(12) United States Patent
Bifulco, Jr. et al.

(10) Patent No.: US 9,434,700 B2
(45) Date of Patent: Sep. 6, 2016

(54) INHIBITORS OF THE FIBROBLAST GROWTH FACTOR RECEPTOR

(71) Applicants: Neil Bifulco, Jr., Sudbury, MA (US); Lucian V. DiPietro, Gloucester, MA (US); Brian L. Hodous, Cambridge, MA (US); Chandrasekhar V. Miduturu, Cambridge, MA (US)

(72) Inventors: Neil Bifulco, Jr., Sudbury, MA (US); Lucian V. DiPietro, Gloucester, MA (US); Brian L. Hodous, Cambridge, MA (US); Chandrasekhar V. Miduturu, Cambridge, MA (US)

(*) Notice: Subject to any disclaimer, the term of this patent is extended or adjusted under 35 U.S.C. 154(b) by 0 days.

(21) Appl. No.: 14/521,909

(22) Filed: Oct. 23, 2014

(65) Prior Publication Data

US 2015/0119405 A1     Apr. 30, 2015

Related U.S. Application Data

(60) Provisional application No. 61/927,782, filed on Jan. 15, 2014, provisional application No. 61/895,472, filed on Oct. 25, 2013.

(51) Int. Cl.
| | | |
|---|---|---|
| *C07D 405/12* | (2006.01) |
| *A61K 31/517* | (2006.01) |
| *C07D 239/84* | (2006.01) |
| *C07D 401/12* | (2006.01) |
| *C07D 403/12* | (2006.01) |
| *C07D 403/14* | (2006.01) |
| *C07D 471/04* | (2006.01) |
| *C07D 401/04* | (2006.01) |
| *C07D 475/00* | (2006.01) |
| *C07D 235/30* | (2006.01) |
| *C07D 409/12* | (2006.01) |
| *C07D 475/08* | (2006.01) |

(52) U.S. Cl.
CPC ........... *C07D 239/84* (2013.01); *C07D 235/30* (2013.01); *C07D 401/04* (2013.01); *C07D 401/12* (2013.01); *C07D 403/12* (2013.01); *C07D 403/14* (2013.01); *C07D 405/12* (2013.01); *C07D 409/12* (2013.01); *C07D 471/04* (2013.01); *C07D 475/00* (2013.01)

(58) Field of Classification Search
None
See application file for complete search history.

(56) References Cited

U.S. PATENT DOCUMENTS

| 6,605,615 | B2 | 8/2003 | Medina et al. |
| 8,802,697 | B2* | 8/2014 | Bifulco et al. ............... 514/303 |
| 9,034,898 | B2 | 5/2015 | Clary-Ceccato et al. |
| 2001/0056096 | A1 | 12/2001 | Medina et al. |
| 2005/0124562 | A1 | 6/2005 | Guiles et al. |
| 2014/0088100 | A1 | 3/2014 | Bifulco, Jr. et al. |
| 2014/0187559 | A1 | 7/2014 | Miduturu |
| 2014/0296233 | A1 | 10/2014 | D'Agostino et al. |
| 2014/0378481 | A1 | 12/2014 | Bifulco, Jr. et al. |
| 2015/0011579 | A1 | 1/2015 | Clary-Ceccato et al. |
| 2015/0119385 | A1 | 4/2015 | Buschmann et al. |
| 2015/0119405 | A1 | 4/2015 | Bifulco, Jr. et al. |
| 2015/0197519 | A1 | 7/2015 | Bifulco, Jr. et al. |

FOREIGN PATENT DOCUMENTS

| EP | 1836174 A2 | 9/2007 |
| EP | 2657233 A1 | 10/2013 |
| WO | 0138315 A1 | 5/2001 |
| WO | 0164646 A2 | 9/2001 |
| WO | 02/076985 A1 | 10/2002 |
| WO | 2004063195 A1 | 7/2004 |
| WO | 2005030131 A2 | 4/2005 |
| WO | 2006039718 A2 | 4/2006 |
| WO | 2009046448 A1 | 4/2009 |
| WO | 2009158571 A1 | 12/2009 |
| WO | 2010028236 A1 | 3/2010 |
| WO | 2010076238 A1 | 7/2010 |
| WO | 2011034907 A2 | 3/2011 |
| WO | 2012158843 A2 | 11/2012 |
| WO | 2013/179034 A1 | 12/2013 |
| WO | 2014011900 A2 | 1/2014 |
| WO | 2014044846 A1 | 3/2014 |
| WO | 2014144737 A1 | 9/2014 |

OTHER PUBLICATIONS

Jain et al. Breast Cancer Research vol. 14,p. 1-9 (2012).*
Cancer Drug Design and Discovery, Neidle, Stephen,ed. (Elsevier/Academic Press), pp. 427-431 (2008).*
Antczak et al. "Structure-activity relationships of 6-(2,6-dichlorophenyl)-8-methyl-2-(phenylamino)pyrido[2,3-d] pyrimidin-7-ones: Toward selective Abl inhibitors" Bioorganic & Medicinal Chemistry Letters (2009) vol. 19, pp. 6872-6876.
Bennett et al, eds. "Cecil Text Book of Medicine" 20th Edition (1996) vol. 1, pp. 1004-1010.
Brown et al. "Cartilage Dysplasia and Tissue Mineralization in the Rat Following Administration of a FGF Receptor Tyrosine Kinase Inhibitor" Toxicologic Pathology 33 (2005) pp. 449-455.
Brunton et al, eds. "Chemotherapy of Neoplastic Diseases" Goodman & Gilman's: The Pharmacological Basis of Therapeutics 11th Edition (2008) pp. 853-908.
Cao et al. "Genome-Wide Identification of PAX3-FKHR Binding Sites in Rhabdomyosarcoma Reveals Candidate Target Genes Important for Development and Cancer" Cancer Research 70 (2010) pp. 6497-6508.
Cohen "The development and therapeutic potential of protein kinase inhibitors" Current Opinions in Chemical Biology (1999) vol. 3, No. 4, pp. 459-465.

(Continued)

*Primary Examiner* — Emily Bernhardt

(57) ABSTRACT

Described herein are inhibitors of FGFR-4, pharmaceutical compositions including such compounds, and methods of using such compounds and compositions.

4 Claims, 2 Drawing Sheets

(56) References Cited

OTHER PUBLICATIONS

Dermer "Another Anniversary for the War on Cancer" Bio/Technology (1994) vol. 12, p. 320.
Ding et al. "Somatic mutations affect key pathways in lung adenocarcinoma" Nature 455 (2008) pp. 1069-1075.
Freshney et al. "Culture of Animal Cells, a Manual of Basic Techniques" Alan R. Liss, Inc. (1983) pp. 1-6.
Golub et al. "Molecular Classification of Cancer: Class Discovery and Class Prediction by Gene Expression Monitoring" Science (1999) vol. 286, pp. 531-537.
Ho et al. "Developing FGFR4 Inhibitors As Potential Anti-Cancer Agents Via In Silico Design, Supported by In Vitro and Cell-Based Testing" Current Medicinal Chemistry (2013) vol. 20, pp. 1203-1217.
Ho et al. "Fibroblast growth factor receptor 4 regulates proliferation, anti-apoptosis and alpha-fetoprotein secretion during hepatocellular carcinoma progression and represents a potential target for therapeutic intervention" Journal of Hepatology 50 (2009) pp. 118-127.
International Search Report and Written Opinion for International Application No. PCT/US2014/061974 dated Dec. 23, 2014, (8 pages).
International Search Report for PCT/US2013/050106 dated Nov. 13, 2013, (6 pages).
Katoh et al. "FGFR2-related pathogenesis and FGFR2-targeted therapuetics" International Journal of Molecular Medicine (2009) vol. 22, pp. 307-311.
Liang et al. "Small molecule inhibition of fibroblast growth factor receptors in cancer" Cytokine & Growth Factor Reviews (2013) vol. 24, pp. 467-475.
Roidl et al. "The FGFR4 Y367C mutant is a dominant oncogene in MDA-MB453 breast cancer cells" Oncogene 29 (2010) pp. 1543-1552.
Sawey et al. "Identification of a Therapeutic Strategy Targeting Amplified FGF19 in Liver Cancer by Oncogenomic Screening" Cancer Cell 19 (2011) pp. 347-358.
Taylor et al. "Identification of FGFR4-activating mutations in human rhabdomyosarcomas that promote metastasis in xenotransplanted models" The Journal of Clinical Investigation 119, 11 (2009) pp. 3395-3407.
Vergnes et al. "Dietl Functions in the FGF15/19 Enterohepatic Signaling Axis to Modulate Bile Acid and Lipid Levels" Cell Metabolism 17 (2013) pp. 916-928.
Wu et al. "A solid-phase Bcr-Abl kinase assay in 96-well hydrogel plates" Analytical Biochemistry (2008) vol. 375, pp. 18-26.
Wu et al. "FGF19-induced Hepatocyte Proliferation Is Mediated through FGFR4 Activation" Journal of Biological Chemistry 285 (2010) pp. 5165-5170.
Zaid et al "Identification of FGFR4 as a Potential Theapeutic Target for Advanced-Stage, High-Grade Serous Ovarian Cancer" Clinical Cancer Research (2013) pp. 809-820.
Zhou et al. "A Structure-Guided Approach to Creating Covalent FGFR Inhibitors". Chemistry & Biology vol. 17, Issue 3 (2010) pp. 285-295.
International Search Report and Written Opinion for International Application No. PCT/US2015/011424 dated May 29, 2015.

* cited by examiner

INHIBITORS OF THE FIBROBLAST GROWTH FACTOR RECEPTOR

CLAIM OF PRIORITY

This application claims priority to U.S. Ser. No. 61/895,472, filed on Oct. 25, 2013, and U.S. Ser. No. 61/927,782, filed on Jan. 15, 2014, which are hereby incorporated by reference in their entirety.

BACKGROUND

Fibroblast growth factor receptor 4 (FGFR-4) is a protein that in humans is encoded by the FGFR-4 gene. This protein is a member of the fibroblast growth factor receptor family, where amino acid sequence was highly conserved between members throughout evolution. FGFR family members 1-4 differ from one another in their ligand affinities and tissue distribution. A full-length representative protein consists of an extracellular region composed of three immunoglobulin-like domains, a single hydrophobic membrane-spanning segment and a cytoplasmic tyrosine kinase domain. The extracellular portion of the protein interacts with fibroblast growth factors, setting in motion a cascade of downstream signals, ultimately influencing mitogenesis and differentiation. The genomic organization of the FGFR-4 gene encompasses 18 exons. Although alternative splicing has been observed, there is no evidence that the C-terminal half of the IgIII domain of this protein varies between three alternate forms, as indicated for FGFR 1-3.

Ectopic mineralization, characterized by inappropriate calcium-phosphorus deposition in soft tissue, has been observed in rats treated with an FGFR-1 inhibitor (Brown, A P et al. (2005), Toxicol. Pathol., p. 449-455). This suggests that selective inhibition of FGFR-4 without inhibition of other isoforms of FGFR, including FGFR-1, may be desirable in order to avoid certain toxicities. FGFR-4 preferentially binds fibroblast growth factor 19 (FGF19) and has recently been associated with the progression of certain sarcomas, renal cell cancer, breast cancer, and liver cancer.

SUMMARY OF THE INVENTION

Figure 1:
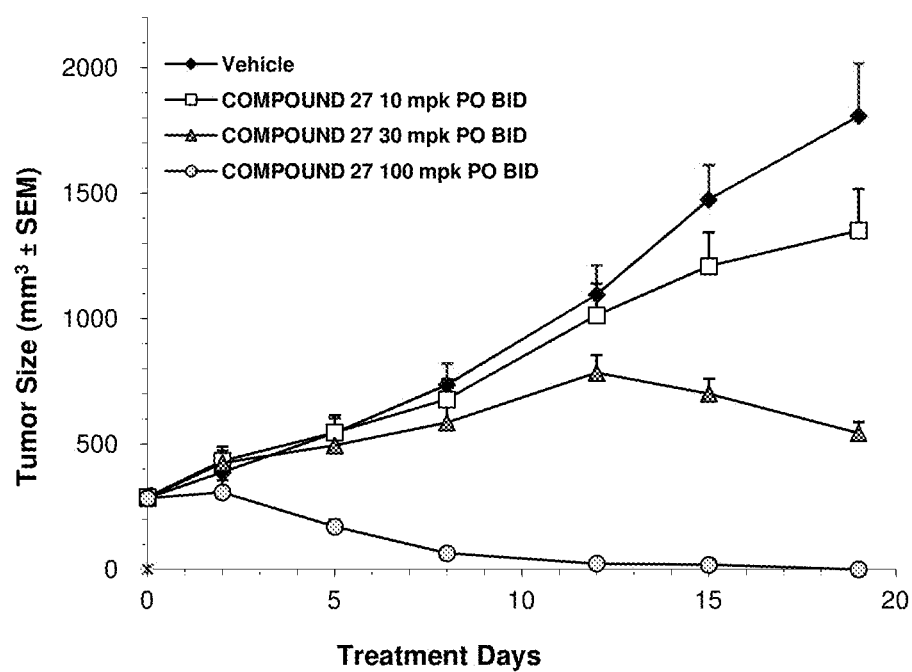
FIG. 1 is a graph depicting the growth inhibition of Compound 27-treated groups against Hep3B xenograft tumors in nude mice.

The present invention describes inhibitors of FGFR-4. The present invention further describes pharmaceutical formulations that include an inhibitor of FGFR-4.

In one aspect, the invention features a compound of Formula I, or a pharmaceutically acceptable salt thereof:

Formula I

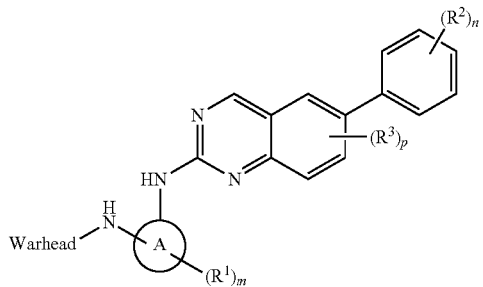

wherein
Warhead is a moiety capable of forming a covalent bond with a nucleophile;
ring A is a 3-8 membered monocyclic or bicyclic cycloalkyl, or heterocyclyl;
each of $R^1$ and $R^2$ is, independently, halo, cyano, $C_{1-6}$ alkoxy, hydroxy, oxo, amino, amido, sulfonyl, sulfonamido, ester, alkyl urea, $C_{1-6}$ alkyl, —C(O)O—, —C(O)—$C_{1-6}$ alkyl, —C(O)—$C_{1-6}$ alkylamino, $C_{1-6}$ heteroalkyl, heterocyclyl, or heterocyclylalkyl, wherein each of $C_{1-6}$ alkoxy, amino, amido, sulfonamido, ester, alkyl urea, $C_{1-6}$ alkyl, $C_{1-6}$ heteroalkyl, heterocyclyl or heterocyclylalkyl is independently substituted with 0-5 occurrences of $R^4$;
$R^3$ is, independently, halo, cyano, $C_{1-6}$ alkoxy, hydroxy, oxo, amino, amido, or $C_{1-6}$ alkyl;
each $R^4$ is, independently, selected from $C_{1-6}$ alkyl, $C_{1-6}$ alkoxy, halo, hydroxy, oxo, amino, cyano, cycloalkyl and heterocyclyl;
m is 0-3;
n is 0-4; and
is 0-2.

In some embodiments, ring A is monocyclic cycloalkyl. In some embodiments, ring A is cyclobutyl, cyclopentyl, or cyclohexyl. In some embodiments, $R^3$ is, independently, halo.

In some embodiments, ring A is bicyclic cycloalkyl.

In some embodiments, ring A is heterocyclyl. In some embodiments, ring A is pyrrolidinyl, piperidinyl, tetrahydrofuranyl, or tetrahydropyranyl. In some embodiments, $R^3$ is, independently, halo.

In another aspect, the invention features a compound of Formula II, or a pharmaceutically acceptable salt thereof:

Formula II

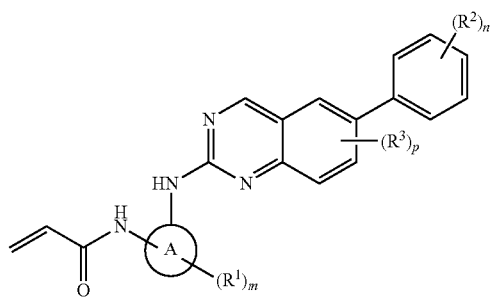

wherein ring A is a 3-6 membered cycloalkyl or heterocyclyl;

$R^1$, is, independently, halo, cyano, $C_{1-6}$ alkoxy, hydroxy, oxo, amino, amido, sulfonyl, sulfonamido, ester, alkyl urea, $C_{1-6}$ alkyl, —C(O)O—, —C(O)—$C_{1-6}$ alkyl, —C(O)—$C_{1-6}$ alkylamino, or $C_{1-6}$ heteroalkyl;

$R^2$ is halo, or $C_{1-6}$ alkoxy;

$R^3$ is halo; and m is 0-1; n is 0-4; and p is 0-1.

In some embodiments, ring A is cycloalkyl.

In some embodiments, ring A is heterocyclyl. In some embodiments, $R^3$ is, independently, halo.

In some embodiments, ring A is cyclobutyl, cyclopentyl, cyclohexyl, pyrrolidinyl, piperidinyl, tetrahydrofuranyl, or tetrahydropyranyl.

In the compounds disclosed herein, a warhead is a moiety that is reactive with a nucleophile, for example, capable of forming a covalent bond with a nucleophile. Examples of warheads include, without limitation, alkyl halides, alkyl sulfonates, heteroaryl halides, epoxides, haloacetamides, maleimides, sulfonate esters, alpha-beta unsaturated ketones, alpha-beta unsaturated esters, vinyl sulfones, propargyl amides, acrylamides. In some of these instances, e.g., acrylamide and propargyl amide, the N of the warhead is the adjacent N in the formulae shown above. Structures of exemplary warheads are shown below:

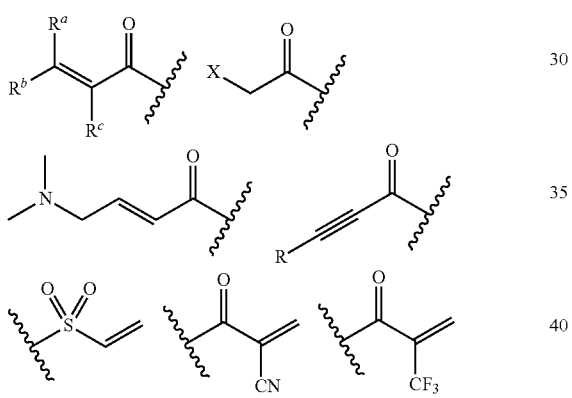

wherein X is a leaving group such as halo, or an activated hydroxyl moiety (e.g., triflate); and each of $R^a$, $R^b$, and $R^c$ is, independently, H, substituted or unsubstituted $C_{1-4}$ alkyl, substituted or unsubstituted $C_{1-4}$ cycloalkyl, or cyano.

In the formulae shown above, the warheads are typically attached to a N atom on the inhibitor. In other embodiments, the warhead can alternatively be attached to an atom other than N. Examples of exemplary warheads include, without limitation,

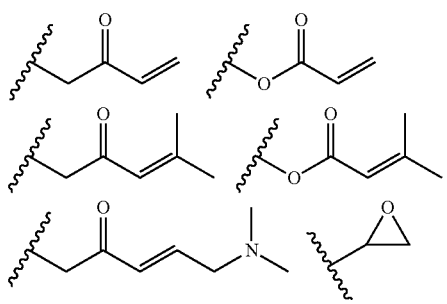

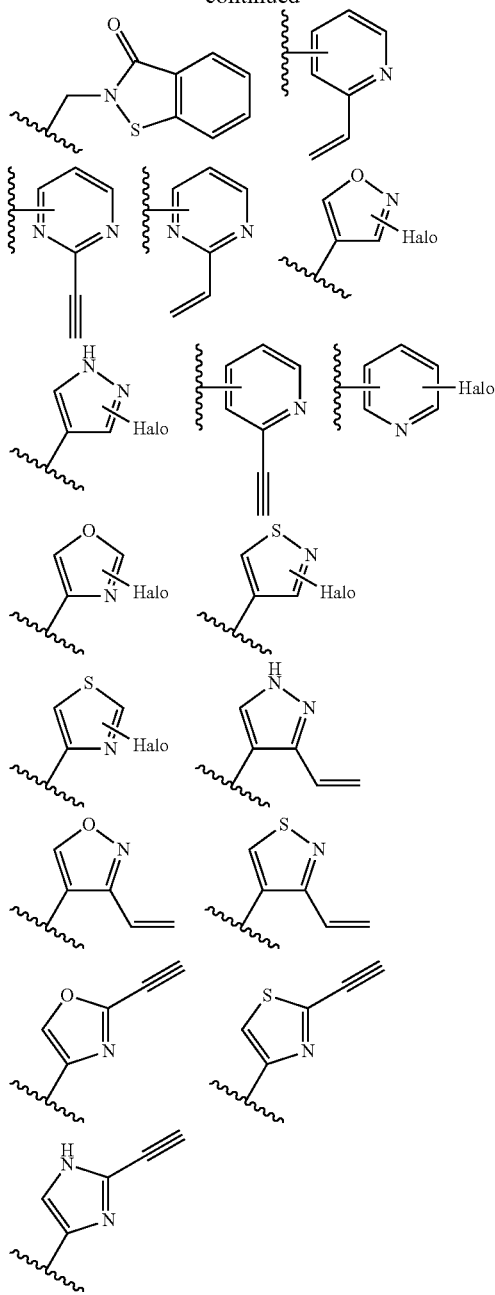

Other examples of warheads can be found, e.g., in WO 2010/028236 and WO 2011/034907.

In certain embodiments, the FGFR-4 inhibitors of the invention inhibit FGFR-4 activity more potently than they inhibit FGFR-1 activity. For example, the FGFR-4 inhibitors of the invention can inhibit FGFR-4 activity at least 10 times, at least 50 times, at least 100 times, at least 200 times, or at least 500 times more potently than they inhibit FGFR-1 activity.

In one aspect, selectivity is measured by comparing the inhibition of FGFR-1 and FGFR-4 caused by the compound of this invention in the same type of assay. In one embodiment, the assays used to measure inhibition of FGFR-1 and FGFR-4 are any of the assays described herein. Typically, inhibition is expressed as $IC_{50}$ (the concentration of inhibitor at which 50% of the activity of the enzyme is inhibited) and thus fold-selectivity is measured by the equation: ($IC_{50}$ FGFR-1)/($IC_{50}$ FGFR-4). The same measurements and calculations can be used to measure selectivity over FGFR-2 and FGFR-3 as well.

Any other assays of FGFR activity may be utilized to determine the relative inhibition of FGFR-1 and FGFR-4 by the compounds of this invention as long as such assays utilize what one of skill in the art would deem to be the same parameters in measuring FGFR activity.

In another aspect, the invention features a pharmaceutical composition comprising a pharmaceutically acceptable carrier and a compound disclosed herein.

In another aspect the invention features a method for treating a condition mediated by FGFR-4, a condition characterized by overexpression of FGFR-4, a condition characterized by amplification of FGFR4, a condition mediated by FGF19, a condition characterized by amplified FGF-19, or a condition characterized by overexpression of FGF19, any of these methods comprising administering a therapeutically effective amount of a compound disclosed herein to a subject.

In another aspect, the invention features a method of treating any of the following conditions by administering a therapeutically effective amount of a compound disclosed herein to a subject: hepatocellular carcinoma, breast cancer, ovarian cancer, lung cancer, liver cancer, a sarcoma, or hyperlipidemia.

The invention includes all possible combinations of the embodiments described above and below.

DETAILED DESCRIPTION OF THE INVENTION

The compounds disclosed below can form a covalent bond with FGFR4 protein; for example, the compounds can form a covalent bond with a cysteine residue of FGFR4, for example, the cysteine at residue 552. FGFRs1-3 do not contain this cysteine. The ability to form a covalent bond between the compound and FGFR4 is therefore an important factor in the selectivity of the compounds disclosed herein for FGFR4.

The details of construction and the arrangement of components set forth in the following description or illustrated in the drawings are not meant to be limiting. Other embodiments and different ways to practice the invention are expressly included. Also, the phraseology and terminology used herein are for the purpose of description and should not be regarded as limiting. The use of "including," "includes," "include," "comprising," or "having," "containing", "involving", and variations thereof herein, is meant to encompass the items listed thereafter and equivalents thereof as well as additional items.

Definitions

"Aliphatic group", as used herein, refers to a straight-chain, branched-chain, or cyclic hydrocarbon group and includes saturated and unsaturated groups, such as an alkyl group, an alkenyl group, and an alkynyl group.

"Alkenyl", as used herein, refers to an aliphatic group containing at least one double bond.

"Alkoxyl" or "alkoxy", as used herein, refers to an alkyl group having an oxygen radical attached thereto. Representative alkoxyl groups include methoxy, ethoxy, propyloxy, tert-butoxy and the like.

Alkyl" refers to a monovalent radical of a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Alkylene" refers to a divalent radical of an alkyl group, e.g., —$CH_2$—, —$CH_2CH_2$—, and $CH_2CH_2CH_2$—.

"Alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

"Alkynylene" refers to an alkynyl having two connecting points. For example, "ethynylene" represents the group —C≡C—. Alkynylene groups can also be in an unsubstituted form or substituted form with one or more substituents.

"Alkylthio", as used herein, refers to a hydrocarbyl group having a sulfur radical attached thereto. In some embodiments, the "alkylthio" moiety is represented by one of —S-alkyl, —S-alkenyl, or —S-alkynyl. Representative alkylthio groups include methylthio, ethylthio, and the like.

"Amido", as used herein, refers to —C(=O)—N($R^1$)($R^2$) or —N($R^1$)—C(=O)—$R^2$ where each of $R^1$ and $R^2$ is H, alkyl, cycloalkyl, alkoxy, or hydroxy.

"Amino", as used herein, refers to —$NH_2$, —NH(alkyl), or —N(alkyl)(alkyl).

"Amplified," as used herein, means additional copies of a gene or chromosome segment are produced in cancer cells that may confer a growth or survival advantage.

"Arylalkyl" or "aralkyl", as used herein, refers to an alkyl group substituted with an aryl group (e.g., an aromatic or hetero aromatic group). Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

"Aryl", as used herein, refers to 5-, 6-, and 7-membered single-ring aromatic groups that may include from zero to four heteroatoms, for example, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls. Each ring can contain, e.g., 5-7 members.

"Carbocyclic ring system" as used herein refers to a monocyclic, bicyclic or polycyclic hydrocarbon ring system, wherein each ring is either completely saturated or contains one or more units of unsaturation, but where no ring is aromatic.

"Carbocyclyl" as used herein refers to a monovalent radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

"Cycloalkyl" as used herein refers to a cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

"Cycloalkylalkyl" as used herein refers to a-(cycloalkyl)-alkyl radical where cycloalkyl and alkyl are as disclosed herein. The "cycloalkylalkyl" is bonded to the parent molecular structure through the cycloalkyl group.

"Cyano" as used herein refers to —CN.

"Covalent inhibitor," as used herein, means an inhibitor that can form a covalent bond with a protein.

"Ester" as used herein refers to —C(=O)—O(R$^1$) or —O—C(=O)—R$^1$ where R$^1$ is H or alkyl.

"FGFR-4" or "FGFR-4 protein" refers to any form of the FGFR-4 protein, including wild type and all variant forms (including, without limitation, mutant forms and splice variants). The FGFR-4 protein is a product of the FGFR-4 gene, and the FGFR-4 protein therefore includes any protein encoded by any form of the FGFR-4 gene, including all aberrations, e.g., point mutations, indels, translocation fusions, and focal amplifications.

"Heteroaromatic ring system" is art-recognized and refers to monocyclic, bicyclic or polycyclic ring system wherein at least one ring is both aromatic and comprises at least one heteroatom (e.g., N, O or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, pyrido[2,3-d]pyrimidine, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

"Heterocyclic ring system" refers to monocyclic, bicyclic and polycyclic ring systems where at least one ring is saturated or partially unsaturated (but not aromatic) and comprises at least one heteroatom. A heterocyclic ring system can be attached to its pendant group at any heteroatom or carbon atom that results in a stable structure and any of the ring atoms can be optionally substituted.

"Heterocyclyl" refers to a monovalent radical of a heterocyclic ring system. Representative heterocylyls include ring systems in which (i) every ring is non-aromatic and at least one ring comprises a heteroatom, e.g., tetrahydrofuranyl, tetrahydropyranyl, tetrahydrothienyl, pyrrolidinyl, pyranyl, thianyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine. In some embodiments, heterocyclyl can include:

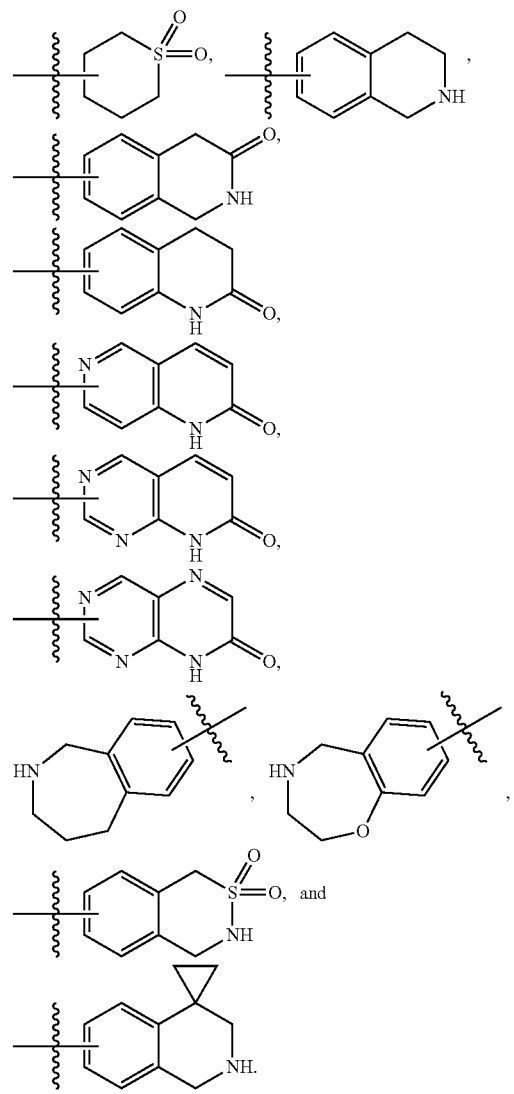

"Heterocyclylalkyl" as used herein refers to an alkyl group substituted with a heterocycl group.

"Heteroarylalkyl" as used herein refers to an alkyl group substituted with a heteroaryl group.

"Hydroxy" or "hydroxyl" as used herein refers to —OH.

"Inhibitor" as used herein refers to a compound that inhibits an enzyme such that a reduction in activity of the enzyme can be observed, e.g., in a biochemical assay. In certain embodiments, an inhibitor has an $IC_{50}$ of less than about 1 µM, less than about 500 nM, less than about 250 nM, less than about 100 nM, less than about 50 nM, or less than about 10 nM. An inhibitor of FGFR-4 refers to a compound that inhibits FGFR-4.

"Nitro" as used herein refers to —$NO_2$.

"Nucleophile" as used herein refers to a species that donates an electron-pair to an electrophile to form a chemical bond in a reaction. In some embodiments, a nucleophile can be an oxygen nucleophile, e.g., water or hydroxyl, a nitrogen nucleophile, e.g., amine, or a sulfur nucleophile, e.g., thiol, such as, for example, the thiol in the side chain of a cysteine residue.

"Overexpressed," as used herein, means there is production of a gene product in a sample that is substantially higher than that observed in a population of control samples (e.g. normal tissue).

"Selective" refers to a compound that inhibits the activity of a target protein, e.g., FGFR-4, more potently than it inhibits activity of other proteins. In this instance, the isoforms FGFR-1, FGFR-2, FGFR-3, and FGFR-4 are all considered distinct proteins. In some embodiments, a compound can inhibit the activity of the target protein, e.g., FGFR-4, at least 1.5, at least 2, at least 5, at least 10, at least 20, at least 30, at least 40, at least 50, at least 60, at least 70, at least 80, at least 90, at least 100, at least 200, at least 500, or at least 1000 or more times potently than it inhibits the activity of a non-target protein.

"Substituted", whether preceded by the term "optionally" or not, refers herein to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like. Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

"Sulfonyl" as used herein refers to —$SO_2$—.

"Sulfonamido" as used herein refers to —S(=O)—N($R^1$)($R^2$) or —N($R^1$)—S(=O)—$R^2$ wherein each of $R^1$ and $R^2$ is independently H or alkyl.

"Warhead moiety" or "warhead" refers to a moiety of an inhibitor which participates, either reversibly or irreversibly, with the reaction of a donor, e.g., a protein, with a substrate. Warheads may, for example, form covalent bonds with the protein, or may create stable transition states, or be a reversible or an irreversible alkylating agent. For example, the warhead moiety can be a functional group on an inhibitor that can participate in a bond-forming reaction, wherein a new covalent bond is formed between a portion of the warhead and a donor, for example an amino acid residue of a protein. The warhead is an electrophile and the "donor" is a nucleophile such as the side chain of a cysteine residue. Examples of suitable warheads include, without limitation, the groups shown below:

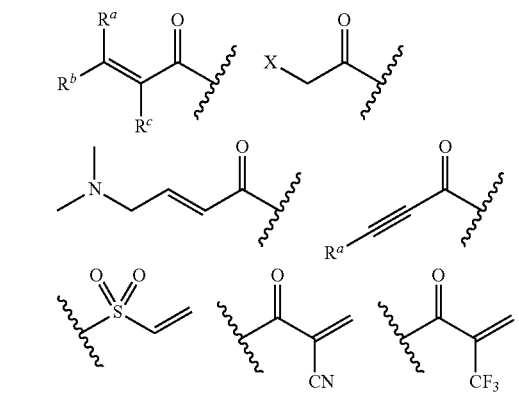

wherein X is a leaving group such as halo, or an activated hydroxyl moiety (e.g., triflate); and each of $R^a$, $R^b$, and $R^c$ is, independently, H, substituted or unsubstituted $C_{1-4}$ alkyl, substituted or unsubstituted $C_{1-4}$ cycloalkyl, or cyano.

The compounds described herein may contain unnatural proportions of atomic isotopes at one or more of the atoms that constitute such compounds. For example, the compounds may be radiolabeled with radioactive isotopes, such as for example tritium ($^3H$) or carbon-14 ($^{14}C$). All isotopic variations of the compounds disclosed herein, whether radioactive or not, are intended to be encompassed within the scope of the present invention. For example, deuterated compounds or compounds containing $^{13}C$ are intended to be encompassed within the scope of the invention.

Certain compounds can exist in different tautomeric forms, and all possible tautomeric forms of all of the compounds described herein are intended to be encompassed within the scope of the invention.

The "enantiomeric excess" or "% enantiomeric excess" of a composition can be calculated using the equation shown below. In the example shown below a composition contains 90% of one enantiomer, e.g., the S-enantiomer, and 10% of the other enantiomer, i.e., the R-enantiomer.

$$ee=(90-10)/100=80\%.$$

Thus, a composition containing 90% of one enantiomer and 10% of the other enantiomer is said to have an enantiomeric excess of 80%. Some of the compositions described herein contain an enantiomeric excess of at least 50%, at least 75%, at least 80%, at least 85%, at least 90%, at least 95%, or at least 99% of Compound 1 (the S-enantiomer). In other words, the compositions contain an enantiomeric excess of the S-enantiomer over the R-enantiomer.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

The compounds described herein can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19.)

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting. In certain embodiments, the compounds provided herein include their hydrates.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable salts of a compound described herein include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds described herein. Water or oil-soluble or dispersible products may be obtained by such quaternization.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; targeting ligands attached to nanoparticles, such as Accurins™; and (22) other non-toxic compatible substances, such as polymer-based compositions, employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intradermally, intraperitoneally, subcutaneously, subcuticularly, or by inhalation.

Indications

FGFR-4 regulates proliferation, survival, and alpha-fetoprotein secretion during hepatocellular carcinoma (HCC) progression; inhibitors of FGFR-4 are therefore promising potential therapeutic agents for this unmet medical need (Ho et al., Journal of Hepatology, 2009, 50:118-27). HCC afflicts more than 550,000 people worldwide every year and has one of the worst 1-year survival rates of any cancer type.

Further evidence of the link between FGFR-4 and HCC is shown through the involvement of FGF19, a member of the fibroblast growth factor (FGF) family, which consists of hormones that regulate glucose, lipid, and energy homeostasis. Increased hepatocyte proliferation and liver tumor formation have been observed in FGF19 transgenic mice. FGF19 activates FGFR-4, its predominant receptor in the liver, and it is believed that activation of FGFR-4 is the mechanism whereby FGF19 can increase hepatocyte proliferation and induce hepatocellular carcinoma formation (Wu et al., J Biol Chem (2010) 285(8):5165-5170). FGF19 has been identified as a driver gene in HCC by others as well (Sawey et al., Cancer Cell (2011) 19: 347-358). It is therefore believed that the compounds disclosed herein, which are potent and selective inhibitors of FGFR-4, can be used to treat HCC and other liver cancers.

Oncogenome screening has identified an activating fibroblast growth factor receptor 4 (FGFR-4) Y367C mutation in the human breast cancer cell line MDA-MB-453. This mutation was shown to elicit constitutive phosphorylation, leading to an activation of the mitogen-activated protein kinase cascade. Accordingly, it has been suggested that FGFR-4 may be a driver of tumor growth in breast cancer (Roidl et al., Oncogene (2010) 29(10):1543-1552). It is therefore believed that the compounds disclosed herein, which are potent and selective inhibitors of FGFR-4, can be used to treat FGFR-4 modulated breast cancer.

Molecular changes (e.g., translocations) in genes upstream of FGFR-4 can lead to activation/overexpression of FGFR-4. For example, a PAX3-FKHR translocation/gene fusion can lead to FGFR-4 overexpression. Overexpression of FGFR-4 due to this mechanism has been associated with rhabdomyosarcoma (RMS) (Cao et al., Cancer Res (2010) 70(16): 6497-6508). Mutations in FGFR-4 itself (e.g., kinase domain mutations) can lead to over-activation of the protein; this mechanism has been associated with a subpopulation of RMS (Taylor et al., J Clin Invest (2009) 119: 3395-3407). It is therefore believed that the compounds disclosed herein, which are potent and selective inhibitors of FGFR-4, can be used to treat FGFR-4 modulated RMS and other sarcomas.

Other diseases have been associated with changes in genes upstream of FGFR-4 or with mutations in FGFR-4 itself. For example, mutations in the kinase domain of FGFR-4 lead to over-activation, which has been associated with lung adenocarcinoma (Ding et al., Nature (2008) 455 (7216): 1069-1075). Amplification of FGFR-4 has been associated with conditions such as renal cell carcinoma (TCGA provisional data). In addition, silencing FGFR4 and inhibiting ligand-receptor binding significantly decrease ovarian tumor growth, suggesting that inhibitors of FGFR4 could be useful in treating ovarian cancer. (Zaid et al., Clin. Cancer Res. (2013) 809).

Pathogenic elevations of bile acid levels have been linked to variations in FGF19 levels (Vergnes et al., Cell Metabolism (2013) 17, 916-28). Reduction in the level of FGF19 may therefore be of benefit in promoting the synthesis of bile acid and thus in the treatment of hyperlipidemia.

Dose Levels

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, doses of the compounds of this invention for a patient will range from about 0.0001 to about 100 mg per kilogram of body weight per day. For example, the dose could be between 10 and 2000 mg per day. Alternatively, the dose can be between 100 and 1000 mg per day, or between 200 and 600 mg per day. If desired, the effective daily dose of the active compound may be administered as one, two, three, four, or more sub-doses administered separately at appropriate intervals throughout the day, optionally, in unit dosage forms.

Combination and Targeted Therapy

Administration of the FGFR-4 inhibitors disclosed herein can be combined with other cancer treatments. For example, the inhibitors can be administered in combination with surgical treatments, radiation, or other therapeutic agents such as antibodies, other selective kinase inhibitors, or chemotherapeutics. The inhibitors may also be administered in combination with RNAi therapy or antisense therapy. The FGFR-4 inhibitors described herein may be combined with one, two, or more other therapeutic agents. In the examples outlined below, it is understood that "second therapeutic agent" also includes more than one therapeutic agent other than the FGFR-4 inhibitor. For instance, the compounds disclosed herein may be combined with an agent such as sorafenib. A FGFR-4 inhibitor described herein may be administered with one, two, or more other therapeutic agents.

The FGFR-4 inhibitors described herein and the second therapeutic agent do not have to be administered in the same pharmaceutical composition, and may, because of different physical and chemical characteristics, be administered by different routes. For example, the FGFR-4 inhibitor can be administered orally, while the second therapeutic agent is administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The FGFR-4 inhibitor and the second therapeutic agent may be administered concurrently (e.g., simultaneously, essentially simultaneously or within the same treatment protocol) or sequentially (i.e., one followed by the other, with an optional time interval in between), depending upon the nature of the proliferative disease, the condition of the patient, and the actual choice of second therapeutic agent to be administered.

In addition, the FGFR-4 inhibitors disclosed herein can be administered as part of an antibody-drug conjugate, where the FGFR-4 inhibitor is the "payload" portion of the conjugate.

Compounds

The table below shows the structures of compounds described herein.

| Compound Number | Structure |
|---|---|
| 1 | 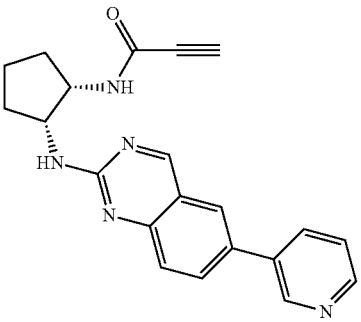 [SMILES: C#CC(=O)N[C@H]1CCC[C@H]1Nc1ncc2cc(-c3cccnc3)ccc2n1] |
| 2 | 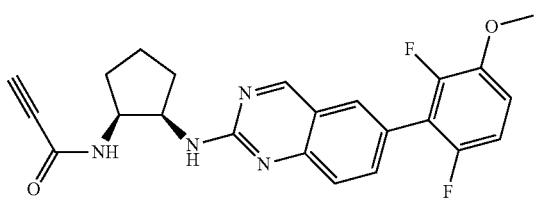 [SMILES: C#CC(=O)N[C@H]1CCC[C@H]1Nc1ncc2cc(-c3c(F)ccc(OC)c3F)ccc2n1] |

-continued
| Compound Number | Structure |
|---|---|
| 3 | 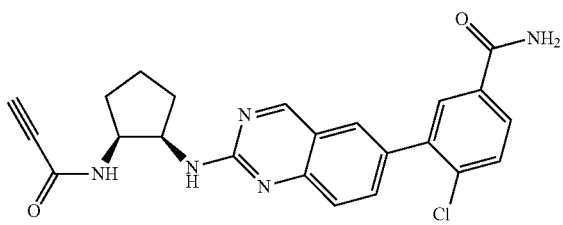 [SMILES: C#CC(=O)N[C@H]1CCC[C@H]1Nc1ncc2cc(-c3cc(C(N)=O)ccc3Cl)ccc2n1] |
| 4 | 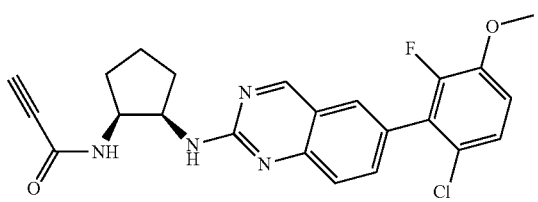 |
| 5 | 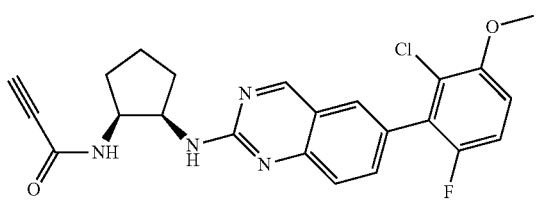 [SMILES: C#CC(=O)N[C@H]1CCC[C@H]1Nc1ncc2cc(-c3c(F)ccc(OC)c3Cl)ccc2n1] |
| 6 | 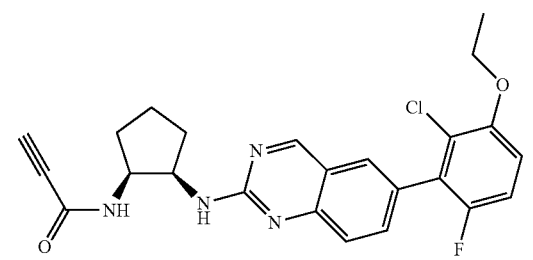 [SMILES: C#CC(=O)N[C@H]1CCC[C@H]1Nc1ncc2cc(-c3c(F)ccc(OCC)c3Cl)ccc2n1] |
| 7 | 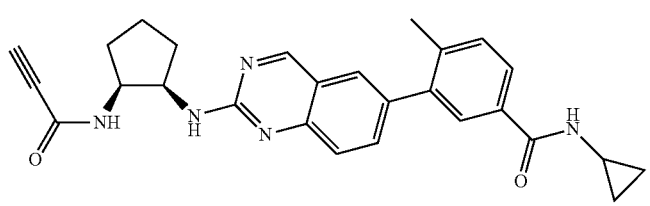 [SMILES: C#CC(=O)N[C@H]1CCC[C@H]1Nc1ncc2cc(-c3cc(C(=O)NC4CC4)ccc3C)ccc2n1] |
| 8 | 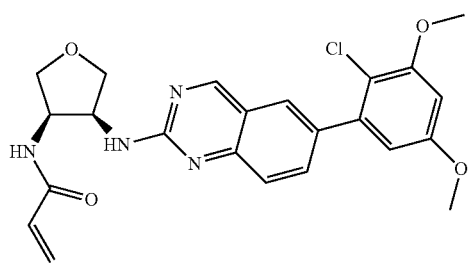 [SMILES: C=CC(=O)N[C@H]1COC[C@H]1Nc1ncc2cc(-c3cc(OC)cc(OC)c3Cl)ccc2n1] |

-continued
| Compound Number | Structure |
|---|---|
| 9 | 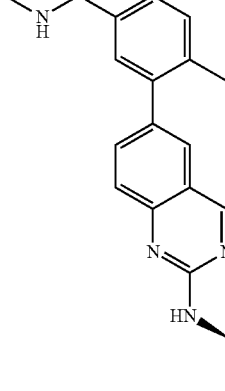 |
| 10 | 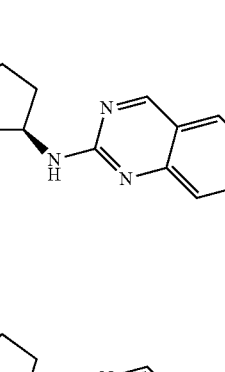 |
| 11 | 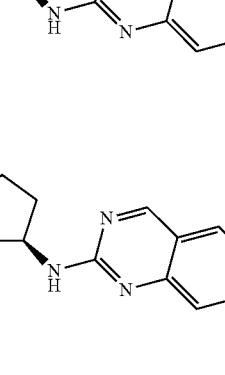 |
| 12 | 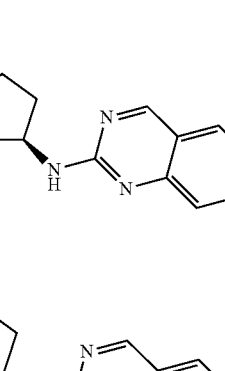 |
| 13 | 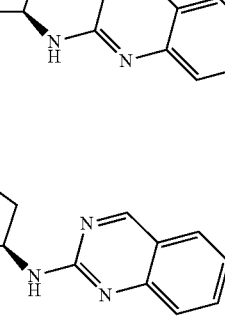 |

-continued
| Compound Number | Structure |
|---|---|
| 14 | 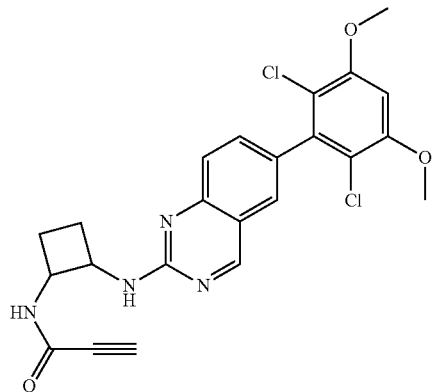<br>cis-racemate |
| 15 | 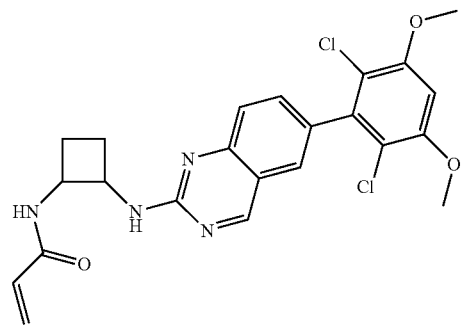<br>cis-racemate |
| 16 | 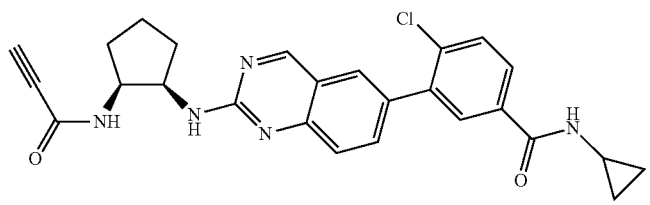 [SMILES: C#CC(=O)N[C@H]1CCC[C@H]1Nc1ncc2cc(-c3cc(C(=O)NC4CC4)ccc3Cl)ccc2n1] |
| 17 | 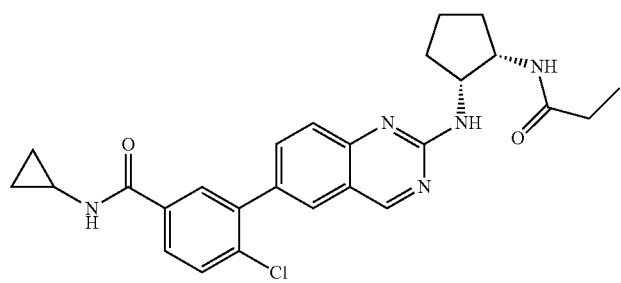 [SMILES: CCC(=O)N[C@H]1CCC[C@H]1Nc1ncc2cc(-c3cc(C(=O)NC4CC4)ccc3Cl)ccc2n1] |
| 18 | 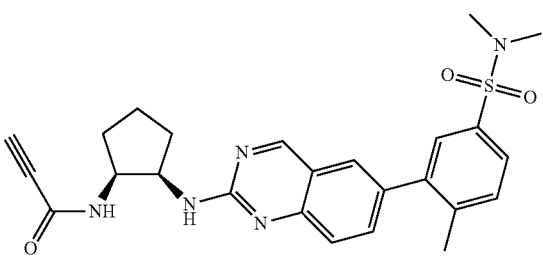 [SMILES: C#CC(=O)N[C@H]1CCC[C@H]1Nc1ncc2cc(-c3cc(S(=O)(=O)N(C)C)ccc3C)ccc2n1] |

-continued
| Compound Number | Structure |
|---|---|
| 19 | 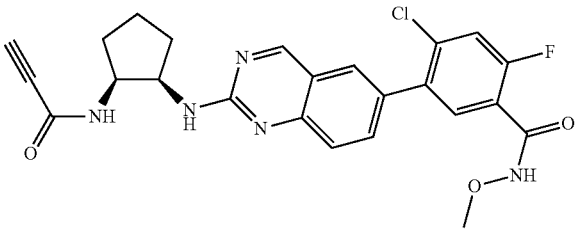 [SMILES: C#CC(=O)N[C@H]1CCC[C@H]1Nc1ncc2cc(-c3cc(C(=O)NOC)c(F)cc3Cl)ccc2n1] |
| 20 | 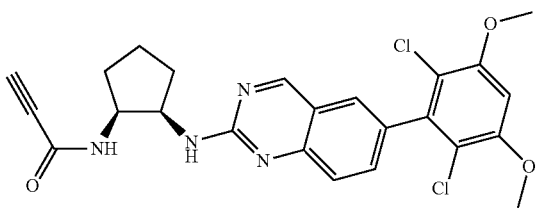 [SMILES: C#CC(=O)N[C@H]1CCC[C@H]1Nc1ncc2cc(-c3c(Cl)c(OC)cc(OC)c3Cl)ccc2n1] |
| 21 | 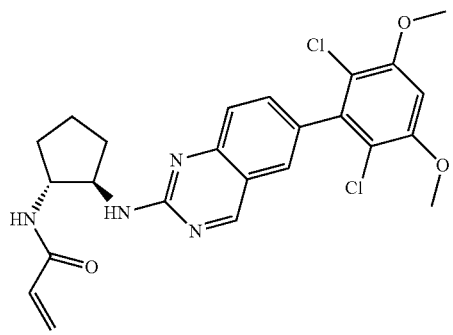 [SMILES: C=CC(=O)N[C@@H]1CCC[C@H]1Nc1ncc2cc(-c3c(Cl)c(OC)cc(OC)c3Cl)ccc2n1] |
| 22 | 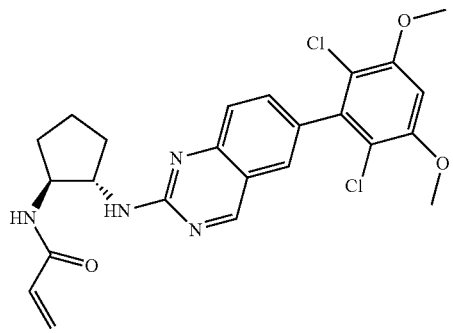 [SMILES: C=CC(=O)N[C@H]1CCC[C@@H]1Nc1ncc2cc(-c3c(Cl)c(OC)cc(OC)c3Cl)ccc2n1] |
| 23 | 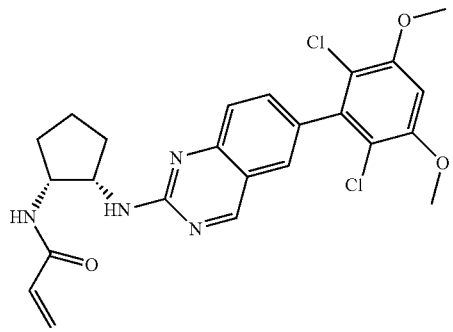 |

-continued
| Compound Number | Structure |
|---|---|
| 24 | 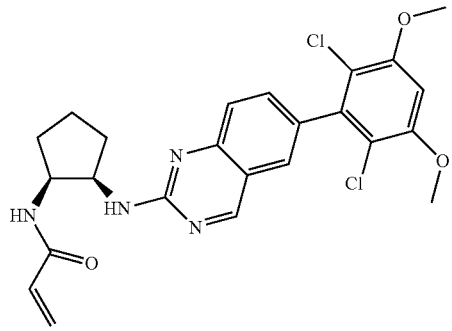 |
| 25 | 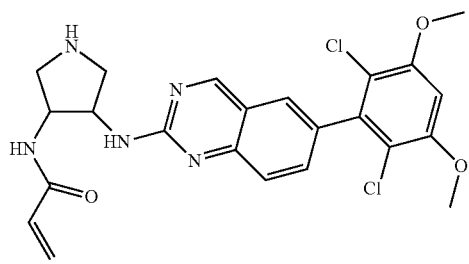
cis-racemate |
| 26 | 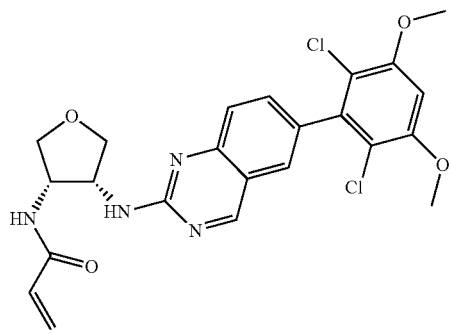 [SMILES: C=CC(=O)N[C@@H]1CCC[C@@H]1Nc1ncc2cc(-c3c(Cl)c(OC)cc(OC)c3Cl)ccc2n1] |
| 27 | 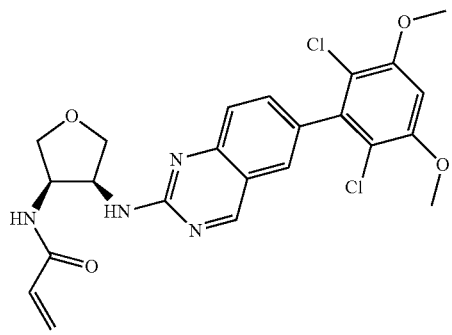 [SMILES: C=CC(=O)N[C@H]1CCC[C@H]1Nc1ncc2cc(-c3c(Cl)c(OC)cc(OC)c3Cl)ccc2n1] |

-continued
| Compound Number | Structure |
|---|---|
| 28 | 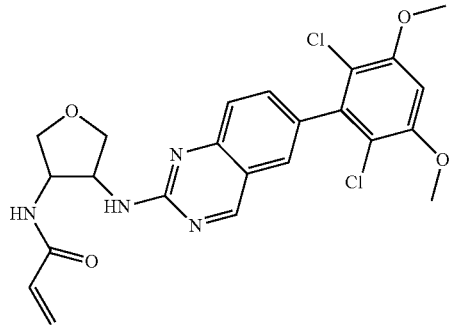 [SMILES: C=CC(=O)N[C@@H]1COC[C@@H]1Nc1ncc2cc(-c3c(Cl)c(OC)cc(OC)c3Cl)ccc2n1]<br>cis-racemate |
| 29 | 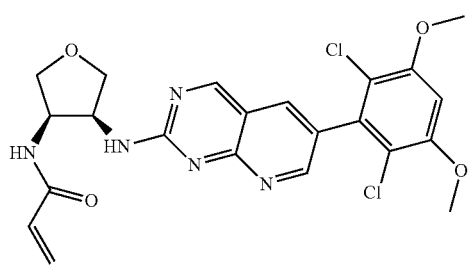 [SMILES: C=CC(=O)N[C@H]1COC[C@H]1Nc1ncc2cc(-c3c(Cl)c(OC)cc(OC)c3Cl)cnc2n1] |
| 30 | 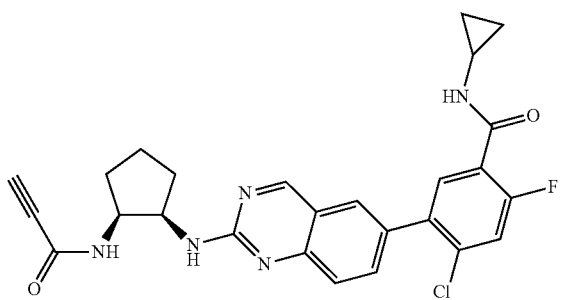 [SMILES: C#CC(=O)N[C@H]1CCC[C@H]1Nc1ncc2cc(-c3cc(C(=O)NC4CC4)c(F)cc3Cl)ccc2n1] |
| 31 | 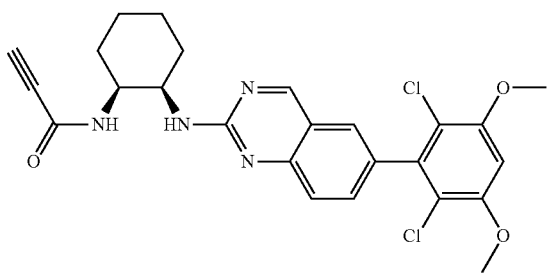 [SMILES: C#CC(=O)N[C@H]1CCCC[C@H]1Nc1ncc2cc(-c3c(Cl)c(OC)cc(OC)c3Cl)ccc2n1] |

| Compound Number | Structure |
|---|---|
| 32 | 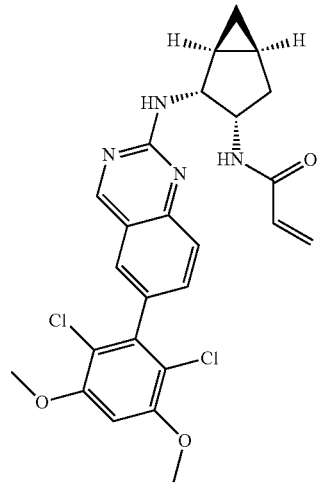 [SMILES: C=CC(=O)N[C@H]1C[C@@H]2C[C@@H]2[C@H]1Nc1ncc2cc(-c3c(Cl)c(OC)cc(OC)c3Cl)ccc2n1] |
| 33 | 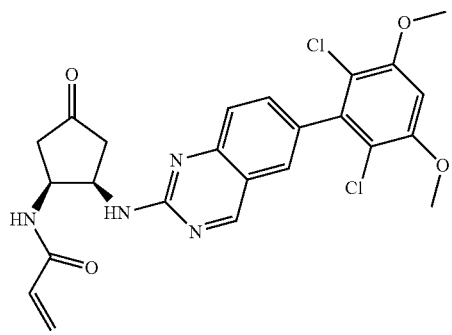 [SMILES: C=CC(=O)N[C@H]1CC(=O)C[C@H]1Nc1ncc2cc(-c3c(Cl)c(OC)cc(OC)c3Cl)ccc2n1] |
| 34 | 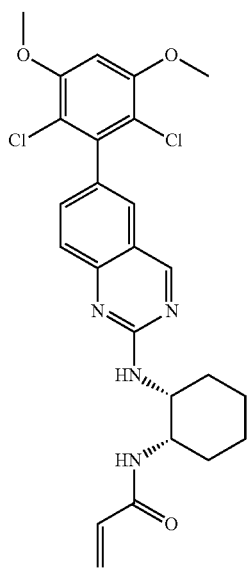 [SMILES: C=CC(=O)N[C@H]1CCCC[C@H]1Nc1ncc2cc(-c3c(Cl)c(OC)cc(OC)c3Cl)ccc2n1] |

-continued
| Compound Number | Structure |
|---|---|
| 35 | 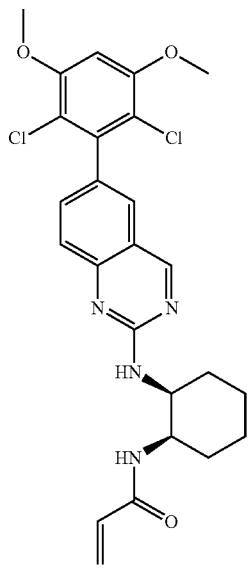 [SMILES: C=CC(=O)N[C@@H]1CCCC[C@@H]1Nc1ncc2cc(-c3c(Cl)c(OC)cc(OC)c3Cl)ccc2n1] |
| 36 | 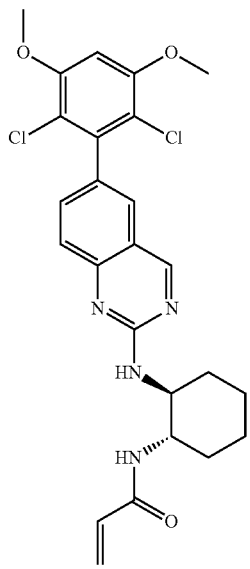 [SMILES: C=CC(=O)N[C@H]1CCCC[C@@H]1Nc1ncc2cc(-c3c(Cl)c(OC)cc(OC)c3Cl)ccc2n1] |

-continued
| Compound Number | Structure |
|---|---|
| 37 | 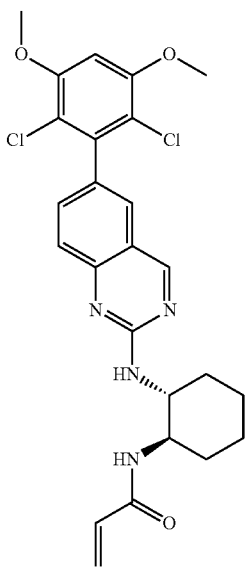 [SMILES: C=CC(=O)N[C@@H]1CCCC[C@H]1Nc1ncc2cc(-c3c(Cl)c(OC)cc(OC)c3Cl)ccc2n1] |
| 38 | 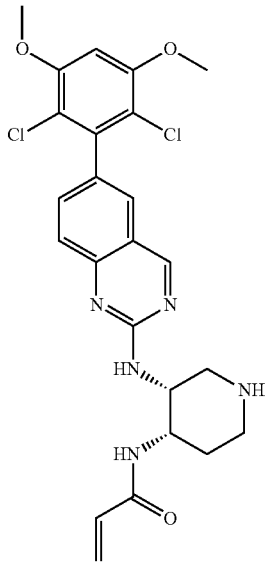 [SMILES: C=CC(=O)N[C@H]1CCNC[C@H]1Nc1ncc2cc(-c3c(Cl)c(OC)cc(OC)c3Cl)ccc2n1] |

-continued
| Compound Number | Structure |
|---|---|
| 39 | 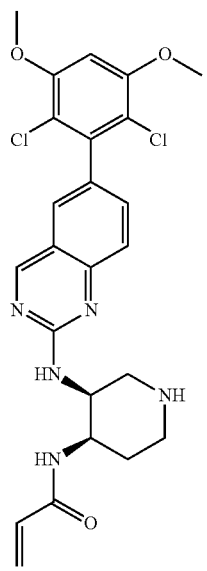 [SMILES: C=CC(=O)N[C@@H]1CCNC[C@@H]1Nc1ncc2cc(-c3c(Cl)c(OC)cc(OC)c3Cl)ccc2n1] |
| 40 | 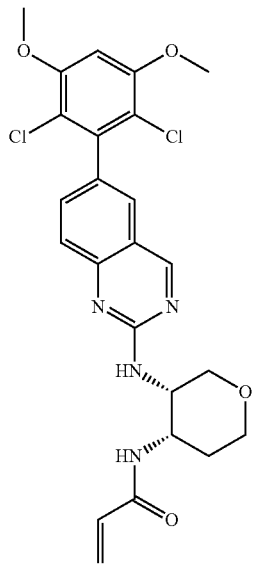 [SMILES: C=CC(=O)N[C@H]1CCOC[C@H]1Nc1ncc2cc(-c3c(Cl)c(OC)cc(OC)c3Cl)ccc2n1] |

| Compound Number | Structure |
|---|---|
| 41 | 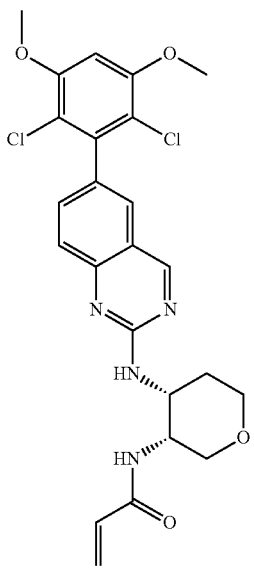 [SMILES: C=CC(=O)N[C@H]1COCC[C@H]1Nc1ncc2cc(-c3c(Cl)c(OC)cc(OC)c3Cl)ccc2n1] |
| 42 | 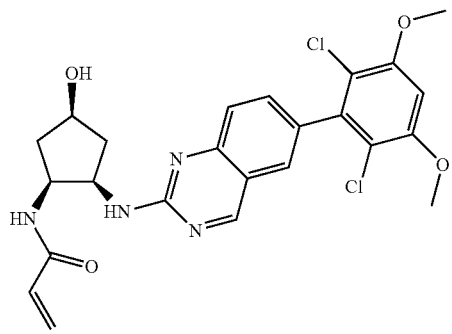 [SMILES: C=CC(=O)N[C@H]1C[C@@H](O)C[C@H]1Nc1ncc2cc(-c3c(Cl)c(OC)cc(OC)c3Cl)ccc2n1] |
| 43 | 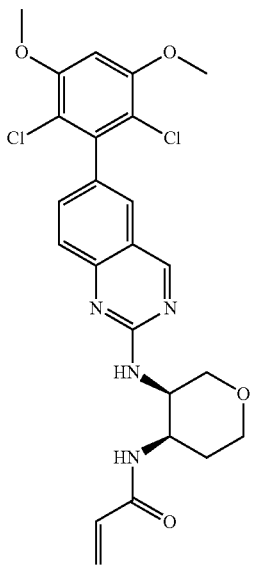 [SMILES: C=CC(=O)N[C@@H]1CCOC[C@@H]1Nc1ncc2cc(-c3c(Cl)c(OC)cc(OC)c3Cl)ccc2n1] |

| Compound Number | Structure |
|---|---|
| 44 | 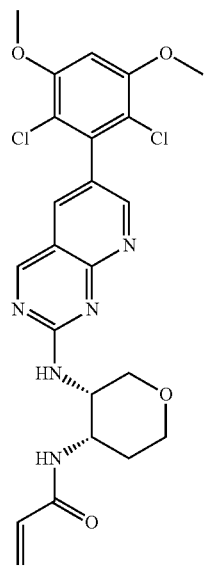 [SMILES: C=CC(=O)N[C@H]1CCOC[C@H]1Nc1ncc2cc(-c3c(Cl)c(OC)cc(OC)c3Cl)cnc2n1] |
| 45 | 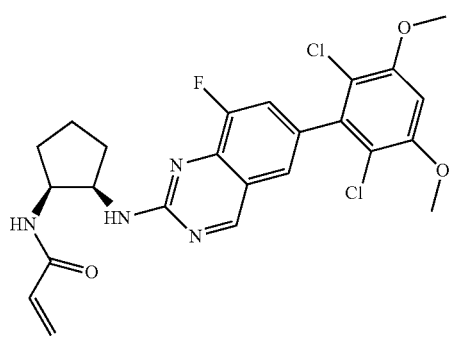 |
| 46 | 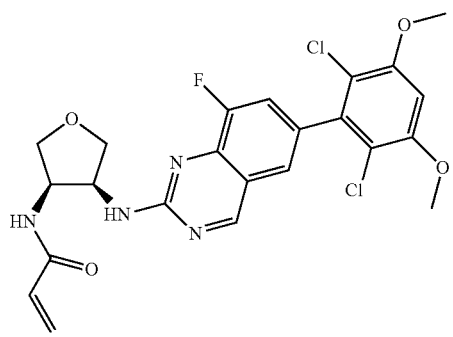 [SMILES: C=CC(=O)N[C@H]1COC[C@H]1Nc1ncc2cc(-c3c(Cl)c(OC)cc(OC)c3Cl)cc(F)c2n1] |
| 47 | 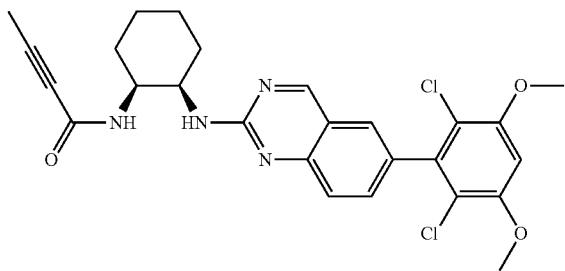 [SMILES: CC#CC(=O)N[C@H]1CCCC[C@H]1Nc1ncc2cc(-c3c(Cl)c(OC)cc(OC)c3Cl)ccc2n1] |

-continued
| Compound Number | Structure |
|---|---|
| 48 | 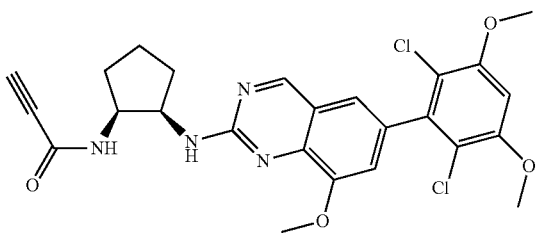 [SMILES: C#CC(=O)N[C@H]1CCC[C@H]1Nc1ncc2cc(-c3c(Cl)c(OC)cc(OC)c3Cl)cc(OC)c2n1] |
| 49 | 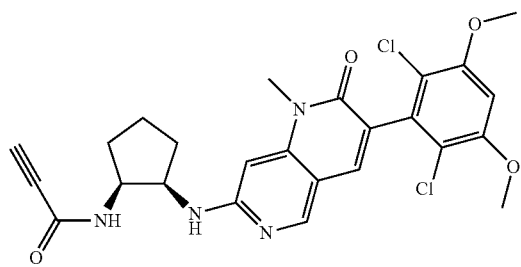 [SMILES: C#CC(=O)N[C@H]1CCC[C@H]1Nc1cc2c(cn1)cc(-c1c(Cl)c(OC)cc(OC)c1Cl)c(=O)n2C] |
| 50 | 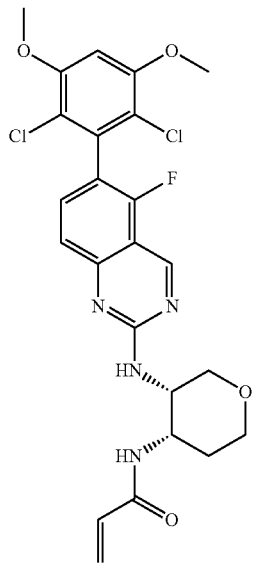 [SMILES: C=CC(=O)N[C@H]1CCOC[C@H]1Nc1ncc2c(F)c(-c3c(Cl)c(OC)cc(OC)c3Cl)ccc2n1] |

-continued
| Compound Number | Structure |
|---|---|
| 51 | 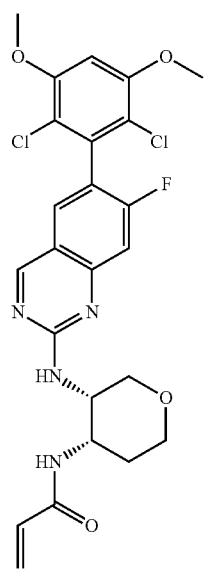 [SMILES: C=CC(=O)N[C@H]1CCOC[C@H]1Nc1ncc2cc(-c3c(Cl)c(OC)cc(OC)c3Cl)c(F)cc2n1] |
| 52 | 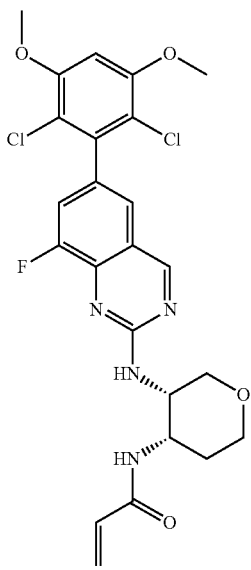 [SMILES: C=CC(=O)N[C@H]1CCOC[C@H]1Nc1ncc2cc(-c3c(Cl)c(OC)cc(OC)c3Cl)cc(F)c2n1] |
| 53 | 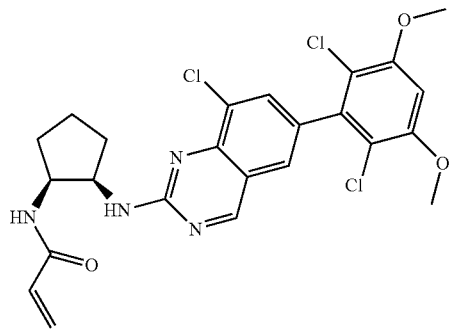 |

-continued

| Compound Number | Structure |
|---|---|
| 54 | 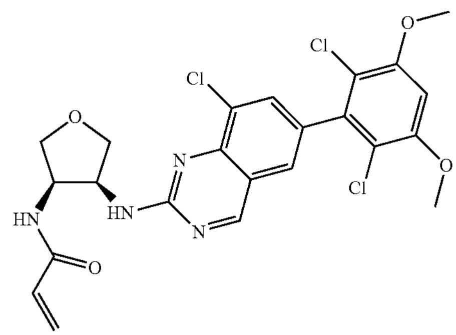 [SMILES: C=CC(=O)N[C@H]1COC[C@H]1Nc1ncc2cc(-c3c(Cl)c(OC)cc(OC)c3Cl)cc(Cl)c2n1] |
| 55 | 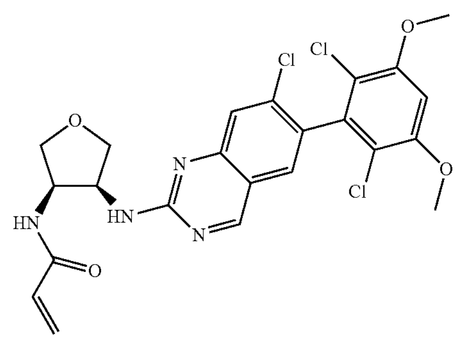 [SMILES: C=CC(=O)N[C@H]1COC[C@H]1Nc1ncc2cc(-c3c(Cl)c(OC)cc(OC)c3Cl)c(Cl)cc2n1] |
| 56 | 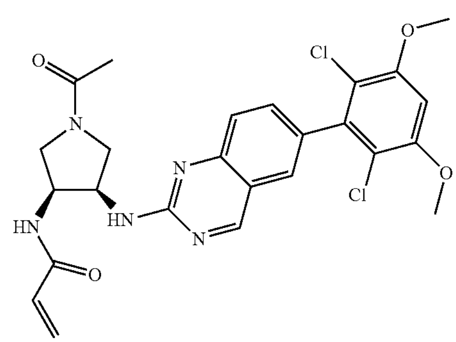 [SMILES: C=CC(=O)N[C@H]1CN(C(C)=O)C[C@H]1Nc1ncc2cc(-c3c(Cl)c(OC)cc(OC)c3Cl)ccc2n1] |
| 57 | 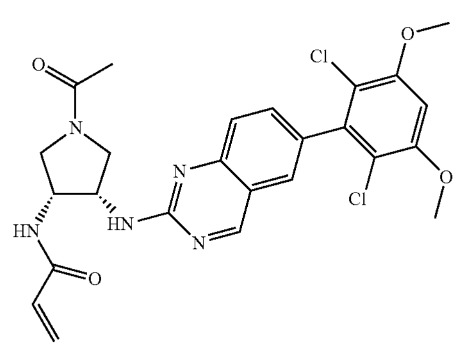 [SMILES: C=CC(=O)N[C@@H]1CN(C(C)=O)C[C@@H]1Nc1ncc2cc(-c3c(Cl)c(OC)cc(OC)c3Cl)ccc2n1] |

-continued
| Compound Number | Structure |
|---|---|
| 58 | 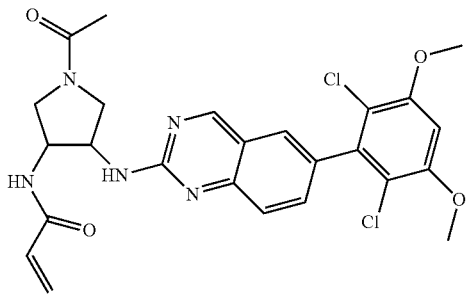 cis-racemate |
| 59 | 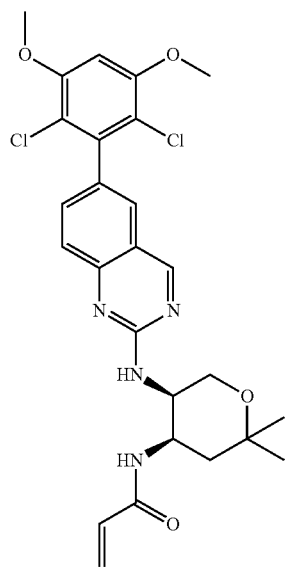 [SMILES: C=CC(=O)N[C@@H]1CC(C)(C)OC[C@@H]1Nc1ncc2cc(-c3c(Cl)c(OC)cc(OC)c3Cl)ccc2n1] |
| 60 | 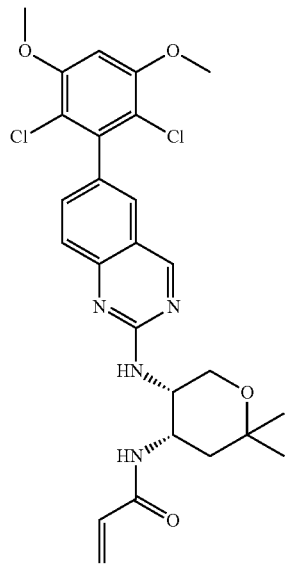 [SMILES: C=CC(=O)N[C@H]1CC(C)(C)OC[C@H]1Nc1ncc2cc(-c3c(Cl)c(OC)cc(OC)c3Cl)ccc2n1] |

-continued
| Compound Number | Structure |
|---|---|
| 61 | 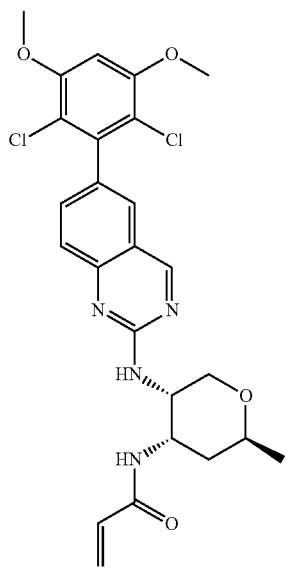 [SMILES: C=CC(=O)N[C@H]1C[C@H](C)OC[C@H]1Nc1ncc2cc(-c3c(Cl)c(OC)cc(OC)c3Cl)ccc2n1] |
| 62 | 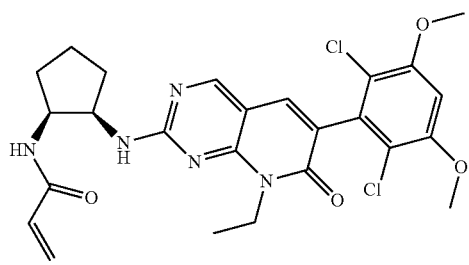 [SMILES: C=CC(=O)N[C@H]1CCC[C@H]1Nc1ncc2cc(-c3c(Cl)c(OC)cc(OC)c3Cl)c(=O)n(CC)c2n1] |
| 63 | 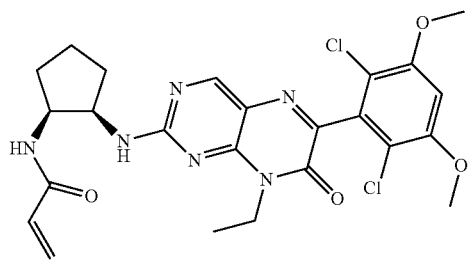 [SMILES: C=CC(=O)N[C@H]1CCC[C@H]1Nc1ncc2nc(-c3c(Cl)c(OC)cc(OC)c3Cl)c(=O)n(CC)c2n1] |

-continued
| Compound Number | Structure |
|---|---|
| 64 | 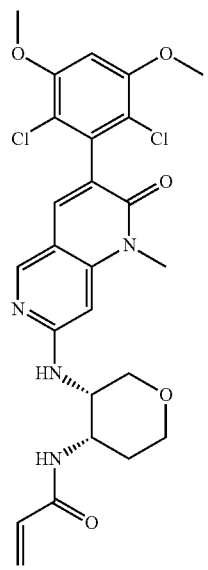 [SMILES: C=CC(=O)N[C@H]1CCOC[C@H]1Nc1cc2c(cn1)cc(-c1c(Cl)c(OC)cc(OC)c1Cl)c(=O)n2C] |
| 65 | 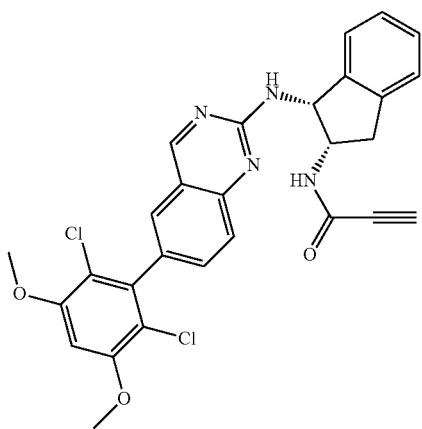 [SMILES: C#CC(=O)N[C@H]1Cc2ccccc2[C@H]1Nc1ncc2cc(-c3c(Cl)c(OC)cc(OC)c3Cl)ccc2n1] |
| 66 | 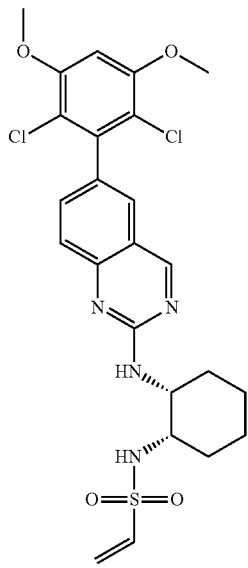 [SMILES: C=CS(=O)(=O)N[C@H]1CCCC[C@H]1Nc1ncc2cc(-c3c(Cl)c(OC)cc(OC)c3Cl)ccc2n1] |

-continued
| Compound Number | Structure |
|---|---|
| 67 | 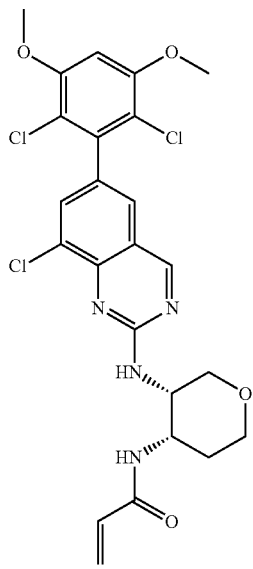 [SMILES: C=CC(=O)N[C@H]1CCOC[C@H]1Nc1ncc2cc(-c3c(Cl)c(OC)cc(OC)c3Cl)cc(Cl)c2n1] |
| 68 | 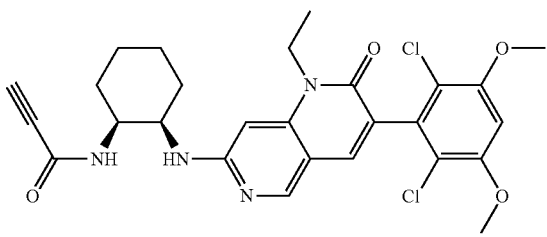 [SMILES: C#CC(=O)N[C@H]1CCCC[C@H]1Nc1cc2c(cn1)cc(-c1c(Cl)c(OC)cc(OC)c1Cl)c(=O)n2CC] |
| 69 | 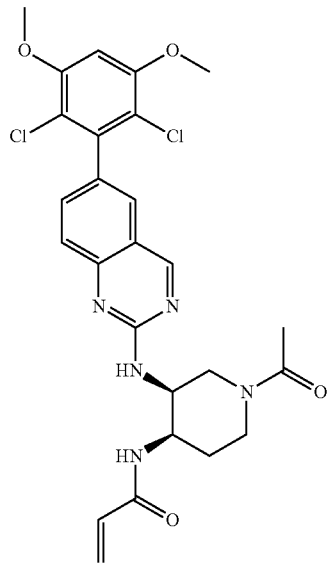 [SMILES: C=CC(=O)N[C@@H]1CCN(C(C)=O)C[C@@H]1Nc1ncc2cc(-c3c(Cl)c(OC)cc(OC)c3Cl)ccc2n1] |

-continued
| Compound Number | Structure |
|---|---|
| 70 | 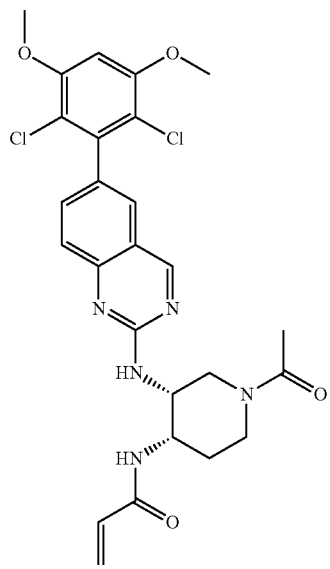 [SMILES: C=CC(=O)N[C@H]1CCN(C(C)=O)C[C@H]1Nc1ncc2cc(-c3c(Cl)c(OC)cc(OC)c3Cl)ccc2n1] |
| 71 | 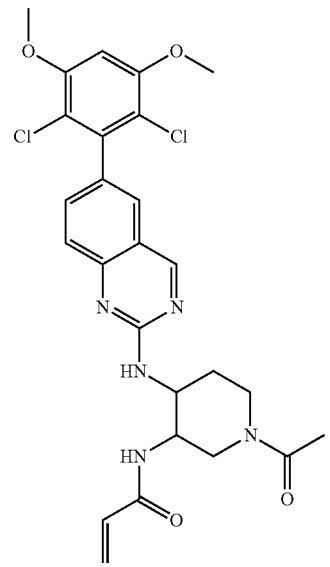<br>cis-racemate |

-continued
| Compound Number | Structure |
|---|---|
| 72 | 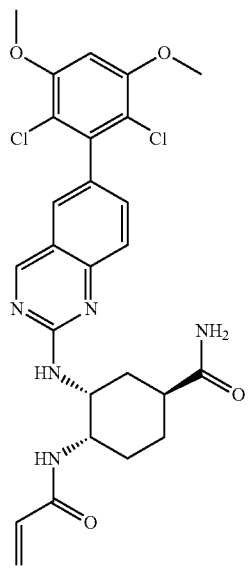<br>racemate |
| 73 | 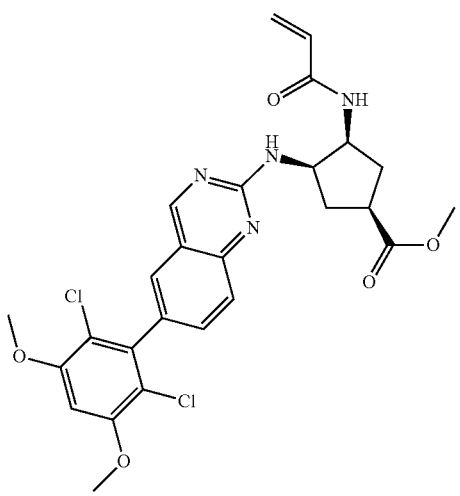 |
| 74 | 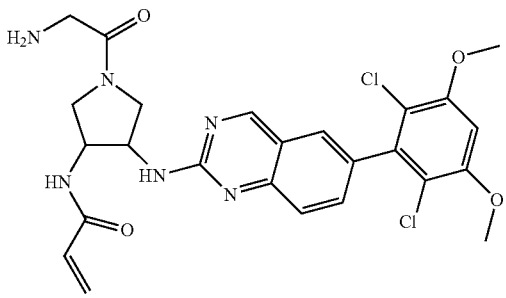<br>cis-racemate |

-continued
| Compound Number | Structure |
|---|---|
| 75 | 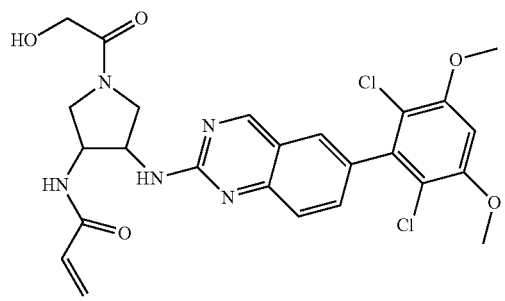 [SMILES: C=CC(=O)NC1CN(C(=O)CO)CC1Nc1ncc2cc(-c3c(Cl)c(OC)cc(OC)c3Cl)ccc2n1] |
| 76 | 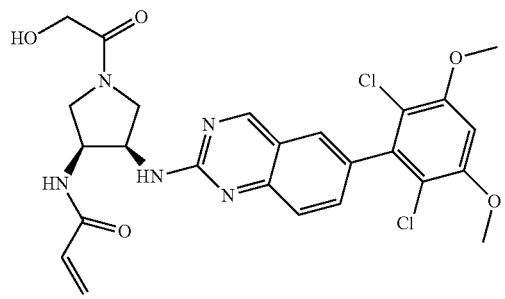 [SMILES: C=CC(=O)N[C@H]1CN(C(=O)CO)C[C@H]1Nc1ncc2cc(-c3c(Cl)c(OC)cc(OC)c3Cl)ccc2n1] |
| 77 | 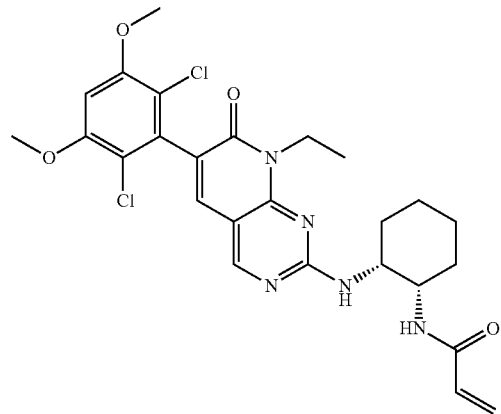 |
| 78 | 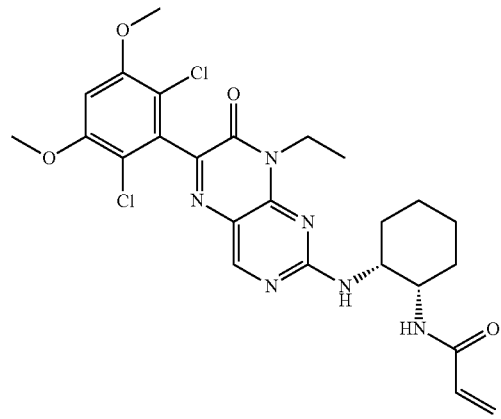 [SMILES: C=CC(=O)N[C@H]1CCCC[C@H]1Nc1ncc2cc(-c3c(Cl)c(OC)cc(OC)c3Cl)c(=O)n(CC)c2n1] |

| Compound Number | Structure |
|---|---|
| 79 | 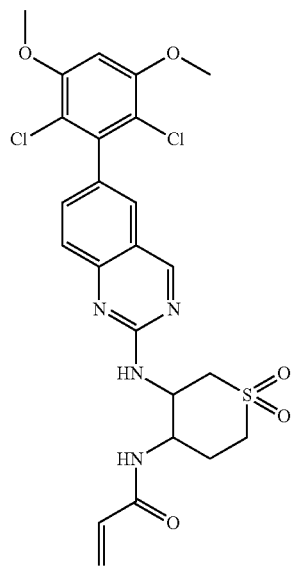 cis-racemate |
| 80 | 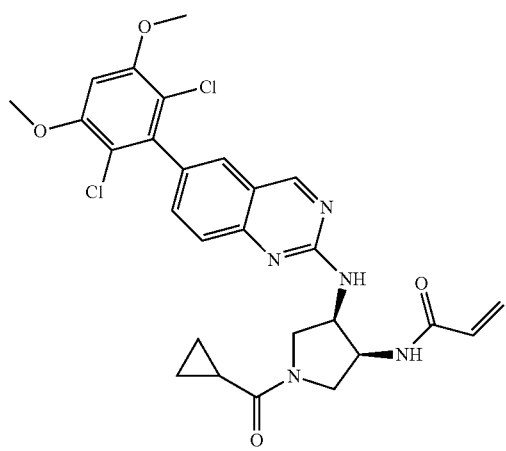 [SMILES: C=CC(=O)N[C@H]1CN(C(=O)C2CC2)C[C@H]1Nc1ncc2cc(-c3c(Cl)c(OC)cc(OC)c3Cl)ccc2n1] |
| 81 | 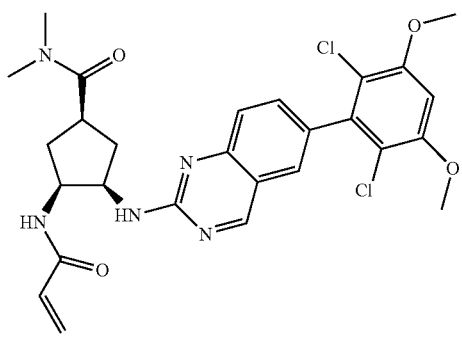 |

-continued
| Compound Number | Structure |
|---|---|
| 82 | 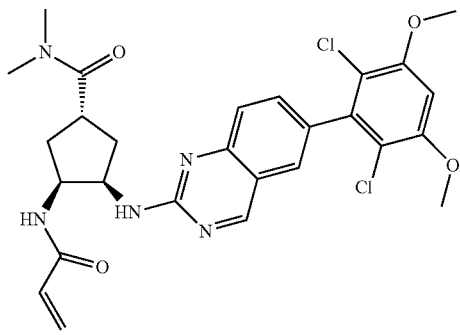 |
| 83 | 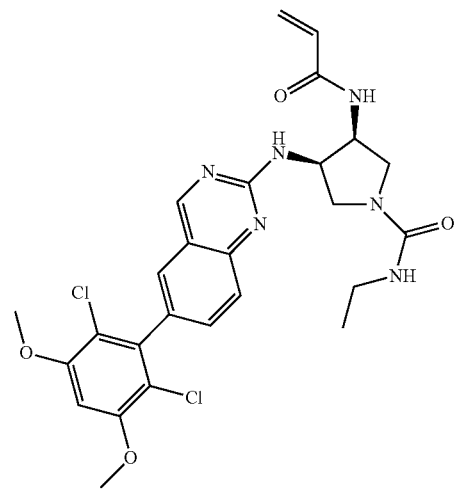 [SMILES: C=CC(=O)N[C@H]1CN(C(=O)NCC)C[C@H]1Nc1ncc2cc(-c3c(Cl)c(OC)cc(OC)c3Cl)ccc2n1] |
| 84 | 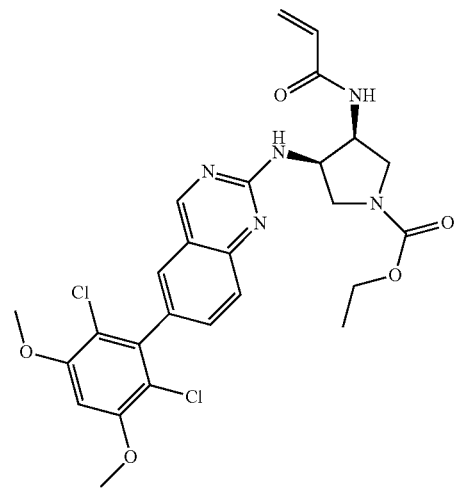 |

| Compound Number | Structure |
|---|---|
| 85 | 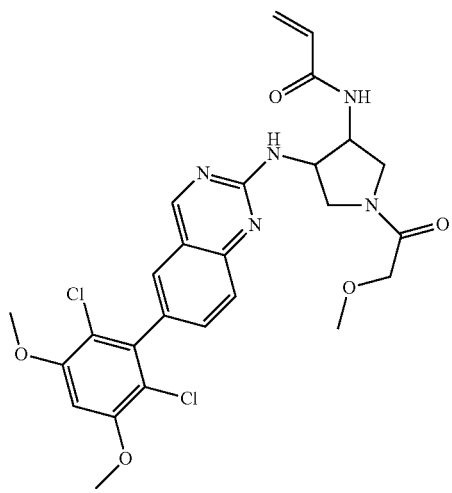<br>cis-racemate |
| 86 | 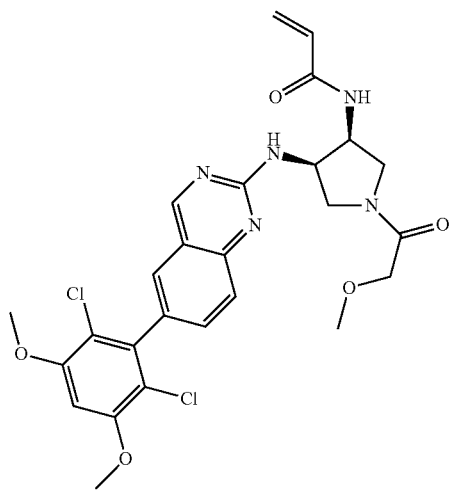 [SMILES: C=CC(=O)N[C@H]1CN(C(=O)COC)C[C@H]1Nc1ncc2cc(-c3c(Cl)c(OC)cc(OC)c3Cl)ccc2n1] |

| Compound Number | Structure |
|---|---|
| 87 | 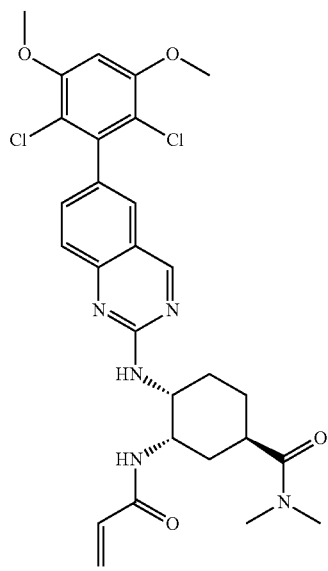 racemate |
| 88 | 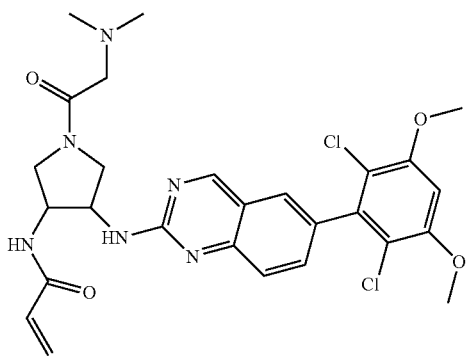 cis-racemate |
| 89 | 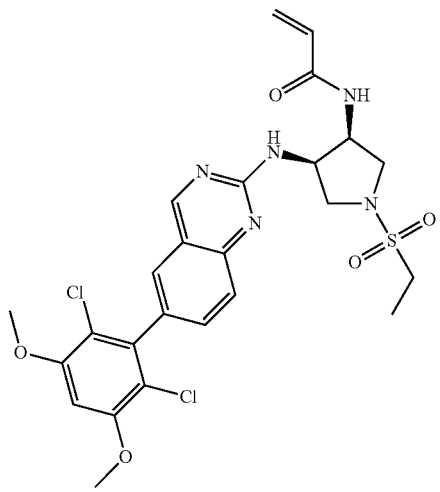 [SMILES: C=CC(=O)N[C@H]1CN(S(=O)(=O)CC)C[C@H]1Nc1ncc2cc(-c3c(Cl)c(OC)cc(OC)c3Cl)ccc2n1] |

-continued
| Compound Number | Structure |
|---|---|
| 90 | 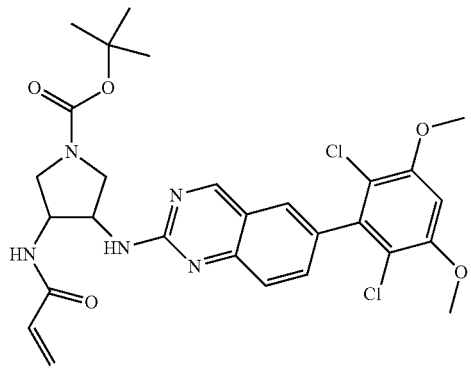<br>cis-racemate |
| 91 | 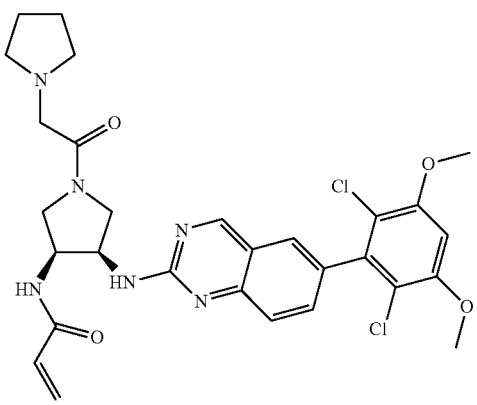 [SMILES: C=CC(=O)N[C@H]1CN(C(=O)CN2CCCC2)C[C@H]1Nc1ncc2cc(-c3c(Cl)c(OC)cc(OC)c3Cl)ccc2n1] |
| 92 | 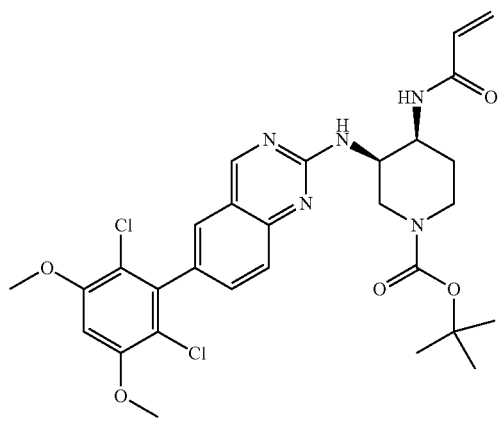 [SMILES: C=CC(=O)N[C@H]1CCN(C(=O)OC(C)(C)C)C[C@H]1Nc1ncc2cc(-c3c(Cl)c(OC)cc(OC)c3Cl)ccc2n1] |

Synthesis

Compounds of the invention, including salts and N-oxides thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2006), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1$H or $^{13}$C), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS: Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Prep LC-MS: Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Silica Gel Chromatography: Silica gel chromatography was performed on either a Teledyne Isco CombiFlash® Rf unit or a Biotage® Isolera Four unit.

Proton NMR: Unless otherwise indicated, all $^1$H NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-d$^6$ solvent as parts-per million (ppm) with respect to residual DMSO (2.50 ppm).

EXAMPLES

The following examples are intended to be illustrative, and are not meant in any way to be limiting.

The below Schemes are meant to provide general guidance in connection with preparing the compounds of the invention. One skilled in the art would understand that the preparations shown in the Schemes can be modified or optimized using general knowledge of organic chemistry to prepare various compounds of the invention.

Synthetic Protocol 1

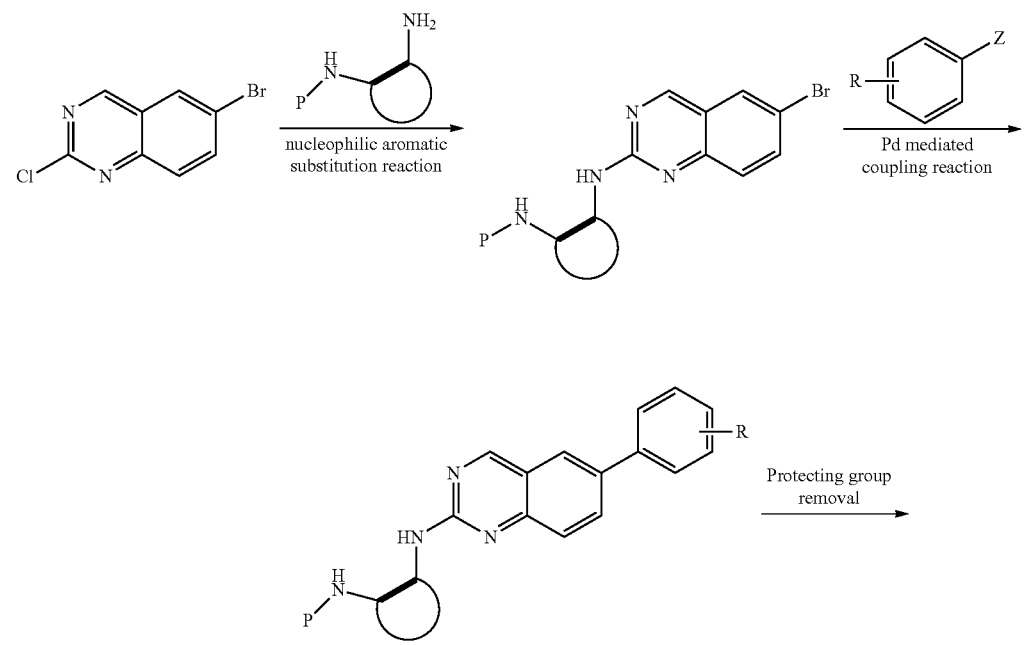

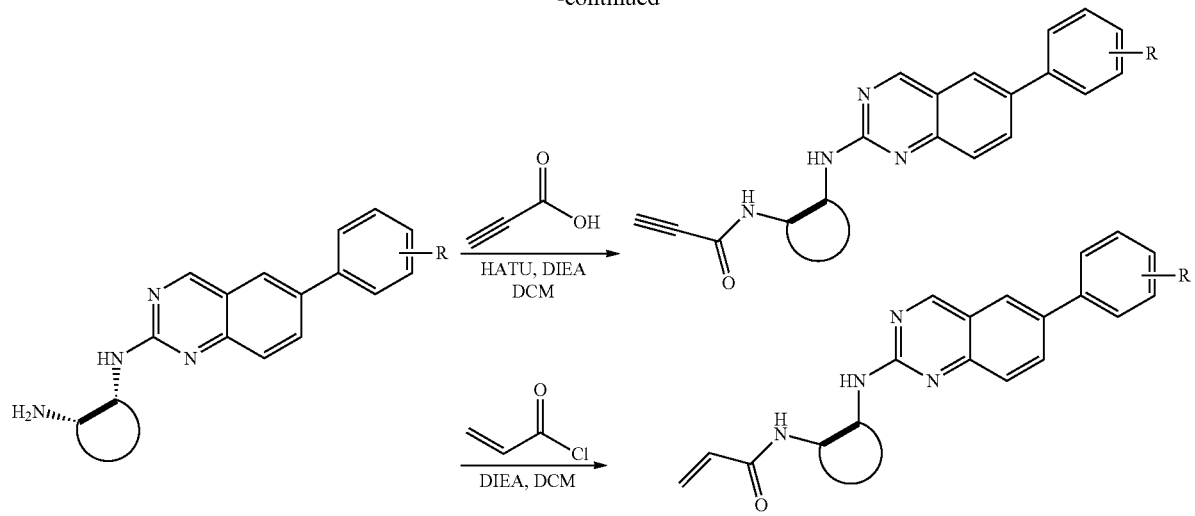

P = Protecting group (e.g. Boc)
Z = B or Sn or Zn reagent 6-bromo-2-chloroquinazoline can be substituted with a 1,2-mono-protected cycloalkyldiamine under nucleophilic aromatic substitution reaction conditions using a base such as diisopropylethylamine (DIPEA) or triethylamine (TEA) in a polar solvent such as dioxane to provide the diamine-substituted quinazoline. The 6-bromoquinazoline can be coupled to a boron, tin or zinc aryl, heteroaryl reagent via a palladium-mediated coupling reaction, e.g., Suzuki, Stille, Negishi coupling, to provide the intermediate which is subsequently de-protected to reveal the amine. The amine on the cycloalkane can be reacted with propiolic acid using amide coupling reaction conditions or reacted with acryloyl chloride to preare the acrylamide. As shown below, Compounds 2 and 6 were prepared using Synthetic Protocol 1.

Example 1

Synthesis of N-((1S,1R)-2-((6-(2,6,-difluoro-3-methoxyphenyl)quinazolin-2-yl)amino)cyclopentyl)propiolamide (Compound 2)

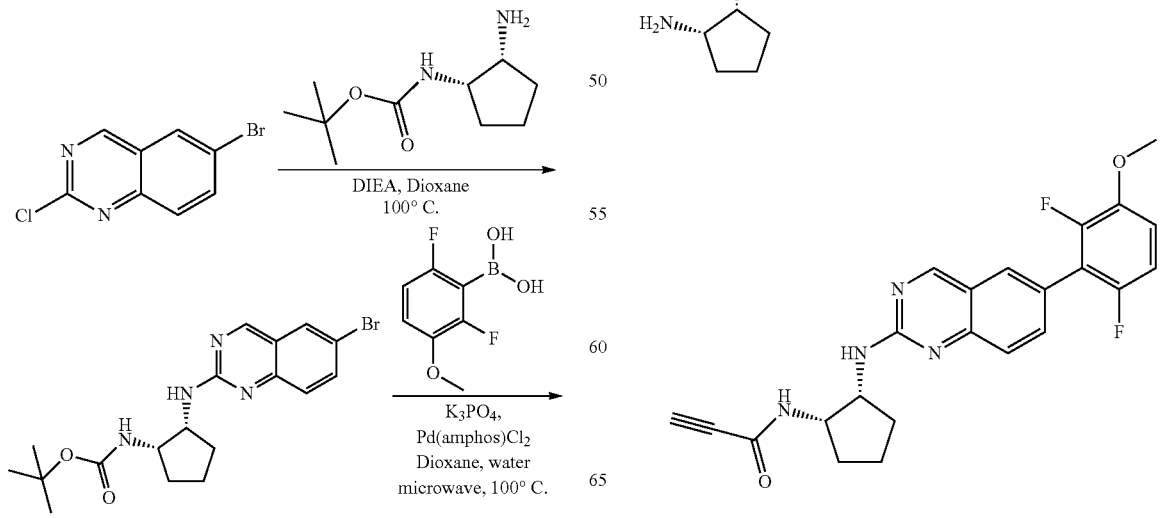

Step 1: Synthesis of tert-butyl ((1S,2R)-2-((6-bromoquinazolin-2-yl)amino)cyclopentyl)carbamate

Step 3: Synthesis of (1R,2S)—N1-(6-(2,6-difluoro-3-methoxyphenyl)quinazolin-2-yl)cyclopentane-1,2-diamine

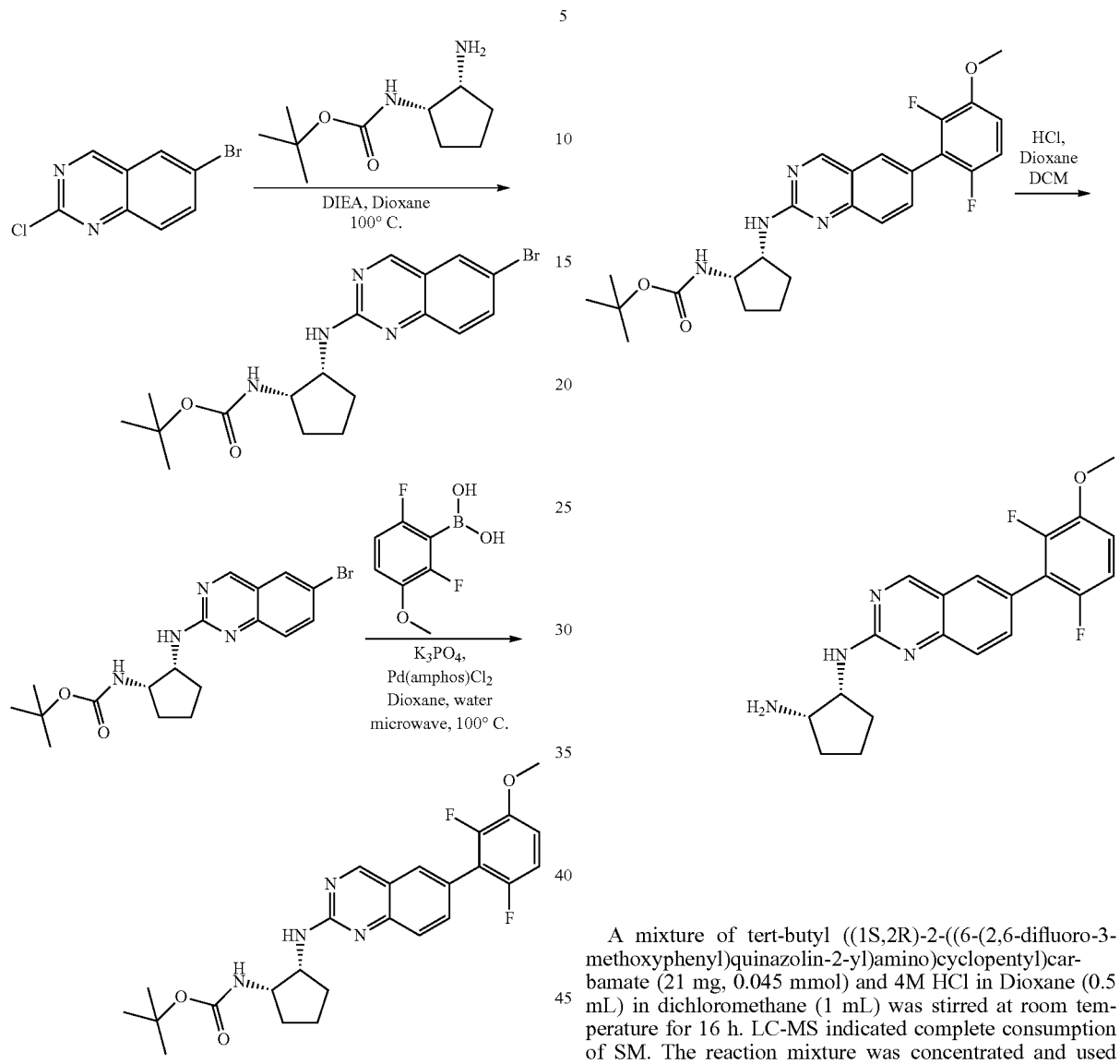

A mixture of tert-butyl ((1S,2R)-2-((6-bromoquinazolin-2-yl)amino)cyclopentyl)carbamate (25 mg, 0.06 mmol), (2,6-difluoro-3-methoxyphenyl)boronic acid (24 mg, 0.12 mmol), Bis(di-tert-butyl(4-dimethylaminophenyl)phosphine)dichloropalladium(II) (3 mg, 0.003 mmol) and potassium phosphate (40 mg, 0.19 mmol) in 1,4-dioxane/water (1 mL/0.2 mL) was degassed with nitrogen for 5 min and stirred at 100° C. for 30 min under microwave. The reaction mixture was cooled to room temperature, diluted with ethyl acetate, washed with saturated ammonium chloride solution and dried with sodium sulfate. The residue was purified by silica gel column chromatography to afford tert-butyl ((1S,2R)-2-((6-(2,6-difluoro-3-methoxyphenyl)quinazolin-2-yl)amino)cyclopentyl)carbamate (21 mg, 37%). MS (ES+) $C_{26}H_{30}N_4O_5$ requires: 470, found: 471 [M+H]+.

A mixture of tert-butyl ((1S,2R)-2-((6-(2,6-difluoro-3-methoxyphenyl)quinazolin-2-yl)amino)cyclopentyl)carbamate (21 mg, 0.045 mmol) and 4M HCl in Dioxane (0.5 mL) in dichloromethane (1 mL) was stirred at room temperature for 16 h. LC-MS indicated complete consumption of SM. The reaction mixture was concentrated and used without further purification in the next step.

Step 4: Synthesis of N-((1S,2R)-2-((6-(2,6-difluoro-3-methoxyphenyl)quinazolin-2-yl)amino)cyclopentyl)propiolamide

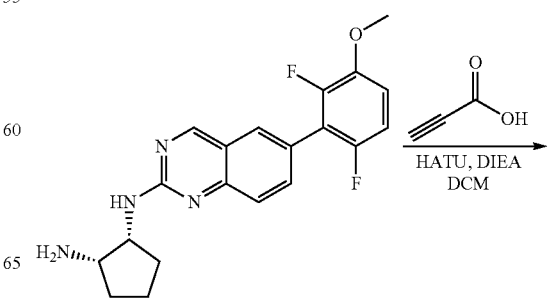

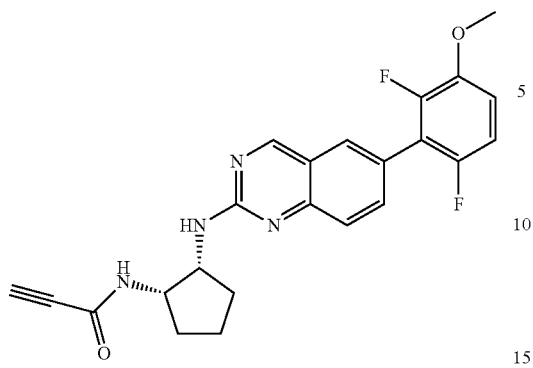
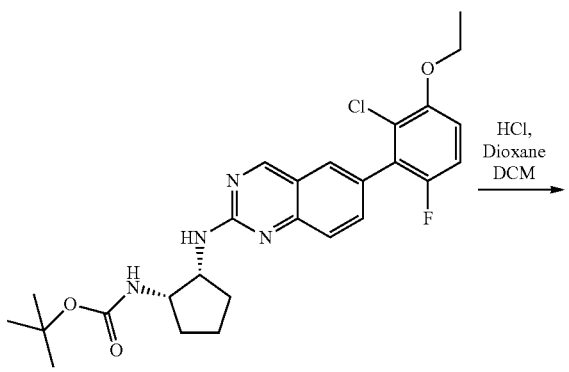

A mixture of (1R,2S)—N1-(6-(2,6-difluoro-3-methoxyphenyl)quinazolin-2-yl)cyclopentane-1,2-diamine (0.045 mmol), propiolic acid (0.004 mL, 0.067 mmol), HATU (25 mg, 0.067 mmol) and DIEA (0.023 mL, 0.135 mmol) in dichloromethane (1 mL) was stirred at room temperature for 60 minutes. LC-MS indicated complete consumption of SM. The reaction mixture was purified by silica gel chromatography to yield N-((1S,2R)-2-((6-(2,6-difluoro-3-methoxyphenyl)quinazolin-2-yl)amino)cyclopentyl)propiolamide (Compound 2) (13 mg, 68%). MS (ES+) $C_{27}H_{27}N_5O_3$ requires: 422, found: 423 [M+H]$^+$.

Example 2

Synthesis of N-((1S,2R)-2-((6-(2-chloro-3-ethoxy-6-fluorophenyl)quinazolin-2-yl)amino)cyclopentyl)propiolamide (Compound 6)

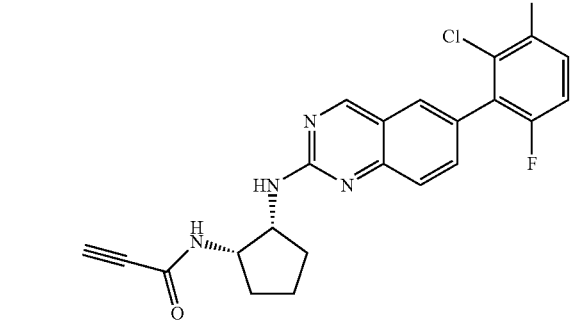

Step 1: Synthesis of tert-butyl ((1S,2R)-2-((6-bromoquinazolin-2-yl)amino)cyclopentyl)carbamate

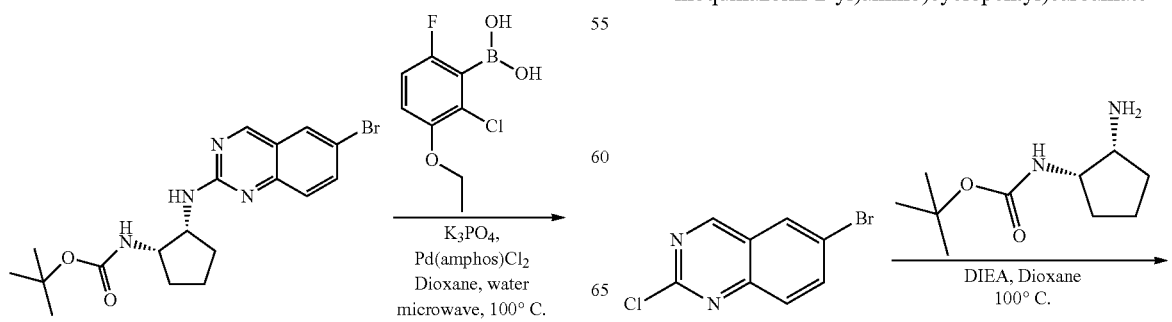

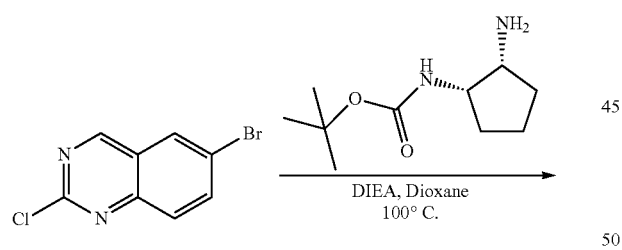

-continued

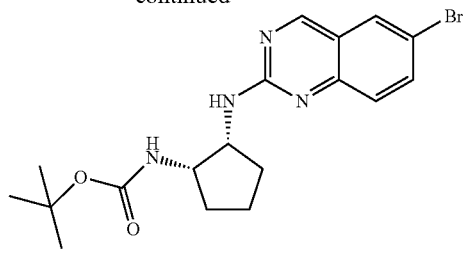

A mixture of 6-bromo-2-chloroquinazoline (1 g, 4.14 mmol) and tert-butyl ((1S,2R)-2-aminocyclopentyl)carbamate (0.826 g, 4.14 mmol) were stirred at 100° C. in Dioxane (10 mL) for 48 h. The reaction mixture was cooled to room temperature, concentrated and the residue was purified by silica gel column chromatography to afford tert-butyl ((1S,2R)-2-((6-bromoquinazolin-2-yl)amino)cyclopentyl)carbamate (1 g, 59%). MS (ES+) $C_{18}H_{23}BrN_4O_2$ requires: 406, found: 407 [M+H]$^+$.

Step 2: Synthesis of tert-butyl ((1S,2R)-2-((6-(2-chloro-3-ethoxy-6-fluorophenyl)quinazolin-2-yl)amino)cyclopentyl)carbamate

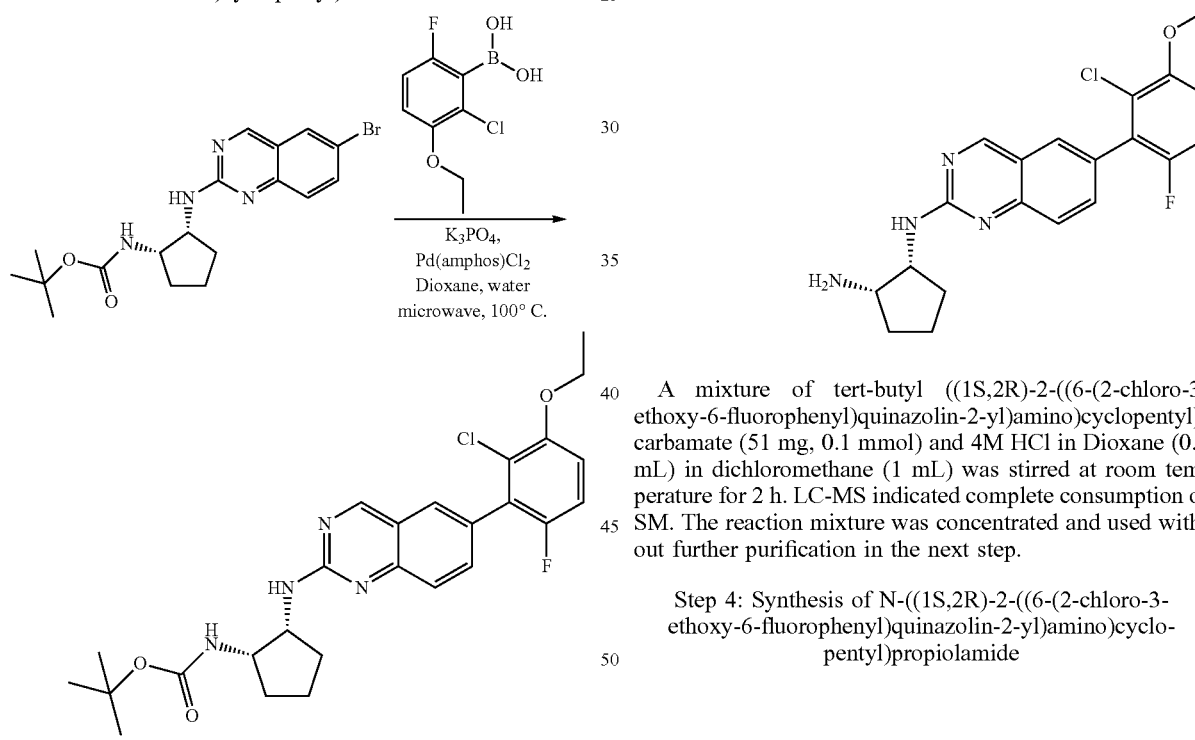

A mixture of tert-butyl ((1S,2R)-2-((6-bromoquinazolin-2-yl)amino)cyclopentyl)carbamate (50 mg, 0.12 mmol), (2-chloro-3-ethoxy-6-fluorophenyl)boronic acid (40 mg, 0.18 mmol), Bis(di-tert-butyl(4-dimethylaminophenyl)phosphine)dichloropalladium(II) (4 mg, 0.005 mmol) and potassium phosphate (78 mg, 0.37 mmol) in 1,4-dioxane/water (1.15 mL/0.15 mL) was degassed with nitrogen for 5 min and stirred at 100° C. for 30 min under microwave. The reaction mixture was cooled to room temperature, diluted with ethyl acetate, washed with saturated ammonium chloride solution and dried with sodium sulfate. The residue was purified by silica gel column chromatography to afford tert-butyl ((1S,2R)-2-((6-(2-chloro-3-ethoxy-6-fluorophenyl)quinazolin-2-yl)amino)cyclopentyl)carbamate (51 mg, 83%). MS (ES+) $C_{26}H_{30}ClFN_4O_3$ requires: 500, found: 501 [M+H]$^+$.

Step 3: Synthesis of (1R,2S)—N1-(6-(2-chloro-3-ethoxy-6-fluorophenyl)quinazolin-2-yl)cyclopentane-1,2-diamine

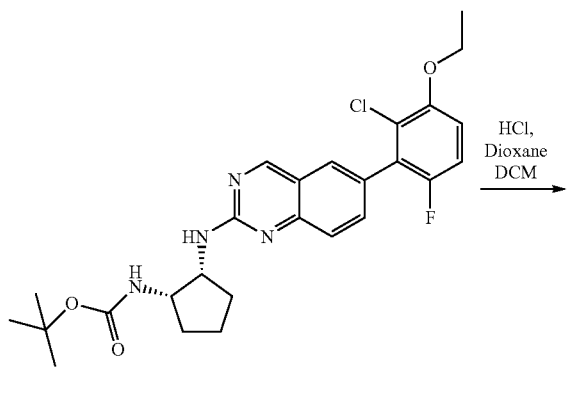

A mixture of tert-butyl ((1S,2R)-2-((6-(2-chloro-3-ethoxy-6-fluorophenyl)quinazolin-2-yl)amino)cyclopentyl)carbamate (51 mg, 0.1 mmol) and 4M HCl in Dioxane (0.5 mL) in dichloromethane (1 mL) was stirred at room temperature for 2 h. LC-MS indicated complete consumption of SM. The reaction mixture was concentrated and used without further purification in the next step.

Step 4: Synthesis of N-((1S,2R)-2-((6-(2-chloro-3-ethoxy-6-fluorophenyl)quinazolin-2-yl)amino)cyclopentyl)propiolamide

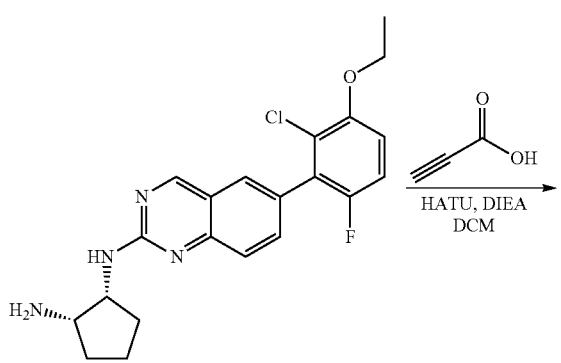

-continued

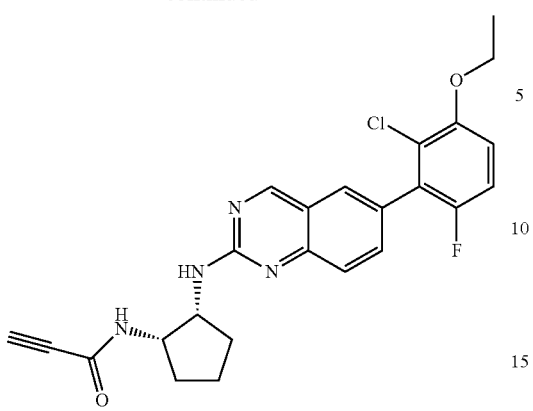

A mixture of (1R,2S)—N1-(6-(2-chloro-3-ethoxy-6-fluorophenyl)quinazolin-2-yl)cyclopentane-1,2-diamine (0.1 mmol), propiolic acid (0.007 mL, 0.12 mmol), HATU (57 mg, 0.15 mmol) and DIEA (0.052 mL, 0.3 mmol) in dichloromethane (1 mL) was stirred at room temperature for 40 minutes. LC-MS indicated complete consumption of SM. The reaction mixture was purified by silica gel chromatography to yield N-((1S,2R)-2-((6-(2-chloro-3-ethoxy-6-fluorophenyl)quinazolin-2-yl)amino)cyclopentyl)propiolamide (Compound 6) (35 mg, 76%). MS (ES+) $C_{24}H_{22}ClFN_4O_2$ requires: 452, found: 453 $[M+H]^+$.

Synthetic Protocol 2

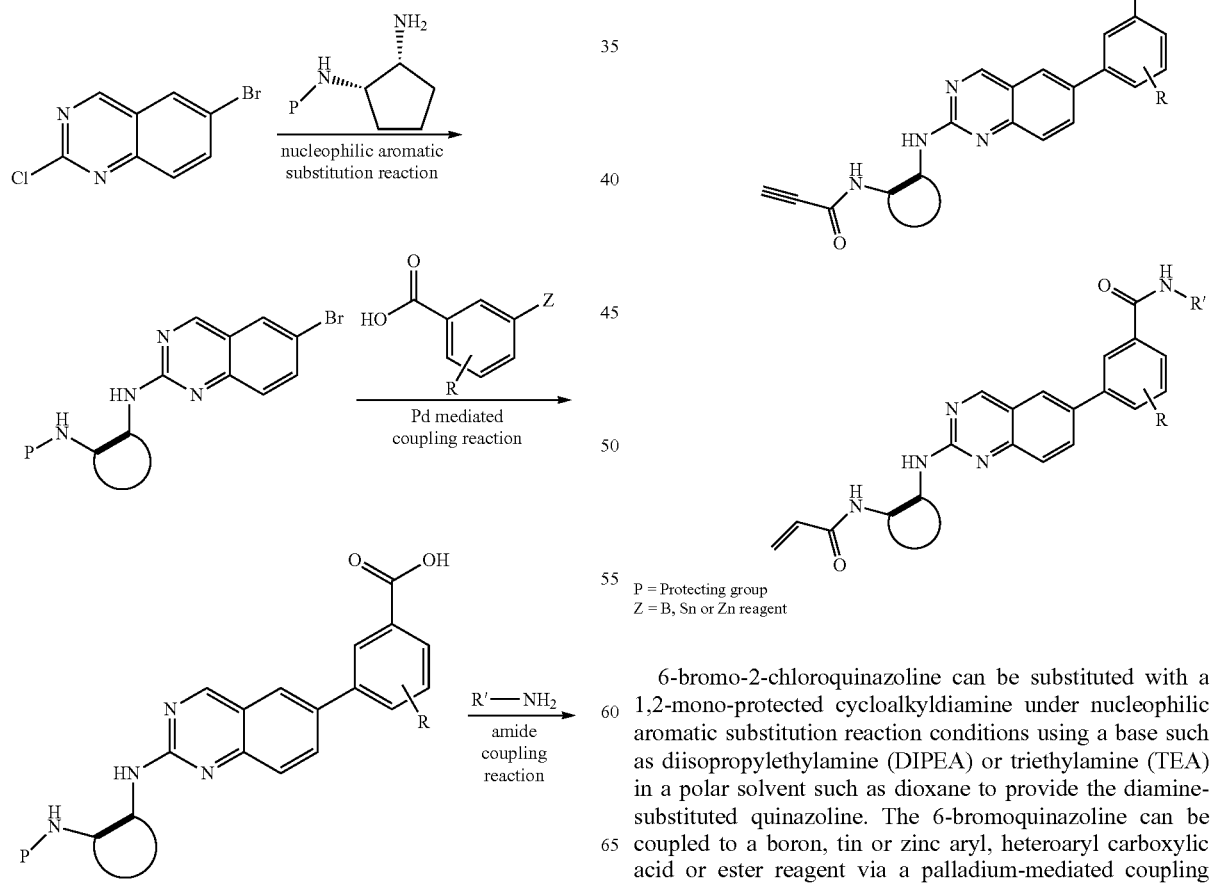

P = Protecting group
Z = B, Sn or Zn reagent 6-bromo-2-chloroquinazoline can be substituted with a 1,2-mono-protected cycloalkyldiamine under nucleophilic aromatic substitution reaction conditions using a base such as diisopropylethylamine (DIPEA) or triethylamine (TEA) in a polar solvent such as dioxane to provide the diamine-substituted quinazoline. The 6-bromoquinazoline can be coupled to a boron, tin or zinc aryl, heteroaryl carboxylic acid or ester reagent via a palladium-mediated coupling reaction, e.g., Suzuki, Stille, Negishi coupling. The carboxylic acid can then be reacted with an amine using amide coupling reaction conditions (such as HATU and diisopropylethylamine) to provide an intermediate which is subsequently de-protected to reveal the amine on the cycloalkane. The amine can be reacted with propiolic acid using amide coupling reaction conditions or reacted with acryloyl chloride to prepare the acrylamide. As shown below, Compound 13 was prepared using Synthetic Protocol 2.

Compound 13

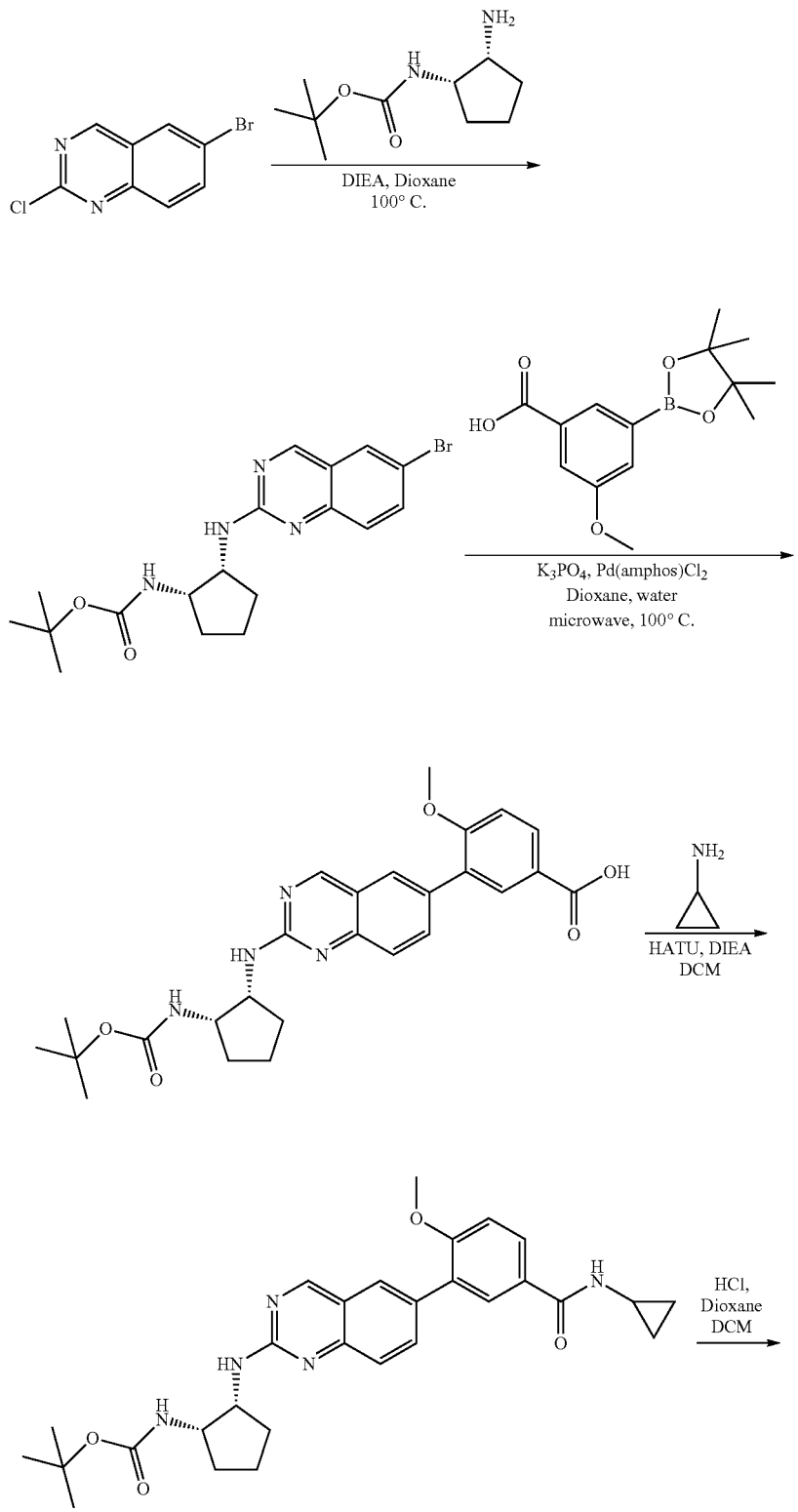

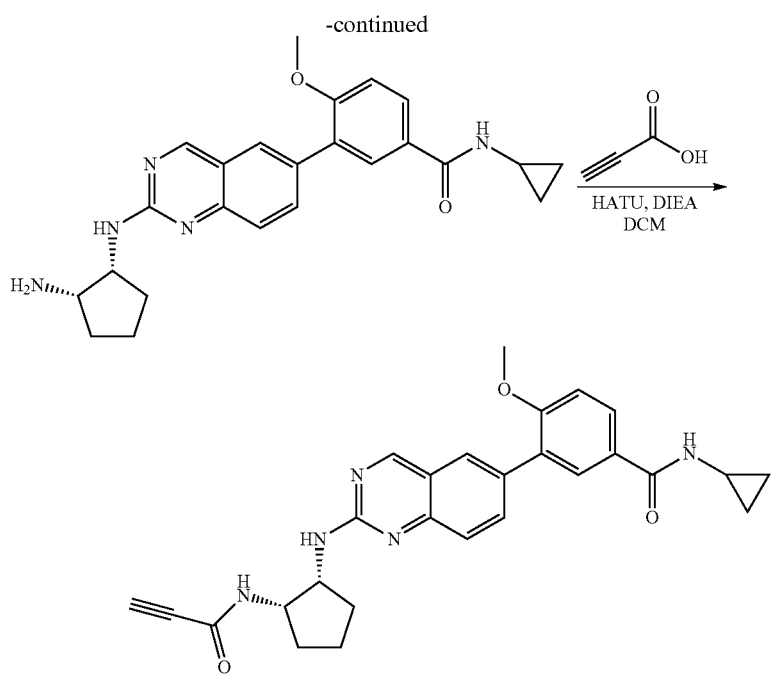

Step 1: Synthesis of tert-butyl ((1S,2R)-2-((6-bromoquinazolin-2-yl)amino)cyclopentyl)carbamate

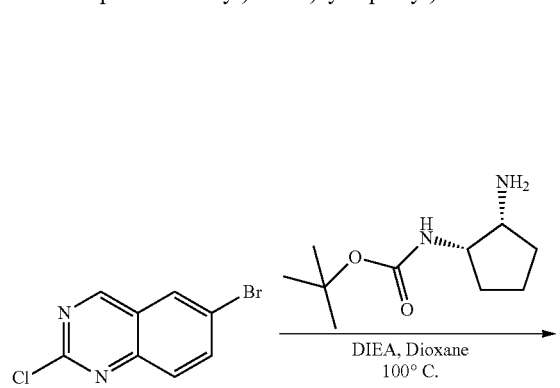

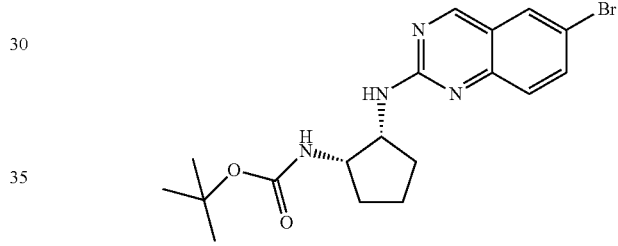

A mixture of 6-bromo-2-chloroquinazoline (1 g, 4.14 mmol) and tert-butyl ((1S,2R)-2-aminocyclopentyl)carbamate (0.826 g, 4.14 mmol) were stirred at 100° C. in Dioxane (10 mL) for 48 h. The reaction mixture was cooled to room temperature, concentrated and the residue was purified by silica gel column chromatography to afford tert-butyl ((1S,2R)-2-((6-bromoquinazolin-2-yl)amino)cyclopentyl)carbamate (1 g, 59%). MS (ES+) $C_{18}H_{23}BrN_4O_2$ requires: 406, found: 407 [M+H]+.

Step 2: Synthesis of 4-(2-((1R,2S)-2-((tert-butoxycarbonyl)amino)cyclopentyl)amino)quinazolin-6-yl)-3-methoxybenzoic acid

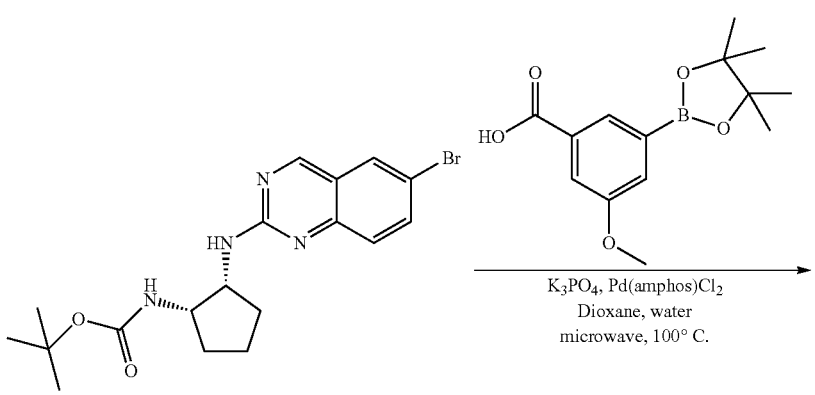

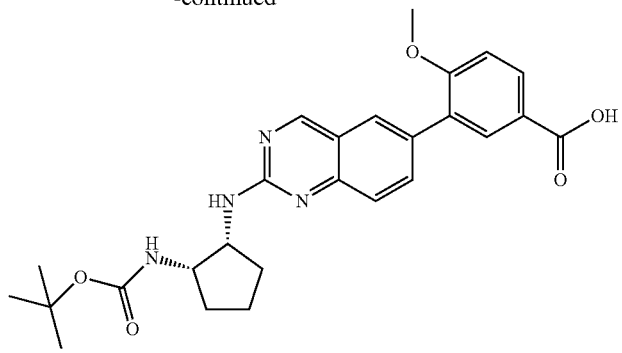

A mixture of tert-butyl ((1S,2R)-2-((6-bromoquinazolin-2-yl)amino)cyclopentyl)carbamate (100 mg, 0.25 mmol), 3-methoxy-5-(4,4,5,5-tetramethyl-1,3,2-dioxaborolan-2-yl)benzoic acid (82 mg, 0.29 mmol), Bis(di-tert-butyl(4-dimethylaminophenyl)phosphine)dichloropalladium(II) (9 mg, 0.01 mmol) and potassium phosphate (157 mg, 0.74 mmol) in 1,4-dioxane/water (2.5 mL/0.25 mL) was degassed with nitrogen for 5 min and stirred at 100° C. for 30 min under microwave. The reaction mixture was cooled to room temperature, diluted with ethyl acetate, washed with saturated ammonium chloride solution and dried with sodium sulfate.

The residue was purified by silica gel column chromatography to afford methyl 4-(2-(((1R,2S)-2-((tert-butoxycarbonyl)amino)cyclopentyl)amino)quinazolin-6-yl)-3-methoxybenzoic acid (114 mg, 96%). MS (ES+) $C_{26}H_{30}N_4O_5$ requires: 478, found: 479 [M+H]$^+$.

Step 3: Synthesis of tert-butyl ((1S,2R)-2-((6-(4-(cyclopropylcarbamoyl)-2-methoxyphenyl)quinazolin-2-yl)amino)cyclopentyl)carbamate

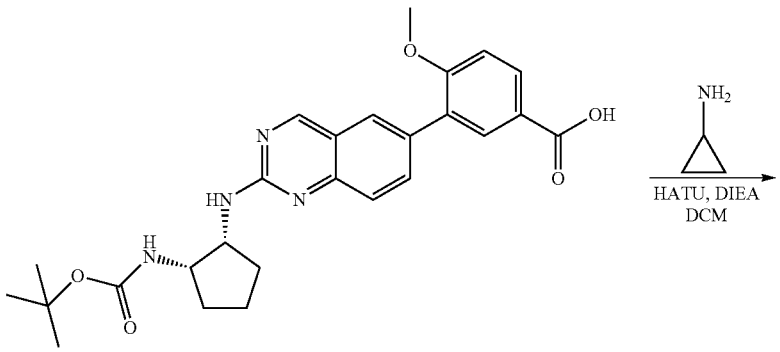

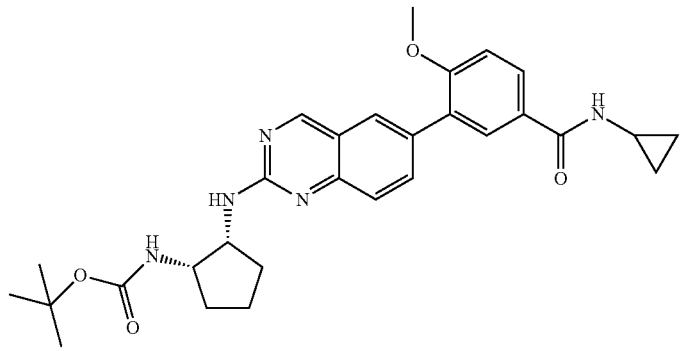

A mixture of 4-(2-(((1R,2S)-2-((tert-butoxycarbonyl)amino)cyclopentyl)amino)quinazolin-6-yl)-3-methoxybenzoic acid (57 mg, 0.12 mmol), cyclopropyl amine (0.012 mL, 0.18 mmol), HATU (68 mg, 0.18 mmol) and DIEA (0.052 mL, 0.30 mmol) in dichloromethane (1.5 mL) was stirred at room temperature for 30 minutes. LC-MS indicated complete consumption of SM. The reaction mixture was purified by silica gel chromatography to yield tert-butyl ((1S,2R)-2-((6-(4-(cyclopropylcarbamoyl)-2-methoxyphenyl)quinazolin-2-yl)amino)cyclopentyl)carbamate (58 mg, 93%). MS (ES+) $C_{29}H_{35}N_5O_4$ requires: 517, found: 518 [M+H]$^+$.

-continued

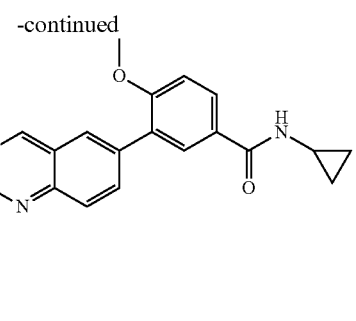

Step 4: Synthesis of 4-(2-(((1R,2S)-2-aminocyclopentyl)amino)quinazolin-6-yl)-N-cyclopropyl-3-methoxybenzamide

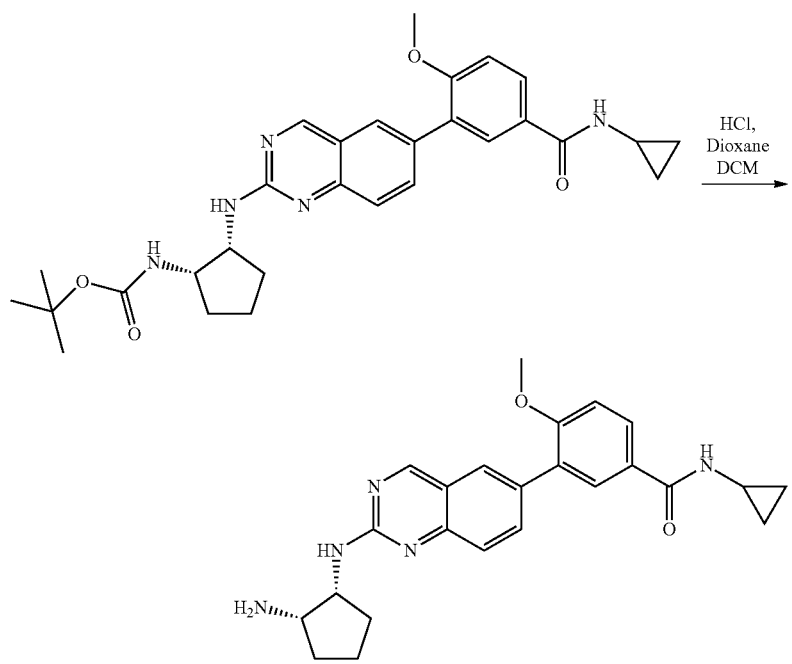

A mixture of tert-butyl ((1S,2R)-2-((6-(4-(cyclopropylcarbamoyl)-2-methoxyphenyl)quinazolin-2-yl)amino)cyclopentyl)carbamate (58 mg, 0.11 mmol) and 4M HCl in Dioxane (0.8 mL) in dichloromethane (1.5 mL) was stirred at room temperature for 120 minutes. LC-MS indicated complete consumption of SM. The reaction mixture was concentrated and used without further purification in the next step.

Step 5: Synthesis of N-cyclopropyl-3-methoxy-4-(2-(((1R,2S)-2-propiolamidocyclopentyl)amino)quinazolin-6-yl)benzamide A mixture of 4-(2-(((1R,2S)-2-aminocyclopentyl)amino)quinazolin-6-yl)-N-cyclopropyl-3-methoxybenzamide (0.11 mmol), propiolic acid (0.010 mL, 0.17 mmol), HATU (64 mg, 0.17 mmol) and DIEA (0.06 mL, 0.34 mmol) in dichloromethane (1.5 mL) was stirred at room temperature for 45 minutes. LC-MS indicated complete consumption of SM. The reaction mixture was purified by silica gel chromatography to yield N-cyclopropyl-3-methoxy-4-(2-(((1R,2S)-2-propiolamidocyclopentyl)amino)quinazolin-6-yl)benzamide (Compound 13) (35 mg, 69%). MS (ES+) $C_{27}H_{27}N_5O_3$ requires: 469, found: 470 [M+H]$^+$.

Synthetic Protocol 3

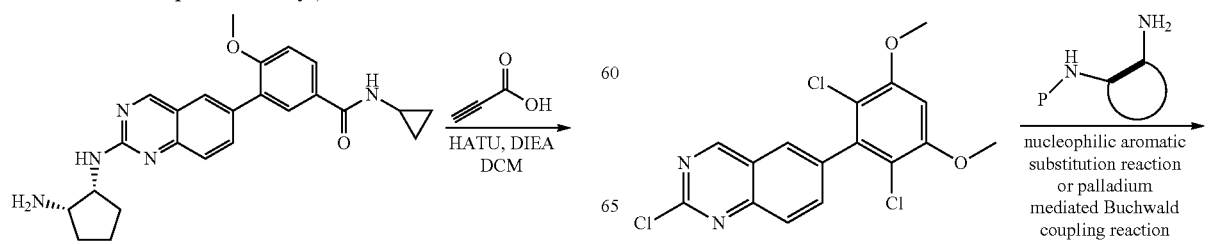

91
-continued

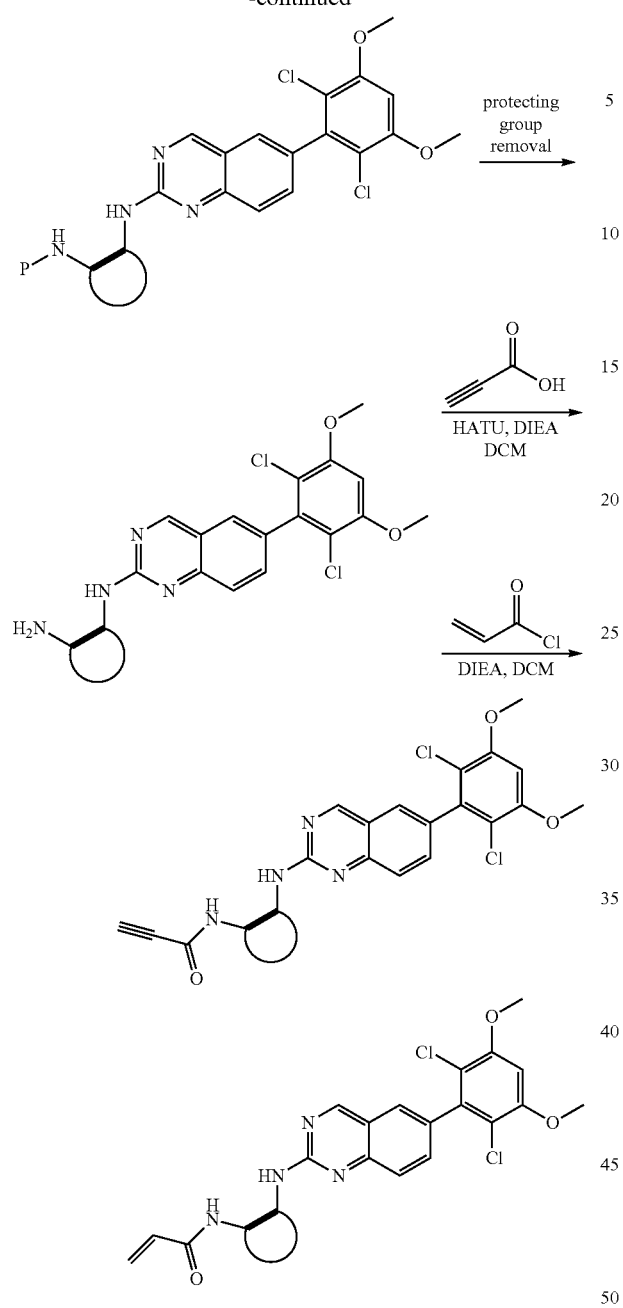

92

Compound 27

Synthesis of N-[(3R,4S)-4-{[6-(2,6-dichloro-3,5-dimethoxyphenyl)quinazolin-2-yl]amino}oxolan-3-yl]prop-2-enamide

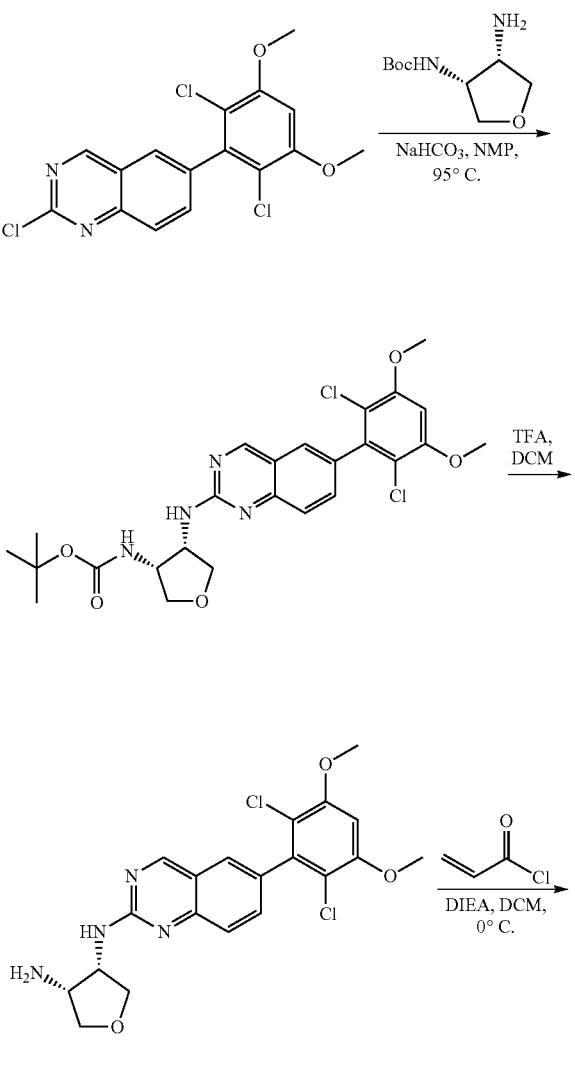

2-chloro-6-(2,6-dichloro-3,5-dimethoxyphenyl)quinazoline (described in WO 2014011900) can be substituted with an 1,2-mono-protected cycloalkyldiamine under various nucleophilic aromatic substitution reaction conditions using a base (such as diisopropylethylamine (DIPEA), DBU or NaHCO₃) in a polar solvent (such as dioxane, CH₃CN or NMP) or via a palladium-mediated Buchwald coupling reaction to provide the diamine-substituted quinazoline. The protecting group on the amine is removed to reveal the amine on the cycloalkane. The amine can be reacted with propiolic acid using amide coupling reaction conditions or reacted with acryloyl chloride to prepare the acrylamide. As shown below, Compounds 27, 32, 34, 36, and 40 were prepared using Synthetic Protocol 3.

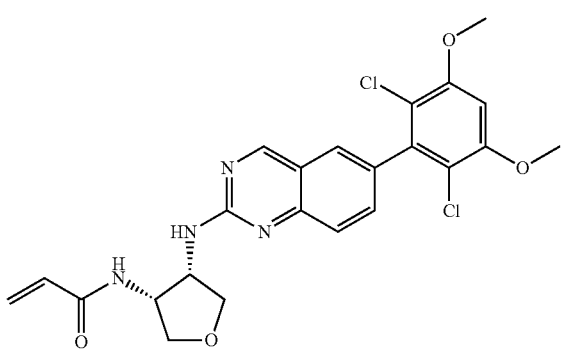

Step 1: Synthesis of tert-butyl ((3R,4S)-4-((6-(2,6-dichloro-3,5-dimethoxyphenyl)quinazolin-2-yl)amino)tetrahydrofuran-3-yl)carbamate as a light yellow foam

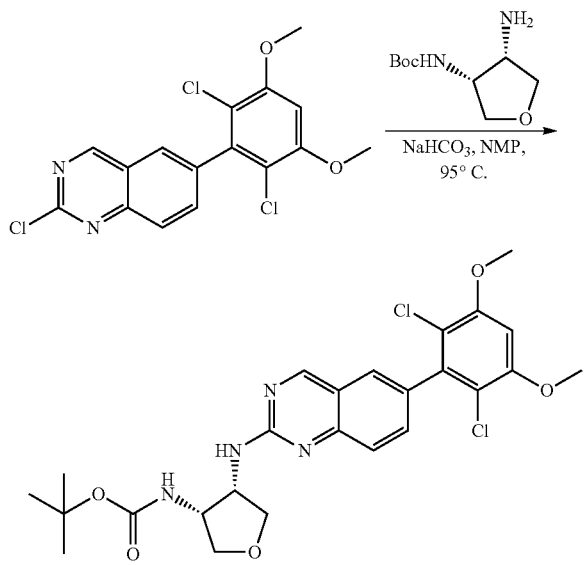

A mixture of 2-chloro-6-(2,6-dichloro-3,5-dimethoxyphenyl)quinazoline (1.02 g, 2.76 mmol), tert-butyl ((3R,4S)-4-aminotetrahydrofuran-3-yl)carbamate (0.85 g, 4.20 mmol), and sodium bicarbonate (0.58 g, 6.90 mmol) was stirred in NMP (5.5 mL, 0.5M) at 95° C. for 12 hours. The reaction was removed from the oil bath and while cooling to room temperature was treated with about 90 mL of water and then sonicated and stirred for 20 minutes. A yellow-orange solid was isolated by filtration, rinsed several times with small amounts of water, and dried under vacuum for nearly 1 hour to yield 3.35 g of crude, which was purified by silica gel chromatography to yield 1.10 g (74.5% yield) of tert-butyl ((3R,4S)-4-((6-(2,6-dichloro-3,5-dimethoxyphenyl)quinazolin-2-yl)amino)tetrahydrofuran-3-yl)carbamate as a light yellow foam. MS (ES+) $C_{25}H_{28}Cl_2N_4O_5$ requires: 534, found: 535 [M+H]+.

Step 2: Synthesis of (3S,4R)—N3-(6-(2,6-dichloro-3,5-dimethoxyphenyl)quinazolin-2-yl)tetrahydrofuran-3,4-diamine

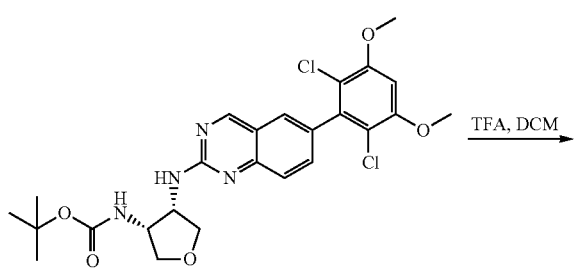

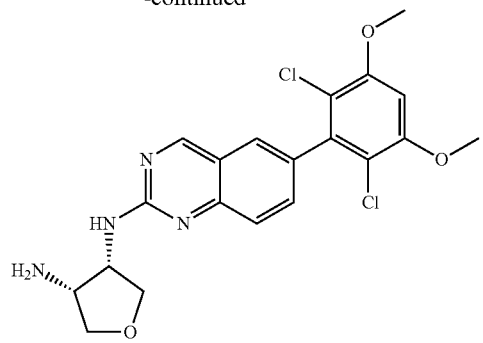

A solution of tert-butyl ((3R,4S)-4-((6-(2,6-dichloro-3,5-dimethoxyphenyl)quinazolin-2-yl)amino)tetrahydrofuran-3-yl)carbamate (1.097 g, 2.049 mmol) in DCM (15 mL, 0.137 M) and TFA (11.7 g, 102 mmol) was stirred about 40 minutes at room temperature. The excess solvents were removed under reduced pressure. The yellow oil was dissolved into DCM (~60 mL) and washed with aqueous 1N NaOH (~30 mL). The aqueous layer was then diluted with brine (~15 mL) and extracted with fresh DCM (3×30 mL). The combined organic layers were dried over sodium sulfate, filtered, concentrated down, and dried to yield (3S,4R)—N3-(6-(2,6-dichloro-3,5-dimethoxyphenyl)quinazolin-2-yl)tetrahydrofuran-3,4-diamine as a very light yellow foam (0.879 g, 99%).

Step 3: Synthesis of N-[(3R,4S)-4-{[6-(2,6-dichloro-3,5-dimethoxyphenyl)quinazolin-2-yl]amino}oxolan-3-yl]prop-2-enamide

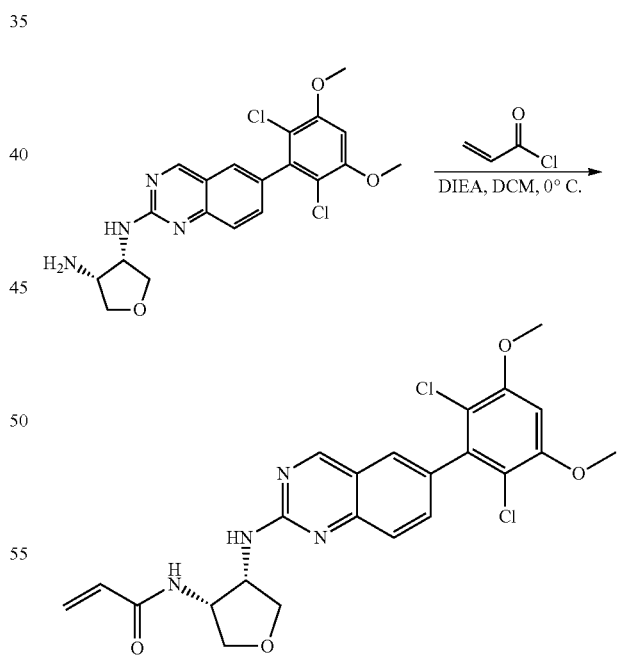

To a solution of (3S,4R)—N3-(6-(2,6-dichloro-3,5-dimethoxyphenyl)quinazolin-2-yl)tetrahydrofuran-3,4-diamine (0.94 g, 2.1 mmol) in dichloromethane (25 mL) at 0° C. was added DIEA (0.37 mL, 2.1 mmol) and acryloyl chloride (0.17 mL, 2.1 mmol) and the reaction was stirred for 3 h. LC-MS indicated complete consumption of SM. The reaction mixture was purified by silica gel chromatography to yield N-((1S,2R)-2-((6-(2,6-dichloro-3,5-dimethoxyphenyl)quinazolin-2-yl)amino)cyclohexyl)acrylamide (Compound 27) (0.8 g, 76%). MS (ES+) $C_{23}H_{22}Cl_2N_4O_4$ requires: 488, found: 489

Compound 32

Synthesis of N-((1S,2R,3S,5S)-2-((6-(2,6-dichloro-3,5-dimethoxyphenyl)quinazolin-2-yl)amino)bicyclo[3.1.0]hexan-3-yl)acrylamide

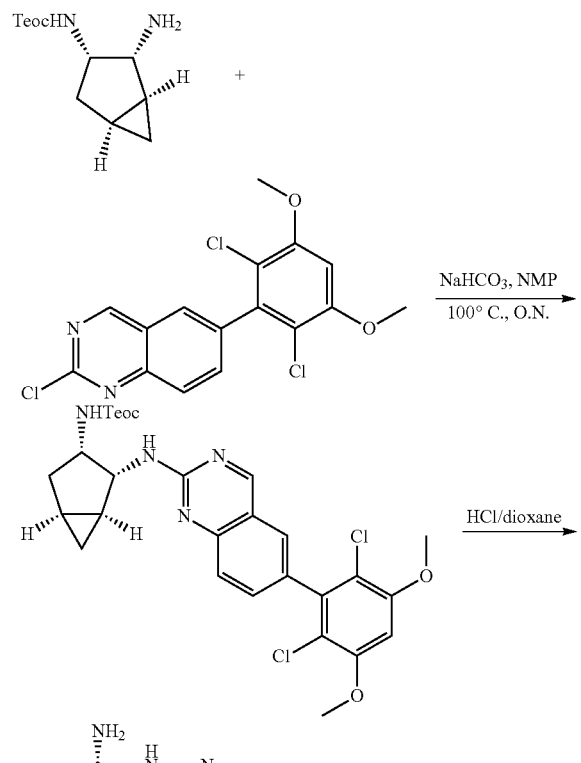

Step 1: Synthesis of 2-(trimethylsilyl)ethyl (1S,2R,3S,5S)-2-(6-(2,6-dichloro-3,5-dimethoxyphenyl)quinazolin-2-ylamino)bicyclo[3.1.0]hexan-3-ylcarbamate

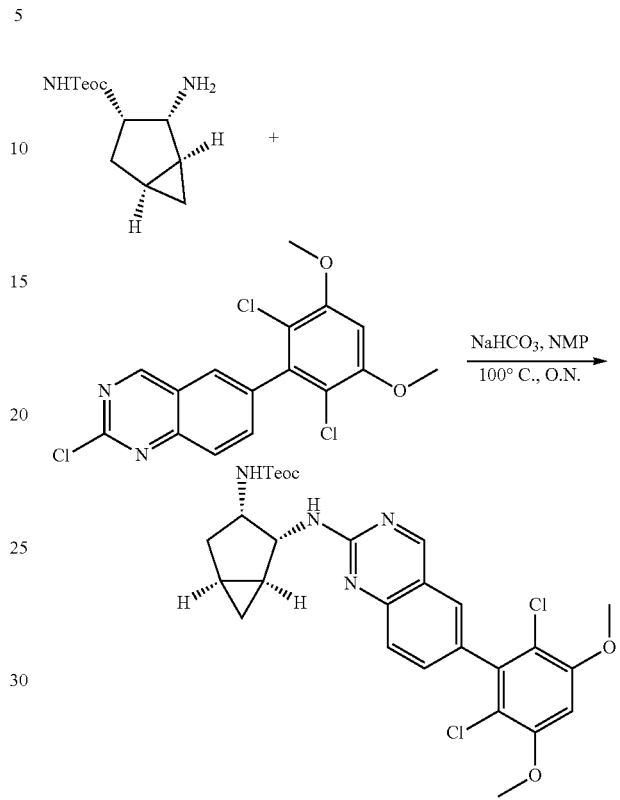

A solution of 2-(trimethylsilyl)ethyl (1S,2R,3S,5S)-2-aminobicyclo[3.1.0]hexan-3-ylcarbamate (250 mg, 0.977 mmol), 2-chloro-6-(2,6-dichloro-3,5-dimethoxyphenyl)quinazoline (300 mg, 0.814 mmol) and sodium bicarbonate (205 mg, 2.442 mmol) in N-methyl-2-pyrrolidone (10 mL) was stirred at 100° C. overnight. The reaction solution was cooled to room temperature, diluted with ethyl acetate (100 mL) and washed with water (eight times) and brine (50 mL). The organic layer was dried over sodium sulfate, filtered and concentrated to afford a crude product, which was purified by silica gel column chromatography (ethyl acetate:petroleum ether=4:2) to afford the title compound (300 mg, 52%) as a yellow solid. MS (ES+) $C_{28}H_{34}Cl_2N_4O_4Si$ requires: 588, 590, found: 589, 591 $[M+H]^+$.

Step 2: Synthesis of (1S,2R,3S,5S)—$N^2$-(6-(2,6-dichloro-3,5-dimethoxyphenyl)quinazolin-2-yl)bicyclo[3.1.0]hexane-2,3-diamine

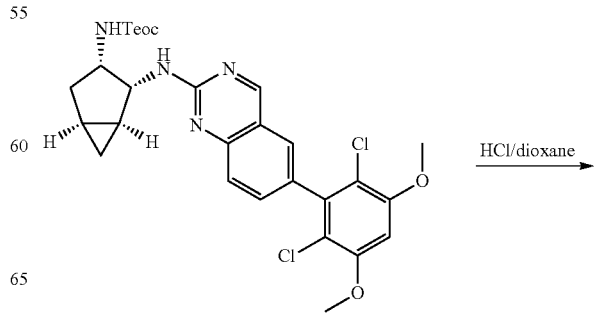

-continued

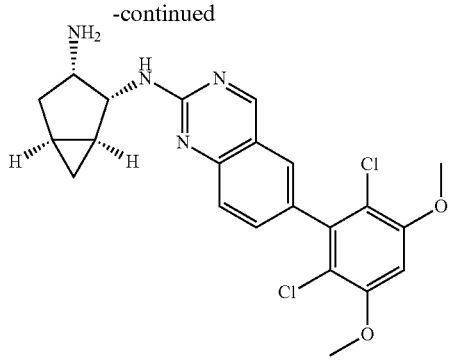

To a solution of 2-(trimethylsilyl)ethyl (1S,2R,3S,5S)-2-(6-(2,6-dichloro-3,5-dimethoxyphenyl)quinazolin-2-ylamino)bicyclo[3.1.0]hexan-3-ylcarbamate (200 mg, 340 mmol) in dioxane (10 mL) was added 12 M conc. HCl (1 mL) at room temperature. The resulting mixture was stirred overnight, then quenched with water (50 mL), and the pH of the solution was brought to pH=8-9 with saturated solution of sodium carbonate. The solution mixture was extracted with ethyl acetate (3×50 mL), and the combined layers were washed with brine (50 mL), dried over sodium sulfate, filtered and concentrated. The residue was purified by thin layer chromatography (Prep-TLC) (dichloromethane:methanol=15:1), and then further purified by silica gel column chromatography (dichloromethane:methanol=20:1) to afford the title compound (70 mg, 46%) as a white solid. MS (ES+) $C_{22}H_{22}Cl_2N_4O_2$ requires: 444, 446, found: 445, 447 [M+H]$^+$.

Step 3: Synthesis of N-((1S,2R,3S,5S)-2-((6-(2,6-dichloro-3,5-dimethoxyphenyl)quinazolin-2-yl)amino)bicyclo[3.1.0]hexan-3-yl)acrylamide To a solution of (1S,2R,3S,5S)—N$^2$-(6-(2,6-dichloro-3,5-dimethoxyphenyl)quinazolin-2-yl)bicyclo[3.1.0]hexane-2,3-diamine (42 mg, 0.094 mmol) in dichloromethane (1.9 mL) at 0° C. was added DIEA (0.025 mL, 0.14 mmol) and acryloyl chloride (0.009 mL, 0.11 mmol) and the reaction was stirred for 1 h. LC-MS indicated complete consumption of SM. The reaction mixture was purified by silica gel chromatography to yield N-((1S,2R,3S,5S)-2-((6-(2,6-dichloro-3,5-dimethoxyphenyl)quinazolin-2-yl)amino)bicyclo[3.1.0]hexan-3-yl)acrylamide (36 mg, 76%) as a pale yellow solid. MS (ES+) $C_{25}H_{24}Cl_2N_4O_3$ requires: 498, found: 499

Compound 34

Synthesis of N-((1S,2R)-2-((6-(2,6-dichloro-3,5-dimethoxyphenyl)quinazolin-2-yl)amino)cyclohexyl)acrylamide

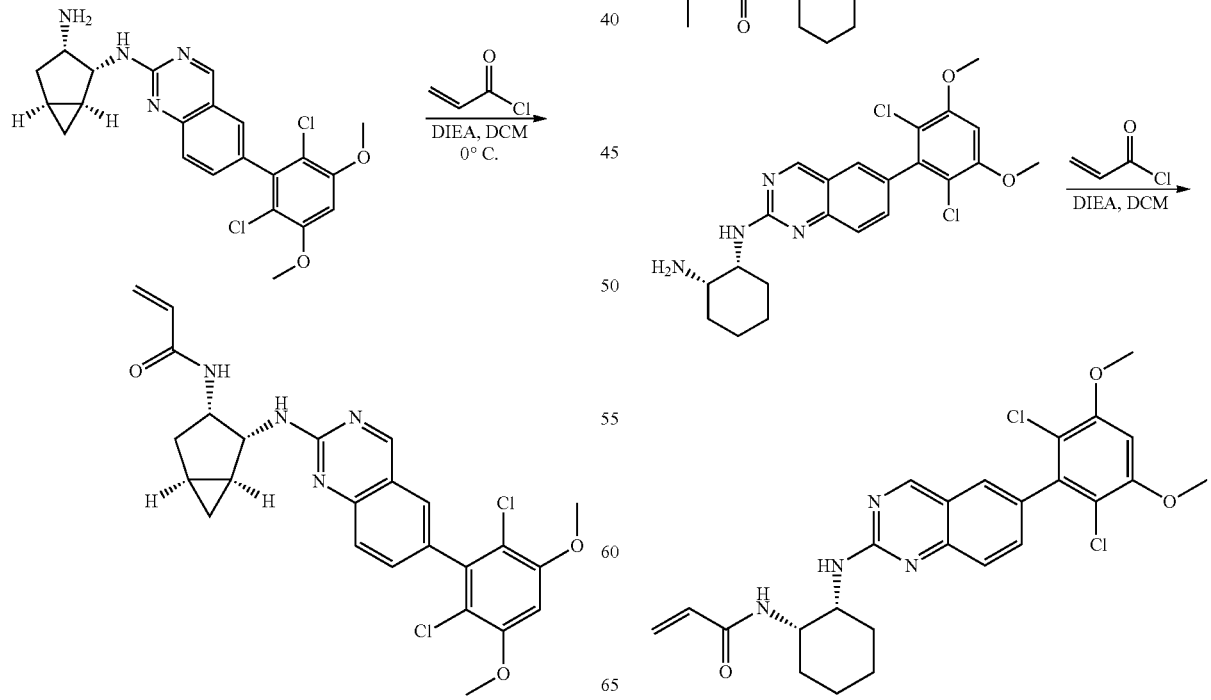

Step 1: Synthesis of tert-butyl ((1S,2R)-2-((6-(2,6-dichloro-3,5-dimethoxyphenyl)quinazolin-2-yl)amino)cyclohexyl)carbamate

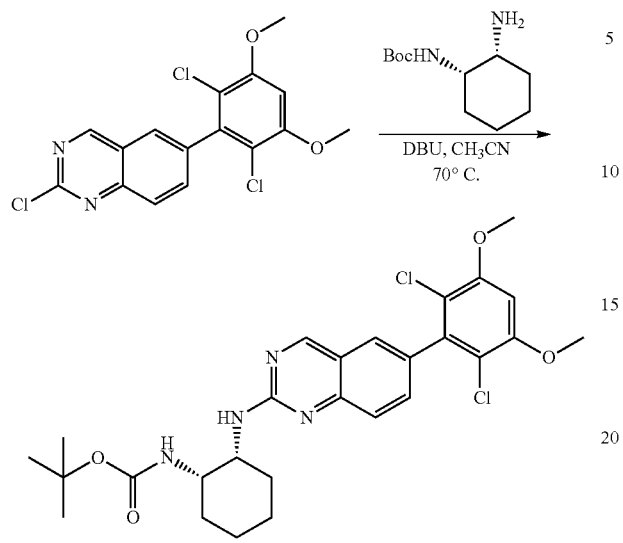

A mixture of 2-chloro-6-(2,6-dichloro-3,5-dimethoxyphenyl)quinazoline (0.95 g, 2.6 mmol), tert-butyl ((1S,2R)-2-aminocyclohexyl)carbamate (1.1 g, 5.14 mmol), and DBU (0.77 mL, 5.14 mmol) in acetonitrile (9 mL) was degassed with $N_2$ for 5 mins and heated at 70° C. for 16 h. The mixture was cooled to room temperature, concentrated and the residue was purified by silica gel column chromatography to afford tert-butyl ((1S,2R)-2-((6-(2,6-dichloro-3,5-dimethoxyphenyl)quinazolin-2-yl)amino)cyclohexyl)carbamate (1.1 g, 81%). MS (ES+) $C_{27}H_{32}Cl_2N_4O_4$ requires: 546, found: 547 $[M+H]^+$.

Step 2: Synthesis of (1R,2S)—N1-(6-(2,6-dichloro-3,5-dimethoxyphenyl)quinazolin-2-yl)cyclohexane-1,2-diamine

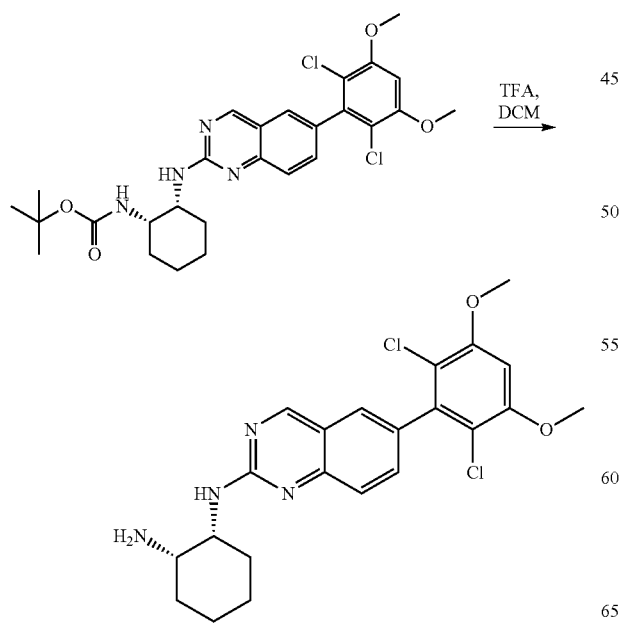

A mixture of tert-butyl ((1S,2R)-2-((6-(2,6-dichloro-3,5-dimethoxyphenyl)quinazolin-2-yl)amino)cyclohexyl)carbamate (1.14 g, 2.1 mmol) and 4N HCl in Dioxane (5.2 mL) in dichloromethane (10 mL) was stirred at room temperature for 30 minutes. LC-MS indicated complete consumption of SM. The reaction mixture was concentrated to give (1R,2S)—N1-(6-(2,6-dichloro-3,5-dimethoxyphenyl)quinazolin-2-yl)cyclohexane-1,2-diamine (0.94 g, 100%) which was used without further purification in the next step.

Step 3: Synthesis of N-((1S,2R)-2-((6-(2,6-dichloro-3,5-dimethoxyphenyl)quinazolin-2-yl)amino)cyclohexyl)acrylamide

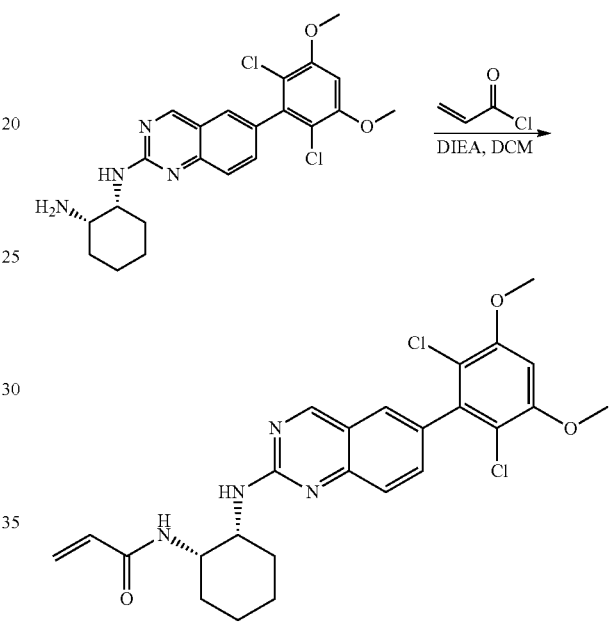

To a solution of (1R,2S)—N1-(6-(2,6-dichloro-3,5-dimethoxyphenyl)quinazolin-2-yl)cyclohexane-1,2-diamine (0.94 g, 2.1 mmol) in dichloromethane (25 mL) at 0° C. was added DIEA (0.37 mL, 2.1 mmol) and acryloyl chloride (0.17 mL, 2.1 mmol) and the reaction was stirred for 3 h. LC-MS indicated complete consumption of SM. The reaction mixture was purified by silica gel chromatography to yield N-((1S,2R)-2-((6-(2,6-dichloro-3,5-dimethoxyphenyl)quinazolin-2-yl)amino)cyclohexyl)acrylamide (0.8 g, 76%). MS (ES+) $C_{25}H_{26}Cl_2N_4O_3$ requires: 500, found: 501.

Compound 36

Synthesis of N-((1S,2S)-2-((6-(2,6-dichloro-3,5-dimethoxyphenyl)quinazolin-2-yl)amino)cyclohexyl)acrylamide

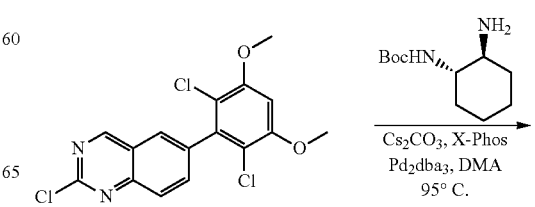

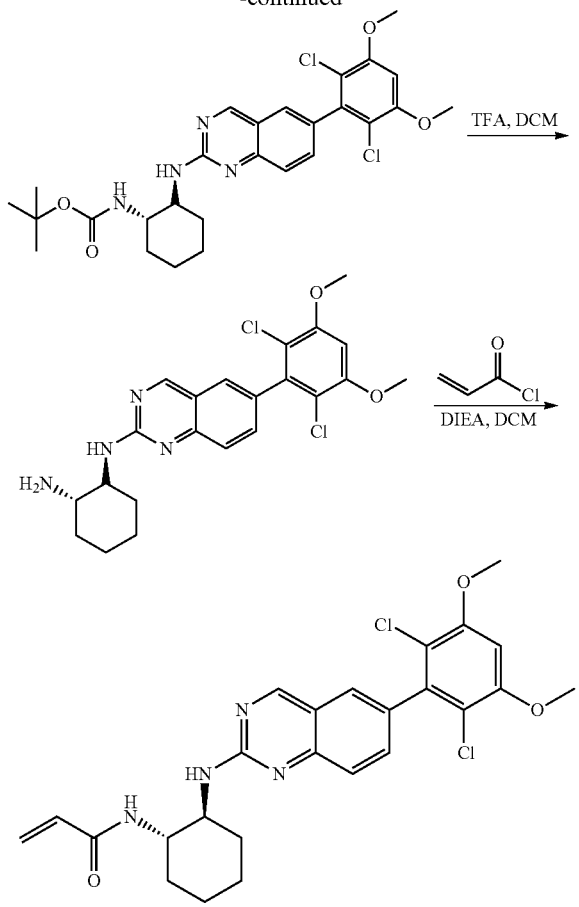

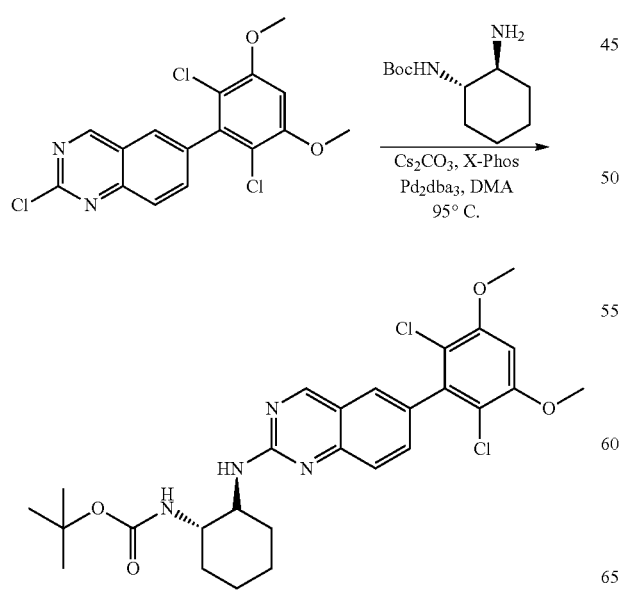

Step 1: Synthesis of tert-butyl ((1S,2R)-2-((6-(2,6-dichloro-3,5-dimethoxyphenyl)quinazolin-2-yl)amino)cyclohexyl)carbamate

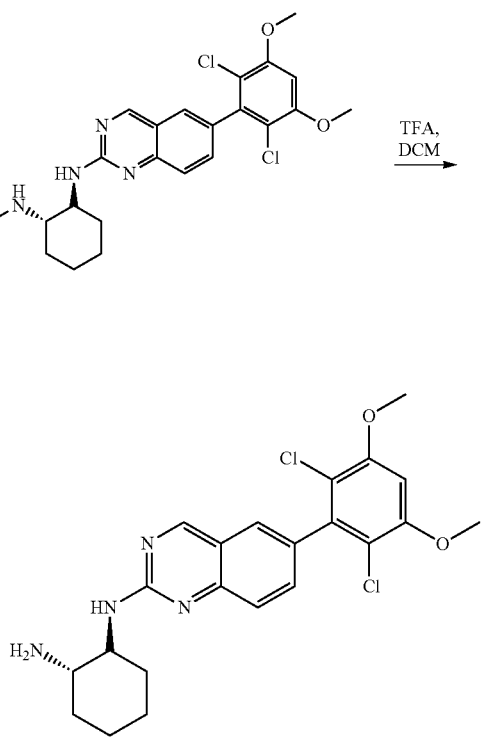

A mixture of 2-chloro-6-(2,6-dichloro-3,5-dimethoxyphenyl)quinazoline (0.1 g, 0.27 mmol), tert-butyl ((1S,2S)-2-aminocyclohexyl)carbamate (75 mg, 0.35 mmol), $Cs_2CO_3$ (176 mg, 0.54 mmol), X-Phos (13 mg, 0.027 mmol) and $Pd_2dba_3$ (12.5 mg, 0.013 mmol) in DMA (1.8 mL) was degassed with $N_2$ for 5 mins and heated in a microwave reactor at 125° C. for 30 mins. The mixture was cooled to room temperature, filtered through celite and washed with water followed by saturated brine solution. The residue was purified by silica gel column chromatography to afford tert-butyl ((1S,2R)-2-((6-(2,6-dichloro-3,5-dimethoxyphenyl)quinazolin-2-yl)amino)cyclohexyl)carbamate (67 mg, 45%). MS (ES+) $C_{27}H_{32}Cl_2N_4O_4$ requires: 546, found: 547 $[M+H]^+$.

Step 2: Synthesis of (1R,2S)—N1-(6-(2,6-dichloro-3,5-dimethoxyphenyl)quinazolin-2-yl)cyclohexane-1,2-diamine A mixture of tert-butyl ((1S,2R)-2-((6-(2,6-dichloro-3,5-dimethoxyphenyl)quinazolin-2-yl)amino)cyclohexyl)carbamate (67 mg, 0.12 mmol) and TFA (0.6 mL) in dichloromethane (0.6 mL) was stirred at room temperature for 60 minutes. LC-MS indicated complete consumption of SM. The reaction mixture was diluted with saturated $NaHCO_3$ and then extracted with dichloromethane. The combined organic layers were dried by $Na_2SO_4$, filtered, concentrated to give (1R,2S)—N1-(6-(2,6-dichloro-3,5-dimethoxyphenyl)quinazolin-2-yl)cyclohexane-1,2-diamine which was used without further purification in the next step.

Step 3: Synthesis of N-((1S,2S)-2-((6-(2,6-dichloro-3,5-dimethoxyphenyl)quinazolin-2-yl)amino)cyclohexyl)acrylamide

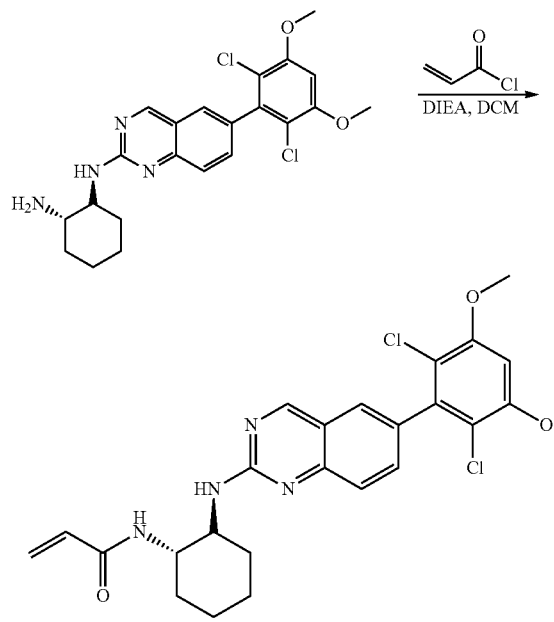

To a solution of (1R,2S)—N1-(6-(2,6-dichloro-3,5-dimethoxyphenyl)quinazolin-2-yl)cyclohexane-1,2-diamine (0.12 mmol) in dichloromethane (1.3 mL) at 0° C. was added DIEA (0.004 mL, 0.02 mmol) and acryloyl chloride (0.012 mL, 0.15 mmol) and the reaction was stirred for 1 h. LC-MS indicated complete consumption of SM. The reaction mixture was purified by silica gel chromatography to yield N-((1S,2S)-2-((6-(2,6-dichloro-3,5-dimethoxyphenyl)quinazolin-2-yl)amino)cyclohexyl)acrylamide (35 mg, 58%). MS (ES+) $C_{25}H_{26}Cl_2N_4O_3$ requires: 500, found: 501.

Compound 40

Synthesis of N-((3S,4S)-3-((6-(2,6-dichloro-3,5-dimethoxyphenyl)quinazolin-2-yl)amino)tetrahydro-2H-pyran-4-yl)acrylamide

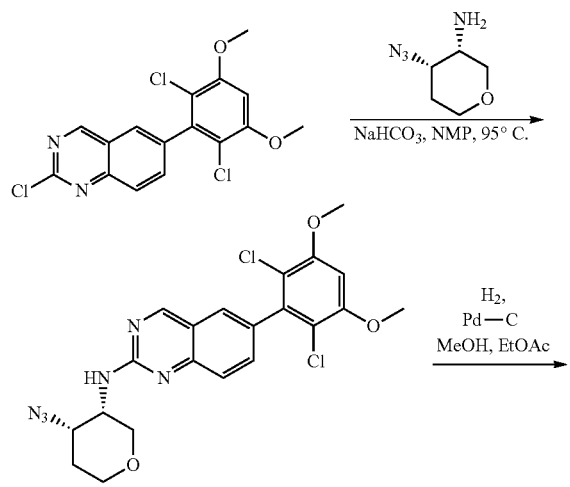

Step 1: Synthesis of N-((3S,4S)-4-azidotetrahydro-2H-pyran-3-yl)-6-(2,6-dichloro-3,5-dimethoxyphenyl)quinazolin-2-amine

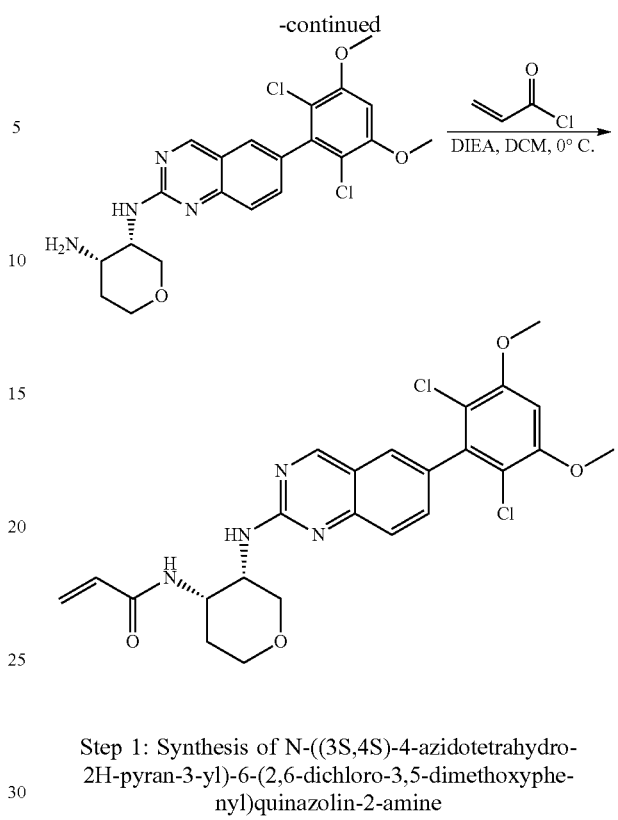

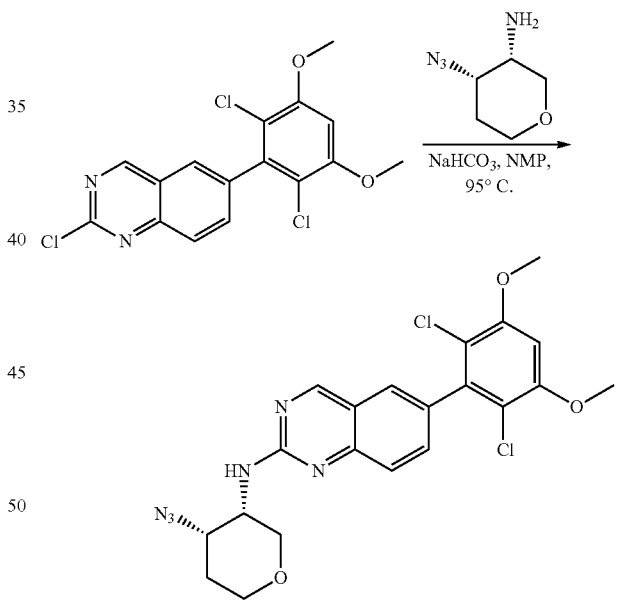

(3S,4S)-4-azidotetrahydro-2H-pyran-3-amine, HCl (0.200 g, 1.120 mmol) and 2-chloro-6-(2,6-dichloro-3,5-dimethoxyphenyl)quinazoline (0.318 g, 0.861 mmol) were taken up in NMP (2 ml) and sodium carbonate (0.217 g, 2.58 mmol) was added. The reaction was heated to 100° C. overnight. After cooling to ambient temperature the reaction was poured into 5 ml of water and stirred for 30 min. The solid layer was filtered off and washed with water and further dried under high vacuum to give N-((3S,4S)-4-azidotetrahydro-2H-pyran-3-yl)-6-(2,6-dichloro-3,5-dimethoxyphenyl)quinazolin-2-amine (0.300 g, 0.631 mmol, 73.3% yield). MS (ES+) $C_{21}H_{20}Cl_2N_6O_3$ requires: 474, found: 475 [M+H]+.

Step 2: Synthesis of (3S,4S)—N3-(6-(2,6-dichloro-3,5-dimethoxyphenyl)quinazolin-2-yl)tetrahydro-2H-pyran-3,4-diamine

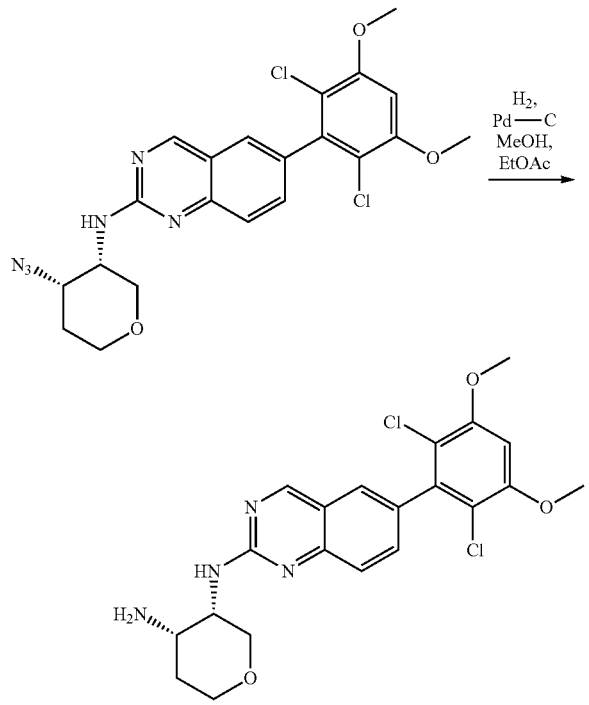

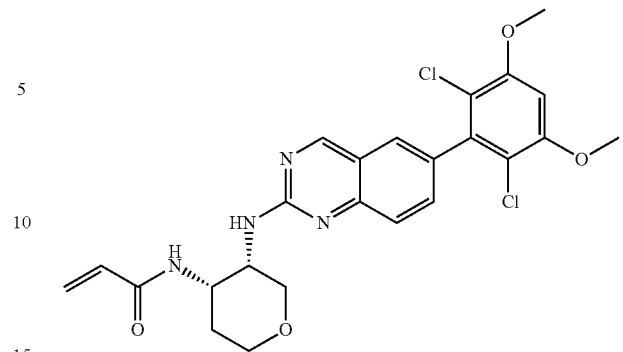

(3S,4S)—N3-(6-(2,6-dichloro-3,5-dimethoxyphenyl)quinazolin-2-yl)tetrahydro-2H-pyran-3,4-diamine (0.060 g, 0.134 mmol) was taken up in $CH_2Cl_2$ (2 ml) and cooled to 0° C., followed by addition of DIEA (0.023 ml, 0.134 mmol) and then acryloyl chloride (0.012 ml, 0.147 mmol) slowly. The reaction was stirred at 0° C. for 30 minutes, then the mixture was loaded directly onto silica and purified by flash chromotography using 0-10% $CH_2Cl_2$/MeOH. N-((3S,4S)-3-((6-(2,6-dichloro-3,5-dimethoxyphenyl)quinazolin-2-yl)amino)tetrahydro-2H-pyran-4-yl)acrylamide (0.041 g, 0.081 mmol, 61% yield) was recovered as an off white solid. MS (ES+) $C_{24}H_{24}Cl_2N_4O_4$ requires: 502, found: 503 [M+H]+.

Synthetic Protocol 4

N-((3S,4S)-4-azidotetrahydro-2H-pyran-3-yl)-6-(2,6-dichloro-3,5-dimethoxyphenyl)quinazolin-2-amine (0.063 g, 0.133 mmol) was taken up in Methanol (7 ml) and EtOAc (7.00 ml), Pd—C (0.014 g, 0.133 mmol) was added and stirred under a $H_2$ balloon for 1 hour. After the reaction was completed, it was filtered through celite and the solvent removed. (3S,4S)—N3-(6-(2,6-dichloro-3,5-dimethoxyphenyl)quinazolin-2-yl)tetrahydro-2H-pyran-3,4-diamine (0.060 g, 0.134 mmol, 101% yield) was recovered as a yellow solid, which was carried on without further purification. MS (ES+) $C_{21}H_{22}Cl_2N_4O_3$ requires: 448, found: 449 [M+H]+.

Step 3: Synthesis of N-((3S,4S)-3-((6-(2,6-dichloro-3,5-dimethoxyphenyl)quinazolin-2-yl)amino)tetrahydro-2H-pyran-4-yl)acrylamide

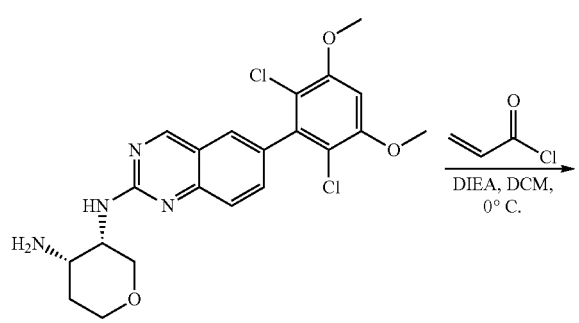

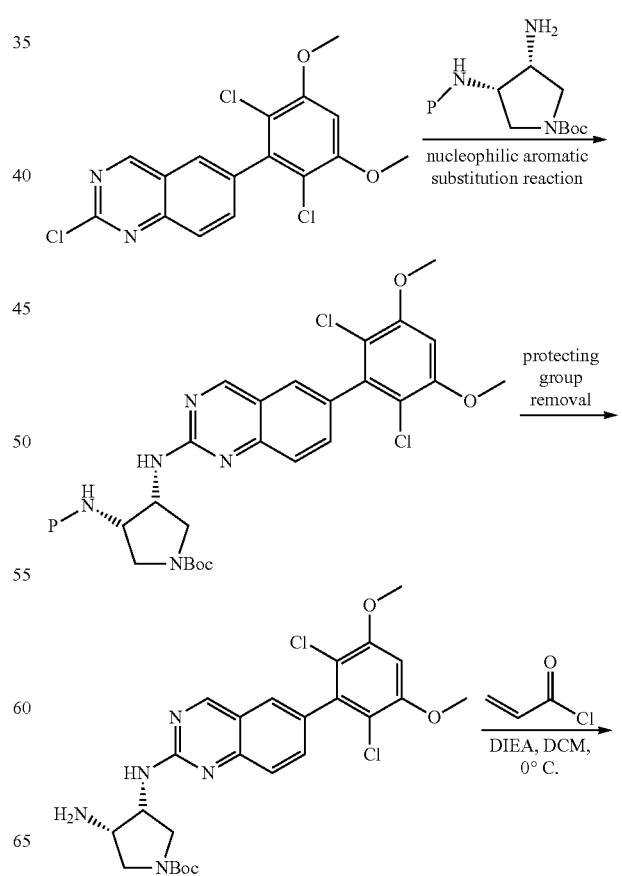

-continued

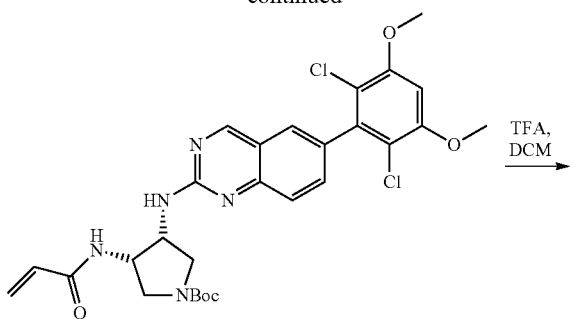

Compound 56

Synthesis of N-((3S,4R)-1-acetyl-4-((6-(2,6-dichloro-3,5-dimethoxyphenyl)quinazolin-2-yl)amino)pyrrolidin-3-yl)acrylamide

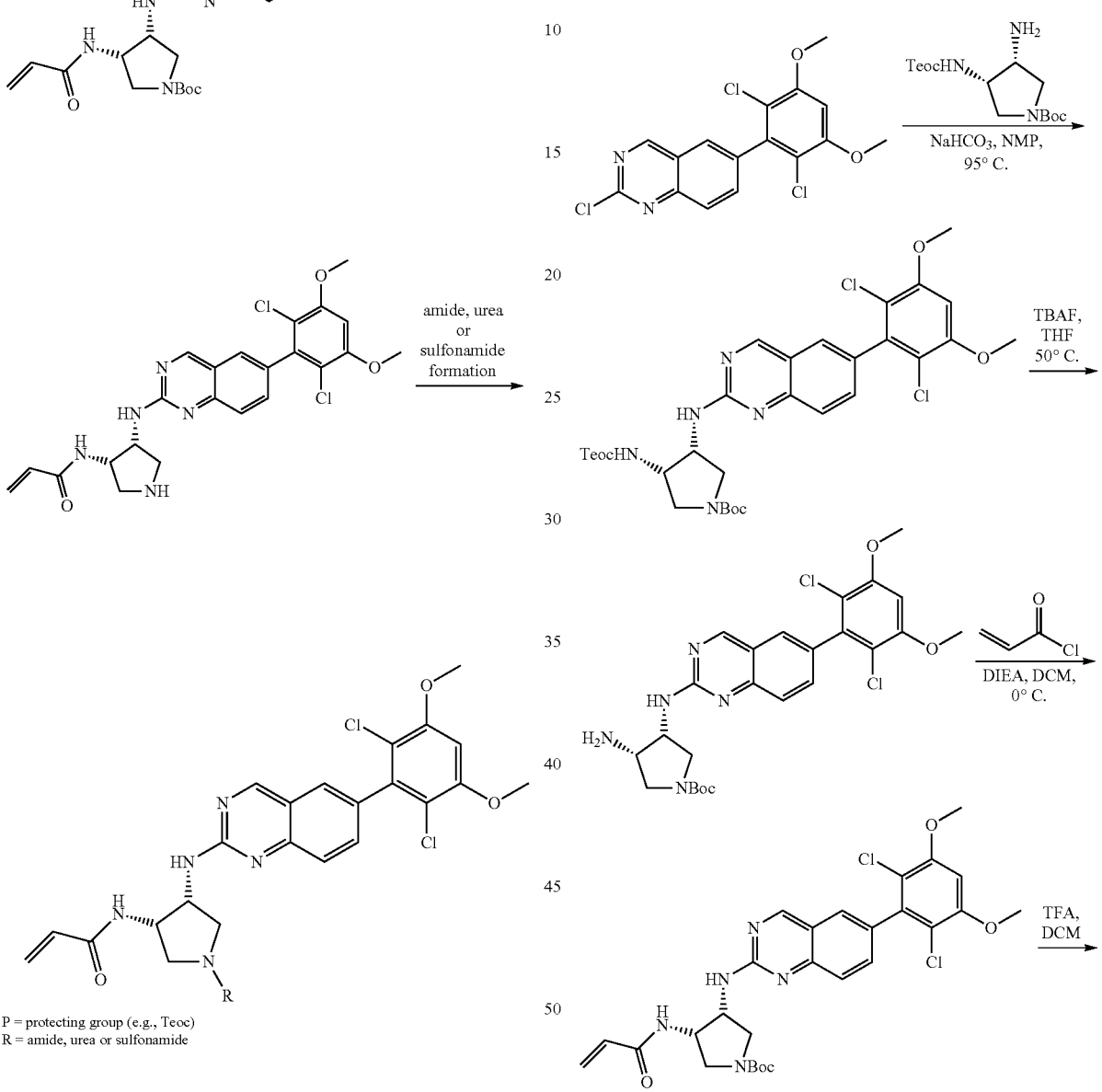

2-chloro-6-(2,6-dichloro-3,5-dimethoxyphenyl)quinazoline (described in WO 2014011900) can be substituted with a 1,2-mono-protected pyrrolidine diamine under nucleophilic aromatic substitution reaction conditions using a base (such as NaHCO₃) in a polar solvent (such as NMP) to provide the diamine-substituted quinazoline. The protecting group on the amine is removed under appropriate conditions to reveal the amine on the pyrrolidine. The amine can be reacted with acryloyl chloride to prepare the acrylamide. As shown below, Compounds 56 and 83 were prepared using Synthetic Protocol 4.

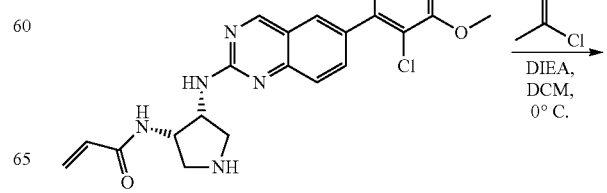

109
-continued

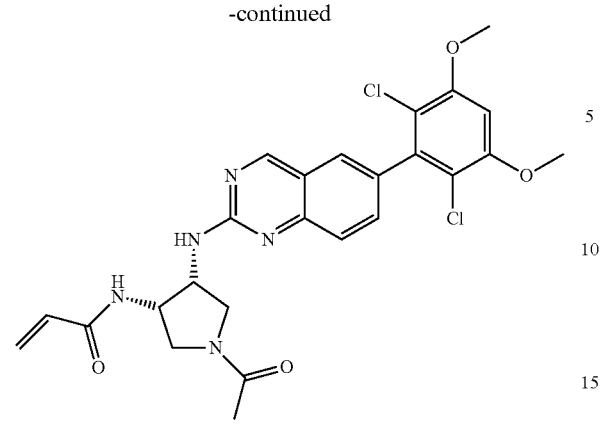

Step 1: Synthesis of tert-butyl (3R,4S)-3-((6-(2,6-dichloro-3,5-dimethoxyphenyl)quinazolin-2-yl)amino)-4-(((2-(trimethylsilyl)ethoxy)carbonyl)amino)pyrrolidine-1-carboxylate

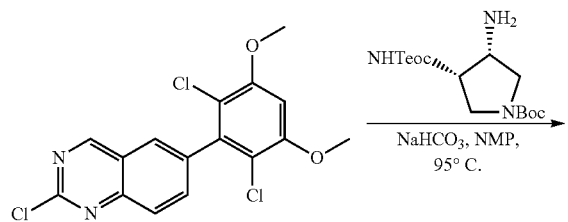

A mixture of 2-chloro-6-(2,6-dichloro-3,5-dimethoxyphenyl)quinazoline (2.65 g, 7.17 mmol), tert-butyl (3R,4S)-3-amino-4-(((2,2,2-trichloroethoxy)carbonyl)amino)pyrrolidine-1-carboxylate (2.97 g, 8.6 mmol), and sodium bicarbonate (2.41 g, 28.7 mmol) was stirred in NMP (40 mL) at 95° C. for 16 hours. The reaction was removed from the oil bath, cooled to room temperature and added to 300 mL of water. A yellow-orange solid was isolated by filtration, rinsed several times with small amounts of water, and dried under vacuum to yield 5 g of crude product, which was purified by silica gel chromatography to yield 2.82 g (58% yield) of tert-butyl (3R,4S)-3-((6-(2,6-dichloro-3,5-dimethoxyphenyl)quinazolin-2-yl)amino)-4-(((2-(trimethylsilyl)ethoxy)carbonyl)amino)pyrrolidine-1-carboxylate. MS (ES+) $C_{31}H_{41}Cl_2N_5O_6Si$ requires: 677, found: 678 [M+H]+.

110

Step 2: Synthesis of tert-butyl (3S,4R)-3-amino-4-((6-(2,6-dichloro-3,5-dimethoxyphenyl)quinazolin-2-yl)amino)pyrrolidine-1-carboxylate

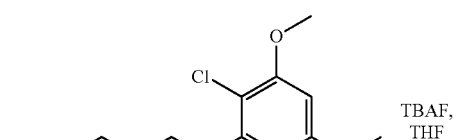

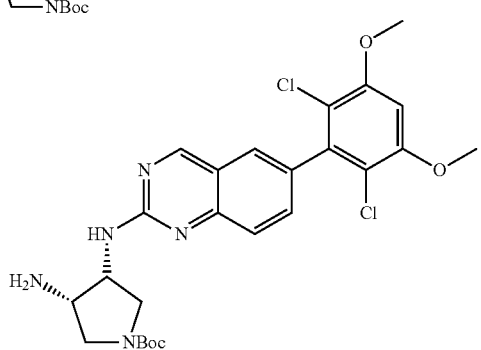

A mixture of tert-butyl (3R,4S)-3-((6-(2,6-dichloro-3,5-dimethoxyphenyl)quinazolin-2-yl)amino)-4-(((2-(trimethylsilyl)ethoxy)carbonyl)amino)pyrrolidine-1-carboxylate (2.77 g, 4.1 mmol) and 1M TBAF in THF (6.1 mL, 6.1 mmol) was stirred in THF (27 mL) at 50° C. for 4 h and then 16 h at room temperature. The reaction mixture was diluted with 10% methanol in dichloromethane (100 mL) and washed with water (50 mL). The aqueous layer was then extracted with fresh dichloromethane (3×20 mL). The combined organic layers were washed with saturated brine solution, dried over sodium sulfate, filtered, concentrated down, and dried to yield tert-butyl (3S,4R)-3-amino-4-((6-(2,6-dichloro-3,5-dimethoxyphenyl)quinazolin-2-yl)amino)pyrrolidine-1-carboxylate as a yellow solid (2.1 g, 94%).

Step 3: Synthesis of tert-butyl (3S,4R)-3-acrylamido-4-((6-(2,6-dichloro-3,5-dimethoxyphenyl)quinazolin-2-yl)amino)pyrrolidine-1-carboxylate

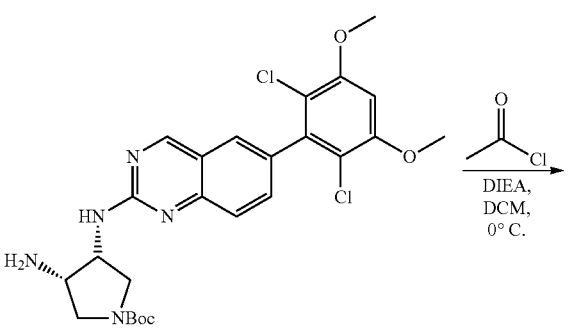

-continued

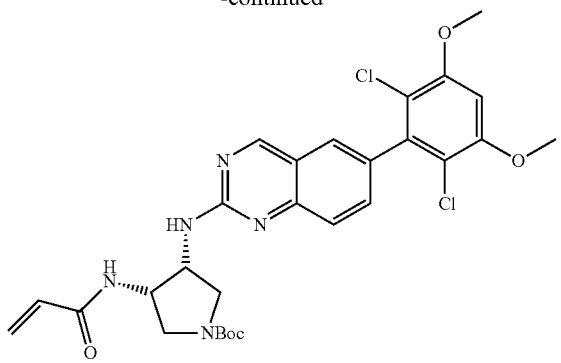

To a solution of (3S,4R)-3-amino-4-((6-(2,6-dichloro-3,5-dimethoxyphenyl)quinazolin-2-yl)amino)pyrrolidine-1-carboxylate (2.1 g, 4.1 mmol) in dichloromethane (82 mL) at 0° C. was added DIEA (1.07 mL, 6.1 mmol) and acryloyl chloride (0.36 mL, 4.5 mmol) and the reaction was stirred for 30 mins. LC-MS indicated complete consumption of SM. The reaction mixture was purified by silica gel chromatography to yield tert-butyl (3S,4R)-3-acrylamido-4-((6-(2,6-dichloro-3,5-dimethoxyphenyl)quinazolin-2-yl)amino)pyrrolidine-1-carboxylate (1.26 g, 52%). MS (ES+) $C_{28}H_{31}Cl_2N_5O_5$ requires: 587, found: 588.

Step 4: Synthesis of N-((3S,4R)-4-((6-(2,6-dichloro-3,5-dimethoxyphenyl)quinazolin-2-yl)amino)pyrrolidin-3-yl)acrylamide A solution of tert-butyl (3S,4R)-3-acrylamido-4-((6-(2,6-dichloro-3,5-dimethoxyphenyl)quinazolin-2-yl)amino)pyrrolidine-1-carboxylate (1.26 g, 2.14 mmol) in DCM (8 mL) and TFA (3 mL, 39 mmol) was stirred 3 h at room temperature. The excess solvents were removed under reduced pressure. The yellow oil was dissolved into DCM (~100 mL) and washed with aqueous saturated sodium bicarbonate solution (~50 mL). The aqueous layer was then extracted with fresh DCM (3×30 mL). The combined organic layers were dried over sodium sulfate, filtered, concentrated down, and dried to yield N-((3S,4R)-4-((6-(2,6-dichloro-3,5-dimethoxyphenyl)quinazolin-2-yl)amino)pyrrolidin-3-yl)acrylamide which was used without further purification in the next step.

Step 5: Synthesis of N-((3S,4R)-1-acetyl-4-((6-(2,6-dichloro-3,5-dimethoxyphenyl)quinazolin-2-yl)amino)pyrrolidin-3-yl)acrylamide

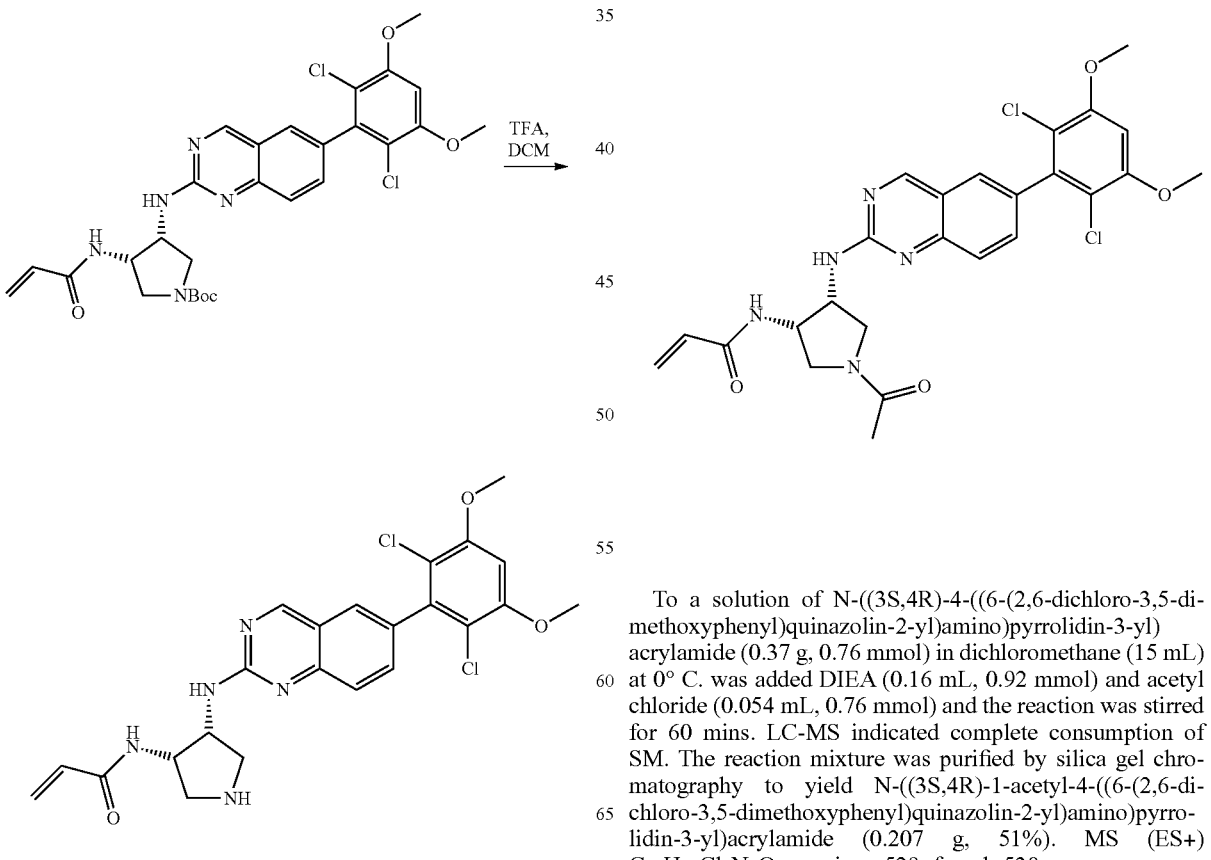

To a solution of N-((3S,4R)-4-((6-(2,6-dichloro-3,5-dimethoxyphenyl)quinazolin-2-yl)amino)pyrrolidin-3-yl)acrylamide (0.37 g, 0.76 mmol) in dichloromethane (15 mL) at 0° C. was added DIEA (0.16 mL, 0.92 mmol) and acetyl chloride (0.054 mL, 0.76 mmol) and the reaction was stirred for 60 mins. LC-MS indicated complete consumption of SM. The reaction mixture was purified by silica gel chromatography to yield N-((3S,4R)-1-acetyl-4-((6-(2,6-dichloro-3,5-dimethoxyphenyl)quinazolin-2-yl)amino)pyrrolidin-3-yl)acrylamide (0.207 g, 51%). MS (ES+) $C_{25}H_{25}Cl_2N_5O_4$ requires: 529, found: 530.

Compound 83

Synthesis of (3S,4R)-3-acrylamido-4-((6-(2,6-di-chloro-3,5-dimethoxyphenyl)quinazolin-2-yl)amino)-N-ethylpyrrolidine-1-carboxamide

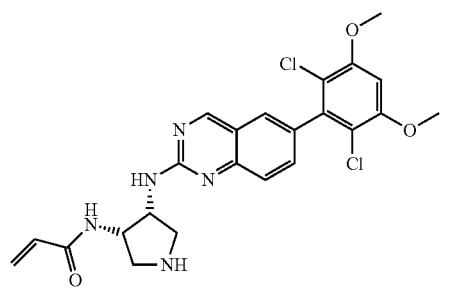

To a solution of N-((3S,4R)-4-((6-(2,6-dichloro-3,5-dimethoxyphenyl)quinazolin-2-yl)amino)pyrrolidin-3-yl)acrylamide (0.040 g, 0.082 mmol) in dichloromethane (1.5 mL) at 0° C. was added TEA (0.014 mL, 0.098 mmol) and ethyl isocyanate (0.008 mL, 0.098 mmol) and the reaction was stirred for 45 mins. LC-MS indicated complete consumption of SM. The reaction mixture was purified by silica gel chromatography to yield (3S,4R)-3-acrylamido-4-((6-(2,6-dichloro-3,5-dimethoxyphenyl)quinazolin-2-yl)amino)-N-ethylpyrrolidine-1-carboxamide (0.035 g, 76%). MS (ES+) $C_{26}H_{28}Cl_2N_6O_4$ requires: 558, found: 559.

Synthetic Protocol 5

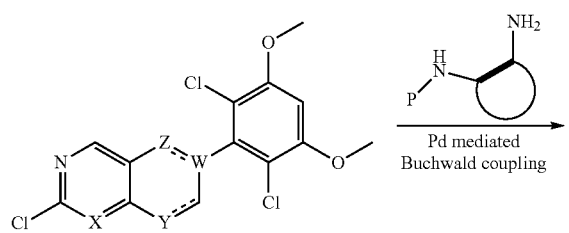

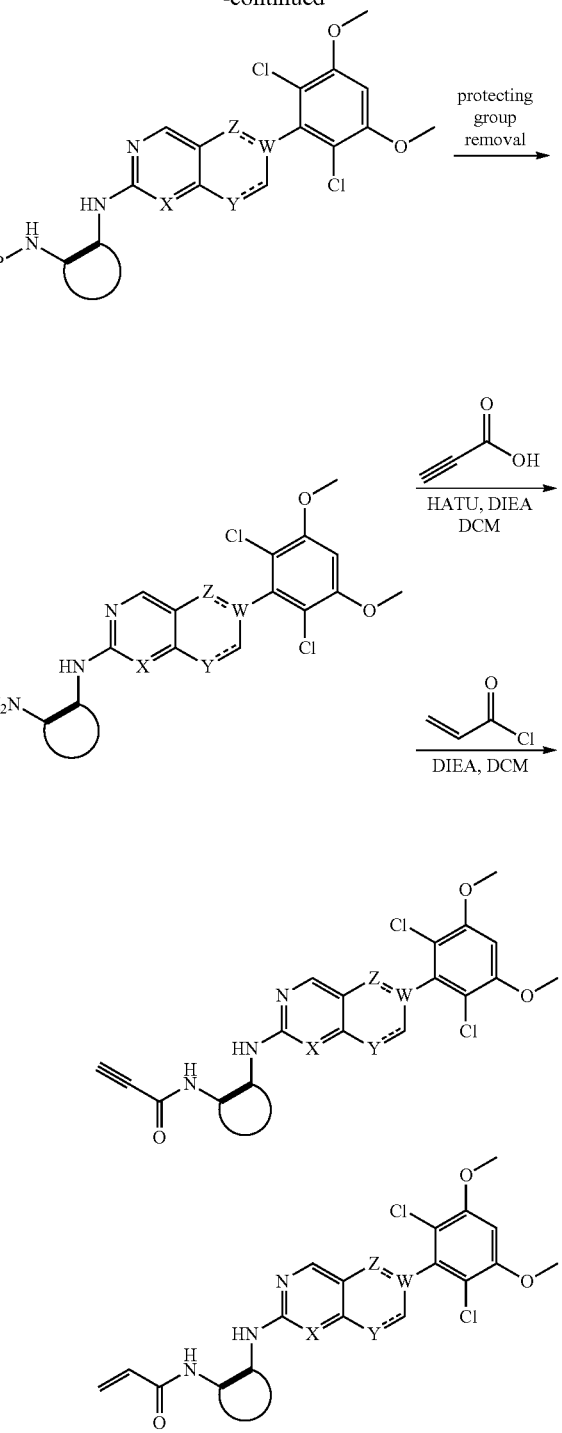

The 2-Cl heterocycle (described in WO 2014/011900) can be substituted with a 1,2-mono-protected diamine via a palladium-mediated Buchwald coupling reaction to provide the diamine-substituted heterocycle. The protecting group on the amine is then removed to reveal the amine on the cycloalkane. The amine can be reacted with propiolic acid using amide coupling reaction conditions to afford the propargyl amide or reacted with acryloyl chloride to provide the acrylamide. As shown below, Compound 62 was prepared using Synthetic Protocol 5.

Compound 62

Synthesis of N-((1S,2R)-2-((6-(2,6-dichloro-3,5-dimethoxyphenyl)-8-ethyl-7-oxo-7,8-dihydropyrido[2,3-d]pyrimidin-2-yl)amino)cyclopentyl)acrylamide

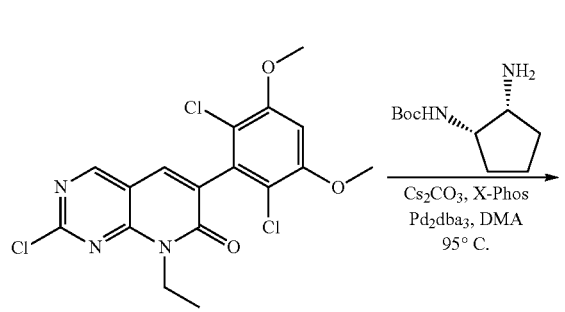

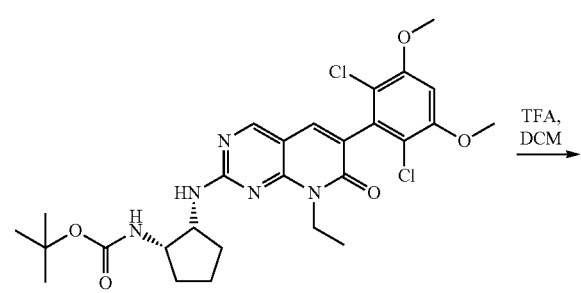

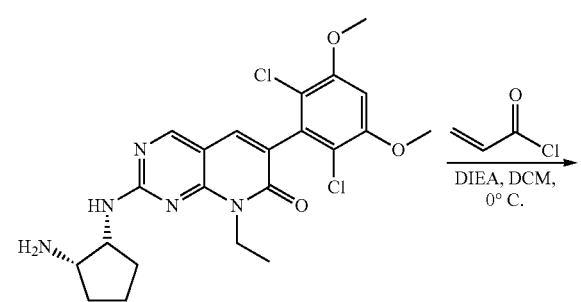

Step 1: Synthesis of tert-butyl ((1S,2R)-2-((6-(2,6-dichloro-3,5-dimethoxyphenyl)-8-ethyl-7-oxo-7,8-dihydropyrido[2,3-d]pyrimidin-2-yl)amino)cyclopentyl)carbamate

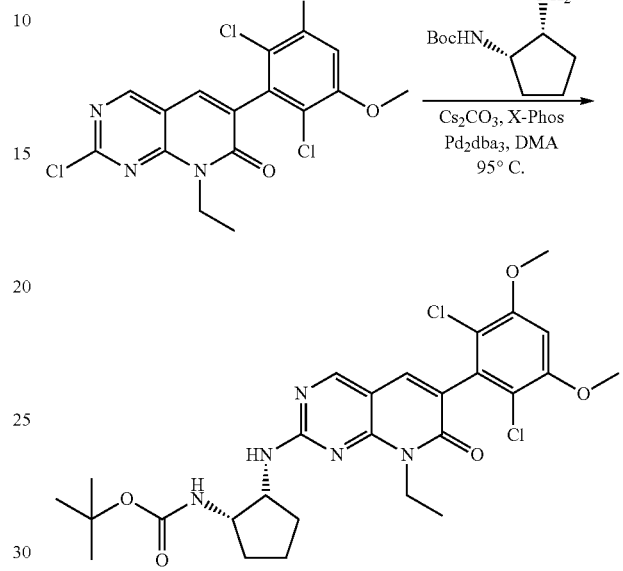

A mixture of 2-chloro-6-(2,6-dichloro-3,5-dimethoxyphenyl)-8-ethylpyrido[2,3-d]pyrimidin-7(8H)-one (0.2 g, 0.48 mmol), tert-butyl ((1S,2R)-2-aminocyclopentyl)carbamate (145 mg, 0.72 mmol), $Cs_2CO_3$ (393 mg, 1.21 mmol), X-Phos (23 mg, 0.048 mmol) and $Pd_2dba_3$ (22 mg, 0.024 mmol) in DMA (3.2 mL) was degassed with $N_2$ for 5 mins and heated in a microwave reactor at 115° C. for 60 mins. The mixture was cooled to room temperature, diluted with EtOAc, filtered through celite and washed with water (4x) followed by saturated brine solution. The residue was purified by silica gel column chromatography to afford tert-butyl tert-butyl ((1S,2R)-2-((6-(2,6-dichloro-3,5-dimethoxyphenyl)-8-ethyl-7-oxo-7,8-dihydropyrido[2,3-d]pyrimidin-2-yl)amino)cyclopentyl)carbamate (60 mg, 22%). MS (ES+) $C_{27}H_{33}Cl_2N_5O_5$ requires: 577, found: 578 $[M+H]^+$.

Step 2: Synthesis of 2-(((1R,2S)-2-aminocyclopentyl)amino)-6-(2,6-dichloro-3,5-dimethoxyphenyl)-8-ethylpyrido[2,3-d]pyrimidin-7(8H)-one

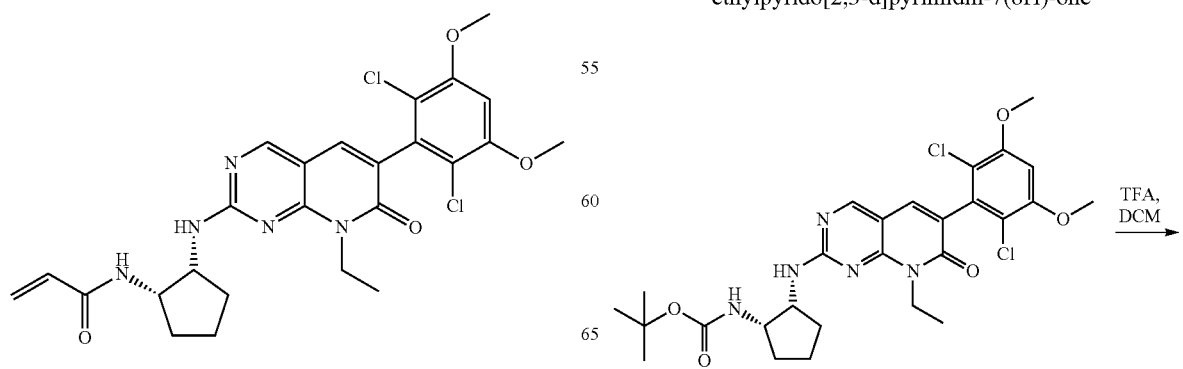

117

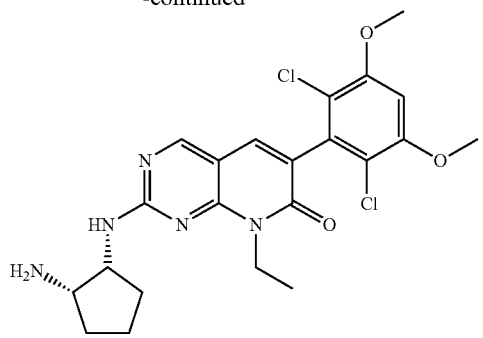

A mixture of tert-butyl tert-butyl ((1S,2R)-2-((6-(2,6-dichloro-3,5-dimethoxyphenyl)-8-ethyl-7-oxo-7,8-dihydropyrido[2,3-d]pyrimidin-2-yl)amino)cyclopentyl)carbamate (60 mg, 0.105 mmol) and TFA (0.5 mL) in dichloromethane (2 mL) was stirred at room temperature for 90 minutes. LC-MS indicated complete consumption of SM. The reaction mixture was diluted with saturated NaHCO₃ and then extracted with dichloromethane. The combined organic layers were dried by Na₂SO₄, filtered, concentrated to give 2-(((1R,2S)-2-aminocyclopentyl)amino)-6-(2,6-dichloro-3,5-dimethoxyphenyl)-8-ethylpyrido[2,3-d]pyrimidin-7(8H)-one which was used without further purification in the next step.

Step 3: Synthesis of N-((1S,2R)-2-((6-(2,6-dichloro-3,5-dimethoxyphenyl)-8-ethyl-7-oxo-7,8-dihydropyrido[2,3-d]pyrimidin-2-yl)amino)cyclopentyl)acrylamide

118

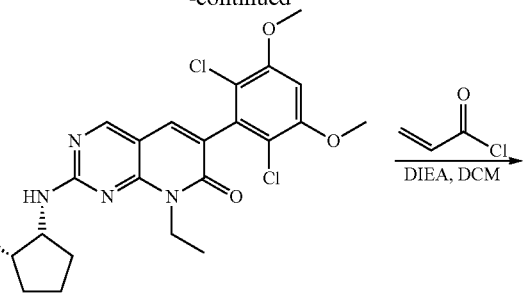

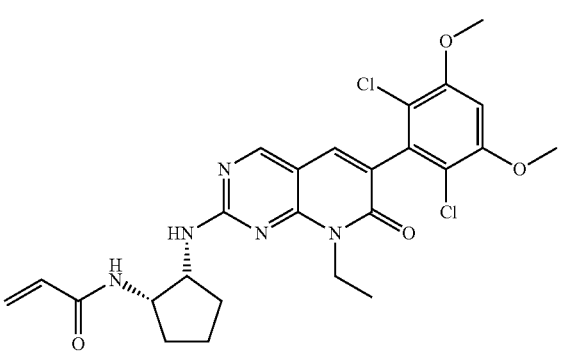

To a solution of 2-(((1R,2S)-2-aminocyclopentyl)amino)-6-(2,6-dichloro-3,5-dimethoxyphenyl)-8-ethylpyrido[2,3-d]pyrimidin-7(8H)-one (0.105 mmol) in dichloromethane (2.1 mL) at −20° C. was added DIEA (0.018 mL, 0.105 mmol) and acryloyl chloride (0.008 mL, 0.105 mmol) and the reaction was stirred for 1 h. LC-MS indicated complete consumption of SM. The reaction mixture was purified by silica gel chromatography to yield N-((1S,2R)-2-((6-(2,6-dichloro-3,5-dimethoxyphenyl)-8-ethyl-7-oxo-7,8-dihydropyrido[2,3-d]pyrimidin-2-yl)amino)cyclopentyl)acrylamide (36 mg, 65%). MS (ES+) $C_{25}H_{27}Cl_2N_5O_4$ requires: 531, found: 532.

Synthetic Protocol 6

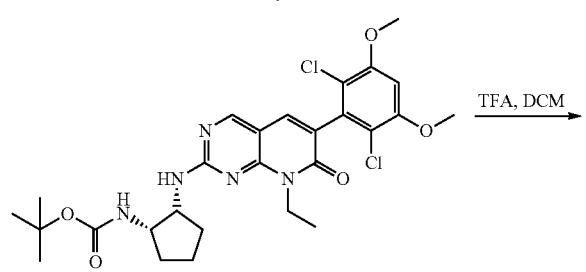

-continued

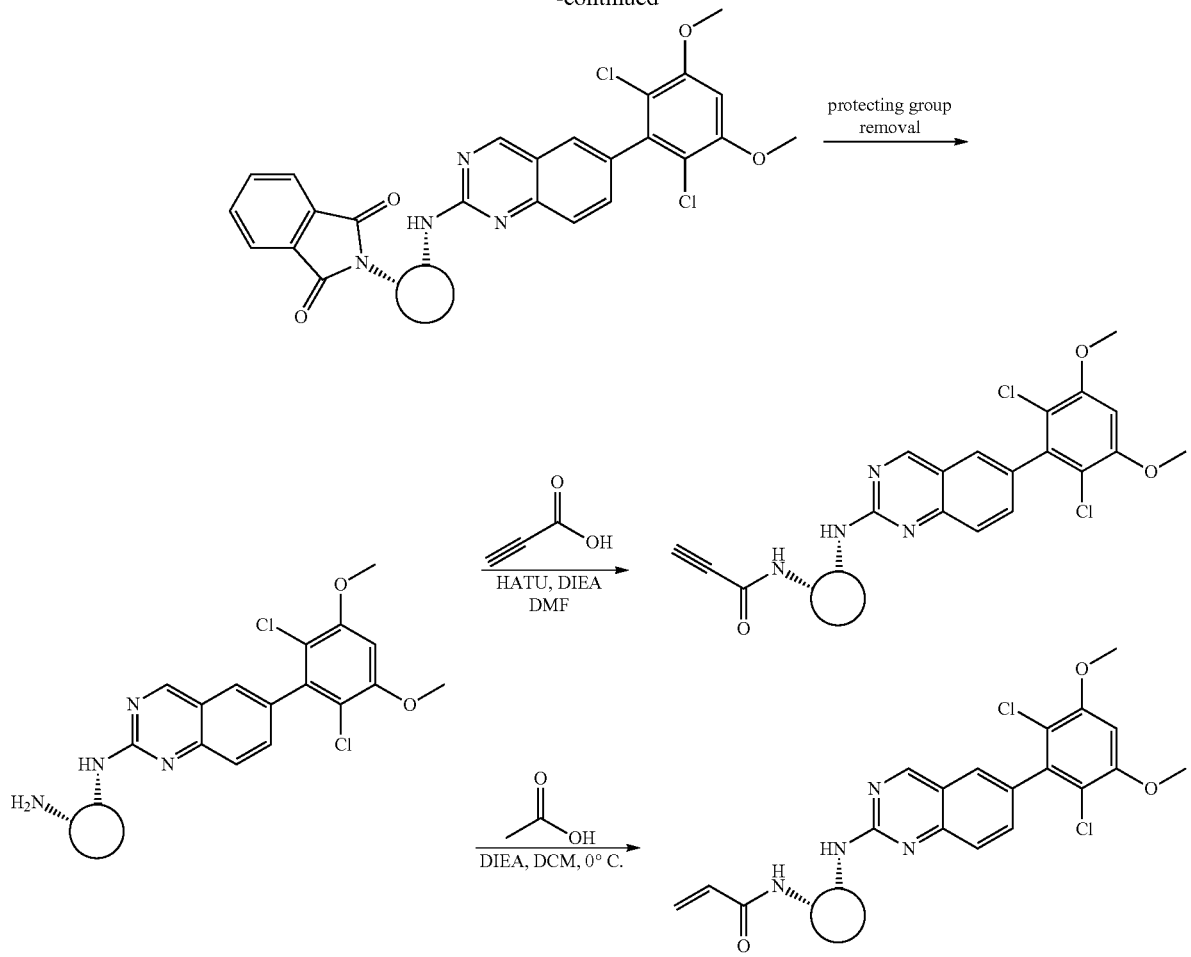

The 2-Cl heterocycle can be substituted with a 1,2-trans-amino alcohol via various nucleophilic aromatic substitution reaction conditions using a base (such as diisopropylethylamine (DIPEA), DBU or NaHCO$_3$) in a polar solvent (such as dioxane, CH$_3$CN or NMP) or via a palladium-mediated Buchwald coupling reaction to provide the substituted quinazoline. The alcohol on the cycloalkane is reacted under nucleophilic substitution reaction conditions (such as Mitusnobu reaction) to afford the protected amine. Removal of the protecting group on the amine (such as hydrazine for the phthalimide protecting group) afforded the amine on the cycloalkane. The amine can be reacted with propargylic acid (using amide coupling conditions such as HATU, DIPEA) or reacted with acryloyl chloride to prepare the final compounds. As shown below, Compounds 81 and 82 were prepared using Synthetic Protocol 6.

Compounds 81 and 82

Synthesis of (1S,3S,4R)-3-acrylamido-4-((6-(2,6-dichloro-3,5-dimethoxyphenyl)quinazolin-2-yl)amino)-N,N-dimethylcyclopentanecarboxamide and (1R,3S,4R)-3-acrylamido-4-((6-(2,6-dichloro-3,5-dimethoxyphenyl)quinazolin-2-yl)amino)-N,N-dimethylcyclopentane-1-carboxamide

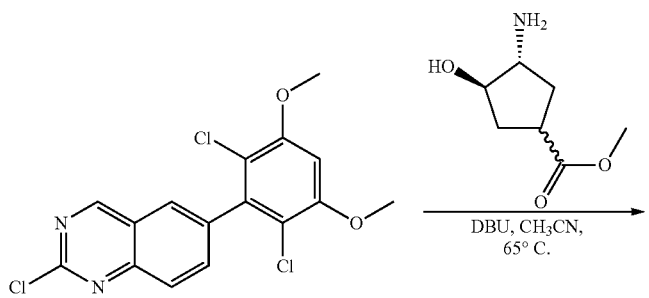

-continued
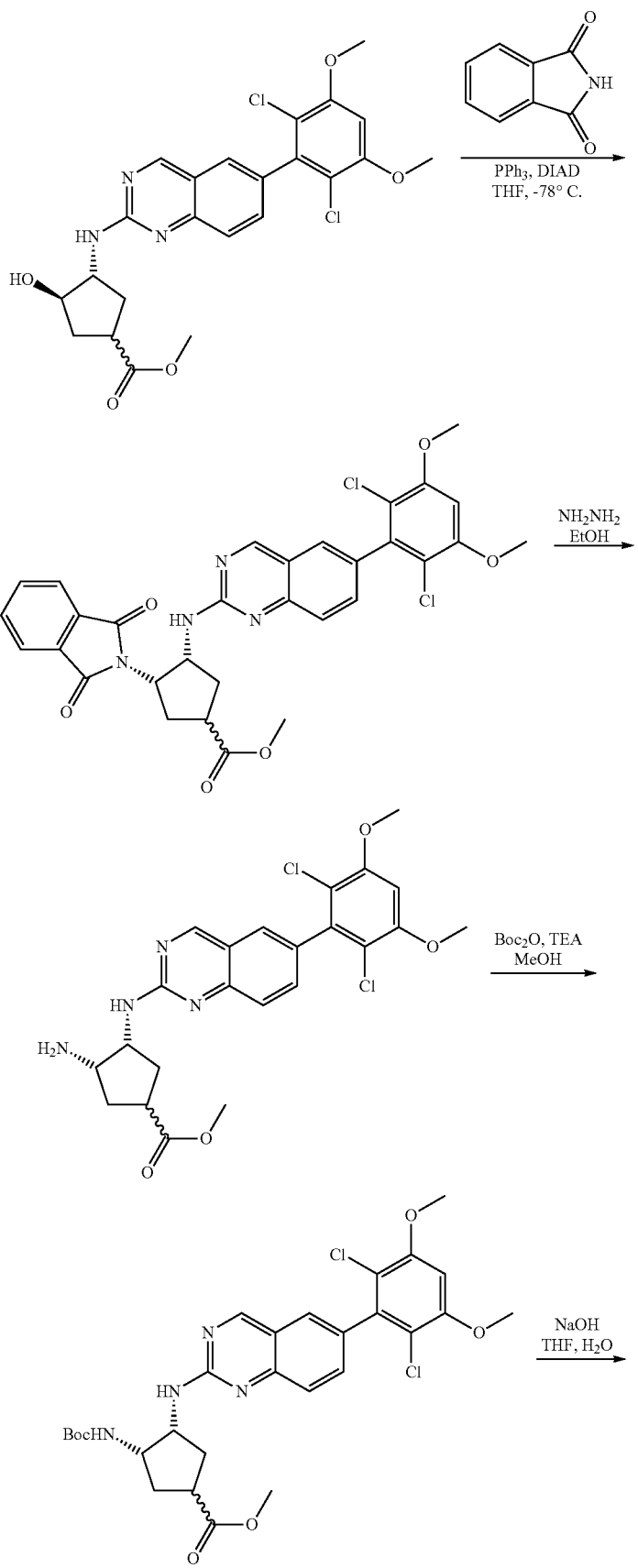

-continued
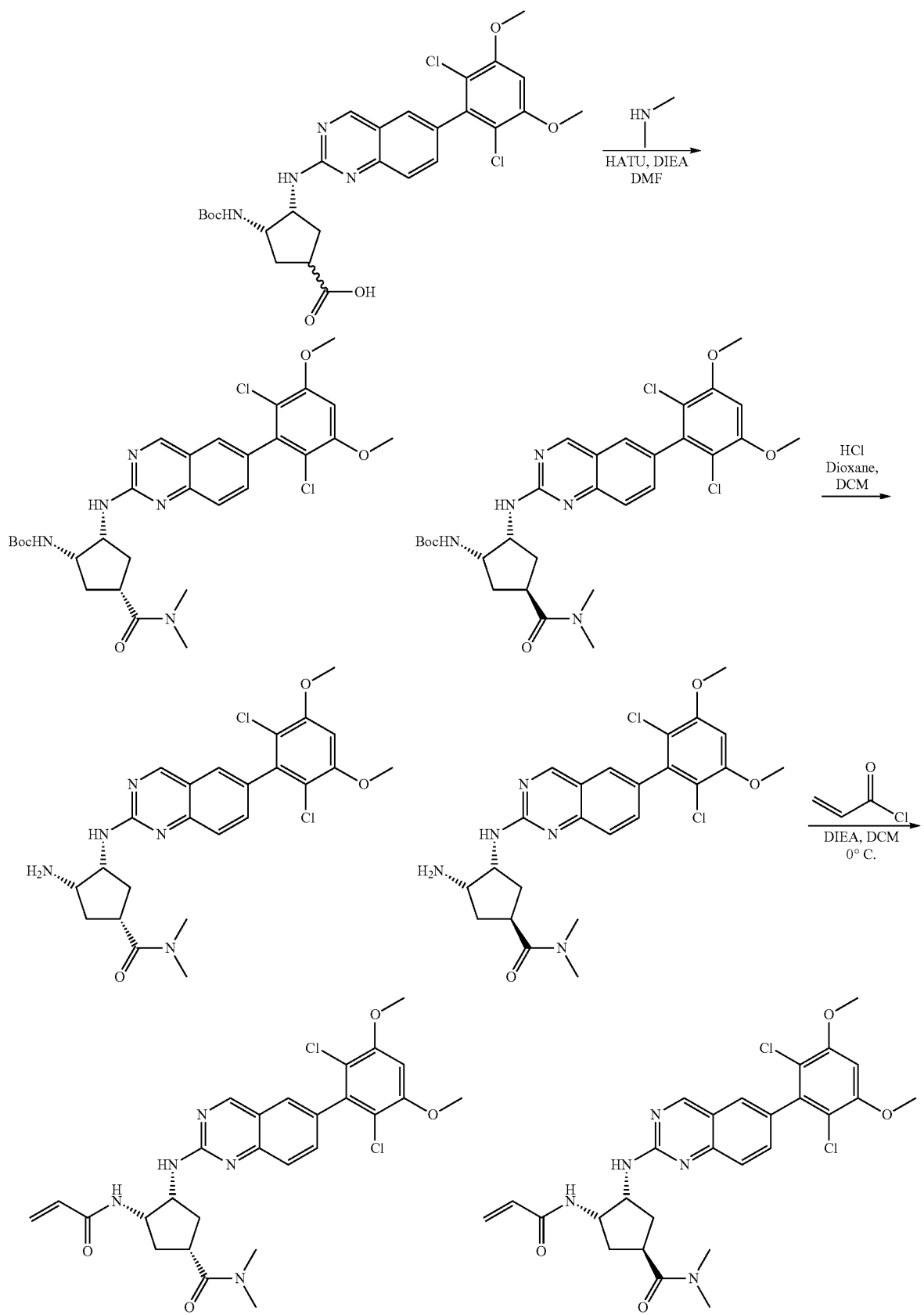

Step 1: Synthesis of racemic methyl (3R,4R)-3-((6-(2,6-dichloro-3,5-dimethoxyphenyl)-quinazolin-2-yl)amino)-4-hydroxycyclopentane-1-carboxylate

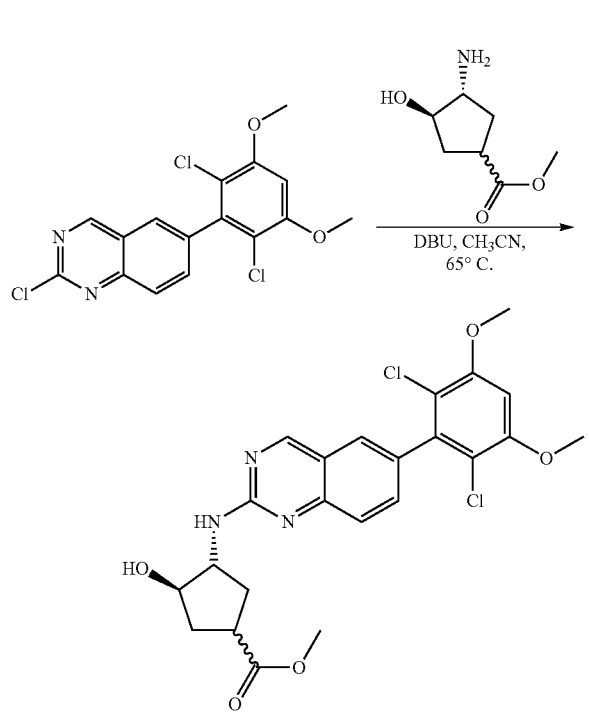

2-chloro-6-(2,6-dichloro-3,5-dimethoxyphenyl)quinazoline (0.576 g, 1.558 mmol), methyl (3R,4R)-3-amino-4-hydroxycyclopentane-1-carboxylate (0.372 g, 2.337 mmol) were taken up in acetonitrile (3 ml) and DBU (0.470 ml, 3.12 mmol) was added. The reaction was purged with $N_2$ for 5 minutes then heated to 65° C. overnight. After cooling to room temperature, the solvent was removed under reduced pressure. The residue was purified via flash chromatography (0-100% Hex/EtOAc; 12 g column), and (1S,3R,4R)-methyl 3-((6-(2,6-dichloro-3,5-dimethoxyphenyl)quinazolin-2-yl)amino)-4-hydroxycyclopentanecarboxylate (0.520 g, 1.056 mmol, 67.8% yield) was recovered. MS (ES+) $C_{23}H_{23}Cl_2N_3O_5$ requires: 492, found: 493 [M+H]+.

Step 2: Synthesis of racemic methyl (3R,4S)-3-((6-(2,6-dichloro-3,5-dimethoxyphenyl)quinazolin-2-yl)amino)-4-(1,3-dioxoisoindolin-2-yl)cyclopentane-1-carboxylate

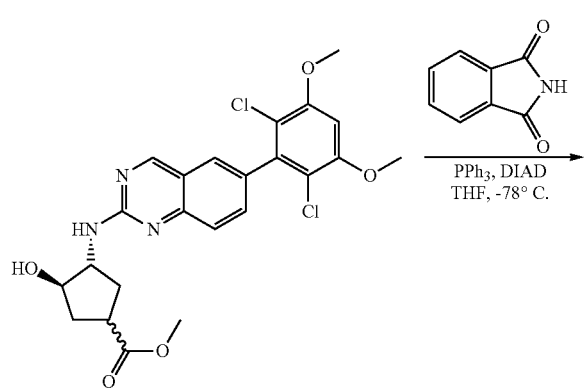

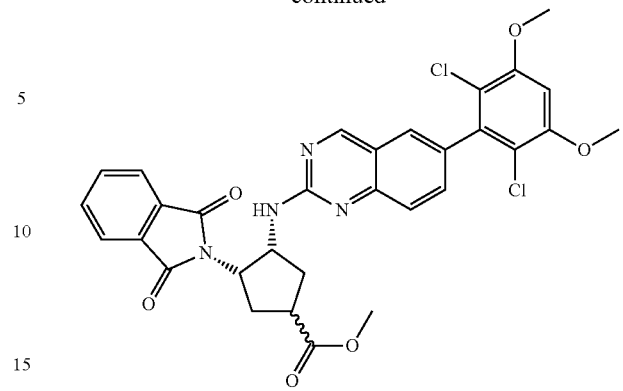

$Ph_3P$ (0.213 g, 0.812 mmol) was taken up in THF (6 ml) and cooled to −78° C. under $N_2$. DIAD (0.126 ml, 0.650 mmol) was added followed by addition of phthalimide (0.105 g, 0.711 mmol) and stirred at −78° C. for 1 hour, followed by addition of (1S,3R,4R)-methyl 3-((6-(2,6-dichloro-3,5-dimethoxyphenyl)quinazolin-2-yl)amino)-4-hydroxycyclopentanecarboxylate (0.100 g, 0.203 mmol) in 4 ml of THF at −78° C. The reaction was stirred overnight while warming to room temperature, after which the solvent was removed under reduced pressure. The residue was purified via flash chromatography (0-100% Hex/EtOAc; 12 g column) to afford methyl (3R,4S)-3-((6-(2,6-dichloro-3,5-dimethoxyphenyl)quinazolin-2-yl)amino)-4-(1,3-dioxoisoindolin-2-yl)cyclopentane-1-carboxylate (0.126 g, 0.203 mmol). MS (ES+) $C_{31}H_{26}Cl_2N_4O_6$ requires: 621, found: 622 [M+H]+.

Step 3: Synthesis of racemic methyl (3S,4R)-3-amino-4-((6-(2,6-dichloro-3,5-dimethoxyphenyl)quinazolin-2-yl)amino)cyclopentane-1-carboxylate

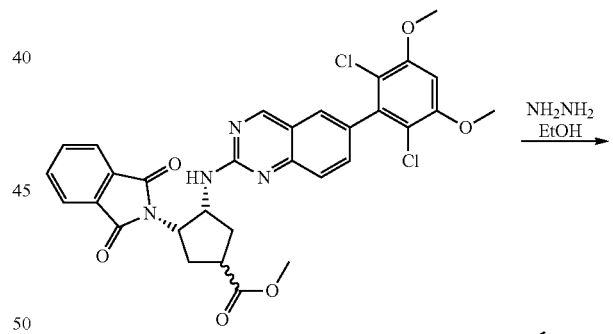

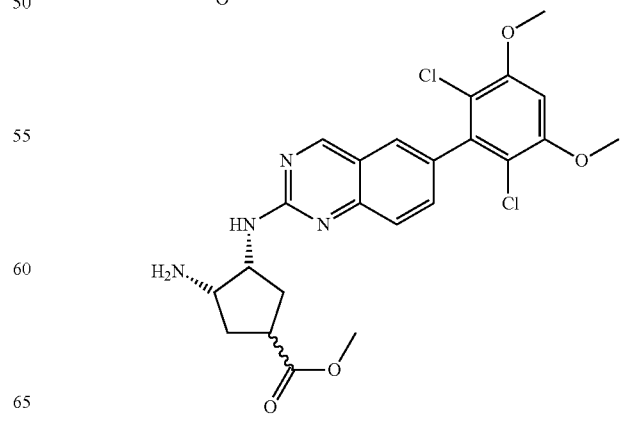

(1S,3R,4S)-methyl 3-((6-(2,6-dichloro-3,5-dimethoxyphenyl)quinazolin-2-yl)amino)-4-(1,3-dioxoisoindolin-2-yl)cyclopentanecarboxylate (0.500 g, 0.805 mmol) was taken up in EtOH (20 ml) and hydrazine monohydrate (0.079 ml, 1.61 mmol) was added. The reaction was stirred overnight at room temperature. A white precipitate was filtered off and solvent was removed under reduced pressure. The precipitate was triturated with ether, followed by removal of the solvent under reduced pressure to give methyl (3S,4R)-3-amino-4-((6-(2,6-dichloro-3,5-dimethoxyphenyl)quinazolin-2-yl)amino)cyclopentane-1-carboxylate (0.395 g, 0.805 mmol) in quantative yield, which was carried on without further purification. MS (ES+) $C_{23}H_{24}Cl_2N_4O_4$ requires: 491, found: 492 [M+H]+.

Step 4: Synthesis of racemic methyl (3S,4R)-3-((tert-butoxycarbonyl)amino)-4-((6-(2,6-dichloro-3,5-dimethoxyphenyl)quinazolin-2-yl)amino)cyclopentane-1-carboxylate

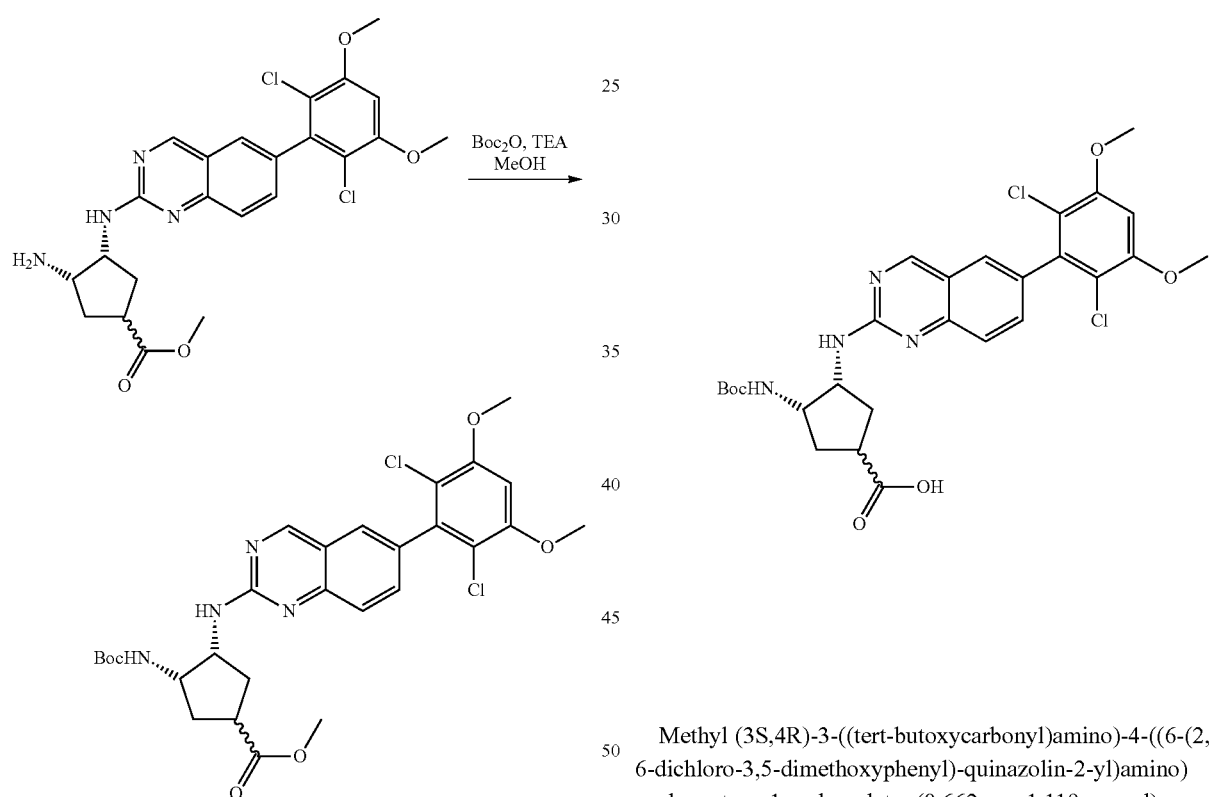

(3S,4R)-3-amino-4-((6-(2,6-dichloro-3,5-dimethoxyphenyl)quinazolin-2-yl)amino)cyclopentane-1-carboxylate (0.550 g, 1.119 mmol) was taken up in methanol (10 ml) followed by addition of Et₃N (0.156 ml, 1.119 mmol) and BOC-Anhydride (0.286 ml, 1.231 mmol). The reaction was stirred at ambient temperature overnight. After removal of the solvent under vacuum, the residue was taken up in DCM and washed with water (2×), dried over sodium sulfate, and the solvent was removed under reduced pressure to give methyl(3S,4R)-3-((tert-butoxycarbonyl)amino)-4-((6-(2,6-dichloro-3,5-dimethoxyphenyl) quinazolin-2-yl)amino)cyclopentane-1-carboxylate (0.662 g, 1.119 mmol), which was carried on without further purification. MS (ES+) $C_{28}H_{32}Cl_2N_4O_6$ requires: 591, found: 592 [M+H]+.

Step 5: Synthesis of racemic (3S,4R)-3-((tert-butoxycarbonyl)amino)-4-((6-(2,6-dichloro-3,5-dimethoxyphenyl)quinazolin-2-yl)amino)cyclopentane-1-carboxylic acid

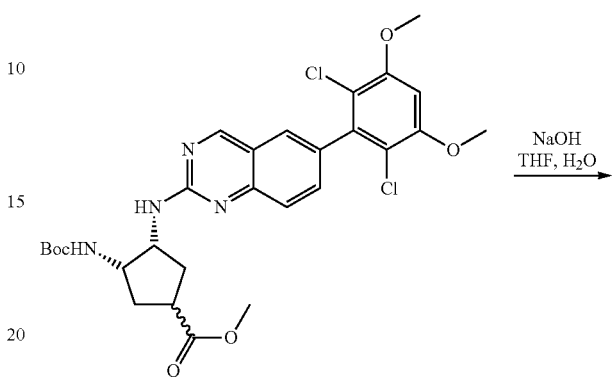

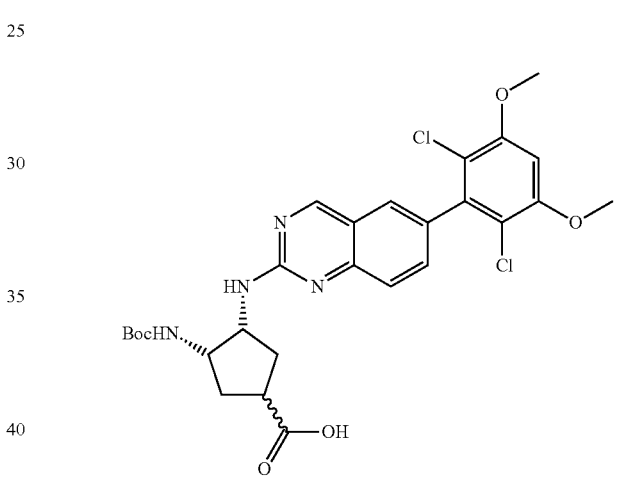

Methyl (3S,4R)-3-((tert-butoxycarbonyl)amino)-4-((6-(2,6-dichloro-3,5-dimethoxyphenyl)-quinazolin-2-yl)amino) cyclopentane-1-carboxylate (0.662 g, 1.119 mmol) was taken up in methanol (10 ml), THF (4 ml) and treated with 10 ml of 1N NaOH. The reaction mixture was stirred at room temperature for 2 hours. The organic solvents were removed under reduced pressure, then the aqueous layer was acidified with 1N HCl to pH ~2. The aqueous layer was extracted with EtOAc×3. The organic layers were combined, dried over sodium sulfate, and the solvent removed to give crude (3S,4R)-3-((tert-butoxycarbonyl)amino)-4-((6-(2,6-dichloro-3,5-dimethoxyphenyl)quinazolin-2-yl)amino)cyclopentane-1-carboxylic acid (0.580 g, 1.00 mmol, 91% yield) which was carried on with further purification. MS (ES+) $C_{27}H_{30}Cl_2N_4O_6$ requires: 577, found: 578 [M+H]+.

Step 6: Synthesis of tert-butyl ((1S,2R,4S)-2-((6-(2,6-dichloro-3,5-dimethoxyphenyl)quinazolin-2-yl)amino)-4-(dimethylcarbamoyl)cyclopentyl)carbamate and tert-butyl ((1S,2R,4R)-2-((6-(2,6-dichloro-3,5-dimethoxyphenyl)quinazolin-2-yl)amino)-4-(dimethylcarbamoyl)cyclopentyl) carbamate Step 7a: Synthesis of (1S,3S,4R)-3-amino-4-((6-(2,6-dichloro-3,5-dimethoxyphenyl)quinazolin-2-yl)amino)-N,N-dimethylcyclopentane-1-carboxamide

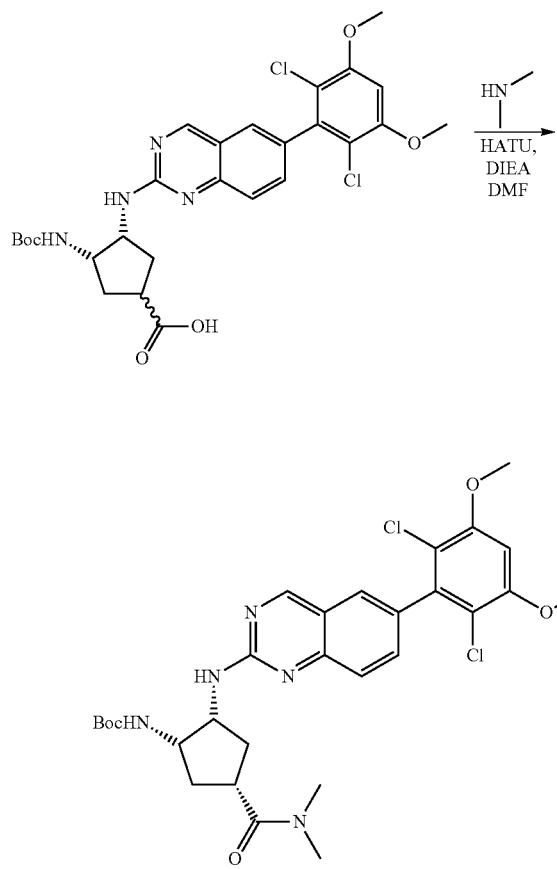

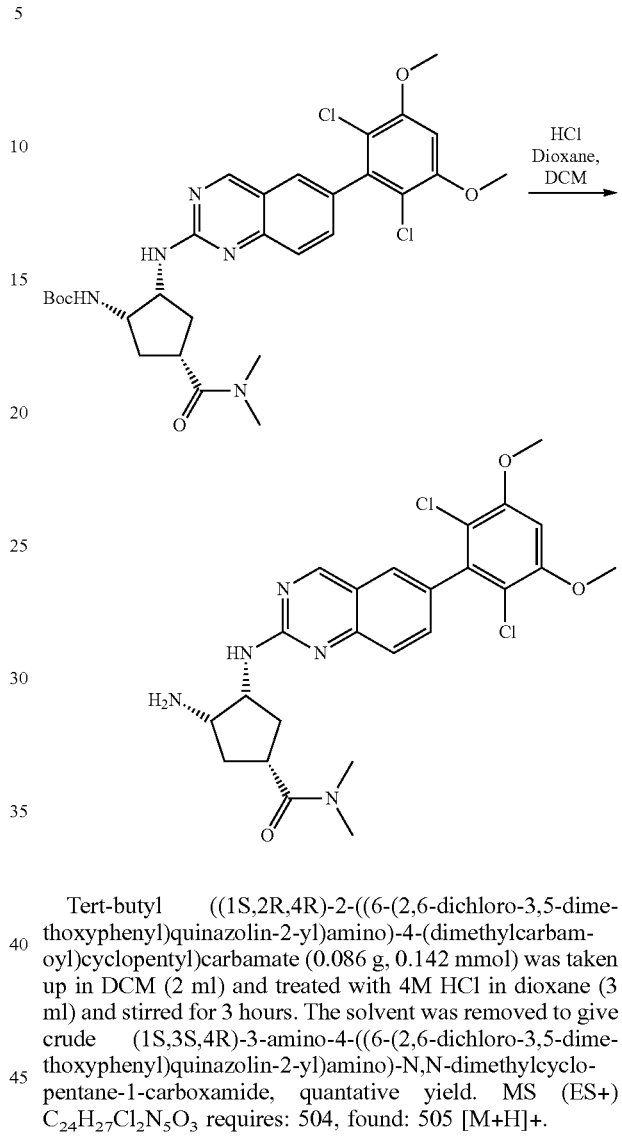

(3S,4R)-3-((tert-butoxycarbonyl)amino)-4-((6-(2,6-dichloro-3,5-dimethoxyphenyl)quinazolin-2-yl)amino)cyclopentane-1-carboxylic acid (0.270 g, 0.468 mmol) was taken up in DMF (3 ml), HATU (0.267 g, 0.701 mmol), dimethylamine 2M in THF (0.250 ml, 0.500 mmol) and DIEA (0.245 ml, 1.403 mmol) were added and stirred at ambient temperature for 30 minutes. The reaction was complete after monitoring by LCMS, which showed two peaks containing the correct mass. The reaction was purified via reverse phase chromatography (5-60% acetonitrile/water+0.01% formic acid; 12 g column). Peak A: tert-butyl ((1S,2R,4R)-2-((6-(2,6-dichloro-3,5-dimethoxyphenyl)quinazolin-2-yl)amino)-4-(dimethylcarbamoyl)cyclopentyl)carbamate (0.086 g, 0.142 mmol) MS (ES+) $C_{29}H_{35}Cl_2N_5O_5$ requires: 604, found: 605 [M+H]+, retention time 3.039. Peak B: tert-butyl ((1S,2R,4S)-2-((6-(2,6-dichloro-3,5-dimethoxyphenyl)quinazolin-2-yl)amino)-4-(dimethylcarbamoyl)cyclopentyl)carbamate (0.062 g, 0.103 mmol) MS (ES+) $C_{29}H_{35}Cl_2N_5O_5$ requires: 604, found: 605 [M+H]+, retention time 2.879. Note: the absolute configuration was assigned arbitrarily.

Tert-butyl ((1S,2R,4R)-2-((6-(2,6-dichloro-3,5-dimethoxyphenyl)quinazolin-2-yl)amino)-4-(dimethylcarbamoyl)cyclopentyl)carbamate (0.086 g, 0.142 mmol) was taken up in DCM (2 ml) and treated with 4M HCl in dioxane (3 ml) and stirred for 3 hours. The solvent was removed to give crude (1S,3S,4R)-3-amino-4-((6-(2,6-dichloro-3,5-dimethoxyphenyl)quinazolin-2-yl)amino)-N,N-dimethylcyclopentane-1-carboxamide, quantative yield. MS (ES+) $C_{24}H_{27}Cl_2N_5O_3$ requires: 504, found: 505 [M+H]+.

Step 8a: Synthesis of (1R,3S,4R)-3-acrylamido-4-((6-(2,6-dichloro-3,5-dimethoxyphenyl)quinazolin-2-yl)amino)-N,N-dimethylcyclopentane-1-carboxamide

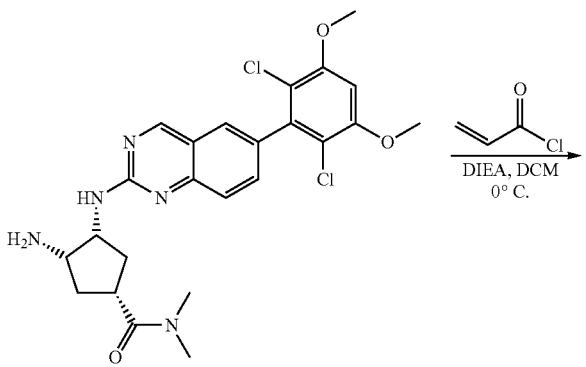

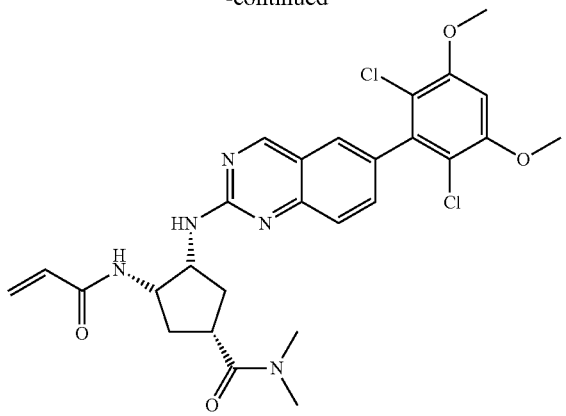

(1S,3S,4R)-3-amino-4-((6-(2,6-dichloro-3,5-dimethoxyphenyl)quinazolin-2-yl)amino)-N,N-dimethylcyclopentanecarboxamide (0.050 g, 0.099 mmol) was taken up in CH$_2$Cl$_2$ (25 ml) and cooled to 0° C., followed by addition of DIEA (0.017 ml, 0.099 mmol) then acryloyl chloride (8.86 µl, 0.109 mmol) slowly. The reaction mixture was stirred at 0° C. for 30 minutes. After the reaction was complete, the reaction mixture was loaded directly onto silica and purified via flash chromatography (0-10% CH$_2$Cl$_2$/MeOH; 12 g column) to afford (1R,3S,4R)-3-acrylamido-4-((6-(2,6-dichloro-3,5-dimethoxyphenyl)quinazolin-2-yl)amino)-N,N-dimethylcyclopentanecarboxamide (0.043 g, 0.077 mmol, 78% yield). MS (ES+) C$_{27}$H$_{29}$Cl$_2$N$_5$O$_4$ requires: 558, found: 559 [M+H]+.

Step 7b: Synthesis of (1R,3S,4R)-3-amino-4-((6-(2,6-dichloro-3,5-dimethoxyphenyl)quinazolin-2-yl)amino)-N,N-dimethylcyclopentane-1-carboxamide tert-butyl ((1S,2R,4S)-2-((6-(2,6-dichloro-3,5-dimethoxyphenyl)quinazolin-2-yl)amino)-4-(dimethylcarbamoyl)cyclopentyl)carbamate (0.062 g, 0.103 mmol) was taken up in DCM (2 ml) and treated with 4M HCl in dioxane (3 ml) and stirred for 3 hours. The solvent was removed to give crude (1S,3S,4R)-3-amino-4-((6-(2,6-dichloro-3,5-dimethoxyphenyl)quinazolin-2-yl)amino)-N,N-dimethylcyclopentane-1-carboxamide, quantative yield. MS (ES+) C$_{24}$H$_{27}$Cl$_2$N$_5$O$_3$ requires: 504, found: 505 [M+H]+.

Step 8b: Synthesis of (1S,3S,4R)-3-acrylamido-4-((6-(2,6-dichloro-3,5-dimethoxyphenyl)quinazolin-2-yl)amino)-N,N-dimethylcyclopentane-1-carboxamide (1R,3S,4R)-3-amino-4-((6-(2,6-dichloro-3,5-dimethoxyphenyl)quinazolin-2-yl)amino)-N,N-dimethylcyclopentanecarboxamide (0.050 g, 0.099 mmol) was taken up in CH$_2$Cl$_2$ (25 ml) and cooled to 0° C., followed by addition of DIEA (0.017 ml, 0.099 mmol) then acryloyl chloride (8.86 µl, 0.109 mmol) slowly. The reaction mixture was stirred at 0° C. for 30 minutes. After the reaction was complete, it was loaded directly onto silica and purified via flash chromatography (0-10% CH$_2$Cl$_2$/MeOH; 12 g column) to afford (1S,3S,4R)-3-acrylamido-4-((6-(2,6-dichloro-3,5-dimethoxyphenyl)quinazolin-2-yl)amino)-N,N-dimethylcyclopentanecarboxamide (0.029 g, 0.052 mmol, 52.4% yield). MS (ES+) C$_{27}$H$_{29}$Cl$_2$N$_5$O$_4$ requires: 558, found: 559 [M+H]+.

Preparation of Common Intermediates

Synthesis of tert-butyl ((3R,4S)-4-aminotetrahydrofuran-3-yl)carbamate

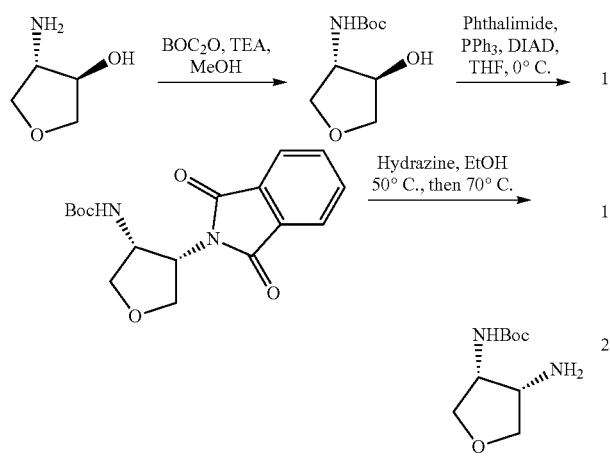

Step 1: Synthesis of tert-butyl ((3S,4R)-4-hydroxytetrahydrofuran-3-yl)carbamate Intermediate (3R,4S)-4-aminotetrahydrofuran-3-ol was prepared as in WO 01/29013 (PCT/US00/28815; pp. 44-45; Example 1). A solution of (3R,4S)-4-aminotetrahydrofuran-3-ol (10.6 g, 103 mmol), triethylamine (26 g, 257 mmol), and BOC anhydride (24.7 g, 113 mmol) in methanol (206 mL, 0.5 M) was stirred at room temperature over 45 hours. The solvents were then removed under reduced pressure. The beige solid was treated with water (about 120 mL). A white crystalline solid was isolated by filtration and dried overnight under vacuum to yield tert-butyl ((3S,4R)-4-hydroxytetrahydrofuran-3-yl)carbamate as a white solid (17.08 g, 82%).

Step 2: Synthesis of tert-butyl ((3R,4S)-4-(1,3-dioxoisoindolin-2-yl)tetrahydrofuran-3-yl)carbamate A mixture of tert-butyl ((3S,4R)-4-hydroxytetrahydrofuran-3-yl)carbamate (15.36 g, 76 mmol), phthalimide (13.34 g, 91 mmol), and triphenylphosphine (23.8 g, 91 mmol) was stirred in THF (378 mL, 0.2 M) at 0° C. for 10 minutes before dropwise addition of DIAD (18.34 g, 91 mmol) over 20 minutes. The reaction was stirred about 40 minutes at 0° C. The solvent was removed under reduced pressure, and the crude oil was treated with less than 50 mL of diethyl ether and sonicated. A white precipitate was formed. The solid was isolated by filtration, washed with small amounts of ether, and dried to yield 10.62 g of white solid. The cooled-down filtrate was refiltered to yield additional 2.54 g of white solid for a total yield of 13.16 g of tert-butyl ((3R,4S)-4-(1,3-dioxoisoindolin-2-yl)tetrahydrofuran-3-yl)carbamate.

Step 3: Synthesis of tert-butyl ((3R,4S)-4-aminotetrahydrofuran-3-yl)carbamate Tert-butyl ((3R,4S)-4-(1,3-dioxoisoindolin-2-yl)tetrahydrofuran-3-yl)carbamate (13.08 g, 39.4 mmol) was dissolved into ethanol (98 mL, 0.4 M)). Hydrazine monohydrate (1.97 g, 39.4 mmol) was added, and the reaction was stirred 30 minutes at 50° C. and then 2 hours at 75° C. The reaction was then cooled to room temperature and the white solid was removed by filtration. The filtrate was concentrated down and dried, then treated with ethanol (about 15 mL). Additional white solid was removed by filtration, then filtrate was concentrated down and dried to yield tert-butyl ((3R,4S)-4-aminotetrahydrofuran-3-yl)carbamate as a thick, clear oil (8.724 g at 90% purity; 99%).

Synthesis of (3S,4S)-4-azidotetrahydro-2H-pyran-3-amine

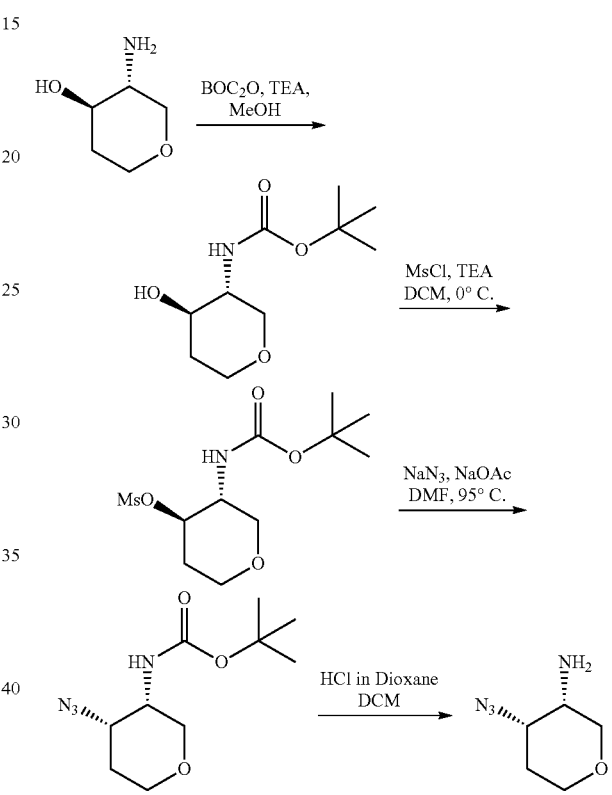

Step 1: Synthesis of (3R,4R)-4-hydroxytetrahydro-2H-pyran-3-yl)carbamate

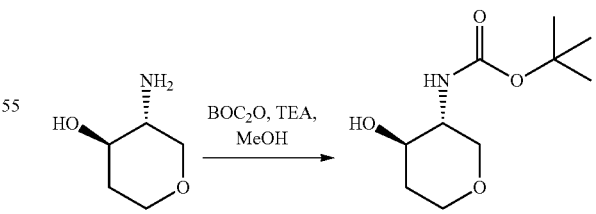

(3R,4R)-3-(((S)-1-phenylethyl)amino)tetrahydro-2H-pyran-4-ol (2.0 g, 9.04 mmol) was taken up in methanol (10 ml) followed by addition of Et$_3$N (1.260 ml, 9.04 mmol) and BOC-anhydride (2.308 ml, 9.94 mmol). The reaction mixture was stirred at room temperature overnight. The solvents were then removed in vacuo and the residue was taken up in DCM (10 ml) and hexane (20 ml) and heated to 80° C. until the solvent level was reduced by half. The reaction mixture was removed from heat and cooled to room temperature while stirring. 5 ml of ether was then added and the reaction was stirred at room temperature for 2 hours. The reaction mixture was filtered to remove the solids, washed with ether and dried to afford tert-butyl ((3R,4R)-4-hydroxytetrahydro-2H-pyran-3-yl)carbamate (1.6 g, 7.36 mmol, 81% yield) as a white solid.

Step 2: Synthesis of (3R,4R)-3-((tert-butoxycarbonyl)amino)tetrahydro-2H-pyran-4-yl methanesulfonate

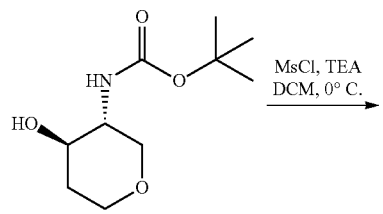

Tert-butyl ((3R,4R)-4-hydroxytetrahydro-2H-pyran-3-yl)carbamate (1.6 g, 7.36 mmol) was taken up in CH$_2$Cl$_2$ (20 ml) and cooled to 0° C. followed by addition of Et$_3$N (1.232 ml, 8.84 mmol). After 5 minutes methanesulfonyl chloride (0.631 ml, 8.10 mmol) in DCM (5 ml) was added dropwise. The reaction mixture was stirred at 0° C. for 30 minutes and allowed to warm to ambient temperature while stirring for 2 hours. The reaction mixture was diluted with water and DCM and the layers were separated. The organic layers were combined and washed with water twice, dried over Na$_2$SO$_4$, and the solvent removed in vacuo. The residue was dried under high vacuum overnight to afford recovered (3R,4R)-3-((tert-butoxycarbonyl)amino)tetrahydro-2H-pyran-4-yl methanesulfonate (2.2 g, 7.45 mmol, 100% yield) as a white solid.

Step 3: Synthesis of tert-butyl ((3S,4S)-4-azidotetrahydro-2H-pyran-3-yl)carbamate

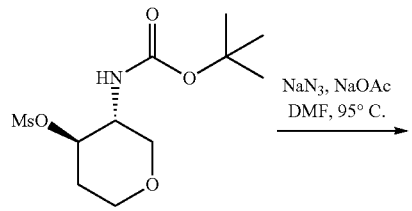

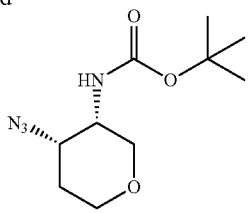

(3R,4R)-3-((tert-butoxycarbonyl)amino)tetrahydro-2H-pyran-4-yl methanesulfonate (2.2 g, 7.45 mmol), sodium azide (0.968 g, 14.90 mmol) and sodium acetate (1.222 g, 14.90 mmol) were taken up in DMF (15 ml). The reaction mixture was heated to 95° C. overnight. The reaction mixture was removed from heat and 20 ml of water was added and stirred while cooling. The reaction mixture was extracted with EtOAc. The organic layers were combined and washed with water. The organics were dried and solvent removed to give tert-butyl ((3S,4S)-4-azidotetrahydro-2H-pyran-3-yl)carbamate (1.8 g, 7.43 mmol, 100% yield) as a yellow oil. MS (ES+) C$_{10}$H$_{18}$N$_4$O$_3$ requires: 242, found: 265 [M+Na]+.

Step 4: Synthesis of (3S,4S)-4-azidotetrahydro-2H-pyran-3-amine

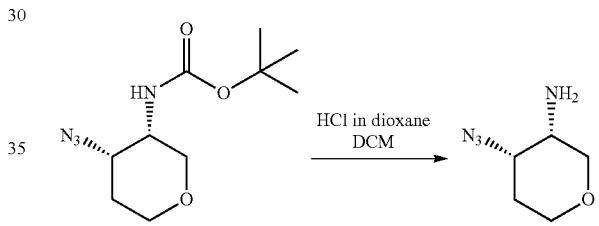

Tert-butyl ((3S,4S)-4-azidotetrahydro-2H-pyran-3-yl)carbamate (1.5 g, 6.19 mmol) was taken up in DCM (5 ml) and 4N HCl dioxane (4.64 ml, 18.57 mmol) added. The reaction mixture was stirred at room temperature for 2 hours. The solvent was removed to give (3S,4S)-4-azidotetrahydro-2H-pyran-3-amine (1.1 g, 6.16 mmol, 99% yield) as an HCl salt. MS (ES+) C$_5$H$_{10}$N$_4$O requires: 142, found: 143 [M+H]+.

Synthesis of 2-(trimethylsilyl)ethyl (1S,2R,3S,5S)-2-aminobicyclo[3.1.0]hexan-3-ylcarbamate

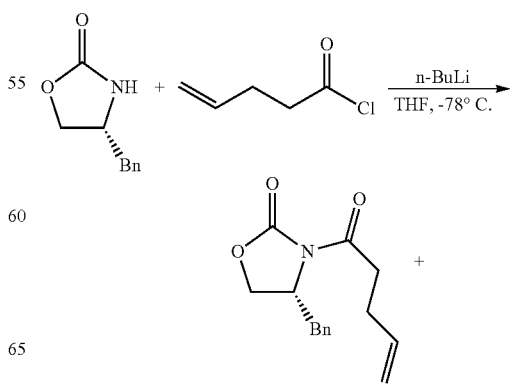

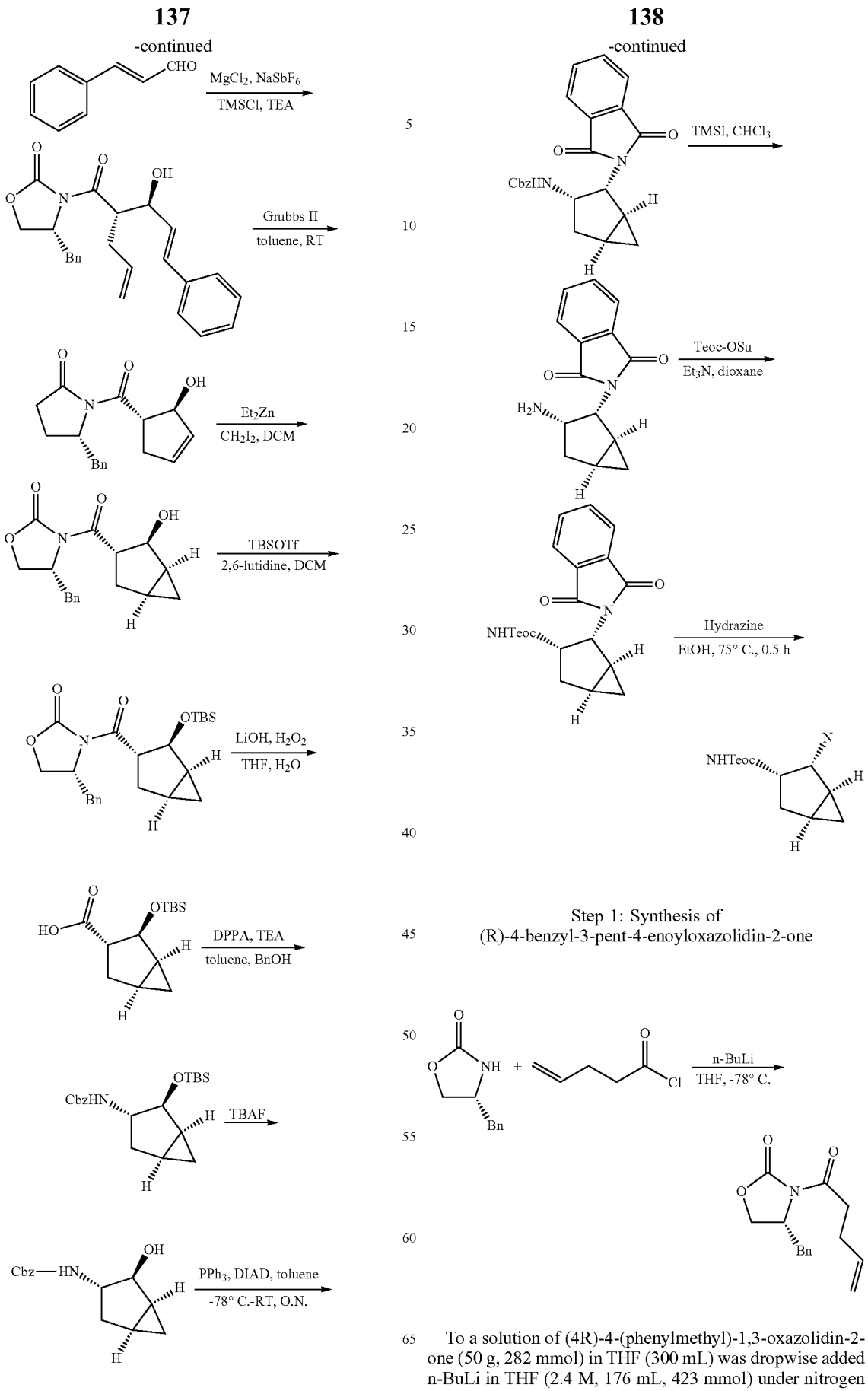
Step 1: Synthesis of
(R)-4-benzyl-3-pent-4-enoyloxazolidin-2-one
To a solution of (4R)-4-(phenylmethyl)-1,3-oxazolidin-2-one (50 g, 282 mmol) in THF (300 mL) was dropwise added n-BuLi in THF (2.4 M, 176 mL, 423 mmol) under nitrogen at −78° C., and the resulting mixture was stirred at −78° C. for 1 hour. Then 4-pentenoyl chloride (49 mL, 423 mmol) was dropwise added. After stirring at −78° C. for another 1 hour, the reaction mixture was allowed to warm up to room temperature and stirred overnight. After diluting with water, the mixture was extracted with ethyl acetate (2×400 mL). The combined ethyl acetate extracts were washed with brine, dried over sodium sulfate, filtered and concentrated under reduced pressure. The crude residue was purified by silica gel column chromatography (ethyl acetate:petroleum ether=1:10) to afford the title compound (68 g, 93%) as a light yellow oil. MS (ES+) $C_{15}H_{17}NO_3$ requires: 259, found: 260 [M+H]⁺.

Step 2: Synthesis of (R)-3-((2S,3S,E)-2-allyl-3-hydroxy-5-phenylpent-4-enoyl)-4-benzyloxazolidin-2-one

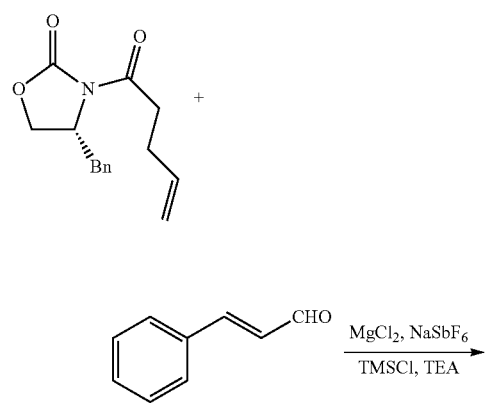

A mixture of (R)-4-benzyl-3-pent-4-enoyloxazolidin-2-one (50 g, 193 mmol), magnesium chloride (18.3 g, 193 mmol), sodium hexafluorostibate(V) (14.9 g, 58 mmol), triethylamine (80 mL, 579 mmol), (trans)-cinnamaldehyde (30.6 g, 232 mmol) and chlorotrimethylsilane (37.2 mL, 290 mmol) in ethyl acetate (500 mL) was stirred at room temperature for 17 hours. The mixture was diluted with ethyl acetate and filtered to remove solids. The filtrate was concentrated to small volume, and then diluted with methanol (500 mL) and a small amount of ethyl acetate. After treatment with trifluoroacetic acid (3 mL), the resulting solution was stirred at room temperature for 1 h, and then concentrated to dryness under reduced pressure. The residue was purified by silica gel column chromatography (ethyl acetate:petroleum ether=1:10) to afford the title compound (60 g, 80%) as a yellow semi-solid. MS (ES+) $C_{24}H_{25}NO_4$ requires: 391, found: 374 [M+H−H$_2$O]⁺.

Step 3: Synthesis of (S)-5-benzyl-1-((1S,2S)-2-hydroxycyclopent-3-enecarbonyl)pyrrolidin-2-one

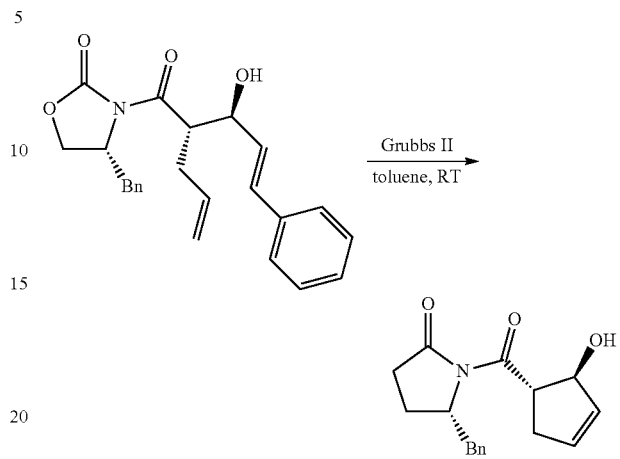

A solution of (R)-3-((2S,3S,E)-2-allyl-3-hydroxy-5-phenylpent-4-enoyl)-4-benzyloxazolidin-2-one (50 g, 128 mmol) and Grubbs 2$^{nd}$ generation catalyst (5.4 g, 6.4 mmol) in toluene (300 mL) was degassed with nitrogen three times, and stirred at room temperature overnight. The reaction mixture was then concentrated to dryness under reduced pressure, and the residue was purified by silica gel column chromatography (ethyl acetate:petroleum ether=1:4) to afford the title compound (32 g, 87%) as a dark brown oil, which solidified upon standing. MS (ES+) $C_{17}H_{19}NO_3$ requires: 285, found: 270 [M+H−H$_2$O]⁺.

Step 4: Synthesis of (R)-4-benzyl-3-((1S,2S,3S,5S)-2-hydroxybicyclo[3.1.0]hexane-3-carbonyl)oxazolidin-2-one

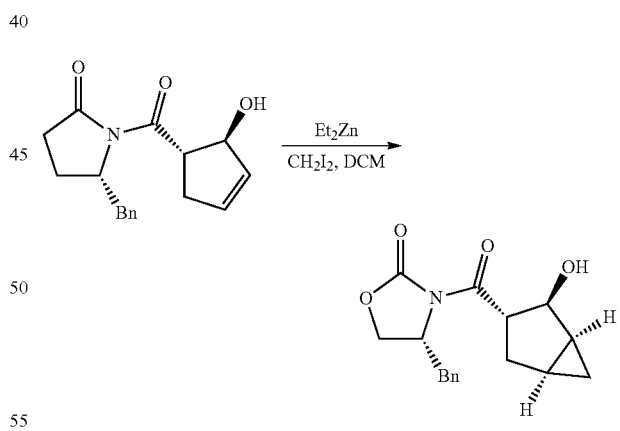

A solution of (S)-5-benzyl-1-((1S,2S)-2-hydroxycyclopent-3-enecarbonyl)pyrrolidin-2-one (25 g, 87.1 mmol) in dichloromethane (300 mL) was cooled in an ice bath and treated with 1 M diethylzinc in hexane (435 mL, 435 mmol) by dropwise addition. After stirring at 0° C. for 20 minutes, diiodomethane (69.6 mL, 871 mmol) was added dropwise. The resulting cloudy solution was stirred at 0° C. for another 20 minutes, and then allowed to warm up to room temperature. After stirring for 6 hours at room temperature, the reaction mixture was quenched with saturated aqueous ammonium chloride and extracted with ethyl acetate. The combined organic extracts were washed with brine, dried over sodium sulfate, filtered and concentrated to dryness under reduced pressure. The crude material was purified by silica gel column chromatography (ethyl acetate:petroleum ether=1:4) to afford the title compound (308 mg, 89%) as a light brown viscous oil. MS (ES+) $C_{17}H_{19}NO_4$ requires: 301, found: 284 [M+H–$H_2O$]$^+$.

Step 5: Synthesis of (R)-4-benzyl-3-((1S,2S,3S,5S)-2-(tert-butyldimethylsilyloxy)-bicyclo[3.1.0]hexane-3-carbonyl)oxazolidin-2-one

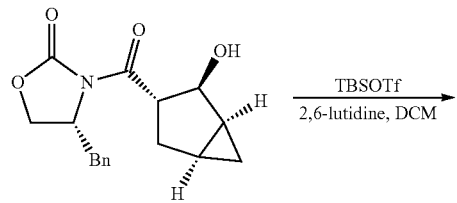

To a stirred solution of (R)-4-benzyl-3-((1S,2S,3S,5S)-2-hydroxybicyclo[3.1.0]hexane-3-carbonyl)oxazolidin-2-one (25 g, 83 mmol) and 2,6-lutidine (38.2 mL, 332 mmol) in dichloromethane (300 mL) was added tert-butyldimethylsilyl trifluoromethanesulfonate (47.6 mL, 207.5 mmol) at 0° C. under nitrogen. The resulting mixture was stirred at 0° C. for 30 minutes and then room temperature for 1 hour. After diluted with methanol (25 mL), the mixture was poured into water and extracted with ether (2×400 mL). The combined ether extracts were washed with brine, dried over sodium sulfate, filtered, concentrated and purified by silica gel column chromatography (ethyl acetate:petroleum ether=1:8) to afford the title compound (29 g, 86%) as a colorless oil. MS (ES+) $C_{23}H_{33}NO_4Si$ requires: 415, found: 416 [M+H–$H_2O$]$^+$.

Step 6: Synthesis of (1S,2S,3S,5S)-2-(tert-butyldimethylsilyloxy)bicyclo[3.1.0]hexane-3-carboxylic acid

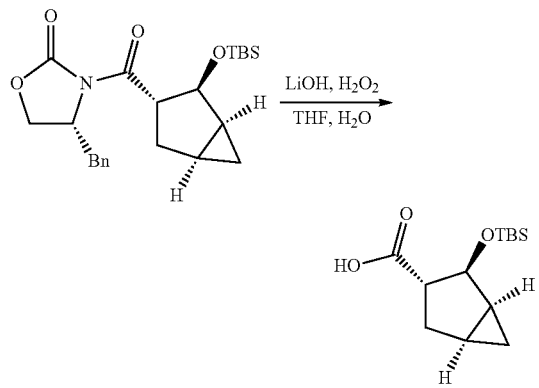

To a solution of (R)-4-benzyl-3-((1S,2S,3S,5S)-2-(tert-butyldimethylsilyloxy)bicyclo[3.1.0]hexane-3-carbonyl)oxazolidin-2-one (40 g, 96.4 mmol) in THF (200 mL) and water (50 mL) was added 30% aqueous hydrogen peroxide (88 mL, 771 mmol) dropwise at 0° C., followed by the addition of a solution of lithium hydroxide monohydrate (16 g, 386 mmol) in water (100 mL). After stirring for 1 hour at 0° C., the reaction mixture was stirred at room temperature overnight. The excess hydrogen peroxide was completely consumed by the addition of saturated aqueous sodium bisulfate. The mixture was then adjusted to pH=14 with 1 N NaOH and washed with ether (400 mL). The aqueous layer was then acidified to pH=3 with 1 M aqueous potassium hydrogen sulfate, and extracted with ethyl acetate (3×400 mL). The combined organic extracts were washed with brine, dried over sodium sulfate, filtered and concentrated to afford the title compound (22 g, 88%) as a colorless oil.

Step 7: Synthesis of benzyl (1S,2S,3S,5S)-2-(tert-butyldimethylsilyloxy)bicyclo[3.1.0]hexan-3-ylcarbamate

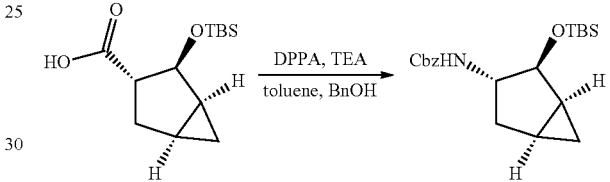

To a solution of (1S,2S,3S,5S)-2-(tert-butyldimethylsilyloxy)bicyclo[3.1.0]hexane-3-carboxylic acid (4 g, 15.625 mmol), triethylamine (22 mL, 156 mmol) and benzyl alcohol (17 mL, 156 mmol) in toluene (50 mL) at room temperature was added diphenyl phosphoryl azide (33.7 mL, 156 mmol) dropwise, and the resulting mixture was stirred at 100° C. overnight. The reaction solution was cooled to room temperature, diluted with ethyl acetate (100 mL) and washed with water (3×50 mL) and brine (50 mL). The organic layer was dried over sodium sulfate, filtered and concentrated to afford a crude product, which was purified by silica gel column chromatography (ethyl acetate:petroleum ether=1:8) to afford the title compound (3.0 g, 54%) as a white solid. MS (ES+) $C_{20}H_{31}NO_3Si$ requires: 361, found: 362 [M+H]$^+$.

Step 8: Synthesis of benzyl (1S,2S,3S,5S)-2-hydroxybicyclo[3.1.0]hexan-3-ylcarbamate

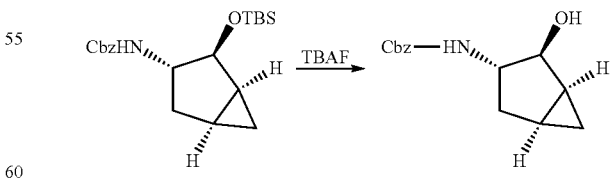

To a solution of benzyl (1S,2S,3S,5S)-2-(tert-butyldimethylsilyloxy)bicyclo[3.1.0]hexan-3-ylcarbamate (2.0 g, 5.540 mmol) in THF (20) at room temperature was added 1 M tetrabutylammonium fluoride in THF (55 mL, 55.4 mmol), and the mixture was stirred at room temperature overnight. The reaction solution was diluted with ethyl acetate (100 mL), and washed with water (3×50 mL) and brine (50 mL). The organic layer was dried over sodium sulfate, filtered and concentrated to afford the title compound (1.2 g, 92%) as a white solid. MS (ES+) $C_{14}H_{17}NO_3$ requires: 247, found: 230 $[M+H-H_2O]^+$.

Step 9: Synthesis of benzyl (1S,2R,3S,5S)-2-(1,3-dioxoisoindolin-2-yl)bicyclo[3.1.0]hexan-3-ylcarbamate

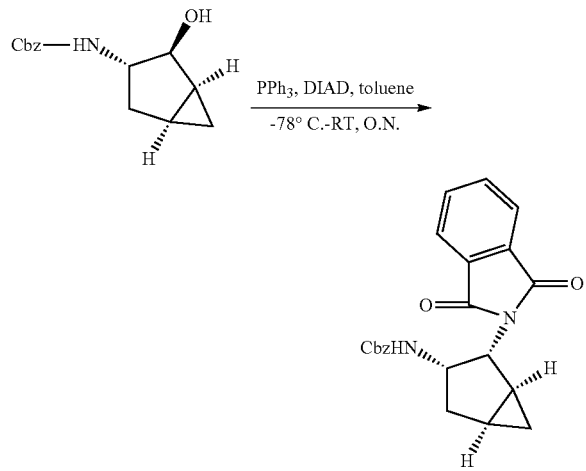

A solution of triphenylphosphine (6.4 g, 24.292 mmol), phthalimide (6.2 g, 42.511 mmol) and benzyl (1S,2S,3S,5S)-2-hydroxybicyclo[3.1.0]hexan-3-ylcarbamate (3.0 g, 12.146 mmol) in toluene (250 mL) was stirred at −78° C. for 30 minutes under nitrogen protection, followed by the addition of diisopropyl azodicarboxylate (8.6 mL, 42.511 mmol) dropwise. The resulting mixture was stirred at −78° C. for another 1 hour and then at room temperature overnight. The reaction mixture was treated with 10 mL of methanol, and the solvents were removed under reduced pressure. The crude material was purified by silica gel column chromatography (ethyl acetate:petroleum ether=1:2) to afford the title compound (3.0 g, 65%) as a light yellow oil. MS (ES+) $C_{22}H_{20}N_2O_4$ requires: 376, found: 399 $[M+23]^+$.

Step 10: Synthesis of 2-((1S,2R,3S,5S)-3-aminobicyclo[3.1.0]hexan-2-yl)isoindoline-1,3-dione

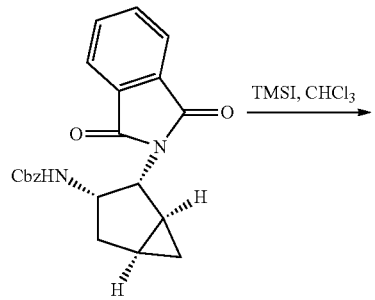

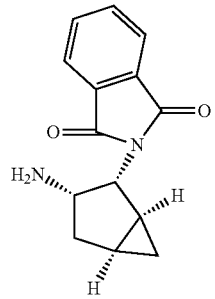

To a solution of benzyl (1S,2R,3S,5S)-2-(1,3-dioxoisoindolin-2-yl)bicyclo[3.1.0]hexan-3-ylcarbamate (4.0 g, 10.638 mmol) in chloroform (30 mL) at room temperature was added trimethylsilyl iodide (14.6 mL, 106.380 mmol) dropwise, and the resulting mixture was stirred at room temperature for 1 hour. The reaction was quenched with methanol (5 mL), diluted with ethyl acetate (150 mL), and washed with water (3×50 mL) and brine (50 mL). The organic layer was dried over sodium sulfate, filtered and concentrated to afford a crude compound, which was directly used in the next reaction without further purification. MS (ES+) $C_{14}H_{14}N_2O_2$ requires: 242, found: 243 $[M+H]^+$.

Step 11: Synthesis of 2-(trimethylsilyl)ethyl (1S,2R,3S,5S)-2-(1,3-dioxoisoindolin-2-yl)bicyclo[3.1.0]hexan-3-ylcarbamate

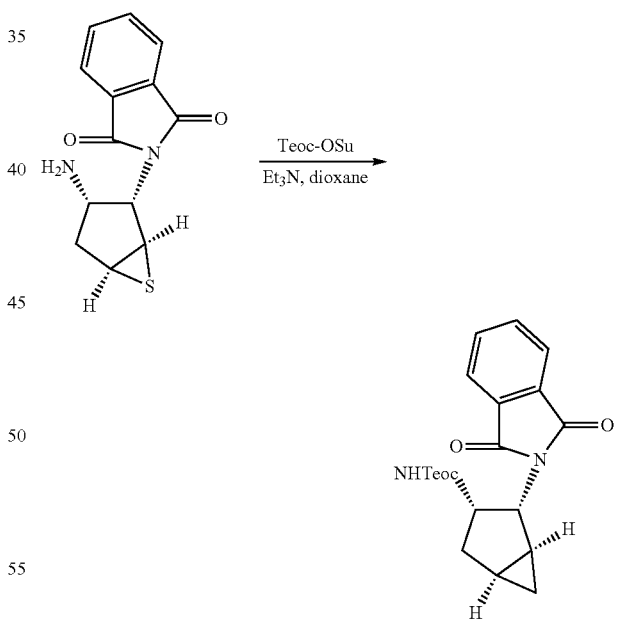

A solution of 2-((1S,2R,3S,5S)-3-aminobicyclo[3.1.0]hexan-2-yl)isoindoline-1,3-dione (2.0 g, 8.264 mmol), 2,5-dioxopyrrolidin-1-yl 2-(trimethylsilyl)ethyl carbonate (3.2 g, 12.396 mmol) and triethylamine (3.4 mL, 24.792 mmol) in dioxane/water (100 mL, v/v=1/1) was stirred at room temperature for 1.5 hours. The reaction mixture was then diluted with ethyl acetate (100 mL), washed by 1 M hydrochloric acid (2×50 mL), saturated sodium bicarbonate solution (2×50 mL) and brine (50 mL). The organic layer was concentrated under reduced pressure, and the residue was purified by silica gel column chromatography (ethyl acetate: petroleum ether=1:4) to afford the title compound (2.5 g, 78%) as a yellow oil. MS (ES+) $C_{20}H_{26}N_2O_4Si$ requires: 386, found: 410 $[M+23]^+$.

Step 12: Synthesis of 2-(trimethylsilyl)ethyl (1S,2R, 3S,5S)-2-aminobicyclo[3.1.0]hexan-3-ylcarbamate

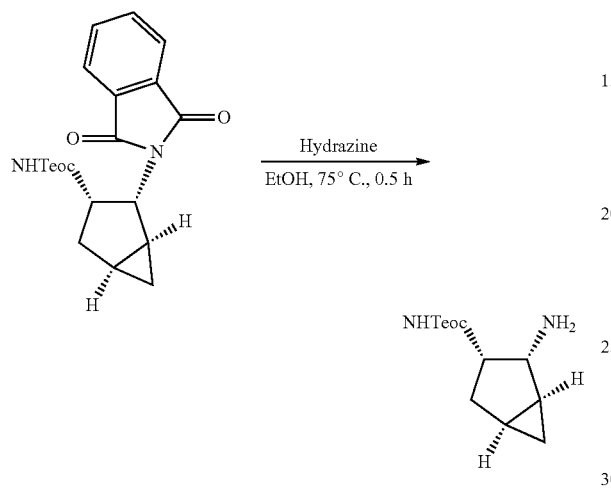

To a solution of 2-(trimethylsilyl)ethyl (1S,2R,3S,5S)-2-(1,3-dioxoisoindolin-2-yl)bicyclo[3.1.0]hexan-3-ylcarbamate (1.5 g, 3.886 mmol) in ethanol (20 mL) at room temperature was added hydrazine (1.9 ml, 38.860 mmol), and the resulting mixture was stirred at 75° C. for 2 hours. The reaction solution was concentrated, and the residue was purified by silica gel column chromatography (ethyl acetate: petroleum ether=1:4) to afford the title compound (800 mg, 80%) as a light yellow semi-solid.

Synthesis of cis-tert-butyl-3-hydroxy-1,1-dioxo-hexahydro-1-thiopyran-4-ylcarbamate

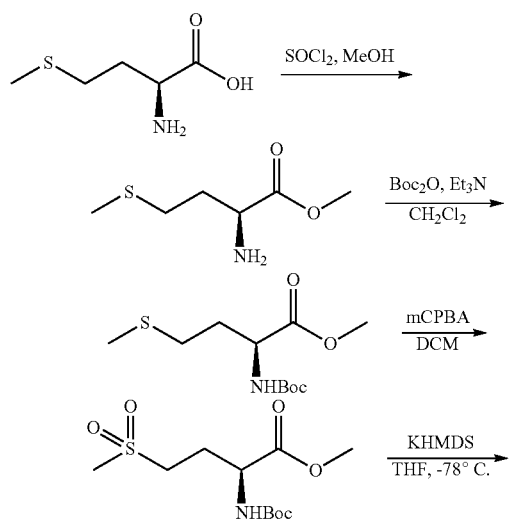

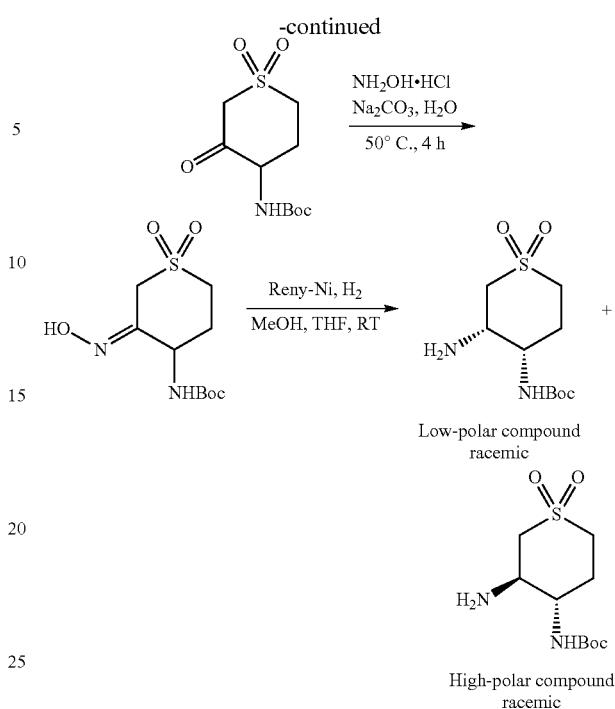

Step 1: Synthesis of (S)-methyl 2-amino-4-(methylthio)butanoate

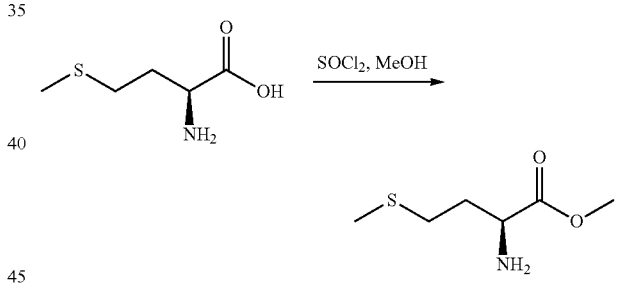

To a flame dried flask under nitrogen was added methanol (60 mL). The stirred solution was cooled to 0° C. before thionyl chloride (7.32 mL, 100.34 mmol) was added dropwise. The solution was stirred at 0° C. for 10 min before methionine (10 g, 33.8 mmol) was added in one portion. The reaction was stirred at room temperature overnight after which time the volatiles were removed under reduced pressure to give the title compound as a yellowish solid.

Step 2: Synthesis of (S)-methyl 2-(tert-butoxycarbonylamino)-4-(methylthio)butanoate -continued

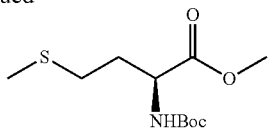

To a solution of (S)-methyl 2-amino-4-(methylthio)butanoate in dichloromethane (300 mL) at 0° C. was added triethylamine (35 mL), followed by the addition of di-tert-butyl dicarbonate (26.98 g, 125 mmol). After stirring at room temperature for 3 h, the reaction mixture was diluted with dichloromethane (200 mL) and washed with water (2*150 mL). The combined organic layers were dried (magnesium sulfate), filtered and concentrated under reduced pressure. The product (Rf=0.5, ethyl acetate:petroleum ether, 1:4) was purified by flash column chromatography to afford the title compound (15 g, 85% yield) as a clear oil.

Step 3: Synthesis of (S)-methyl 2-(tert-butoxycarbonylamino)-4-(methylsulfonyl)butanoate

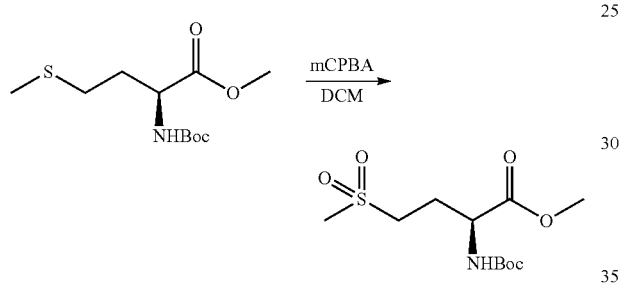

N-(tert-Butoxycarbonyl)-L-methionine methyl ester (8.76 g, 33.3 mmol) was added to a 1000 mL round bottom flask and dissolved in dichloromethane (150 mL). The stirred solution was cooled to 0° C., followed by the addition of 3-chloroperoxybenzoic acid (70%, 18.0 g, 7.32 mmol) in 30 mL of dichloromethane over a period of 5 min. The reaction mixture was stirred at room temperature for 1.5 hours at which time it was diluted with dichloromethane (200 mL) and sodium hydrogen carbonate (300 mL of a saturated aqueous solution). The organic layer was separated, washed successively with sodium hydrogen carbonate (2*300 mL of a saturated aqueous solution), dried (magnesium sulfate), filtered, and concentrated under reduced pressure. The product was purified by flash column chromatography (ethyl acetate:petroleum ether, 6:4) to afford the title compound (5 g, 51% yield) as a yellow solid.

Step 4: Synthesis of tert-butyl (1,1-dioxido-3-oxo-tetrahydro-2H-thiopyran-4-yl)carbamate

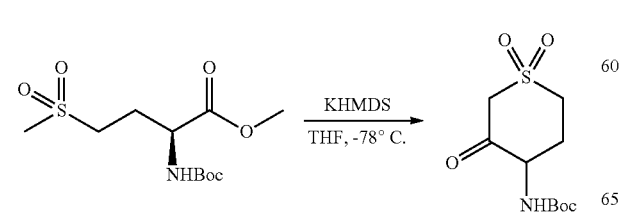

A solution of (S)-methyl 2-(tert-butoxycarbonylamino)-4-(methylsulfonyl)butanoate (2 g, 6.78 mmol) in tetrahydrofuran (50 mL) was cooled to −78° C., to which potassium bis(trimethylsilyl)amide (1.0 M, toluene solution, 15 ml) was added dropwise, and the mixture was stirred at −78° C. for 2 hours and at room temperature for another 2 hours. An aqueous solution of ammonium chloride (1 M) was added, and the mixture was stirred. The reaction mixture was subjected to liquid separation. The resultant organic layer was then washed with water and brine, and dried over anhydrous magnesium sulfate. The solvent was removed under reduced pressure, and the formed solid was collected by filtration to obtain the title compound. The water layer separated previously was extracted twice with ethyl acetate. The resultant organic layers were combined, washed with water and brine, and dried over anhydrous magnesium sulfate. The ethyl acetate extracts were combined, dried and then concentrated under reduced pressure to obtain the title compound. The combined product was purified by flash column chromatography (ethyl acetate:petroleum ether, 3:1) to afford the title compound (55 mg, yield 22%) as a yellow solid.

Step 5: Synthesis of (Z)-tert-butyl (3-(hydroxyimino)-1,1-dioxidotetrahydro-2H-thiopyran-4-yl)carbamate

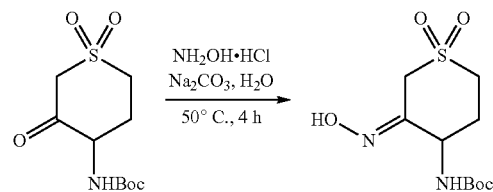 [SMILES: CC(C)(C)OC(=O)NC1CCS(=O)(=O)CC1=O ; CC(C)(C)OC(=O)NC1CCS(=O)(=O)C/C1=N\O]

Hydroxylamine hydrochloride (26 mg, 0.379 mmol) was added to a mixture of compound 5 (50 mg, 0.189 mmol) and sodium carbonate (64 mg, 0.757 mmol) in water (5 mL). After stirred at 50° C. for 4 h, the reaction mixture was cooled to RT and filtered to get the title compound (50 mg, 95% yield) as a white solid. MS (ES+) $C_{10}H_{18}H_2O_5S$ requires: 278, found: 179 [M+H−100]$^+$, 223 [M+H−56]$^+$.

Step 6: Synthesis of cis-tert-butyl-3-hydroxy-1,1-dioxohexahydro-1-thiopyran-4-ylcarbamate

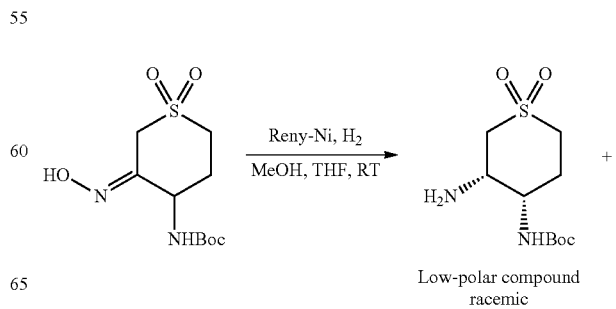

Low-polar compound
racemic

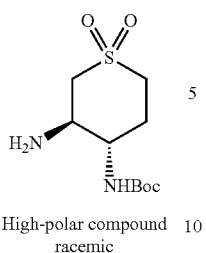

High-polar compound racemic

A mixture of compound (Z)-tert-butyl (3-(hydroxyimino)-1,1-dioxidotetrahydro-2H-thiopyran-4-yl)carbamate (2.5 g, 7.6 mmol) and Raney-Nickel (excessive amount) in methanol (200 mL) and THF (200 mL) was stirred at room temperature under hydrogen balloon for 24 hours. The mixture was filtered, and the filtrate was concentrated. The residue was purified by flash column chromatography (methanol:dichloromethane, 1:2) to afford a low-polar compound racemic mixture (400 mg, 16% yield) and a high-polar compound (600 mg, 25% yield).

Step 7: Synthesis of (3R,4S)-tert-butyl 3-amino-4-(benzyloxycarbonylamino)piperidine-1-carboxylate and (3S,4R)-tert-butyl 3-amino-4-(benzyloxycarbonylamino)piperidine-1-carboxylate

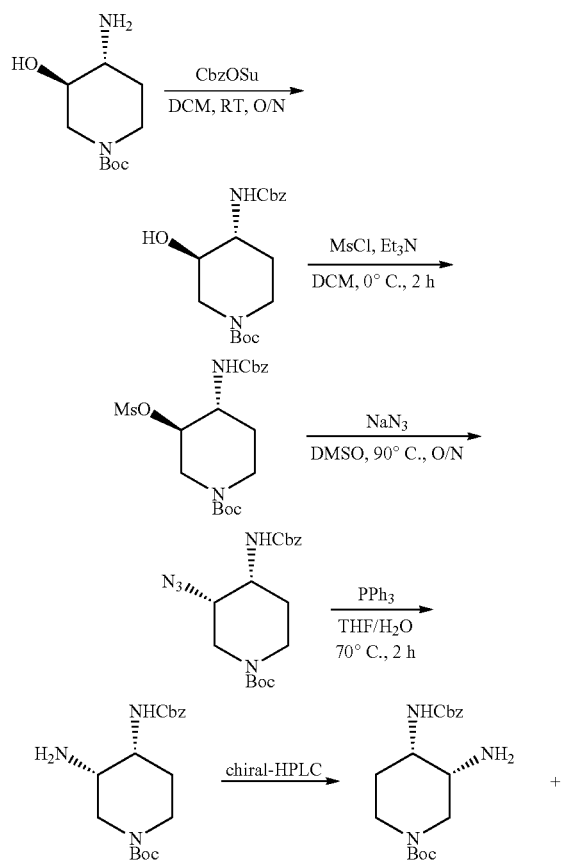

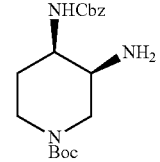

Step 8: Synthesis of trans-tert-butyl 4-(benzyloxycarbonylamino)-3-hydroxypiperidine-1-carboxylate

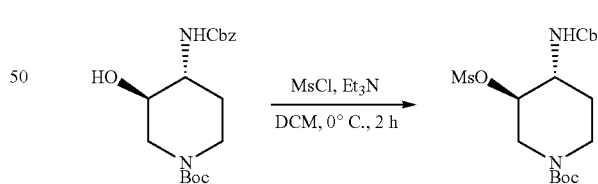

To a stirred mixture of trans-tert-butyl 4-amino-3-hydroxypiperidine-1-carboxylate (1.05 g, 4.86 mmol) in 80 mL of dichloromethane was added triethyl amine (5.89 g, 5.83 mmol), followed by the addition of N-(benzyloxycarbonyloxy)succinimide (1.27 g, 5.10 mmol) at 0° C. The reaction was stirred at room temperature for 16 hours and then diluted with 100 mL of dichloromethane. The solution mixture was washed with 5% citric acid solution (2×100 mL), 5% potassium carbonate solution (2×100 mL) and brine (200 mL). The organic layer was dried over anhydrous sodium sulfate and filtered, followed by concentration under reduced pressure. The resultant oily matter was purified by silica gel column chromatography (ethyl acetate: petroleum ether=1:4~1:2) to afford the title compound (1.7 g, ~100%, crude) as a colorless oil. MS (ES+) $C_{18}H_{26}N_2O_5$ requires: 350, found: 251 [M+H−100]$^+$.

Step 9: Synthesis of trans-tert-butyl 4-(benzyloxycarbonylamino)-3-(methylsulfonyloxy)-piperidine-1-carboxylate To a solution of trans-tert-butyl 4-(benzyloxycarbonylamino)-3-hydroxypiperidine-1-carboxylate (5.0 g, 14.3 mmol) and triethylamine (4.5 g, 43.0 mmol) in dichloromethane (100 mL) was added methanesulfonyl chloride (4.9 g, 43.0 mmol) at 0° C., and the mixture was stirred at 0° C. for 2 hours. The solution was washed with water (150 mL×3) and brine, dried over anhydrous sodium sulfate and filtered, followed by concentration under reduced pressure to give the title compound (6.0 g, crude) as a yellow oil. MS (ES+) $C_{19}H_{28}H_2O_7S$ requires: 428, found: 329 [M+H−100]$^+$.

Step 10: Synthesis of trans-tert-butyl 3-azido-4-(benzyloxycarbonylamino)piperidine-1-carboxylate

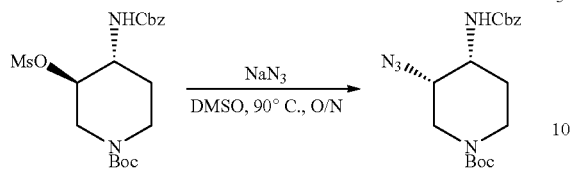

To a solution of trans-tert-butyl 4-(benzyloxycarbonylamino)-3-(methylsulfonyloxy)piperidine-1-carboxylate (6.0 g, 14 mmol) in dimethyl sulfoxide (40 mL) was added sodium azide (9.11 g, 140 mmol), and the reaction mixture was stirred at 90° C. overnight under $N_2$. The solution mixture was cooled to ~30° C., diluted with ethyl acetate (~300 mL), and washed with water (700 mL×3) and brine. The organic layer was dried over anhydrous sodium sulfate, filtered and concentrated to the title compound (3.8 g, 72%) as a yellow oil. MS (ES+) $C_{18}H_{25}N_5O_4$ requires: 375, found: 276 $[M+H-100]^+$, 373 $[M+Na]^+$.

Step 11: Synthesis of (3R,4S)-tert-butyl 3-amino-4-(benzyloxycarbonylamino)piperidine-1-carboxylate and (3S,4R)-tert-butyl 3-amino-4-(benzyloxycarbonylamino)piperidine-1-carboxylate

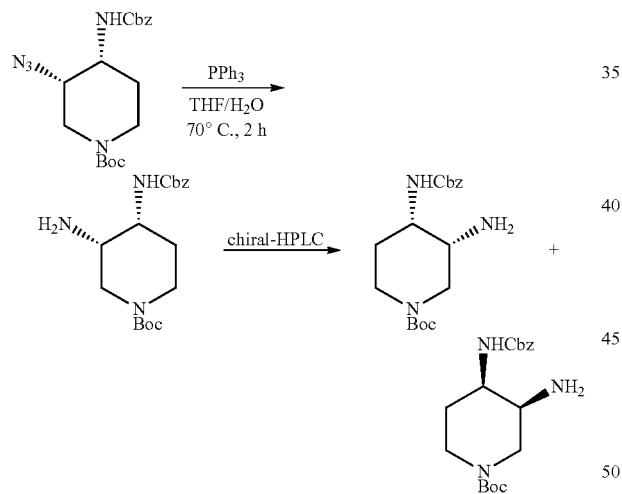

A mixture of crude trans-tert-butyl 3-azido-4-(benzyloxycarbonylamino)piperidine-1-carboxylate (12 g, ~32 mmol) and triphenylphosphine (41.9 g, 160 mmol) in THF (100 mL) and water (5 mL) was stirred at 70° C. for 2 hours. The reaction mixture was cooled to room temperature and diluted with ethyl acetate (500 mL). The organic layer was washed with brine (50 mL) and directly evaporated under reduced pressure. The residue was purified by silica gel column chromatography (petroleum ether/ethyl acetate=4/1~1:1) to afford trans-tert-butyl 3-amino-4-(benzyloxycarbonylamino)piperidine-1-carboxylate (5.0 g, 44%) as a yellow oil. MS (ES+) $C_{18}H_{27}N_3O_4$ requires: 349, found: 350 $[M+H]^+$.

2 g of the above racemic sample was separated by Chiral-HPLC to afford (3R,4S)-tert-butyl 3-amino-4-(benzyloxycarbonylamino)piperidine-1-carboxylate (550 mg, peak 1 in chiral-HPLC) and (3S,4R)-tert-butyl 3-amino-4-(benzyloxycarbonylamino)piperidine-1-carboxylate (620 mg, peak 2 in chiral-HPLC).

Synthesis of cis-tert-butyl-4-amino-3-(((2-(trimethylsilyl)ethoxy)carbonyl)amino)piperidine-1-carboxylate

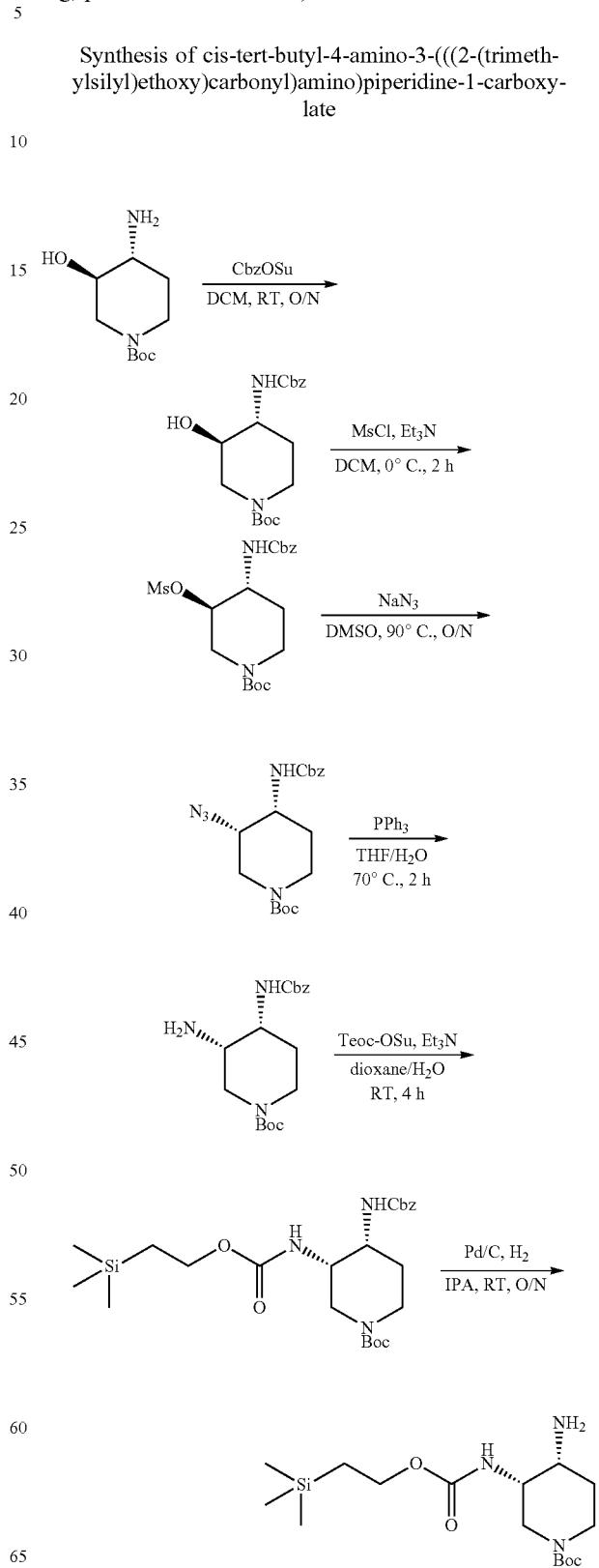

Step 1: Synthesis of trans-tert-butyl 4-(benzyloxycarbonylamino)-3-hydroxypiperidine-1-carboxylate

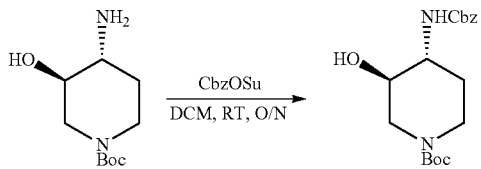 [SMILES: CC(C)(C)OC(=O)N1CC[C@@H](N)[C@H](O)C1 ; CC(C)(C)OC(=O)N1CC[C@@H](NC(=O)OCc2ccccc2)[C@H](O)C1]

To a stirred mixture of trans-tert-butyl 4-amino-3-hydroxypiperidine-1-carboxylate (1.05 g, 4.86 mmol) in 80 mL of dichloromethane was added triethylamine (5.89 g, 5.83 mmol), followed by the addition of N-(benzyloxycarbonyloxy)succinimide (1.27 g, 5.10 mmol) at 0° C. The reaction mixture was stirred at room temperature for 16 hours and then diluted with 100 mL of dichloromethane. The solution mixture was washed with 5% citric acid solution (2×100 mL), 5% potassium carbonate solution (2×100 mL) and brine (200 mL). The organic layer was dried over anhydrous sodium sulfate and filtered, followed by concentration under reduced pressure. The resultant oily matter was purified by silica gel column chromatography (ethyl acetate: petroleum ether=1:4~1:2) to afford the title compound (1.7 g, ~100%, crude) as a colorless oil. MS (ES+) $C_{18}H_{26}N_2O_5$ requires: 350, found: 251 [M+H−100]$^+$.

Step 2: Synthesis of trans-tert-butyl 4-(benzyloxycarbonylamino)-3-(methylsulfonyloxy)piperidine-1-carboxylate

To a solution of trans-tert-butyl 4-(benzyloxycarbonylamino)-3-hydroxypiperidine-1-carboxylate (5.0 g, 14.3 mmol) and triethylamine (4.5 g, 43.0 mmol) in dichloromethane (100 mL) was added methanesulfonyl chloride (4.9 g, 43.0 mmol) at 0° C., and the mixture was stirred at 0° C. for 2 hours. The solution was washed with water (150 mL×3) and brine, dried over anhydrous sodium sulfate and filtered, followed by concentration under reduced pressure to give the title compound (6.0 g, crude) as a yellow oil. MS (ES+) $C_{19}H_{28}N_2O_7S$ requires: 428, found: 329 [M+H−100]$^+$.

Step 3: Synthesis of cis-tert-butyl 3-azido-4-(benzyloxycarbonylamino)piperidine-1-carboxylate

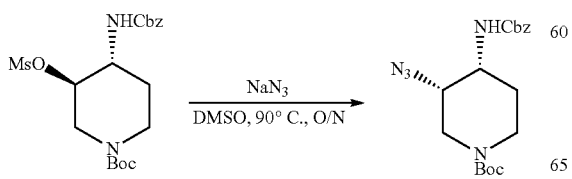

To a solution of trans-tert-butyl 4-(benzyloxycarbonylamino)-3-(methylsulfonyloxy)piperidine-1-carboxylate (6.0 g, 14 mmol) in dimethyl sulfoxide (40 mL) was added sodium azide (9.11 g, 140 mmol), and the reaction mixture was stirred at 90° C. overnight under $N_2$. The solution mixture was cooled to ~30° C., diluted with ethyl acetate (~300 mL), and washed with water (700 mL×3) and brine. The organic layer was dried over anhydrous sodium sulfate, filtered and concentrated to the title compound (3.8 g, 72%) as a yellow oil. MS (ES+) $C_{18}H_{25}N_5O_4$ requires: 375, found: 276 [M+H−100]$^+$, 373 [M+Na]$^+$.

Step 4: Synthesis of cis-tert-butyl 3-amino-4-(benzyloxycarbonylamino)piperidine-1-carboxylate and (3S,4R)-tert-butyl 3-amino-4-(benzyloxycarbonylamino)piperidine-1-carboxylate

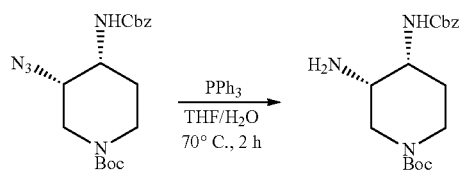 [SMILES: CC(C)(C)OC(=O)N1CC[C@@H](NC(=O)OCc2ccccc2)[C@@H](N=[N+]=[N-])C1 ; CC(C)(C)OC(=O)N1CC[C@@H](NC(=O)OCc2ccccc2)[C@@H](N)C1 ; "PPh3"]

A mixture of crude cis-tert-butyl 3-azido-4-(benzyloxycarbonylamino)piperidine-1-carboxylate (12 g, ~32 mmol) and triphenylphosphine (41.9 g, 160 mmol) in THF (100 mL) and water (5 mL) was stirred at 70° C. for 2 hours. The reaction mixture was cooled to room temperature and diluted with ethyl acetate (500 mL). The organic layer was washed with brine (50 mL) and directly evaporated under reduced pressure. The residue was purified by silica gel column chromatography (petroleum ether/ethyl acetate=4/1~1:1) to afford the title compound (racemate, 5.0 g, 44%) as a yellow oil. MS (ES+) $C_{18}H_{27}N_3O_4$ requires: 349, found: 350 [M+H]$^+$.

Step 5: Synthesis of cis-tert-butyl 4-(benzyloxycarbonylamino)-3-((2-(trimethylsilyl)ethoxy)-carbonylamino)piperidine-1-carboxylate

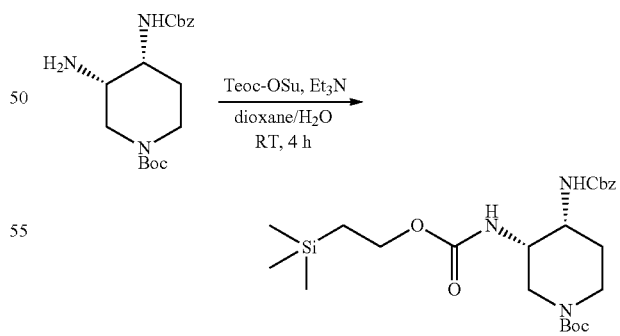

A solution of cis-tert-butyl 3-amino-4-(benzyloxycarbonylamino)piperidine-1-carboxylate (3.0 g, 8.6 mmol), 2,5-dioxopyrrolidin-1-yl 2-(trimethylsilyl)ethyl carbonate (2.5 g, 9.5 mmol) and triethylamine in dioxane/water (40 mL, v/v=1/1) was stirred at room temperature for 4 hours. After that, the solution was diluted with ethyl acetate (200 mL), and washed by 1 M hydrochloric acid (50 mL), saturated sodium bicarbonate solution (50 mL) and brine (50 mL). The organic layer was dried over sodium sulfate, filtered and concentrated. The residue was purified by silica gel column chromatography (petroleum ether/ethyl acetate=4/1) to afford the title compound (3.5 g, 83%) as a white solid. MS (ES+) $C_{24}H_{39}N_3O_6Si$ requires: 493, found: 516 $[M+23]^+$.

Step 6: Synthesis of cis-tert-butyl 4-amino-3-((2-(trimethylsilyl)ethoxy)-carbonylamino)piperidine-1-carboxylate

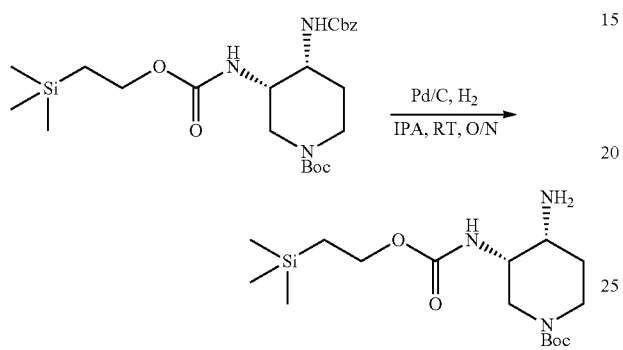

A mixture of cis-tert-butyl 4-(benzyloxycarbonylamino)-3-((2-(trimethylsilyl)ethoxy)carbonylamino)piperidine-1-carboxylate (1.8 g, 3.6 mmol) and 10% palladium on carbon (180 mg) in isopropanol (60 mL) was stirred under 1 atm hydrogen atmosphere (hydrogen balloon) at room temperature for 3 hours. After that, the mixture was filtered through a pad of celite. The filtrate was concentrated and purified by silica gel column chromatography (methanol/dichloromethane=1/30 to 1/10) to afford the title compound (800 mg, 61%) as a yellow oil. MS (ES+) $C_{16}H_{33}N_3O_4Si$ requires: 359, found: 360 $[M+H]^+$.

Synthesis of Racemate-ethyl 4-amino-3-(tert-butoxycarbonylamino)cyclohexanecarboxylate

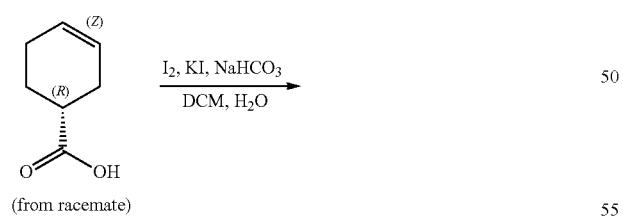

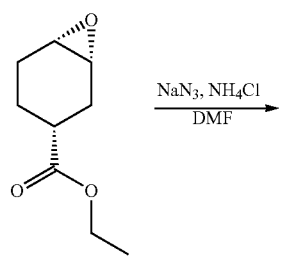

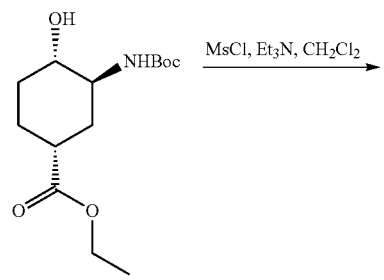

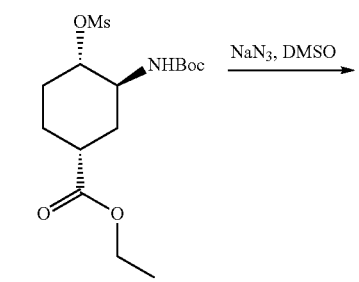

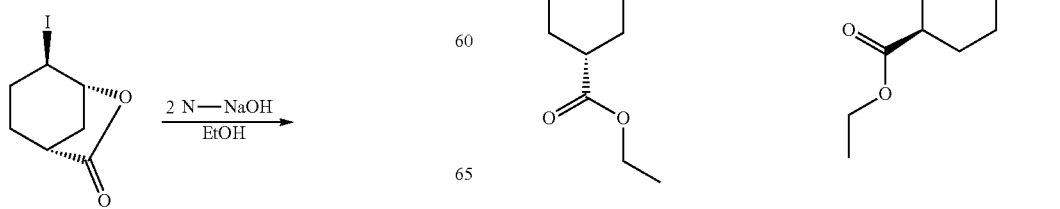

Step 1: Synthesis of Racemate-4-iodo-6-oxa-bicyclo[3.2.1]octan-7-one

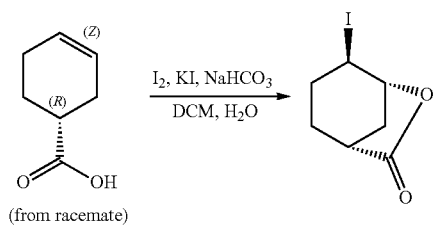

(from racemate)

To a mixture of cyclohex-3-enecarboxylic acid (racemate, 42.0 g, 333 mmol), potassium iodide (72.0 g, 433 mmol) and sodium hydrogencarbonate (36.4 g, 433 mmol) in methylene chloride (750 mL) and water (750 mL) was added iodine (110.0 g, 433 mmol) at an internal temperature of 5° C., and the reaction mixture was stirred at room temperature for 3 hours. After quenched with 1 N aqueous sodium thiosulfate (1500 mL), the resulting mixture was extracted with methylene chloride (1000 mL×2). The combined organic layers were washed with aqueous sodium hydrogencarbonate (1000 mL), water (2000 mL) and brine (1000 mL), dried over anhydrous magnesium sulfate, filtered, then concentrated under reduced pressure. The precipitated crystals were collected by filtration and washed with hexane, followed by drying, to thereby give the title compound (80.2 g, 95%) as a white solid.

Step 2: Synthesis of Racemate-ethyl 7-oxa-bicyclo[4.1.0]heptane-3-carboxylate

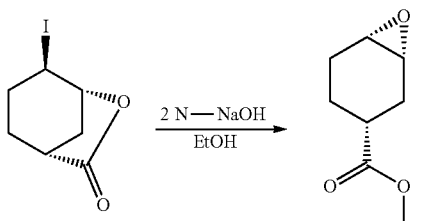

To a suspension of Racemate-4-iodo-6-oxa-bicyclo[3.2.1]octan-7-one (45.0 g, 180 mmol) in ethanol (400 mL) was added 2 N aqueous sodium hydroxide (110 mL, 220 mmol) at room temperature while being stirred, and the resulting mixture was stirred for 3 hours. The reaction mixture was concentrated in a bath at a temperature of 35° C. under reduced pressure. Water (500 mL) was added to the resultant oily matter, and the resulting mixture was extracted with ethyl acetate (500 mL). The organic layer was washed with water (500 mL), dried over anhydrous sodium sulfate, filtered and followed by concentration under reduced pressure. The resultant oily matter was purified by silica gel column chromatography (ethyl acetate:petroleum ether=1:10~1:5), to thereby give the tile compound (15.9 g, 52%) as a pale yellow oil.

Step 3: Synthesis of Racemate-ethyl 3-azido-4-hydroxycyclohexanecarboxylate

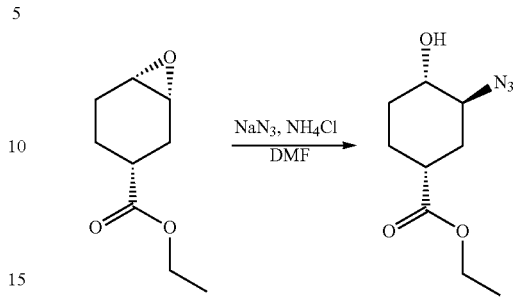

A mixture of Racemate-ethyl 7-oxa-bicyclo[4.1.0]heptane-3-carboxylate (24.0 g, 140 mmol), ammonium chloride (13.6 g, 210 mmol) and sodium azide (13.7 g, 210 mmol) in N,N-dimethylformamide (120 mL) was stirred at 76° C. for 13 hours. After any insoluble matter was collected by filtration, the filtrate was concentrated under reduced pressure while not allowing the solvent to evaporate to dryness. The residue was combined with the solid matter collected by the previous filtration, and the thus-obtained mixture was dissolved in water (500 mL). The solution was extracted with ethyl acetate (500 mL). The extract was washed with water (500 mL×5) and saturated brine, dried over anhydrous sodium sulfate, filtered and concentrated to afford the tile compound (28 g, crude) as an yellow oil. MS (ES+) $C_9H_{15}N_3O_3$ requires: 213, found: 214 $[M+H]^+$, 236 $[M+Na]^+$.

Step 4: Synthesis of Racemate-ethyl 3-(tert-butoxycarbonylamino)-4-hydroxycyclohexanecarboxylate

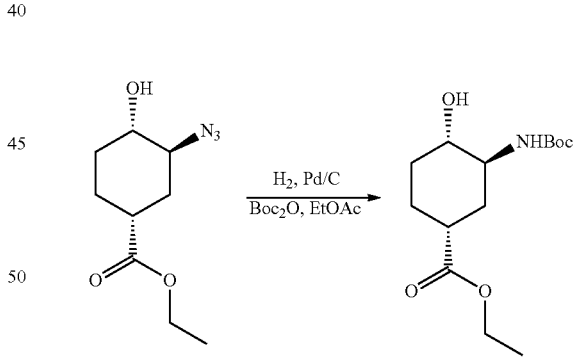

A mixture of Racemate-ethyl 3-azido-4-hydroxycyclohexanecarboxylate (14.0 g, 66 mmol), di-tert-butyldicarbonate (18.5 g, 85 mmol) and 5% palladium on carbon (50% wet, 2.5 g) in ethyl acetate (300 mL) was stirred at room temperature overnight at a hydrogen pressure of ~1 atm. After the reaction mixture was filtered, the filtrate was concentrated, and the thus-obtained oily matter was purified by silica gel column chromatography (petroleum ether:ethyl acetate=4:1-3:1). The thus-obtained compound was crystalized from hexane to thereby give the title compound (12.0 g, 62%) as a white solid. MS (ES+) $C_{14}H_{25}NO_5$ requires: 287, found: 188 $[M+H-100]^+$.

Step 5: Synthesis of Racemate-ethyl 3-(tert-butoxycarbonylamino)-4-(methylsulfonyloxy)cyclohexanecarboxylate

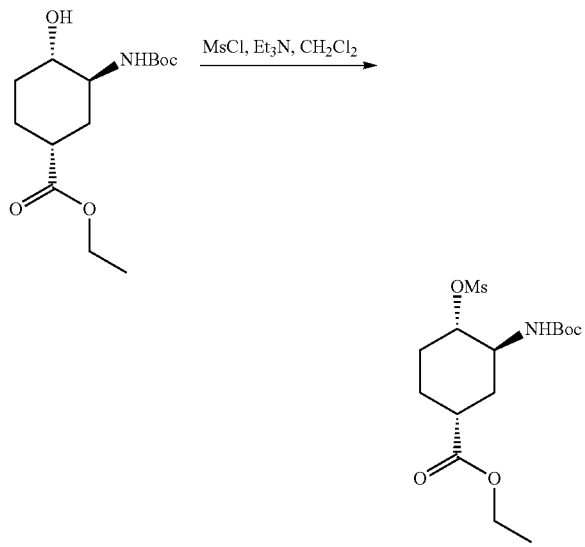

To a solution of Racemate-ethyl 3-(tert-butoxycarbonylamino)-4-hydroxycyclohexanecarboxylate (12.0 g, 42 mmol) and triethylamine (12.7 g, 126 mmol) in dichloromethane (150 mL) was added methanesulfonyl chloride (9.5 g, 84 mmol) dropwise at 0° C., and the mixture was stirred at 0° C. for 3 hours. The solution was washed with water (100 mL×3) and brine, dried over anhydrous sodium sulfate, filtered and concentrated to afford the title compound (15 g, crude) as a yellow oil. MS (ES+) $C_{15}H_{27}NO_7S$ requires: 365, found: 266 [M+H−100]$^+$.

Step 6: Synthesis of Racemate-ethyl 4-azido-3-(tert-butoxycarbonylamino)-cyclohexanecarboxylate

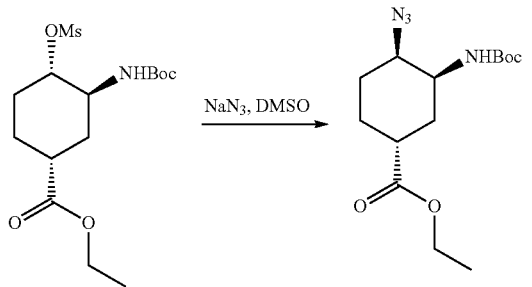 [SMILES: CCOC(=O)[C@@H]1CC[C@H](OS(C)(=O)=O)[C@@H](NC(=O)OC(C)(C)C)C1 ; CCOC(=O)[C@@H]1CC[C@@H](N=[N+]=[N-])[C@@H](NC(=O)OC(C)(C)C)C1]

To a solution of Racemate-ethyl 3-(tert-butoxycarbonylamino)-4-(methylsulfonyloxy)cyclohexanecarboxylate (11.0 g, 30 mmol) in dimethyl sulfoxide (110 mL) was added sodium azide (20 g, 300 mmol), and the mixture was stirred at 90° C. overnight under $N_2$. The solution was cooled to ~30° C., dissolved in ethyl acetate (~500 mL), washed with water (500 mL×5) and brine, dried over anhydrous sodium sulfate, filtered and concentrated. The residue was purified by silica gel column chromatography (petroleum ether:ethyl acetate=4:1~2:1) to thereby give the title compound (4.1 g, 44%) as an colorless oil. MS (ES+) $C_{14}H_{24}N_4O_4$ requires: 312, found: 213 [M+H−100]$^+$.

Step 7: Synthesis of Racemate-ethyl 4-amino-3-(tert-butoxycarbonylamino)-cyclohexanecarboxylate

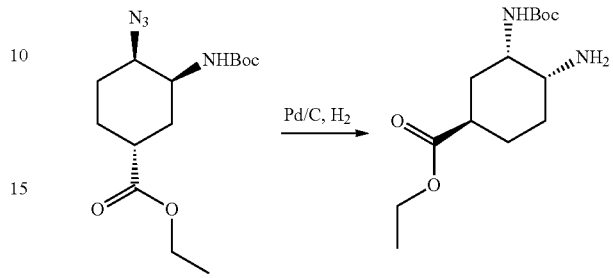

A mixture of Racemate-ethyl 4-azido-3-(tert-butoxycarbonylamino)cyclohexanecarboxylate (14.0 g, 66 mmol) and 5% palladium on carbon (50% wet, 1.0 g) in ethyl acetate (100 mL) was stirred at room temperature overnight at a hydrogen pressure of ~1 atm. After the reaction mixture was filtered, the filtrate was concentrated. The resulting oily residue was purified by silica gel column chromatography (petroleum ether:ethyl acetate=4:1~1:1) to thereby give the title compound (2.0 g, 59%) as a yellow solid.

Synthesis of Racemate-4-amino-3-(6-(2,6-dichloro-3,5-dimethoxyphenyl)quinazolin-2-ylamino)cyclohexanecarboxamide

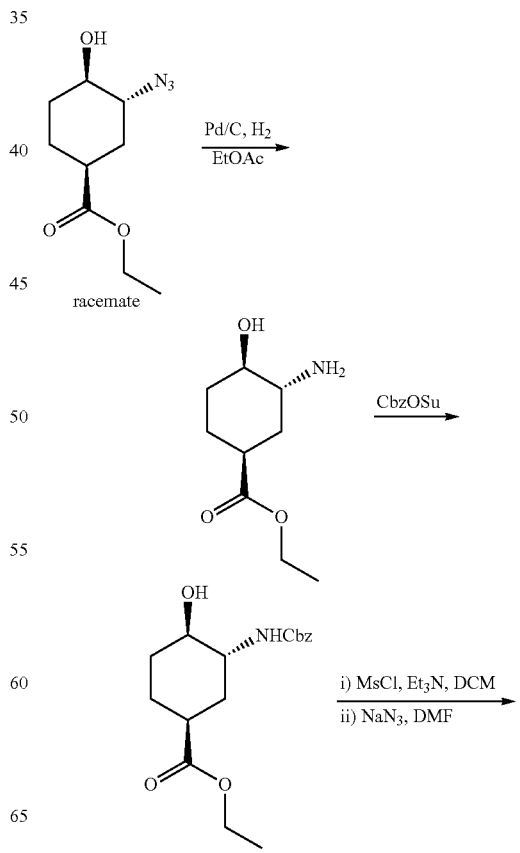

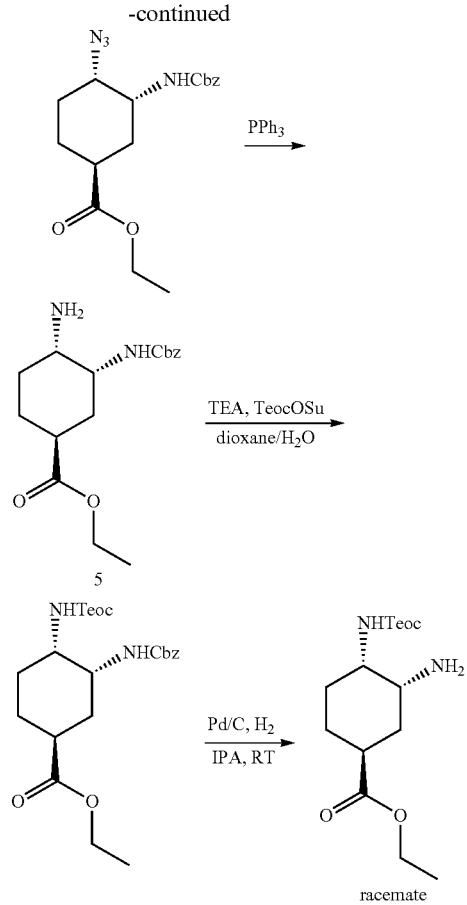

Step 2: Synthesis of Racemate-ethyl 3-(benzyloxy-carbonylamino)-4-hydroxycyclohexanecarboxylate

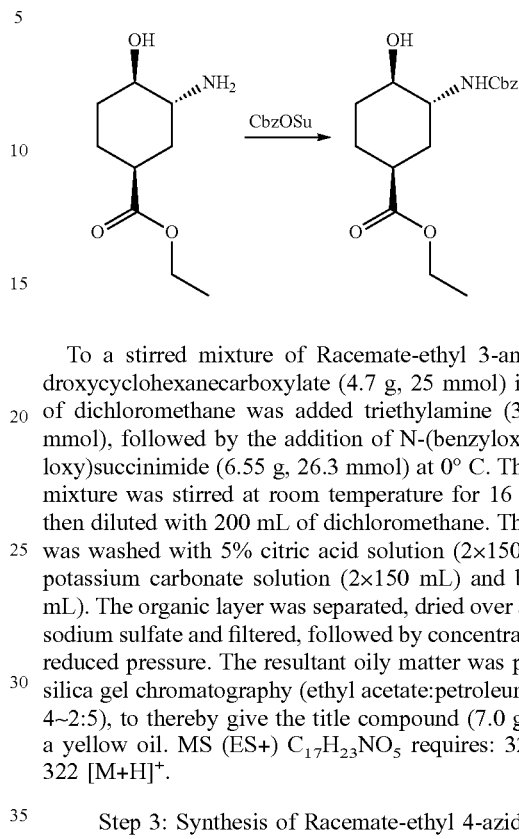

To a stirred mixture of Racemate-ethyl 3-amino-4-hydroxycyclohexanecarboxylate (4.7 g, 25 mmol) in 120 mL of dichloromethane was added triethylamine (3.03 g, 30 mmol), followed by the addition of N-(benzyloxycarbonyloxy)succinimide (6.55 g, 26.3 mmol) at 0° C. The reaction mixture was stirred at room temperature for 16 hours and then diluted with 200 mL of dichloromethane. The solution was washed with 5% citric acid solution (2×150 mL), 5% potassium carbonate solution (2×150 mL) and brine (200 mL). The organic layer was separated, dried over anhydrous sodium sulfate and filtered, followed by concentration under reduced pressure. The resultant oily matter was purified by silica gel chromatography (ethyl acetate:petroleum ether=1:4~2:5), to thereby give the title compound (7.0 g, 87%) as a yellow oil. MS (ES+) $C_{17}H_{23}NO_5$ requires: 321, found: 322 $[M+H]^+$.

Step 3: Synthesis of Racemate-ethyl 4-azido-3-(benzyloxycarbonylamino)-cyclohexanecarboxylate

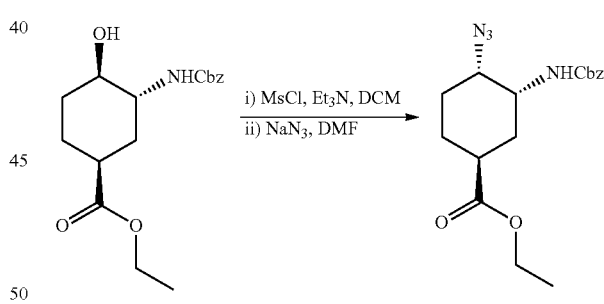

To a solution of Racemate-ethyl 3-(benzyloxycarbonylamino)-4-hydroxycyclohexanecarboxylate (7.0 g, 22 mmol) and triethylamine (6.7 g, 66 mmol) in dichloromethane (100 mL) was dropwise added methanesulfonyl chloride (5.1 g, 44 mmol) at 0° C., and the mixture was stirred at this temperature for 2 hours. The reaction mixture was washed with water (200 mL×3) and brine. The organic layer was dried over anhydrous sodium sulfate, filtered and concentrated to thereby give crude product (8.0 g, crude) as a yellow oil. A mixture of the above residue (8.0 g, 20 mmol) and sodium azide (7.8 g, 120 mmol) in dimethylsulfoxide (50 mL) was stirred at 100° C. for 18 hours. The reaction mixture was cooled to ~30° C., dissolved in water (~300 mL) and extracted with ethyl acetate (200 mL×2). The combined organic layers were washed with brine (~200 mL), dried over anhydrous sodium sulfate, filtered and

Step 1: Synthesis of Racemate-ethyl 3-amino-4-hydroxycyclohexanecarboxylate

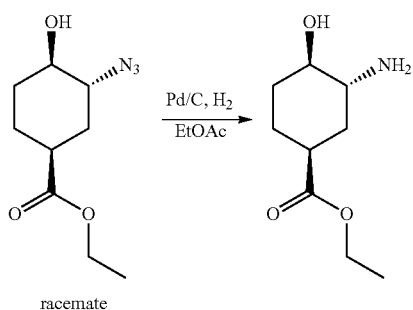

A suspension mixture of Racemate-ethyl 3-azido-4-hydroxycyclohexanecarboxylate (8.0 g, 37.5 mmol) and 5% palladium on carbon (50% wet, 2.0 g) in ethyl acetate (250 mL) was stirred under hydrogen atmosphere (~1 atm) at room temperature overnight. After the reaction mixture was filtered, the filtrate was concentrated to thereby give the title compound (5.8 g, 83%) as a yellow solid. MS (ES+) $C_9H_{17}NO_3$ requires: 187, found: 188 $[M+H]^+$.

Step 4: Synthesis of Racemate-ethyl 3-(tert-butoxy-carbonylamino)-4-hydroxycyclohexanecarboxylate

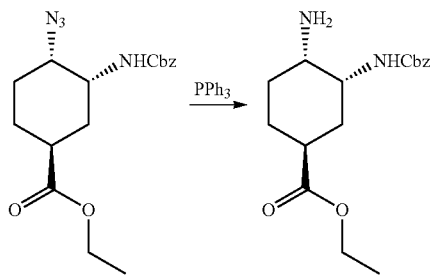 [SMILES: CCOC(=O)[C@H]1CC[C@H](N=[N+]=[N-])[C@H](NC(=O)OCc2ccccc2)C1 ; CCOC(=O)[C@H]1CC[C@H](N)[C@H](NC(=O)OCc2ccccc2)C1 ; "PPh3"]

A mixture of Racemate-ethyl 4-azido-3-(benzyloxycarbonylamino)cyclohexanecarboxylate (3.5 g, 10 mmol) and triphenylphosphine (10.4 g, 40 mmol) in THF (200 mL) and water (10 mL) was stirred at 65° C. for 18 hours. The reaction mixture was cooled to room temperature, then diluted with ethyl acetate (200 mL), washed with brine (200 mL) and evaporated in vacuo. The residue was purified by silica gel chromatography (petroleum ether/ethyl acetate=2/1~dichloromethane/methanol=10:1) to afford the title compound (2.4 g, 75%) as a yellow oil. MS (ES+) $C_{17}H_{24}N_2O_4$ requires: 320, found: 321 $[M+H]^+$.

Step 5: Synthesis of Racemate-ethyl 3-(benzyloxycarbonylamino)-4-((2-(trimethylsilyl)ethoxy)carbonylamino)cyclohexanecarboxylate

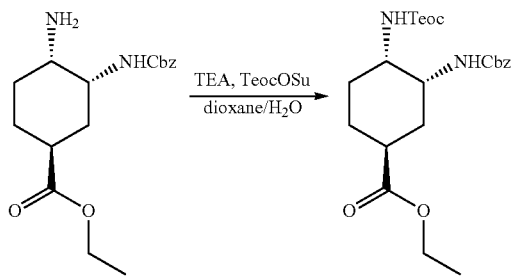

A solution of Racemate-ethyl 3-(tert-butoxycarbonylamino)-4-hydroxycyclohexanecarboxylate (1.6 g, 5.0 mmol), 1,3-dioxoisoindolin-2-yl 2-(trimethylsilyl)ethyl carbonate (1.42 g, 5.5 mmol) and triethylamine (760 mg, 7.5 mmol) in dioxane/water (25/25 mL) was stirred at room temperature for 3 hours. The reaction mixture was diluted with ethyl acetate (200 mL), and washed by 1 M hydrochloric acid (100 mL), saturated sodium bicarbonate solution (100 mL) and brine (100 mL). The organic layer was concentrated and purified by silica gel chromatography (petroleum ether/ethyl acetate=4/1) to afford the title compound (2.3 g, 99%) as a white solid. MS (ES+) $C_{23}H_{36}N_2O_6Si$ requires: 464, found: 487 $[M+Na]^+$.

Step 6: Synthesis of Racemate-ethyl 3-amino-4-((2-(trimethylsilyl)ethoxy)carbonylamino)cyclohexanecarboxylate

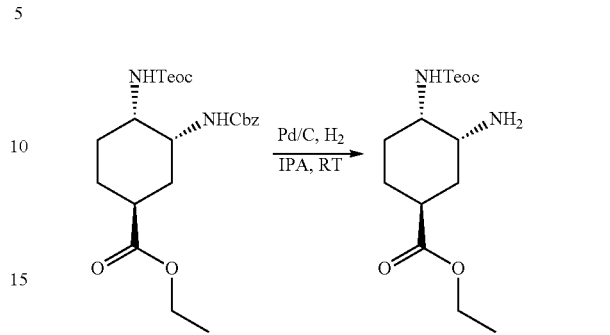

A mixture of Racemate-ethyl 3-(benzyloxycarbonylamino)-4-((2-(trimethylsilyl)ethoxy)carbonylamino)cyclohexanecarboxylate (1.7 g, 3.7 mmol) and 5% palladium on carbon (50% wet, 300 mg) in isopropanol (35 mL) was stirred under 1 atm hydrogen atmosphere at room temperature for 18 hours. The mixture was filtered through a pad of celite. The filtrate was concentrated and purified by silica gel chromatography (methanol/dichloromethane=1/30 to 1/10) to afford the title compound (1.0 g, 89%) as a yellow oil. MS (ES+) $C_{15}H_{30}H_2O_4Si$ requires: 330, found: 331 $[M+H]^+$.

Synthesis of tert-butyl (4S,5S)-5-amino-2,2-dimethyl-tetrahydro-2H-pyran-4-ylcarbamate and tert-butyl (4R,5R)-5-amino-2,2-dimethyl-tetrahydro-2H-pyran-4-ylcarbamate

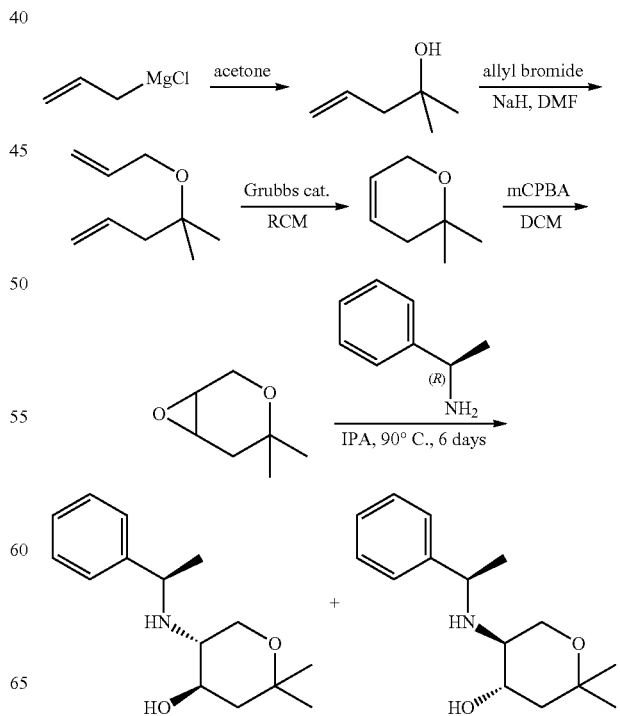

Step 2: Synthesis of 4-(allyloxy)-4-methylpent-1-ene

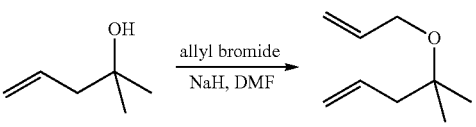

To a suspension of sodium hydride (60%, 24 g, 60 mmol) in N,N-dimethylformamide (150 mL) at 0° C. was slowly added 2-methylpent-4-en-2-ol (20.0 g, 200 mmol). After 1 hour at 0° C., allyl bromide (48.0 g 400 mmol) was slowly added at 0~5° C., and the reaction mixture was stirred at 0° C. for another 1 hour. The reaction was quenched with aq. ammonium chloride solution and extracted with tert-butyl methyl ether. The combined organic layers were washed with water and brine, dried over sodium sulfate, filtered and concentrated under reduced pressure to give the title compound (44 g, crude) as a yellow oil, which was directly used in the next step without further purification.

Step 3: Synthesis of 2,2-dimethyl-3,6-dihydro-2H-pyran

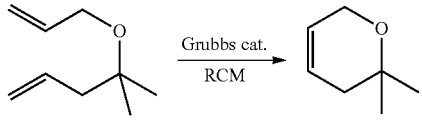

Grubbs II catalyst (1.20 g, 1.43 mmol) was added to a solution of 4-(allyloxy)-4-methylpent-1-ene (10.0 g, 71.4 mmol) in dichloromethane (300 mL) and the reaction mixture was refluxed overnight. After the solvent was evaporated, the residue was distilled under reduced pressure to give the title compound (4.0 g, 50%) as a colorless oil.

Step 4: Synthesis of 4,4-dimethyl-3,7-dioxa-bicyclo[4.1.0]heptane

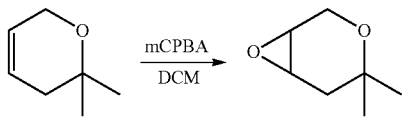

To a solution of 2,2-dimethyl-3,6-dihydro-2H-pyran (4.0 g, 36 mmol) in dichloromethane (20 mL) was added 3-chloroperoxybenzoic acid (18.4 g, 107 mmol), and the mixture was stirred at room temperature overnight. The reaction mixture was then diluted with dichloromethane, and washed with saturated aqueous sodium sulfite and brine. The organic layer was dried over sodium sulfate, filtered, and concentrated under reduced pressure to give the title compound (5.0 g, crude) as a yellow oil, which was directly used in the next step without further purification.

-continued

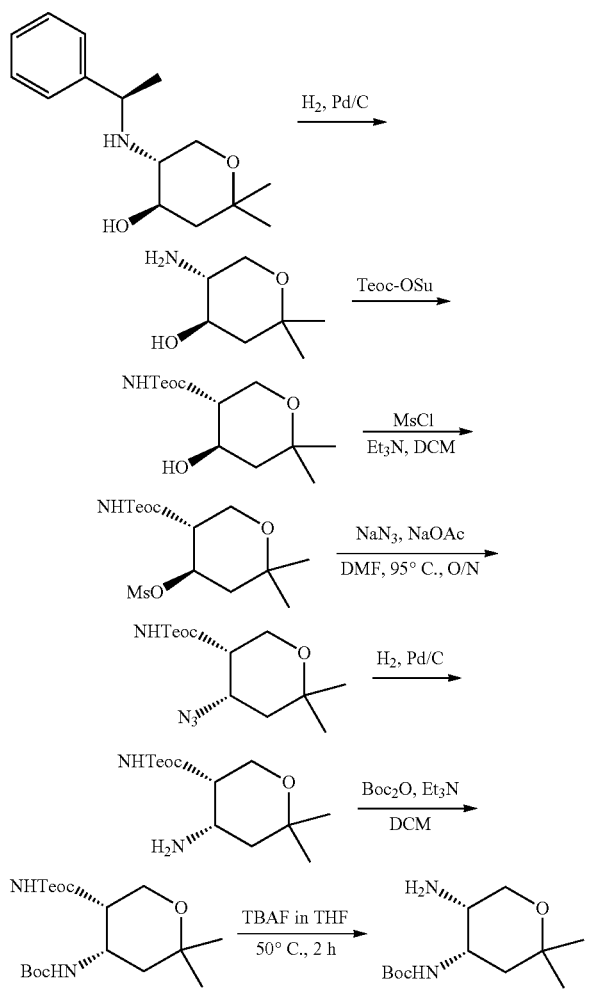

Step 1: Synthesis of 2-methylpent-4-en-2-ol

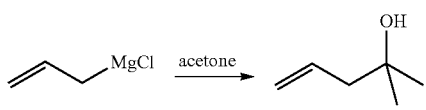

To a solution of allylmagnesium chloride in anhydrous THF (1.7 M, 200 mL, 340 mmol) was slowly added acetone (13.2 g, 227 mmol) at 0° C. After stirring for 15 min at 0° C., the reaction mixture was stirred at room temperature for another 2 hours. The reaction was quenched with aq. ammonium chloride solution and extracted with tert-butyl methyl ether. The combined organic layers were washed with water and brine, dried over sodium sulfate, filtered and concentrated under reduced pressure The residue was purified by distillation under reduced pressure (~10-15 bars, b.p. 50° C.) to give the title compound (15 g, 66%) as a colorless oil.

Step 5: Synthesis of (4R,5R)-2,2-dimethyl-5-((R)-1-phenylethylamino)-tetrahydro-2H-pyran-4-ol (6a) and (4S,5S)-2,2-dimethyl-5-((R)-1-phenylethylamino)-tetrahydro-2H-pyran-4-ol (6b)

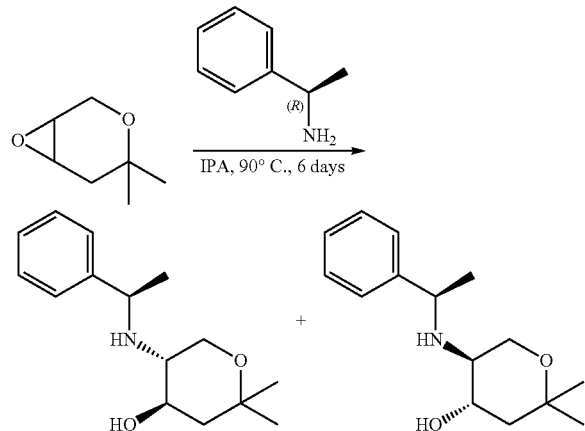

A mixture of 4,4-dimethyl-3,7-dioxa-bicyclo[4.1.0]heptane (7.0 g, 54 mmol) and (R)-1-phenylethanamine (9.9 g, 82 mmol) in isopropanol (50 mL) was stirred at 80° C. for 6 days. The reaction mixture was cooled to room temperature and concentrated under reduced pressure. The residue was purified by silica gel chromatography (elute:petroleum ether:dichloromethane containing 1% ammonia-methanol (7 M), 10:1 to dichloromethane containing 1% ammonia/methanol (7 M) to afford (4R,5R)-2,2-dimethyl-5-((R)-1-phenylethylamino)-tetrahydro-2H-pyran-4-ol (6a) (more polar fraction, 1.5 g) and (4S,5S)-2,2-dimethyl-5-((R)-1-phenylethylamino)-tetrahydro-2H-pyran-4-ol (6b) (less polar fraction, 1.7 g) as a yellow oil. Note: The absolute configuration of the products was assigned randomly. MS (ES+) $C_{15}H_{23}NO_2$ requires: 249, found: 250 [M+H]$^+$. Mobile phase for TLC: ethyl acetate/dichloromethane=2/1.

Step 6: Synthesis of (4R,5R)-5-amino-2,2-dimethyl-tetrahydro-2H-pyran-4-ol

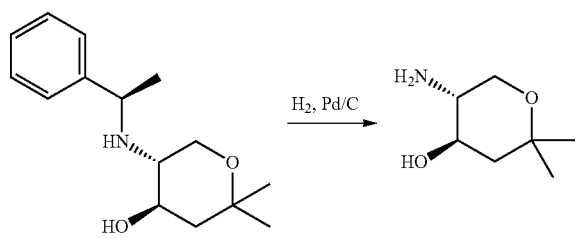

A mixture of (4R,5R)-2,2-dimethyl-5-((R)-1-phenylethylamino)-tetrahydro-2H-pyran-4-ol (600 mg, 2.40 mmol) and 10% palladium on carbon (100 mg) in methanol (50 mL) was stirred at room temperature under hydrogenation overnight. After that, the mixture was filtered through a pad of celite, and the filtrate was concentrated to afford the title compound (550 mg, crude) as a yellow oil, which was used directly for the next step without further purification.

Step 7: Synthesis of 2-(trimethylsilyl)ethyl (3R,4R)-4-hydroxy-6,6-dimethyl-tetrahydro-2H-pyran-3-ylcarbamate

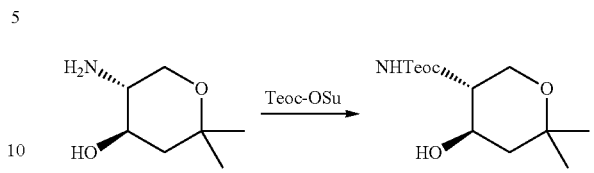

To a solution of (4R,5R)-5-amino-2,2-dimethyl-tetrahydro-2H-pyran-4-ol (550 mg, 2.40 mmol) and triethylamine (484 mg, 4.80 mmol) in dioxane (5 mL) and water (5 mL) was added 2-(trimethylsilyl)ethyl 2,5-dioxopyrrolidine-1-carboxylate (750 mg, 2.90 mmol) at room temperature. The reaction mixture was stirred at room temperature for 4 hours. After that, the solution was diluted with ethyl acetate and washed with brine. The organic layer was concentrated, and the residue was purification by silica gel column with petroleum ether/ethyl acetate=4/1 to 1/1 to afford the title compound (360 mg, 52% for 2 steps) as a gray solid.

Step 8: Synthesis of (4R,5R)-2,2-dimethyl-5-((2-(trimethylsilyl)ethoxy)carbonylamino)-tetrahydro-2H-pyran-4-yl methanesulfonate

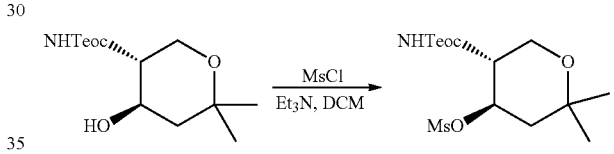

To a solution of 2-(trimethylsilyl)ethyl (3R,4R)-4-hydroxy-6,6-dimethyl-tetrahydro-2H-pyran-3-ylcarbamate (360 mg, 1.25 mmol) and triethylamine (378 mg, 3.75 mmol) in dichloromethane (5 mL) was dropwise added mesyl chloride (213 mg, 1.87 mmol) at 0° C. The reaction mixture was stirred at room temperature for 4 h, and then diluted with dichloromethane (100 mL). The organic layer was washed with water (50 mL) and brine (50 mL), dried over sodium sulfate, filtered and concentrated to afford the title compound (550 mg, crude) as a yellow oil, which was directly used in the next step without further purification.

Step 9: Synthesis of 2-(trimethylsilyl)ethyl (3S,4S)-4-azido-6,6-dimethyl-tetrahydro-2H-pyran-3-ylcarbamate

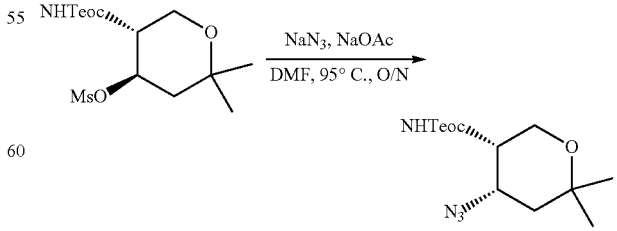

To a solution of (4R,5R)-2,2-dimethyl-5-((2-(trimethylsilyl)ethoxy)carbonylamino)-tetrahydro-2H-pyran-4-yl methanesulfonate (550 mg, 1.25 mmol) in N,N-dimethylformamide (10 mL) was added sodium azide (812 mg, 12.5 mmol) and sodium acetate (1.05 mg, 12.5 mmol) at room temperature. The resultant mixture was stirred at 95° C. for 2 days. After that, the mixture was cooled to room temperature and diluted with ethyl acetate (100 mL). The organic phase was washed with water (100 mL×8) and brine (50 mL), dried over sodium sulfate, filtered, and concentrated to afford the title compound (510 mg, crude) as a yellow oil which was directly used in the next step without further purification.

Step 10: Synthesis of 2-(trimethylsilyl)ethyl (3S, 4S)-4-amino-6,6-dimethyl-tetrahydro-2H-pyran-3-ylcarbamate

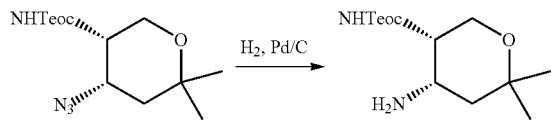

A mixture of 2-(trimethylsilyl)ethyl (3S,4S)-4-azido-6,6-dimethyl-tetrahydro-2H-pyran-3-ylcarbamate (510 mg, 1.25 mmol), 10% palladium on carbon (50 mg) in methanol (10 mL) was stirred at room temperature under 1 atm hydrogen atmosphere (hydrogen balloon) overnight. After that, the mixture was filtered through a pad of celite. The filtrate was concentrated to get the title compound (450 mg, crude) as a brown oil, which was used directly for the next step without further purification.

Step 11: Synthesis of 2-(trimethylsilyl)ethyl (3S, 4S)-(4-tert-butoxycarbonylamino)-6,6-dimethyl-tetrahydro-2H-pyran-3-ylcarbamate

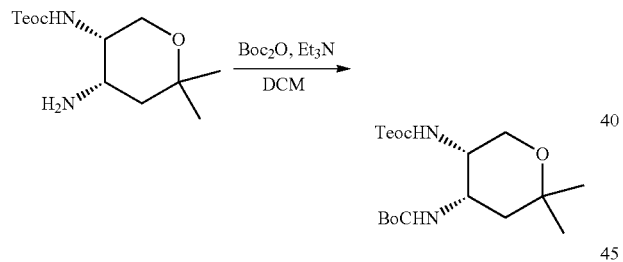

To a solution of 2-(trimethylsilyl)ethyl (3S,4S)-4-amino-6,6-dimethyl-tetrahydro-2H-pyran-3-ylcarbamate (450 mg, 1.25 mmol) and triethylamine (379 mg, 3.75 mmol) in dichloromethane (10 mL) at room temperature was added di-tert-butyl dicarbonate (410 mg, 1.88 mmol). The reaction mixture was stirred at room temperature for 2 hours. After that, the solution was concentrated, and the residue was purified by silica gel chromatography using petroleum ether/ ethyl acetate=4/1 as the eluent to afford the title compound (160 mg, 33% for 4 steps) as a yellow solid.

Step 12: Synthesis of tert-butyl (4S,5S)-5-amino-2, 2-dimethyl-tetrahydro-2H-pyran-4-ylcarbamate

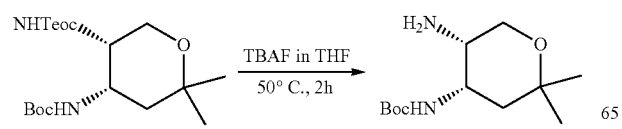

To a solution of compound 2-(trimethylsilyl)ethyl (3S, 4S)-(4-tert-butoxycarbonylamino)-6,6-dimethyl-tetrahydro-2H-pyran-3-ylcarbamate (160 mg, 0.41 mmol) in tetrahydrofuran (2 mL) at room temperature was added tetrabutylammonium fluoride in tetrahydrofuran (1 M, 1.23 mL, 1.23 mmol). The reaction mixture was stirred 50° C. for 2 hours. After that, the solution was concentrated, and the residue was purified by silica gel chromatography with ethyl acetate as the eluent to afford the title compound (110 mg, crude) as a yellow oil.

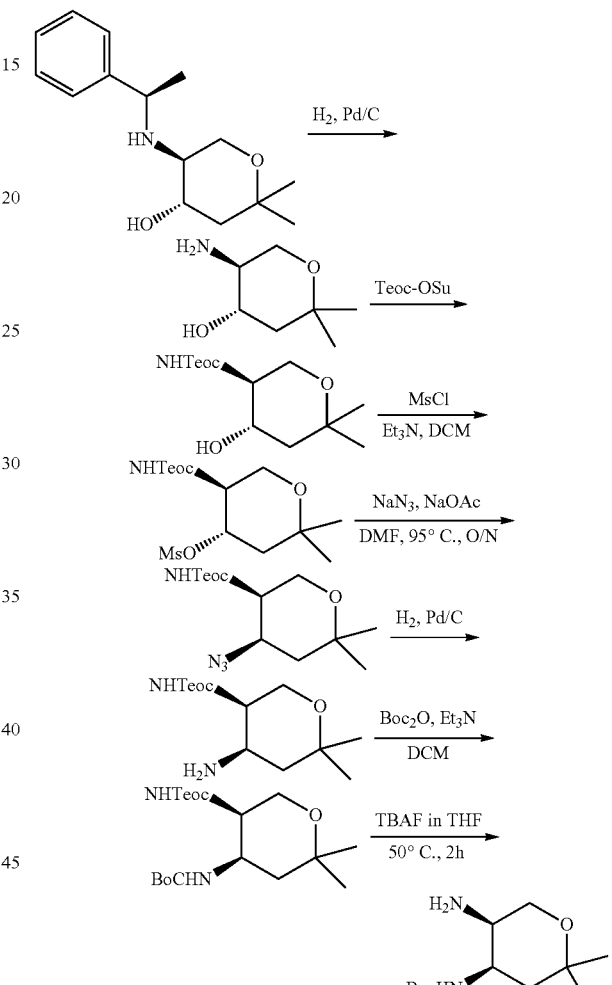

Step 1: Synthesis of (4S,5S)-5-amino-2,2-dimethyl-tetrahydro-2H-pyran-4-ol

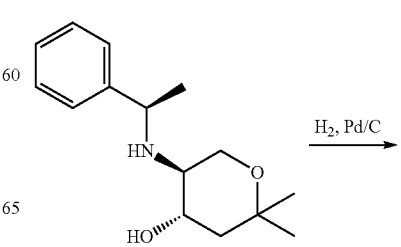

-continued

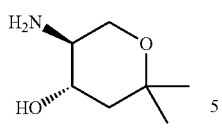

A suspension mixture of (4S,5S)-2,2-dimethyl-5-((R)-1-phenylethylamino)-tetrahydro-2H-pyran-4-ol (1.0 g, 4.0 mmol) and 10% palladium on carbon (200 mg) in methanol (20 mL) was stirred at room temperature under 1 atm hydrogen atmosphere (hydrogen balloon) overnight. After that, the mixture was filtered through a pad of celite, and the filtrate was concentrated to get the title compound (1.1 g, crude) as a yellow oil, which was used directly for the next step without further purification.

Step 2: Synthesis of 2-(trimethylsilyl)ethyl (3S,4S)-4-hydroxy-6,6-dimethyl-tetrahydro-2H-pyran-3-ylcarbamate

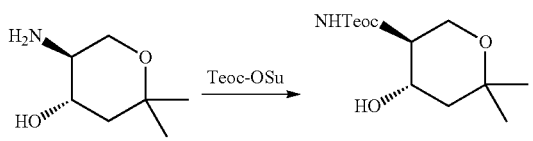

To a solution of (4S,5S)-5-amino-2,2-dimethyl-tetrahydro-2H-pyran-4-ol (1.1 g, 4.0 mmol) and triethylamine (1.1 mL, 8.0 mmol) in a mixed solvent of dioxane (5 mL) and water (5 mL) at room temperature was added 2-(trimethylsilyl)ethyl 2,5-dioxopyrrolidine-1-carboxylate (1.2 g, 4.8 mmol). The reaction mixture was stirred at room temperature for 4 hours. After that, the solution was diluted with ethyl acetate and washed with brine. The organic layer was separated and concentrated. The resulting residue was purified by silica gel chromatography using petroleum ether/ethyl acetate=4/1 to 1/1 as the eluent to afford the title compound (1.0 g, 86% for 2 steps) as a yellow oil.

Step 3: Synthesis of (4S,5S)-2,2-dimethyl-5-((2-(trimethylsilyl)ethoxy)carbonylamino)-tetrahydro-2H-pyran-4-yl methanesulfonate

To a solution of 2-(trimethylsilyl)ethyl (3S,4S)-4-hydroxy-6,6-dimethyl-tetrahydro-2H-pyran-3-ylcarbamate (1.0 g, 3.5 mmol) and triethylamine (1.4 mL, 10 mmol) in dichloromethane (10 mL) at 0° C. was dropwise added mesyl chloride (600 mg, 5.20 mmol). The reaction mixture was stirred at room temperature for 4 hours and then diluted with dichloromethane (100 mL). The organic layer was washed with water (50 mL) and brine (50 mL), dried over sodium sulfate, filtered and concentrated to afford the title compound (1.6 g, crude) as a yellow oil which was directly used in the next step without further purification.

Step 4: Synthesis of 2-(trimethylsilyl)ethyl (3R,4R)-4-azido-6,6-dimethyl-tetrahydro-2H-pyran-3-ylcarbamate

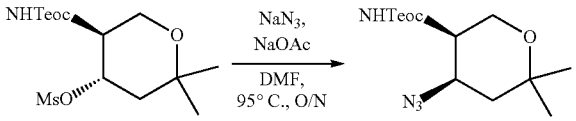

To a solution of (4S,5S)-2,2-dimethyl-5-((2-(trimethylsilyl)ethoxy)carbonylamino)-tetrahydro-2H-pyran-4-yl methanesulfonate (1.6 g, 3.5 mmol) in N,N-dimethylformamide (10 mL) was added sodium azide (2.3 g, 35 mmol) and sodium acetate (2.8 g, 35 mmol) at room temperature. The resultant mixture was stirred at 95° C. for 2 days. After that, the mixture was cooled to room temperature and diluted with ethyl acetate (100 mL). The organic layer was washed by water (100 mL×8) and brine (50 mL), dried over sodium sulfate, filtered and concentrated to afford the title compound (1.3 g, crude) as a yellow oil, which was directly used in the next step without further purification.

Step 5: Synthesis of 2-(trimethylsilyl)ethyl (3R,4R)-4-amino-6,6-dimethyl-tetrahydro-2H-pyran-3-ylcarbamate

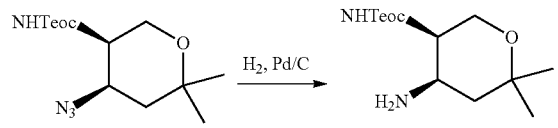

A mixture of 2-(trimethylsilyl)ethyl (3R,4R)-4-azido-6,6-dimethyl-tetrahydro-2H-pyran-3-ylcarbamate (1.3 g, 3.5 mmol) and 10% palladium on carbon (200 mg) in methanol (10 mL) was stirred at room temperature under 1 atm hydrogen atmosphere (hydrogen balloon) overnight. After that, the mixture was filtered through a pad of celite. The filtrate was concentrated to get the title compound (1.2 g, crude) as a yellow oil, which was used directly for the next step without further purification.

Step 6: Synthesis of 2-(trimethylsilyl)ethyl (3R,4R)-(4-tert-butoxycarbonylamino)-6,6-dimethyl-tetrahydro-2H-pyran-3-ylcarbamate

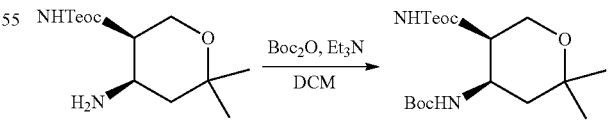

To a solution of 2-(trimethylsilyl)ethyl (3R,4R)-4-amino-6,6-dimethyl-tetrahydro-2H-pyran-3-ylcarbamate (1.2 g, 3.5 mmol) and triethylamine (1.4 mL, 10.5 mmol) in dichloromethane (10 mL) was added di-tert-butyl dicarbonate (1.1 g, 5.2 mmol) at room temperature. The reaction mixture was stirred at room temperature for 2 hours. After that, the mixture was directly concentrated and purified by silica gel chromatography using petroleum ether/ethyl acetate=4/1 as the eluent to afford the title compound (440 mg, 32% for 4 steps) as a gray solid.

Step 7: Synthesis of tert-butyl (4R,5R)-5-amino-2,2-dimethyl-tetrahydro-2H-pyran-4-ylcarbamate

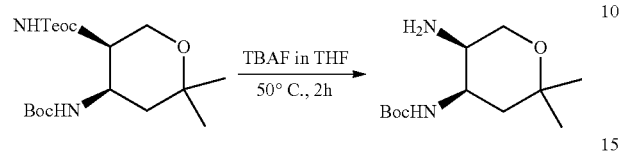

To a solution of 2-(trimethylsilyl)ethyl (3R,4R)-(4-tert-butoxycarbonylamino)-6,6-dimethyl-tetrahydro-2H-pyran-3-ylcarbamate (440 mg, 1.13 mmol) in tetrahydrofuran (2 mL) at room temperature was added tetrabutylammonium fluoride in tetrahydrofuran (1 M, 3.4 mL, 3.4 mmol). The reaction mixture was stirred 50° C. for 2 hours. After that, the solution was cooled to room temperature, concentrated and purified by silica gel chromatography using ethyl acetate as the elute to afford the title compound (80 mg, 29%) as a yellow oil.

Synthesis of tert-butyl (2S,4S,5S)-5-amino-2-methyltetrahydro-2H-pyran-4-ylcarbamate

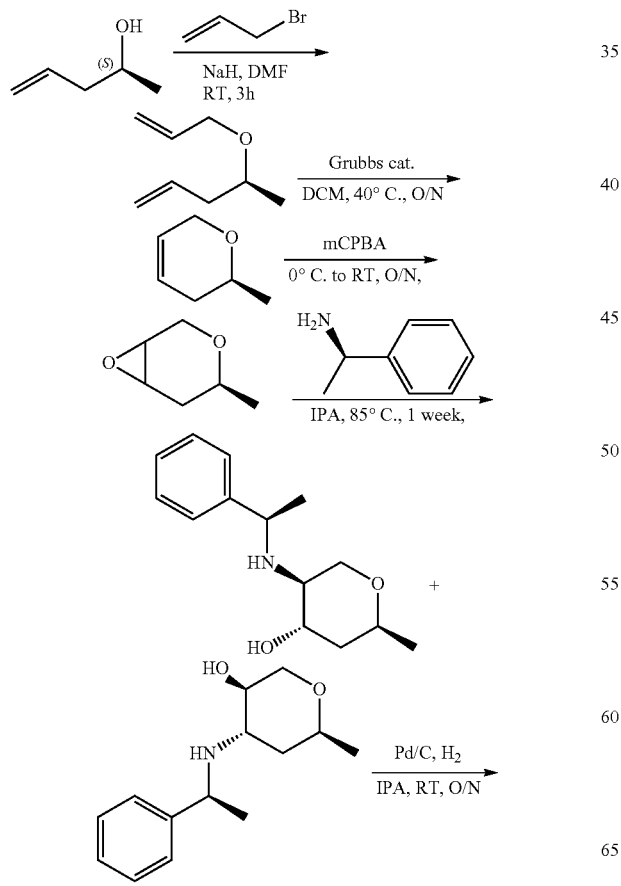

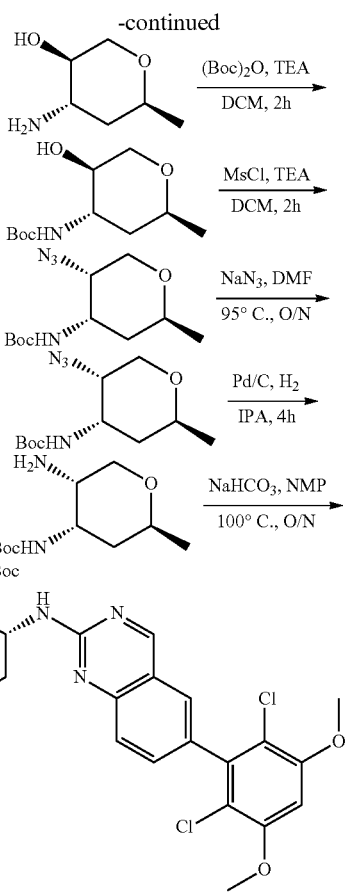

Step 1: Synthesis of (S)-4-(allyloxy)pent-1-ene

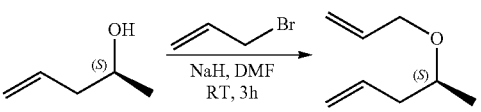

To a suspension of sodium hydride (21 g, 34 mmol) in N,N-dimetylformamide (100 mL) was dropwise added (S)-pent-4-en-2-ol (10 g, 116 mmol) at 0° C. The reaction mixture was stirred at 0° C. for 1 hour. After that, allyl bromide (14.0 g, 116.2 mmol) was dropwise added to the mixture at 0° C. The resultant mixture was stirred at 0° C. for another 3 h, and the mixture was quenched by saturate ammonium chloride solution (500 mL). The aqueous layer was extracted with tert-butyl methyl ether (200 mL×3), and the combined organic layers were washed with water (100 mL×3) and brine (100 mL), dried over sodium sulfate, filtered and concentrated to afford (S)-4-(allyloxy)pent-1-ene (~20 ml tert-butyl methyl ether solution), which was used in the next step without further purification.

Step 2: Synthesis of
(S)-2-methyl-3,6-dihydro-2H-pyran

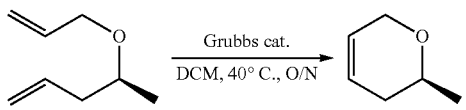

A mixture of (S)-4-(allyloxy)pent-1-ene (~20 mL solution, 116 mmol), $2^{nd}$ generation Grubbs catalyst (1.8 g) in dichloromethane (500 mL) was stirred at 40° C. overnight. After that, the solution was cooled to room temperature and the title compound (~3.5 g, 31% for 2 steps) was obtained by vacuum distillation.

Step 3: Synthesis of
(4S)-4-methyl-3,7-dioxabicyclo[4.1.0]heptane

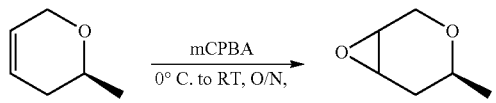

To a solution of (S)-2-methyl-3,6-dihydro-2H-pyran (~1 g, 10 mmol) in dichloromethane (20 mL) was added 3-chloroperoxybenzoic acid (1.8 g, 20 mmol) at 0° C. The resultant mixture was stirred at room temperature overnight. After that, the mixture was washed by saturated sodium sulfite solution (15 mL), sodium carbonate (15 mL) and brine (15 mL). The organic layer was dried over sodium sulfate and concentrated to get the title compound (~3 mL dichloromethane solution), which was used directly for the next step without further purification.

Step 4: Synthesis of (3R,4S,6S)-6-methyl-4-((S)-1-phenylethylamino)tetrahydro-2H-pyran-3-ol

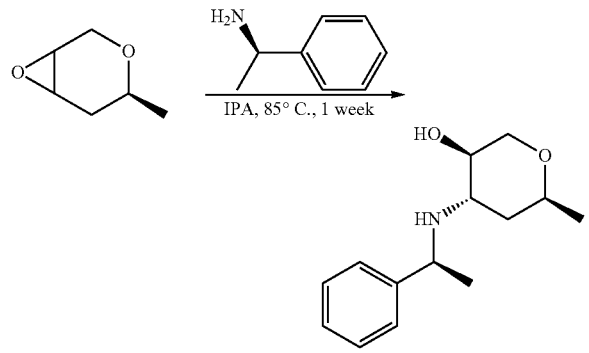

A mixture of (4S)-4-methyl-3,7-dioxabicyclo[4.1.0]heptane (~3 mL dichloromethane solution, 10 mmol) and (R)-1-phenylethanamine (2.4 g, 20 mmol) in isopropyl alcohol (20 mL) was stirred at 85° C. for 1 week. After that, the solution was cooled to room temperature and purified by prep-HPLC to get the title compound (more polar, 120 mg, 10% for 2 steps) as a yellow solid and a side product (less polar, 400 mg, 32% for 2 steps) as a white solid. MS (ES+) $C_{14}H_{21}NO_2$ requires: 235, found: 236 [M+H]$^+$.

Step 5: Synthesis of (3R,4S,6S)-4-amino-6-methyl-tetrahydro-2H-pyran-3-ol

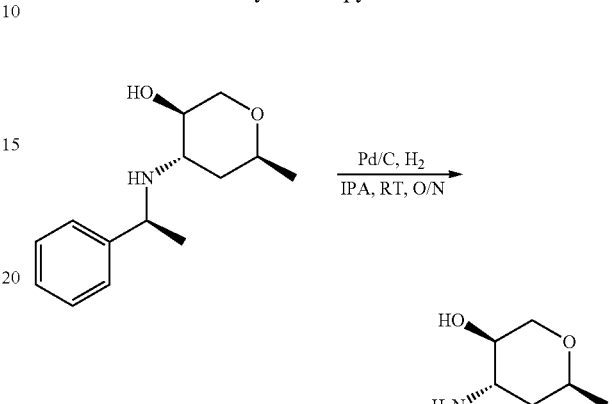

A mixture of (3S,4R)-tert-butyl tert-butyl (2S,4S,5R)-5-hydroxy-2-methyltetrahydro-2H-pyran-4-ylcarbamate (200 mg, 0.85 mmol) and 10% palladium on carbon (50 mg) in isopropanol (10 mL) was stirred at room temperature under hydrogenation overnight. After that, the mixture was filtered through a pad of celite and concentrated to get the title compound (150 mg, crude) as a yellow oil, which was used directly for the next step without further purification.

Step 6: Synthesis of tert-butyl (2S,4S,5R)-5-hydroxy-2-methyltetrahydro-2H-pyran-4-ylcarbamate

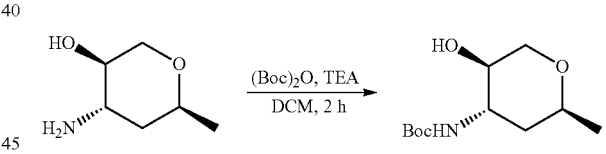

To a solution of (3R,4S,6S)-4-amino-6-methyltetrahydro-2H-pyran-3-ol (150 mg, 1.1 mmol) and triethylamine (333 mg, 3.3 mmol) in dichloromethane (80 mL) at 0° C. was dropwise added di-tert-butyl dicarbonate (475 mg, 2.2 mmol). The reaction mixture was stirred at room temperature for 4 hours. After that, the solution was concentrated and purified by silica gel column with methanol/dichloronethane=1/30 to 1/15 as elute to afford the title compound (130 mg, 51% for 2 steps) as a yellow oil.

Step 7: Synthesis of tert-butyl (2S,4S,5S)-5-azido-2-methyltetrahydro-2H-pyran-4-ylcarbamate

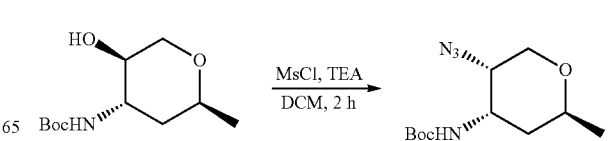

To a solution of tert-butyl (2S,4S,5R)-5-hydroxy-2-methyltetrahydro-2H-pyran-4-ylcarbamate 7 (130 mg, 0.6 mmol) and triethylamine (202 mg, 2.0 mmol) in dichloromethane (10 mL) at 0° C. was dropwise added mesyl chloride (194 mg, 1.7 mmol). The reaction mixture was stirred at room temperature for 4 hours and then diluted with dichloromethane (100 mL). The organic layers were washed with water (50 mL) and brine (50 mL), dried over sodium sulfate, filtered and concentrated to afford the title compound (190 mg, crude) as a yellow oil (4.0 g, 98%), which was directly used in the next step without further purification.

Step 8: Synthesis of tert-butyl (2S,4S,5S)-5-azido-2-methyltetrahydro-2H-pyran-4-ylcarbamate

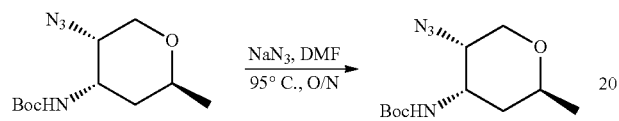

To a solution of tert-butyl (2S,4S,5S)-5-azido-2-methyltetrahydro-2H-pyran-4-ylcarbamate (190 mg, 0.6 mmol) in N,N-dimethylformamide (10 mL) was added sodium azide (375 mg, 5.6 mmol) and sodium acetate (459 mg, 5.6 mmol) at room temperature. The resultant mixture was stirred at 95° C. for 2 days. After that, the mixture was diluted with ethyl acetate (100 mL), washed by water (50 mL) and brine (50 mL), dried over sodium sulfate, filtered and concentrated to afford the title compound (180 mg, crude) as a yellow oil (4.0 g, 98%), which was directly used in the next step without further purification.

Step 9: Synthesis of tert-butyl (2S,4S,5S)-5-amino-2-methyltetrahydro-2H-pyran-4-ylcarbamate

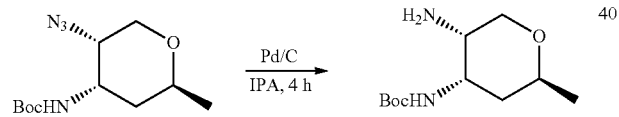

A mixture of tert-butyl (2S,4S,5S)-5-azido-2-methyltetrahydro-2H-pyran-4-ylcarbamate (1.8 g, 3.6 mmol) and 10% palladium on carbon (50 mg) in isopropanol (10 mL) was stirred at room temperature under hydrogenation overnight. After that, the mixture was filtered through a pad of celite. Concentrated to get the title compound (150 mg, crude) as a yellow oil, which was used directly for the next step without further purification.

Synthesis of 2,8-dichloro-6-(2,6-dichloro-3,5-dimethoxyphenyl)quinazoline

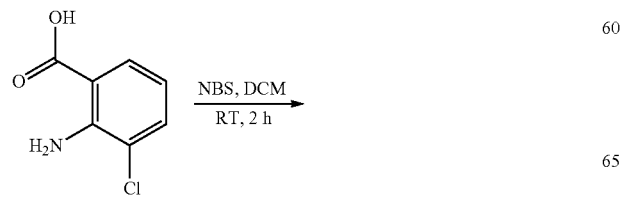

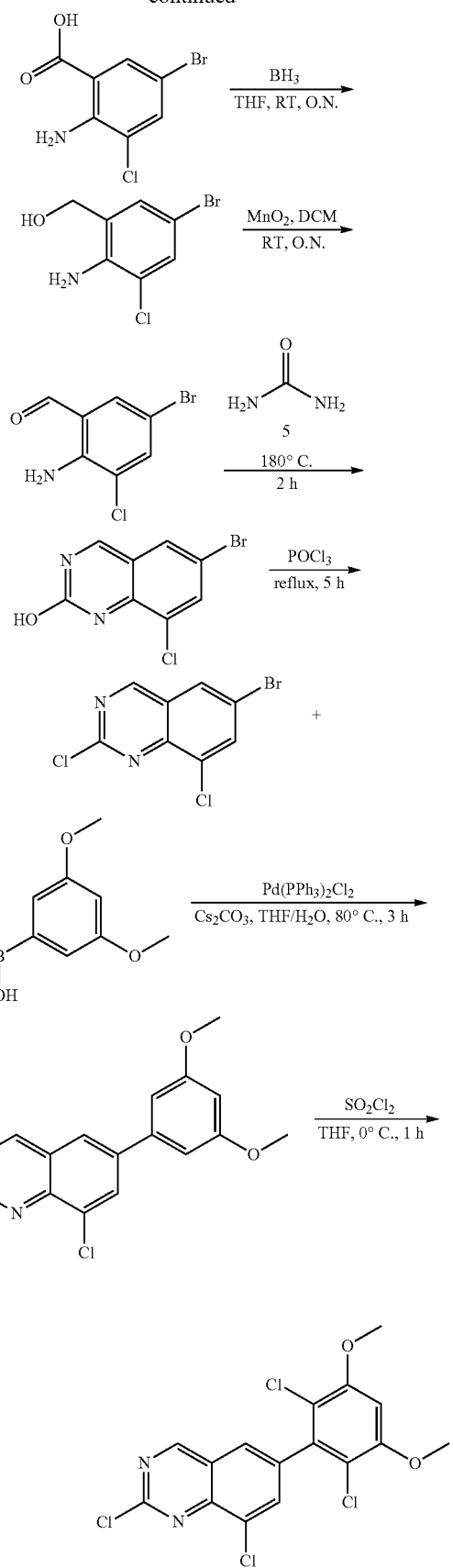

Step 1: Synthesis of 2-amino-5-bromo-3-chlorobenzoic acid

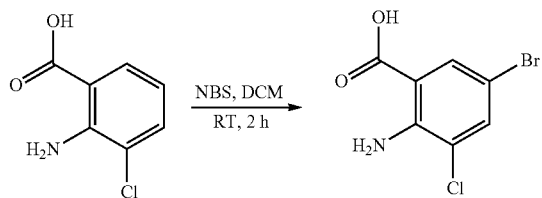 [SMILES: Nc1c(Cl)cccc1C(=O)O ; Nc1c(Cl)cc(Br)cc1C(=O)O]

To a solution of 2-amino-3-fluorobenzoic acid (10.0 g, 58.5 mmol) in dichloromethane (150 mL) was added N-bromosuccinimide (10.4 g, 58.5 mmol), and the mixture was stirred at room temperature for 2 hours. LCMS showed the reaction was completed. The solid was filtered and washed with dichloromethane (100 mL×3) to give the title compound as a white solid (13.0 g, 89%), which was directly used in the next step without further purification. MS (ES+) $C_7H_5BrClNO_2$ requires: 249, 251, found: 250, 252 $[M+H]^+$.

Step 2: Synthesis of (2-amino-5-bromo-3-chlorophenyl)methanol

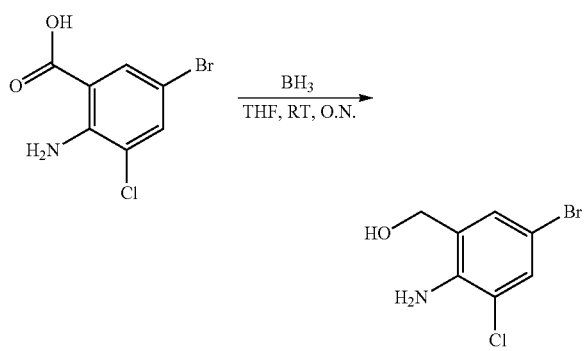

To a solution of 2-amino-5-bromo-3-chlorobenzoic acid (13.0 g, 52.0 mmol) in THF (200 mL) was added borohydride in THF (300 mL, 1N) at ice/water bath, and the reaction mixture was stirred at room temperature overnight. The mixture was quenched with methanol (100 mL) and concentrated to a volume of 50 mL. The residue was diluted with aqueous sodium bicarbonate (400 mL) and extracted with ethyl acetate (200 mL×3). The organic layers were separated, combined, washed by brine (100 mL), dried over sodium sulfate, filtered and concentrated to afford the title product (10.0 g, 82%). MS (ES+) $C_7H_7BrClNO$ requires: 234, 236, found: 236, 238 $[M+H]^+$.

Step 3: Synthesis of 2-amino-5-bromo-3-chlorobenzaldehyde

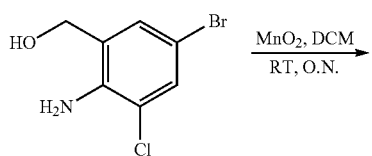

-continued

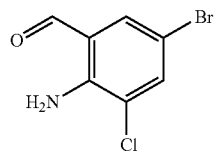

A mixture of (2-amino-5-bromo-3-chlorophenyl)methanol (10.0 g, 42.5 mmol) and manganese oxide (21.9 g, 255 mmol) in dichloromethane (400 mL) was stirred at room temperature overnight. The solid was filtered off, and the filtrate was concentrated to give the title compound as a light yellow solid (9.0 g, 91%), which was directly used in the next step without further purification.

Step 4: Synthesis of 6-bromo-8-chloroquinazolin-2-ol

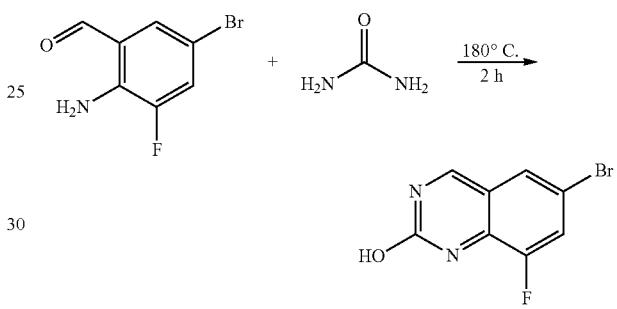

A mixture of 2-amino-5-bromo-3-chlorobenzaldehyde (9.0 g, 38.6 mmol) and urea (34.7 g, 579 mmol) was heated to 180° C. and stirred for 2 hours. The reaction mixture was cooled to room temperature, and the resulting precipitate was diluted with water (1 L) and stirred for 2 hours. The resulting precipitate was filtered, and the moisture trapped was completely removed by the co-evaporation with toluene three times. The title compound (9.0 g, 90%) was obtained as a yellow solid. MS (ES+) $C_8H_4BrClN_2O$ requires: 257, 259, found: 258, 260 $[M+H]+$.

Step 5: Synthesis of 6-bromo-2,8-dichloroquinazoline

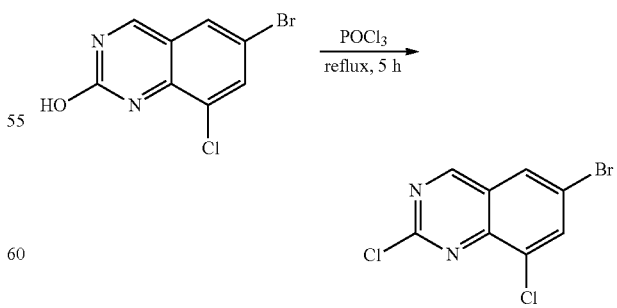

A solution of 6-bromo-8-chloroquinazolin-2-ol (9.0 g, 35 mmol) in phosphorus oxychloride (100 mL) was refluxed for 5 hours. Most of phosphorus oxychloride was removed under reduced pressure, and the residue was added to a stirring ice water (500 mL). The resulting precipitate was collected via filtration and then refluxed in THF. The solid was filtered off, and the filtrate was concentrated to give the title compound a yellow solid (7.0 g, 78%). MS (ES+) $C_8H_4BrClN_2$ requires: 275, 277, found: 276, 278 $[M+H]^+$.

Step 6: Synthesis of 2,8-dichloro-6-(3,5-dimethoxyphenyl)quinazoline

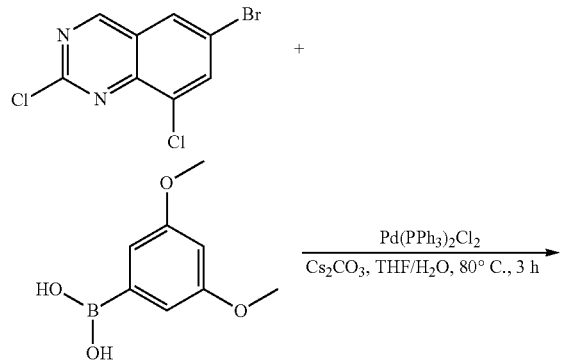

A mixture of 6-bromo-2,8-dichloroquinazoline (4.0 g, 14.5 mmol), 3,5-dimethoxyphenylboronic acid (4.23 g, 16.0 mmol), cesium carbonate (9.42 g, 29.0 mmol) and Pd(PPh$_3$)$_2$Cl$_2$ (220 mg, 0.70 mmol) in THF (200 mL) and water (10 mL) was degassed with nitrogen three times, and stirred at 80° C. for 5 hours. The reaction mixture was cooled to room temperature, directly concentrated and purified by silica gel chromatography (petroleum ether: dichloromethane=2:1~1:1) to get the title compound as a yellow solid (2.0 g, 41%). MS (ES+) $C_{16}H_{12}Cl_2N_2O_2$ requires: 334, 336, found: 335, 337 $[M+H]^+$.

Step 7: Synthesis of 2,8-dichloro-6-(2,6-dichloro-3,5-dimethoxyphenyl)quinazoline

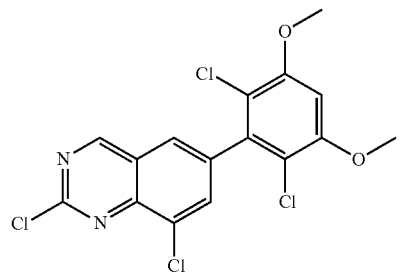

To a solution of 2,8-dichloro-6-(3,5-dimethoxyphenyl)quinazoline (2.0 g, 6.0 mmol) in dry THF (40 mL) was dropwise added sulfuryl chloride (1.59 g, 1.75 mmol) at 0° C., and the mixture was stirred for 30 min at 0° C. The reaction was quenched with water (1 mL), and the precipitate was collected via filtration to give the title compound (1.3 g, 54%) as a yellow solid. MS (ES+) $C_{16}H_{10}Cl_4N_2O_2$ requires: 402, 404, found: 403, 405 $[M+H]^+$; $^1$H-NMR (400 MHz, CDCl$_3$) δ ppm 9.36 (s, 1H), 7.94 (s, 1H), 7.79 (s, 1H), 6.69 (s, 1H), 4.01 (s, 6H).

Synthesis of 2,7-dichloro-6-(2,6-dichloro-3,5-dimethoxyphenyl)quinazoline

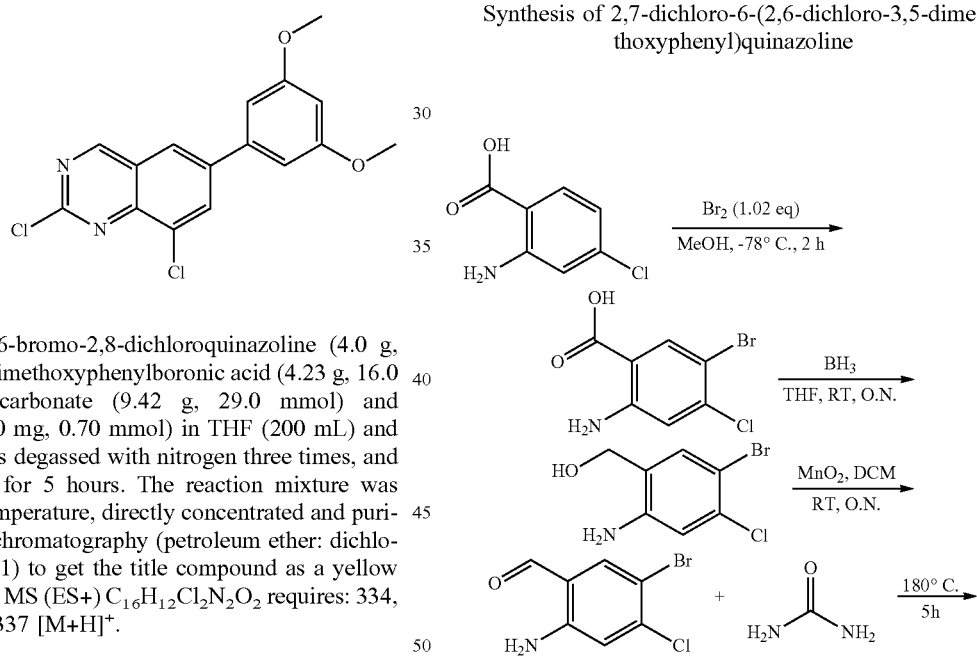

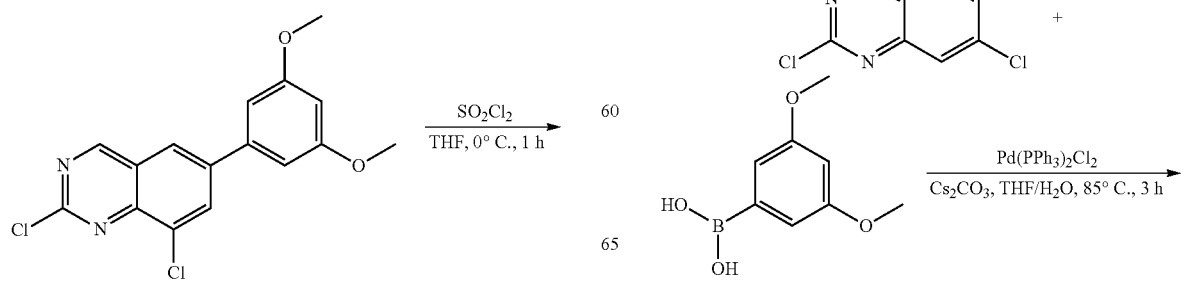

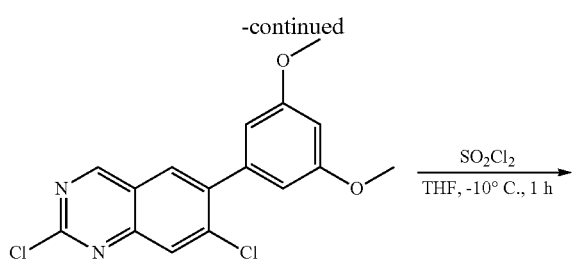

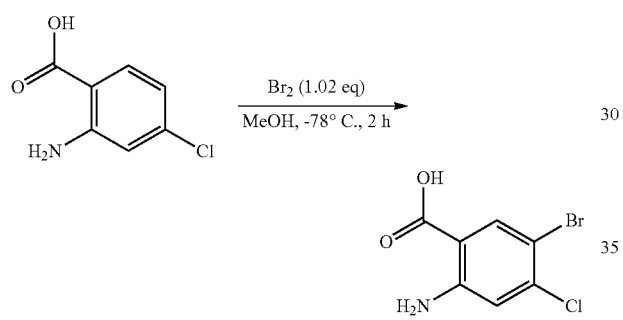

Step 1: Synthesis of 2-amino-5-bromo-4-chlorobenzoic acid

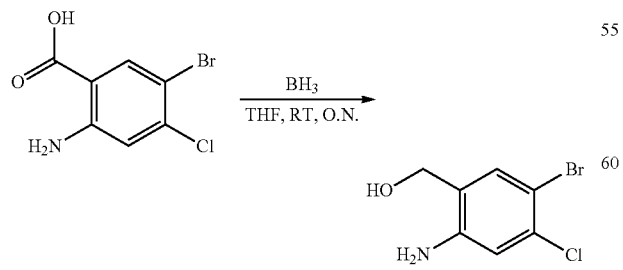

To a solution of 2-amino-4-chlorobenzoic acid (10.0 g, 58.5 mmol) in methanol (150 mL) was added bromine (15.7 mL) at −78° C., and the reaction mixture was stirred at −78° C. for 2 hours. The reaction mixture was quenched with ice water (100 mL) and aq. sodium thiosulfate, and extracted with ethyl acetate (150 mL×3). The organic layers were separated, combined, washed with water (100 mL) and brine (100 mL), dried over sodium sulfate, filtered and concentrated to afford the title compound (9 g, 62%).

Step 2: Synthesis of (2-amino-5-bromo-4-chlorophenyl)methanol

To a solution of 2-amino-5-bromo-4-chlorobenzoic acid (9.0 g, 36.0 mmol) in THF (150 mL) was added borohydride in THF (144 mL, 1 M) at room temperature, and the reaction mixture was stirred overnight. The reaction mixture was quenched with methanol (50 mL), and concentrated to a volume of 50 mL. The residue was diluted with water (100 mL) and extracted with ethyl acetate (150 mL×3). The organic layers were separated, combined, washed with water (100 mL) and brine (100 mL), dried over sodium sulfate, filtered and concentrated to afford the title compound (crude, 6 g, 71%).

Step 3: Synthesis of 2-amino-5-bromo-4-chlorobenzaldehyde

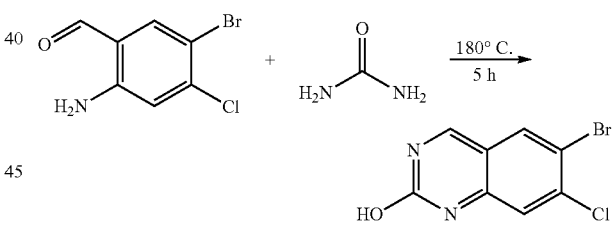

A mixture of (2-amino-5-bromo-4-chlorophenyl)methanol (6 g, 25.5 mmol) and manganese(IV) oxide (15.5 g, 0.178 mol) in dichloromethane (100 mL) was stirred at room temperature overnight. The solid was filtered off, and the filtrate was concentrated to give the title compound as a light yellow solid (5 g, 81%). MS (ES+) $C_7H_5BrClNO$ requires: 233, 235, found: 234, 236 $[M+H]^+$.

Step 4: Synthesis of 6-bromo-7-chloroquinazolin-2-ol

A mixture of 2-amino-5-bromo-4-chlorobenzaldehyde (5 g, 21.46 mmol) and urea (18 g, 300.0 mmol) was stirred at 180° C. for 5 hours. LCMS monitored the reaction was completed. The mixture was cooled to room temperature, washed with water (100 mL×3) and filtered. The filtration cake was dried to get the title compound as a yellow solid (6 g (crude, 100%). MS (ES+) $C_8H_4BrClN_2O$ requires: 258, 260, found: 259, 261 $[M+H]^+$.

Step 5: Synthesis of 6-bromo-2,7-dichloroquinazoline

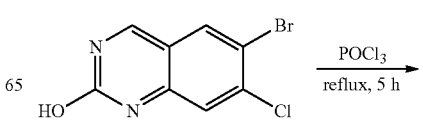

-continued

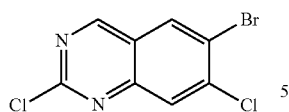

A solution of 6-bromo-7-chloroquinazolin-2-ol (6.0 g, 23 mmol) in phosphorus oxychloride (50 mL) was refluxed for 5 hours. The reaction was cooled to room temperature, and most of phosphorus oxychloride was removed under reduced pressure. The residue was dropwise added to ice water (500 mL), and the resulting precipitate was collected by the filtration to give the title compound as a yellow solid (3 g, 48%).

Step 6: Synthesis of 2,7-dichloro-6-(3,5-dimethoxyphenyl)quinazoline

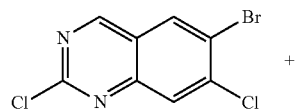

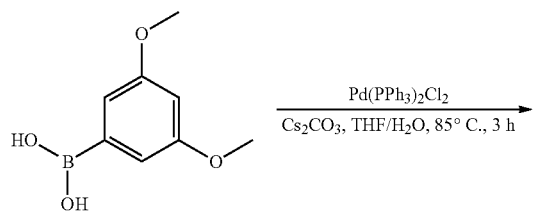

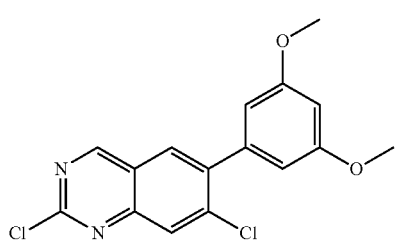

A mixture of 6-bromo-2,7-dichloroquinazoline (3 g, 10.8 mmol), 3,5-dimethoxyphenylboronic acid (2.2 g, 11.9 mmol), cesium carbonate (1.06 g, 32.4 mmol) and Pd(PPh$_3$)$_2$Cl$_2$ (702 mg, 1.08 mmol) in THF (50 mL) and water (10 mL) was degassed with nitrogen three times, and the reaction mixture was stirred at 85° C. for 3 hours. The reaction mixture was cooled to room temperature and directly concentrated. The residue was purified by silica gel chromatography (petroleum ether:ethyl acetate=10:1~4:1) to give the title compound (2.0 g, yield: 55%) as a yellowish solid. MS (ES+) requires: 334, 336, C$_{16}$H$_{12}$Cl$_2$N$_2$O$_2$, found: 335, 337 [M+H]$^+$.

Step 7: Synthesis of 2,7-dichloro-6-(2,6-dichloro-3,5-dimethoxyphenyl)quinazoline

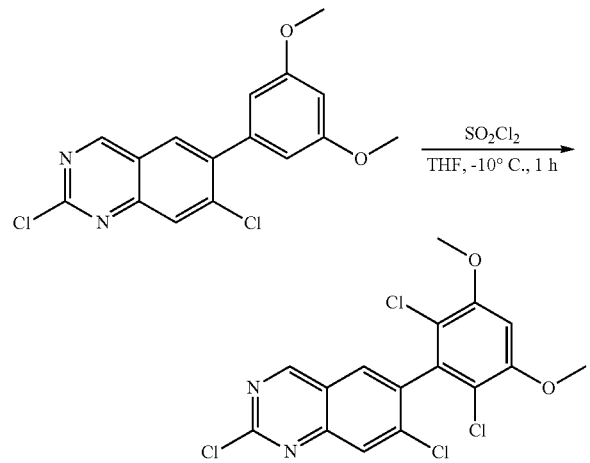

To a solution of 2,7-dichloro-6-(3,5-dimethoxyphenyl)quinazoline (2.0 g, 6.0 mmol) in THF (30 mL) was added sulfuryl chloride (1.77 g, 13.2 mmol) at −10° C., and the mixture was stirred at −10° C. for 1 hour. The solution was quenched with water (1 mL) and concentrated under reduced pressure. The residue was purified by silica gel chromatography (petroleum ether:ethyl acetate=10:1~4:1) to the title compound (1.2 g, 50%) as a white solid. MS (ES+) C$_{16}$H$_{10}$Cl$_4$N$_2$O$_2$ requires: 402, 404, found: 403, 405 [M+H]$^+$.

Step 8: Synthesis of 2-chloro-6-(2,6-dichloro-3,5-dimethoxyphenyl)pyrido[2,3-d]pyrimidine

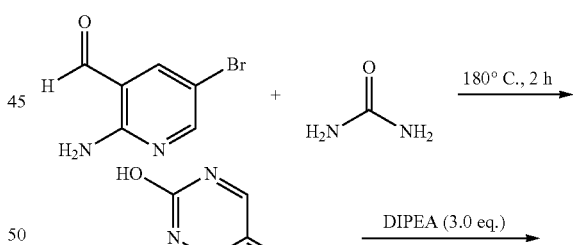

-continued

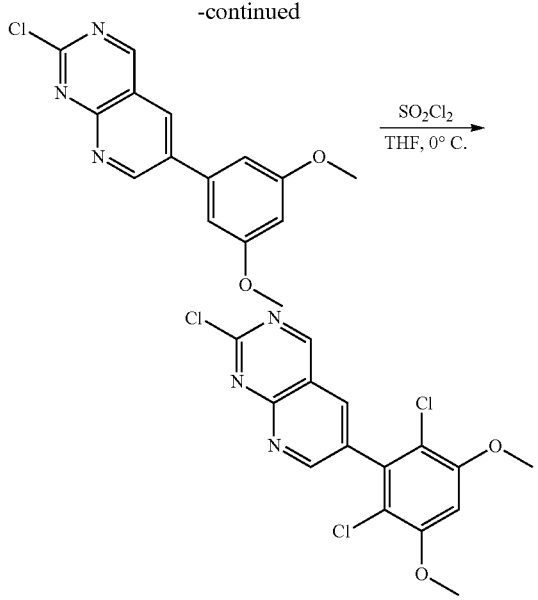

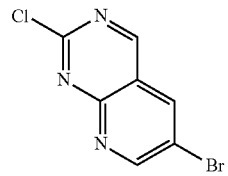

To a stirred mixture of 6-bromopyrido[2,3-d]pyrimidin-2-ol (1.1 g, 4.9 mmol) in 30 mL of phosphoryl trichloride was added diisopropylethylamine (1.6 g, 12.2 mmol) at room temperature, and the reaction mixture was then stirred at 120° C. for 12 hours. Most of phosphoryl trichloride was removed under reduced pressure. The residue was diluted with ethyl acetate (200 mL) and added to saturated sodium bicarbonate solution (300 mL) at 0° C. The mixture was extracted with ethyl acetate (200 mL×3). The combined organic layers were dried over anhydrous sodium sulfate, filtered and concentrated to afford the title compound (800 mg, 67%) as a yellow solid. MS (ES+) $C_7H_3BrClN_3$ requires: 243, 245, found: 244, 246 [M+H]$^+$.

Step 11: Synthesis of 2-chloro-6-(3,5-dimethoxyphenyl)pyrido[2,3-d]pyrimidine

Step 9: Synthesis of 6-bromopyrido[2,3-d]pyrimidin-2-ol

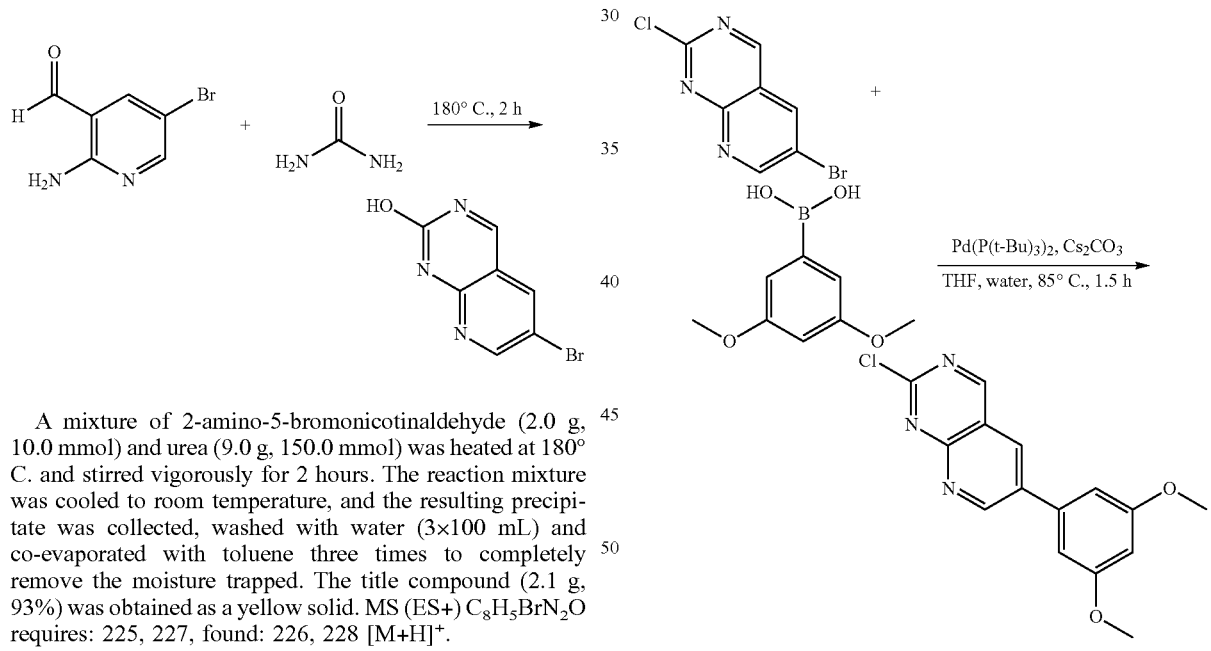

A mixture of 2-amino-5-bromonicotinaldehyde (2.0 g, 10.0 mmol) and urea (9.0 g, 150.0 mmol) was heated at 180° C. and stirred vigorously for 2 hours. The reaction mixture was cooled to room temperature, and the resulting precipitate was collected, washed with water (3×100 mL) and co-evaporated with toluene three times to completely remove the moisture trapped. The title compound (2.1 g, 93%) was obtained as a yellow solid. MS (ES+) $C_8H_5BrN_2O$ requires: 225, 227, found: 226, 228 [M+H]$^+$.

Step 10: Synthesis of 6-bromo-2-chloropyrido[2,3-d]pyrimidine

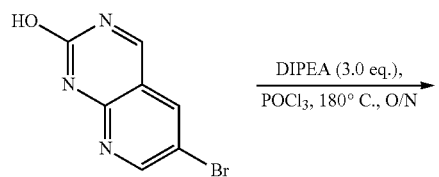

A mixture of 6-bromo-2-chloropyrido[2,3-d]pyrimidine (800 mg, 3.3 mmol), 3,5-dimethoxyphenylboronic acid (655 mg, 3.6 mmol), bis(tri-tert-butylphosphine)palladium (83 mg, 0.16 mmol) and cesium carbonate (1.06 g, 3.3 mmol) in THF (30 mL) and water (6 mL) was degassed with nitrogen for three times and then heated at 85° C. for 0.5 hour. The mixture was cooled to room temperature and concentrated under reduced pressure. The residue was purified by silica gel column chromatography (dichloromethane/ethyl acetate=3/1) to get the title product as a yellow solid (460 mg, 47%) as a yellow solid. MS (ES+) $C_{15}H_{12}ClN_3O_2$ requires: 301, 302, found: 302, 304 [M+H]$^+$.

Step 12: Synthesis of 2-chloro-6-(2,6-dichloro-3,5-dimethoxyphenyl)pyrido[2,3-d]pyrimidine

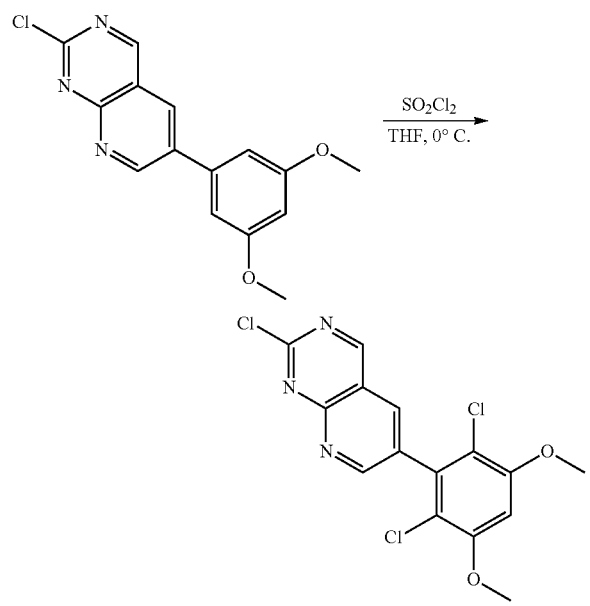

To a solution of 2-chloro-6-(3,5-dimethoxyphenyl)pyrido[2,3-d]pyrimidine (300 mg, 1.0 mmol) in THF (30 mL) was dropwise added sulfuryl chloride (337 mg, 2.5 mmol) at 0° C., and the mixture was stirred for 20 min at 0° C. The reaction mixture was quenched with water (50 mL) and extracted with ethyl acetate (100 mL×3). The combined organic layers were washed with brine (100 mL), dried over sodium sulfate, filtered and concentrated. The residue was purified by silica gel chromatography (dichloromethane/ethyl acetate=5/1) to get the title product as a tan solid (240 mg, 65%). MS (ES+) $C_{15}H_{10}Cl_3N_3O_2$ requires: 369, found: 370, 372 [M+H]$^+$.

Synthesis of 2-chloro-6-(2,6-dichloro-3,5-dimethoxyphenyl)-7-fluoroquinazoline

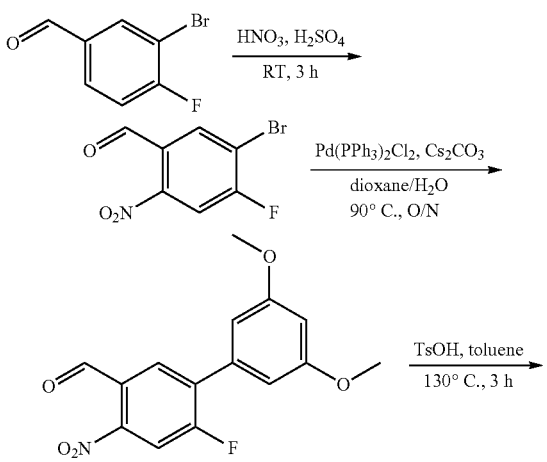

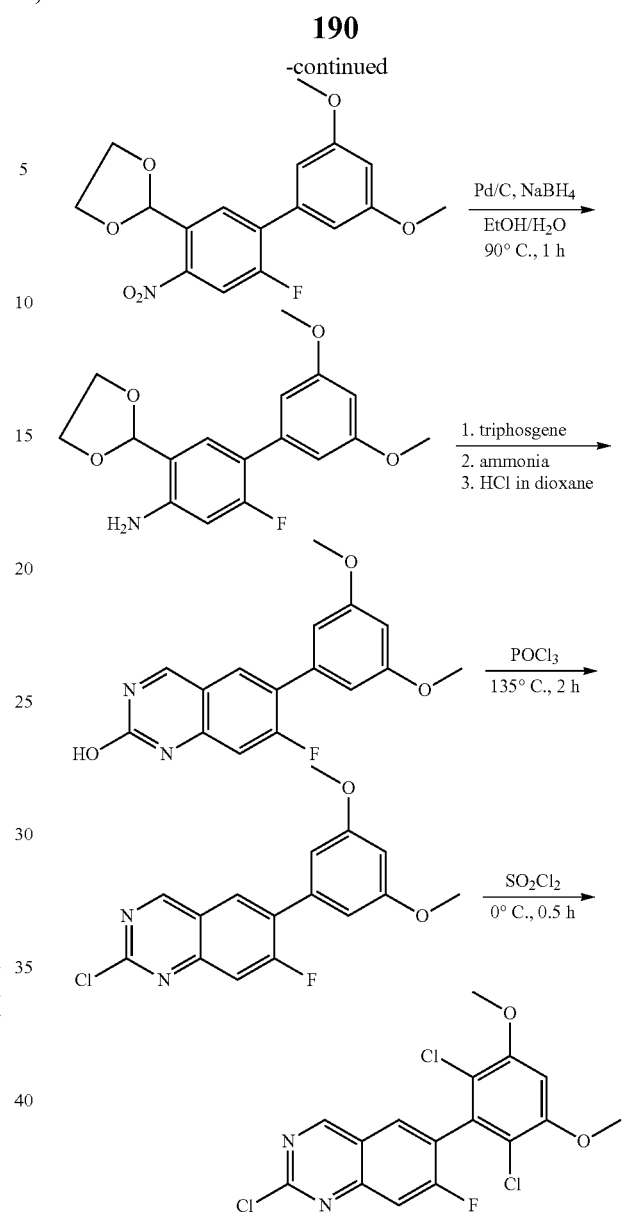

Step 1: Synthesis of 5-bromo-4-fluoro-2-nitrobenzaldehyde

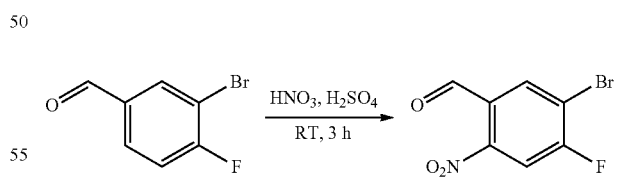

To a stirred solution of concentrated nitric acid (6.8 mL, 101.0 mmol) in concentrated sulfuric acid (60 mL) was slowly added 3-bromo-4-fluorobenzaldehyde (10 g, 49.5 mmol) at 0° C. After the addition was completed, the ice bath was removed, and the reaction was allowed to warm to room temperature and stirred for 3 hours. The mixture was poured into ice water and extracted with ethyl acetate (200 mL). The organic layer was concentrated to give the title compound as a yellow solid (crude, 12 g, 100%), which was used directly for the next step without further purification.

Step 2: Synthesis of 6-fluoro-3',5'-dimethoxy-4-nitrobiphenyl-3-carbaldehyde

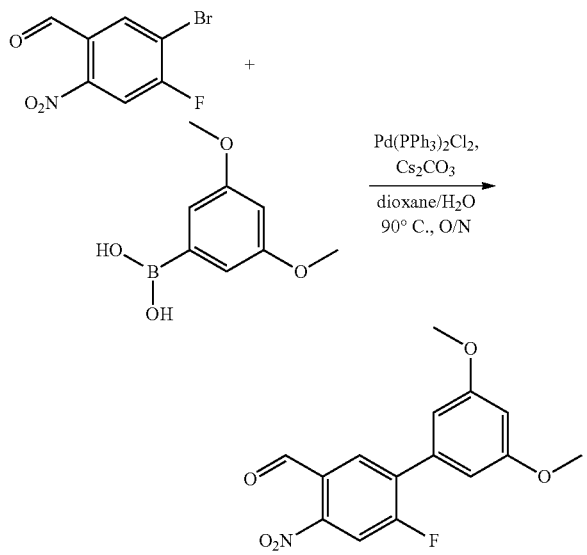

A mixture of 5-bromo-4-fluoro-2-nitrobenzaldehyde (10.0 g, 40.0 mmol), 3,5-dimethoxyphenylboronic acid (7.3 g, 40.0 mmol), bis(triphenylphosphino) palladium(II) chloride (1.4 g, 2.0 mmol) and cesium carbonate (32.6 g, 100.0 mmol) in dioxane/water (550 mL, v/v=10/1) was degassed with nitrogen for three times and heated at 90° C. for 3 hours. The mixture was cooled to room temperature, concentrated, diluted with ethyl acetate (1000 mL), and washed by water (500 mL) and brine (500 mL). The organic layer was dried, concentrated, and the residue was purified by silica gel column chromatography (petroleum ether/ethyl acetate=8/1 to 5/1) to afford the title compound (9 g, 61%) as a yellow solid. MS (ES+) $C_{15}H_{12}FNO_5$ requires: 305, found: 306 [M+H]$^+$.

Step 3: Synthesis of 2-(6-fluoro-3',5'-dimethoxy-4-nitrobiphenyl-3-yl)-1,3-dioxolane

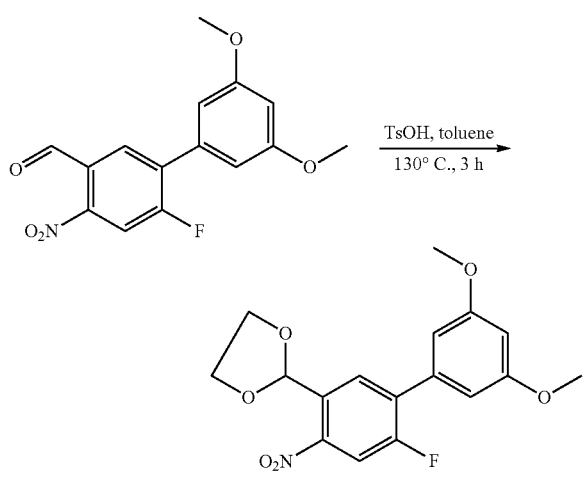

A mixture of 6-fluoro-3',5'-dimethoxy-4-nitrobiphenyl-3-carbaldehyde (1.7 g, 5.6 mmol) and 4-toluenesulfonic acid (95.8 mg, 0.6 mmol) in 1,2-ethanediol (4.3 mL) and toluene (60 mL) was heated at 130° C. for 3 hours. After that, the reaction mixture was cooled to room temperature, diluted with ethyl acetate (100 mL), and washed by water (100 mL*3) and brine (100 mL). The combined organic layers were dried over sodium sulfate, filtered and concentrated. The residue was purified by silica gel column chromatography (petroleum ether/ethyl acetate=8/1 to 5/1) to afford the title compound (1.8 g, 89%) as a yellow solid. MS (ES+) $C_{17}H_{16}FNO_6$ requires: 349, found: 350 [M+H]$^+$.

Step 4: Synthesis of 5-(1,3-dioxolan-2-yl)-2-fluoro-3',5'-dimethoxybiphenyl-4-amine

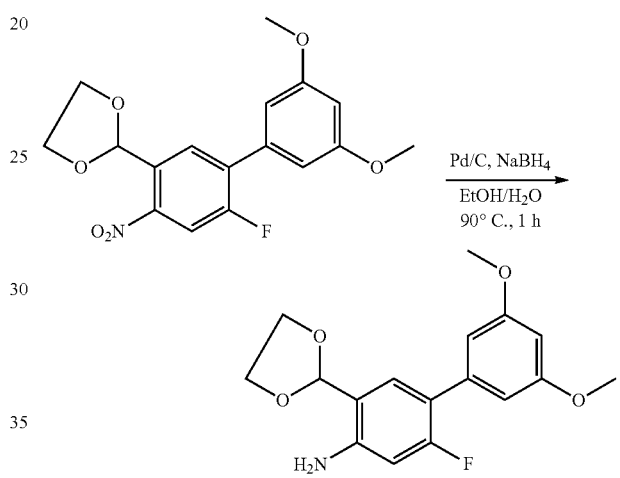

A mixture of 2-(6-fluoro-3',5'-dimethoxy-4-nitrobiphenyl-3-yl)-1,3-dioxolane (1.8 g, 5.2 mmol), sodium borohydride (587.9 mg, 15.5 mmol) and 10% palladium on carbon (0.2 g) in ethanol/water (33 mL, v/v=10/1) was heated at 90° C. for 1 hour. After that, the mixture was diluted with ethyl acetate (150 mL), and washed by water (50 mL) and brine (50 mL). The organic layer was dried over sodium, filtered and concentrated. The residue was purified by silica gel column chromatography (petroleum ether/ethyl acetate=5/1 to 4/1) to afford the title compound (1.4 g, 88%) as a yellow solid. MS (ES+) $C_{17}H_{18}FNO_4$ requires: 319, found: 320 [M+H]$^+$.

Step 5: Synthesis of 6-(3,5-dimethoxyphenyl)-7-fluoroquinazolin-2-ol

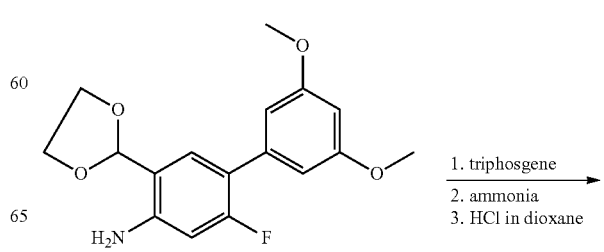

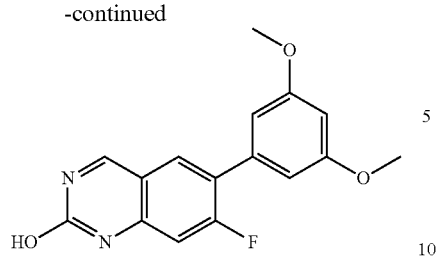

To a solution of 5-(1,3-dioxolan-2-yl)-2-fluoro-3',5'-dimethoxybiphenyl-4-amine (1.9 g, 6.0 mmol) and triethylamine (3.0 mL, 21.4 mmol) in THF (20 mL) at 0° C. was added triphosgene (0.6 g, 2.0 mmol), and stirred at 0° C. for 0.5 hour. After that, ammonia in methanol (3 mL, 21 mmol, 7 mol/L) was added. The reaction was stirred at 0° C. for 30 mins and quickly warmed to ambient temperature. After stirred for additional 30 mins at room temperature, the reaction mixture was acidified with 4 mol/L HCl in dioxane (8.2 mL) to pH 2 and then stirred at room temperature for 1 hour. Then the resultant solution was concentrated and purified by silica gel column chromatography (dichloromethane/methanol=50/1 to 10/1) to afford the title compound (2.0 g, 99%) as a yellow solid. MS (ES+) $C_{16}H_{13}FN_2O_3$ requires: 300, found: 301 $[M+H]^+$.

Step 6: Synthesis of 2-chloro-6-(3,5-dimethoxyphenyl)-7-fluoroquinazoline

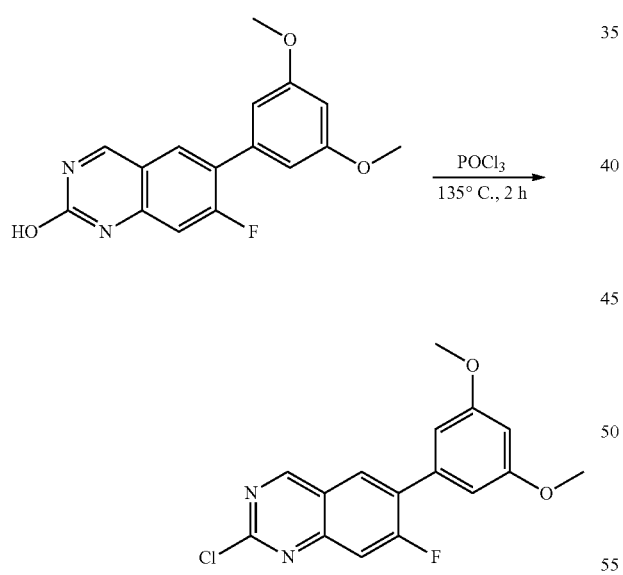

A solution of 6-(3,5-dimethoxyphenyl)-7-fluoroquinazolin-2-ol (2.0 g, 6.7 mmol) in POCl₃ (30 mL) was heated at 135° C. for 2 hours. After that, the reaction solution was cooled to room temperature and dropwise added to saturated sodium bicarbonate solution (800 mL) at 0° C. The mixture was extracted with ethyl acetate (200 mL*3). The combined organic layers were dried over anhydrous sodium sulfate, filtered and concentrated to afford the title compound (1.1 g, 52%) as a pale yellow solid. MS (ES+) $C_{16}H_{12}ClFN_2O_2$ requires: 318, found: 319 $[M+H]^+$.

Step 7: Synthesis of 2-chloro-6-(2,6-dichloro-3,5-dimethoxyphenyl)-7-fluoroquinazoline

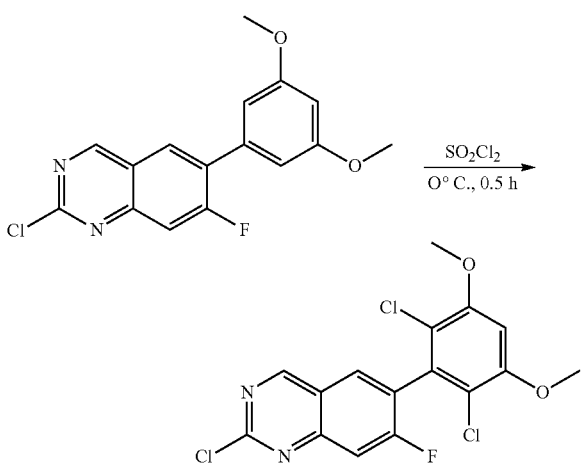

To a solution of 2-chloro-6-(3,5-dimethoxyphenyl)-7-fluoroquinazoline (1.2 g, 3.8 mmol) in acetonitrile/tetrahydrofuran (200 mL, v/v=1/1) was added sulfuryl chloride (1.7 mL, 18.9 mmol) at 0° C. The resultant solution was stirred at 0° C. for 0.5 hour. After that, the solution was concentrated and diluted with ethyl acetate (500 mL). The organic phase was washed by saturated sodium bicarbonate solution (200 mL) and brine (200 mL), dried over anhydrous sodium sulfate, filtered and concentrated to afford the title compound (946 mg, 65%) as a yellow solid. MS (ES+) $C_{16}H_{10}Cl_3FN_2O_2$ requires: 386, found: 387 $[M+H]^+$.

Step 8: Synthesis of 2-chloro-6-(2,6-dichloro-3,5-dimethoxyphenyl)-8-fluoroquinazoline

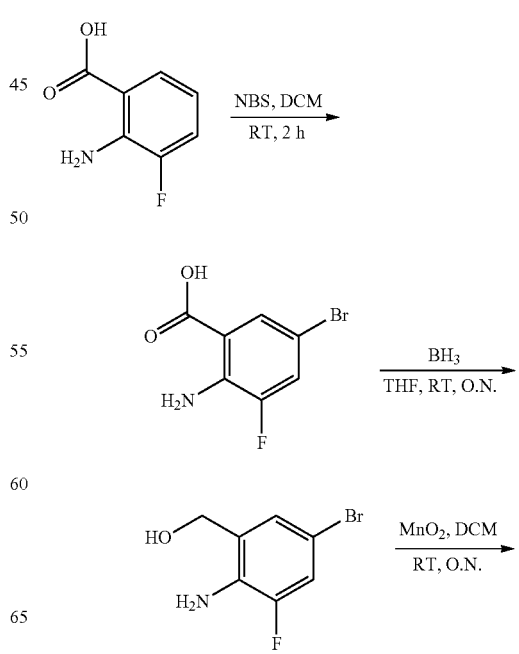

-continued

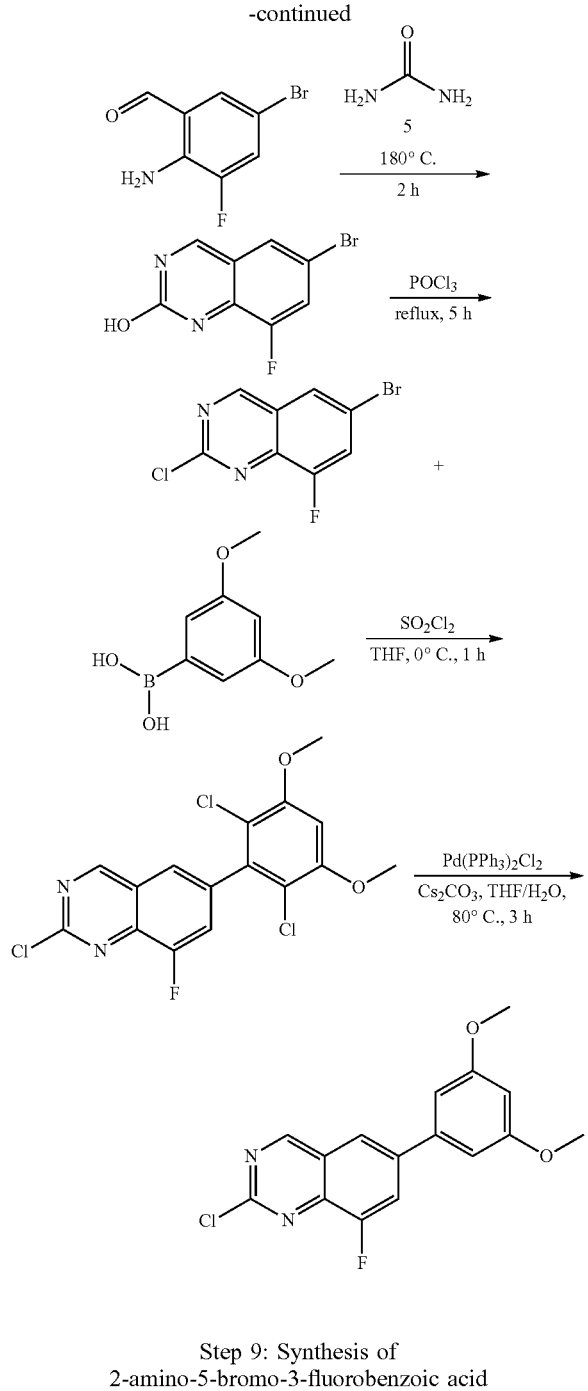

Step 9: Synthesis of 2-amino-5-bromo-3-fluorobenzoic acid

A solution of 2-amino-3-fluorobenzoic acid (10.85 g, 70 mmol) in dichloromethane (175 mL) was added N-bromosuccinimide (12.46 g, 70 mmol), and the mixture was stirred at room temperature for 2 hours. The precipitate was filtered and washed with dichloromethane (100 mL*3) to give the title compound (12.7 g, 78%) as a grey solid, which was directly used in the next step without further purification. MS (ES+) C₇H₅BrFNO₂ requires: 233, 235, found: 232, 234 [M+H]⁺.

Step 10: Synthesis of (2-amino-5-bromo-3-fluorophenyl)methanol

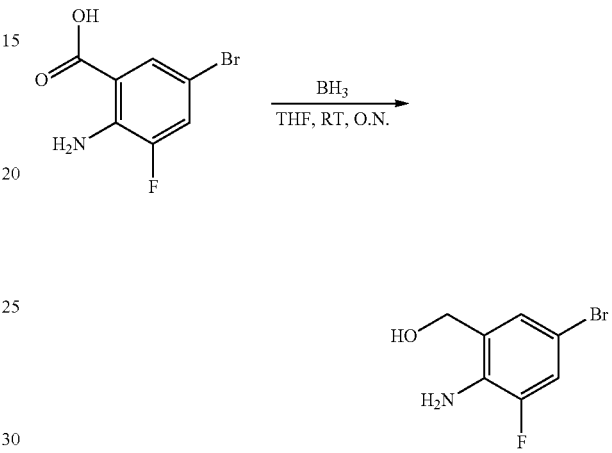

To a solution of 2-amino-5-bromo-3-fluorobenzoic acid (14.5 g, 62.2 mmol) in THF (150 mL) at 0° C. was added borohydride in THF (1 M, 310 mL), and the reaction mixture was stirred at room temperature overnight. The reaction was quenched with methanol (150 mL), concentrated in vacuum, diluted with aqueous sodium bicarbonate (400 mL) and extracted with ethyl acetate (200 mL*3). The organic layers were separated, combined, washed with water (200 mL) and brine (200 mL), dried over sodium sulfate, filtered and concentrated to afford the title compound (13.0 g, crude), which was directly used in the next step without the further purification. MS (ES+) C₇H₇BrFNO requires: 219, 221, found: 220, 222 [M+H]⁺.

Step 11: Synthesis of 2-amino-5-bromo-3-fluorobenzaldehyde

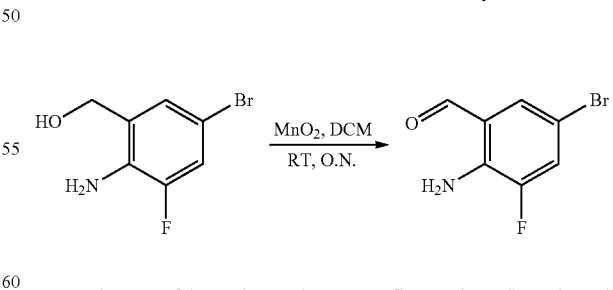

A mixture of (2-amino-5-bromo-3-fluorophenyl)methanol (13 g, 59.4 mmol) and manganese oxide (31 g, 356.4 mmol) in dichloromethane (400 mL) was stirred at room temperature overnight. The solid was filtered off, and the filtrate was concentrated to give the title compound (11 g, 85%) as a light yellow solid, which was directly used in the next step without further purification.

Step 12: Synthesis of 6-bromo-8-fluoroquinazolin-2-ol

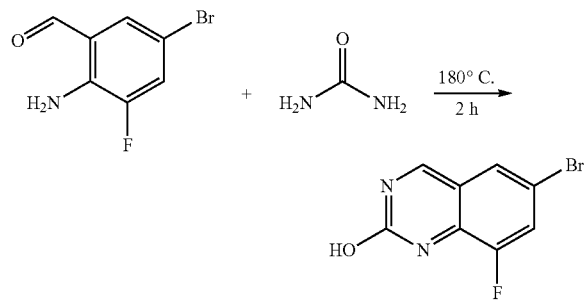

A stirred mixture of 2-amino-5-bromo-3-fluorobenzaldehyde (2.17 g, 10 mmol) and urea (9 g, 150 mmol) was heated at 180° C. for 2 hours. The reaction mixture was cooled to room temperature, and the resulting precipitate was filtered and washed with water (500 mL*3). The moisture trapped was completely removed by the co-evaporation with toluene three times. The title compound (2 g, 83%) was obtained as a yellow solid. MS (ES+) $C_8H_4BrFN_2O$ requires: 242, 244, found: 243, 245 [M+H]+.

Step 13: Synthesis of 6-bromo-2-chloroquinazoline

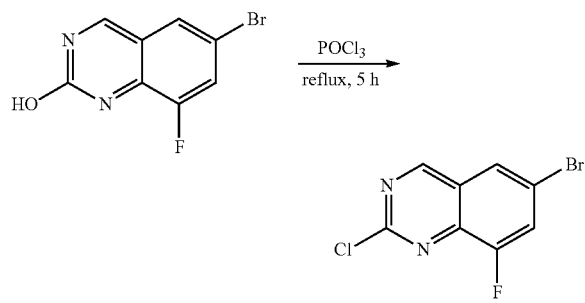

A solution of 6-bromoquinazolin-2-ol (9.72 g, 40 mmol) in phosphorus oxychloride (100 mL) was refluxed for 5 hours. The reaction was cooled to room temperature, and most of phosphorus oxychloride was removed under reduced pressure. The residue was dropwise added to ice water (500 mL), and the resulting precipitate was collected by the filtration to give the title compound (9 g, 87%) as a yellow solid. MS (ES+) $C_8H_3BrClFN_2$ requires: 260, 262, found: 261, 263 [M+H]+.

Step 14: Synthesis of 2-chloro-6-(3,5-dimethoxyphenyl)-8-fluoroquinazoline

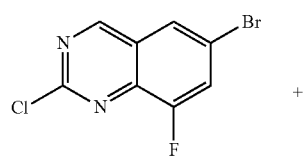

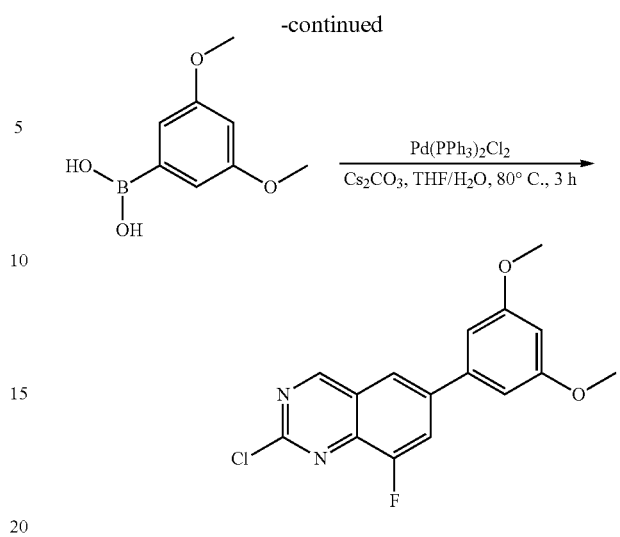

A mixture of 6-bromo-2-chloro-8-fluoroquinazoline (4.0 g, 15.4 mmol), 3,5-dimethoxyphenylboronic acid (4.47 g, 16.9 mmol), cesium carbonate (10.0 g, 30.8 mmol) and $Pd(PPh_3)_2Cl_2$ (236 mg, 0.77 mmol) in THF (200 mL) and water (10 mL) was degassed with nitrogen three times, and stirred at 80° C. for 3 hours. The reaction mixture was cooled to room temperature and directly concentrated. The residue was purified by silica gel chromatography (petroleum ether:dichloromethane=2:1 to 1:1) to afford the title compound (2.5 g, 51%) as a yellow solid. MS (ES+) $C_{16}H_{12}ClFN_2O_2$ requires: 318/320, found: 319/321 [M+H]+.

Step 15: Synthesis of 2-chloro-6-(2,6-dichloro-3,5-dimethoxyphenyl)-8-fluoroquinazoline

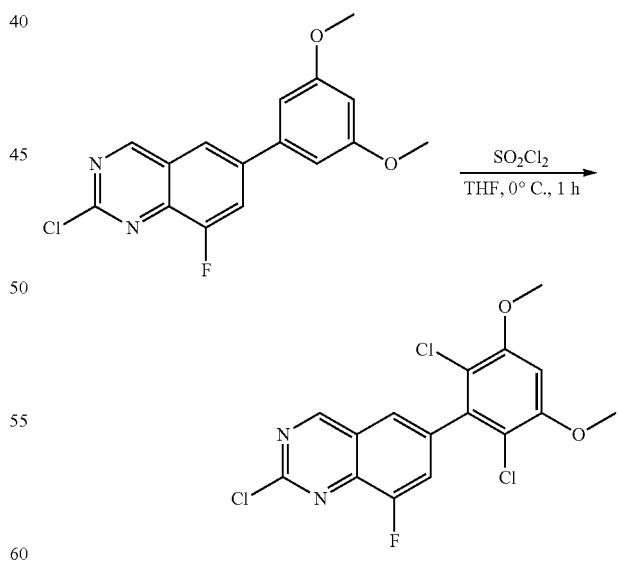

To a solution of 2-chloro-6-(3,5-dimethoxyphenyl)-8-fluoroquinazoline (1.5 g, 4.7 mmol) in dry THF (40 mL) was dropwise added sulfuryl chloride (1.59 g, 1.75 mmol) at 0° C., and the mixture was stirred for 1 hour. The reaction was quenched with water (1 mL), and the solvents were removed under reduced pressure. The residue was washed with acetonitrile and dried to give the title compound (700 mg, 38%) as a white solid. (MS (ES+) C$_{16}$H$_{10}$Cl$_3$FN$_2$O$_2$ requires: 386, 388, found: 387, 389 [M+H]$^+$.

Synthesis of 2-chloro-6-(2,6-dichloro-3,5-dimethoxyphenyl)-5-fluoroquinazoline

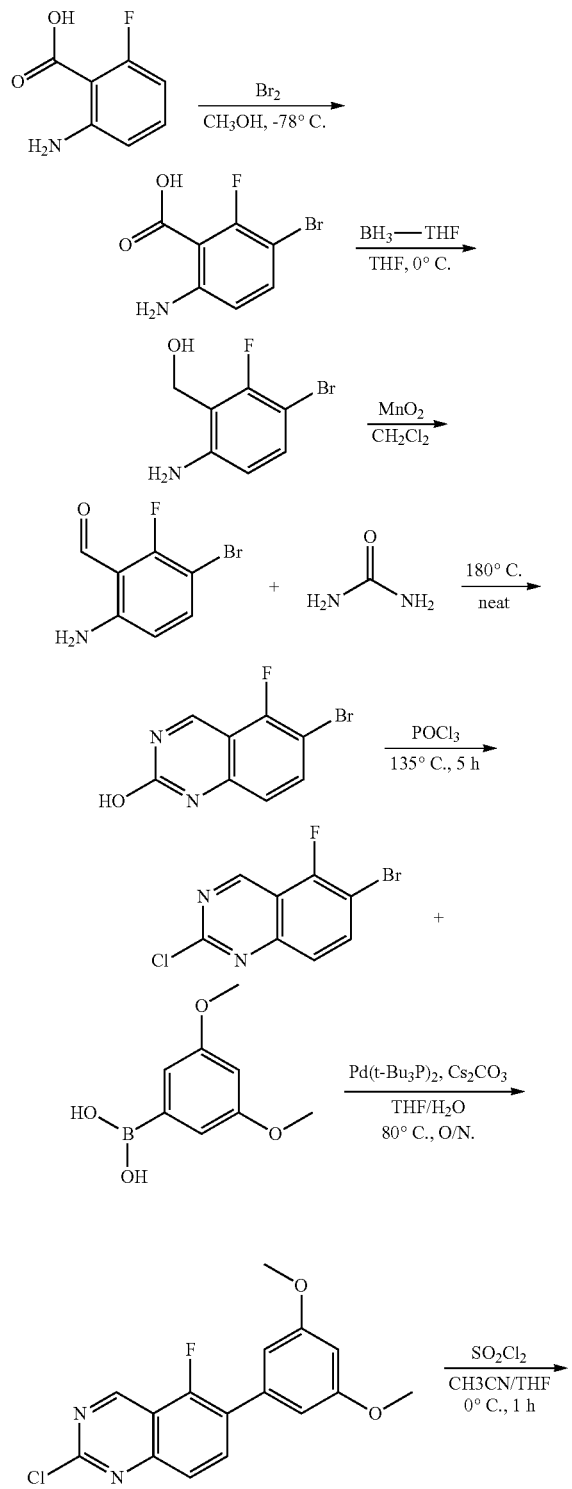

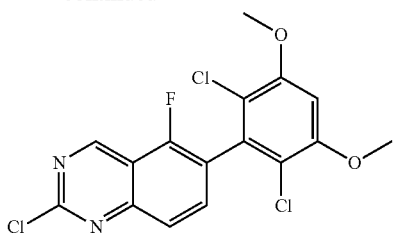

Step 1: Synthesis of 6-amino-3-bromo-2-fluorobenzoic acid

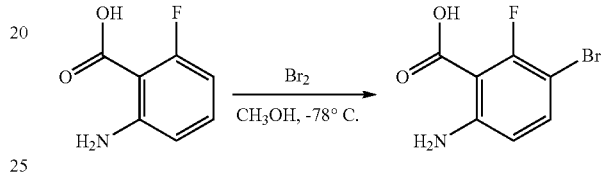

To a solution of 2-amino-6-fluorobenzoic acid (12.0 g, 77.35 mmol) in methanol (150 mL) was added bromine (15.7 mL) at −78° C., and the mixture was stirred 2 hours at −78° C. The reaction mixture was quenched with ice-water (100 mL) and aqueous solution of sodium sulfothioate, and extracted with ethyl acetate (150 mL×3). The organic layers were separated, combined, washed with water (100 mL) and brine (100 mL), dried over sodium sulfate, filtered and concentrated to afford the title crude product (9.0 g, 50%). MS (ES+) C$_7$H$_5$BrFNO$_2$ requires: 232, found: 233, 235 [M+H]$^+$.

Step 2: Synthesis of (6-amino-3-bromo-2-fluorophenyl)methanol

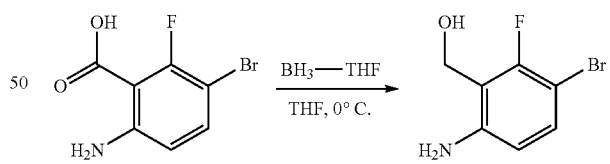

To a solution of 6-amino-3-bromo-2-fluorobenzoic acid (9.0 g, 38.46 mmol) in THF (150 mL) was added BH$_3$-THF (1 M, 193 mL) at 0° C., and the mixture was stirred at room temperature overnight. The reaction was slowly quenched with methanol (50 mL), and the solvents were removed under reduced pressure. The residue was diluted with 200 mL of ethyl acetate, washed with water (200 mL) and brine (200 mL), dried over sodium sulfate, filtered and concentrated to afford the title product (8.3 g, 98%), which was directly used in the next step without further purification. MS (ES+) C$_7$H$_7$BrFNO requires: 219, found: 220, 222 [M+H]$^+$.

Step 3: Synthesis of 6-amino-3-bromo-2-fluorobenzaldehyde

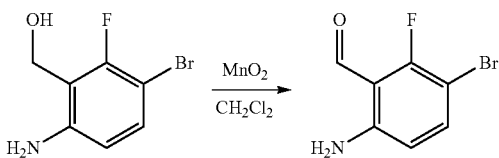

A suspension mixture of (6-amino-3-bromo-2-fluorophenyl)methanol (8.3 g, 37.72 mmol) and manganese(IV) oxide (19.68 g, 226.32 mmol) in dichloromethane (400 mL) was stirred at room temperature overnight. The solid was filtered off, and the filtrate was concentrated to give the title product as a light yellow solid (6.0 g, 73%), which was directly used in the next step without further purification. MS (ES+) $C_7H_5BrFNO$ requires: 217, found: 218, 220 $[M+H]^+$.

Step 4: Synthesis of 6-bromo-5-fluoroquinazolin-2-ol

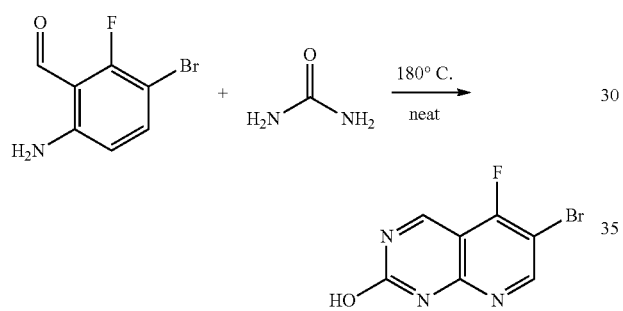

A mixture of 6-amino-3-bromo-2-fluorobenzaldehyde (3.0 g, 13.76 mmol) and urea (12.40 g, 206.40 mmol) was heated to 180° C. and stirred for 2 hours. The reaction mixture was cooled to room temperature. The resulting precipitate was collected, washed with water (3×100 mL) and co-evaporated with toluene three times to completely remove the moisture trapped. The title compound (3.3 g, 99%) was obtained as a yellow solid. MS (ES+) $C_8H_4BrFN_2O$ requires: 242, found: 243, 245 $[M+H]^+$.

Step 5: Synthesis of 6-bromo-2-chloro-5-fluoroquinazoline

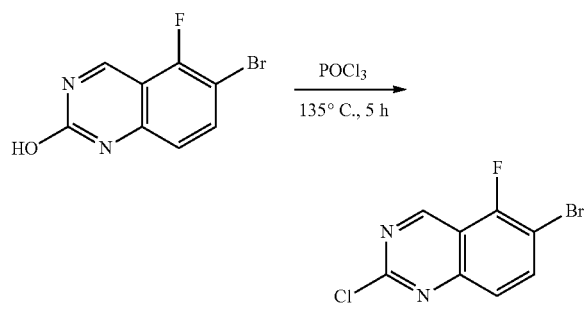

A solution of 6-bromo-5-fluoroquinazolin-2-ol (3.0 g, 12.34 mmol) in phosphoryl trichloride (10 mL) was refluxed at 135° C. for 5 hours. Most of phosphoryl trichloride was removed under reduced pressure, and the residue was dropwise added to ice water (200 mL). The resulting precipitate was collected via filtration as a yellow solid (3.1 g, 96%). MS (ES+) $C_8H_3BrClFN_2$ requires: 260, found: 261, 263 $[M+H]^+$.

Step 6: Synthesis of 2-chloro-6-(3,5-dimethoxyphenyl)-5-fluoroquinazoline

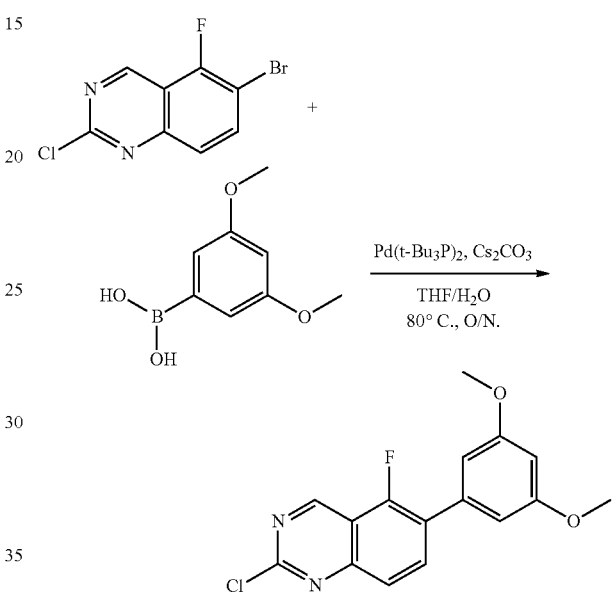

A mixture of 6-bromo-2-chloro-5-fluoroquinazoline (1.5 g, 5.74 mmol), 3,5-dimethoxyphenylboronic acid (1.15 g, 6.31 mmol), cerium carbonate (1.87 g, 5.74 mmol) and bis(tri-tert-butylphosphine)palladium (148 mg, 0.29 mmol) in THF (30 mL) and water (3 mL) was degassed with nitrogen for three times and stirred at 80° C. overnight. The mixture was cooled to room temperature and extracted with ethyl acetate (3×200 mL). The combined organic layers were washed with water and brine, dried over sodium sulfate, filtered and concentrated. The residue was purified by silica gel chromatography (petroleum ether:ethyl acetate=8:1) to get the title product as a white solid (1.3 g, 70%). MS (ES+) $C_{16}H_{12}ClFN_2O_2$ requires: 318, found: 319, 321 $[M+H]^+$.

Step 7: Synthesis of 2-chloro-6-(2,6-dichloro-3,5-dimethoxyphenyl)-5-fluoroquinazoline

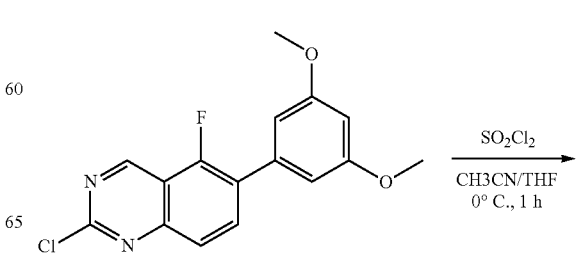

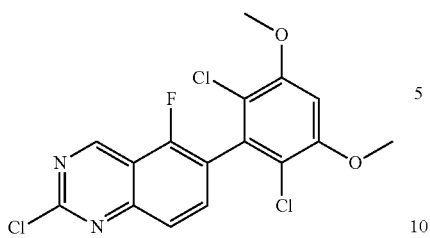

To a solution of 2-chloro-6-(3,5-dimethoxyphenyl)-5-fluoroquinazoline (1.25 g, 3.92 mmol) in dry acetontrile/THF (20 mL/10 mL) was dropwise added sulfuryl chloride (1.32 g, 9.80 mmol) at −20° C., and the mixture was stirred for 1 hour. The reaction was quenched with water (1 mL), and the solvents were removed under reduced pressure. The precipitate was washed with acetontrile and dried to give the title product (886.5 mg, 56%) as a white solid. MS (ES+) $C_{16}H_{10}Cl_3FN_2O_2$ requires: 386, found: 387, 389 [M+H]$^+$.

Synthesis of 2-chloro-6-(2,6-dichloro-3,5-dimethoxyphenyl)-7-methoxyquinazoline

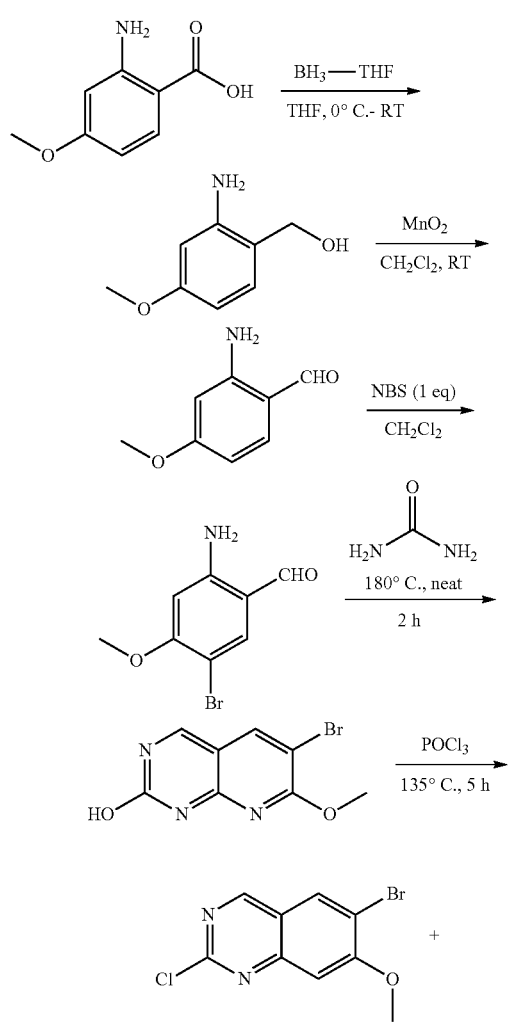

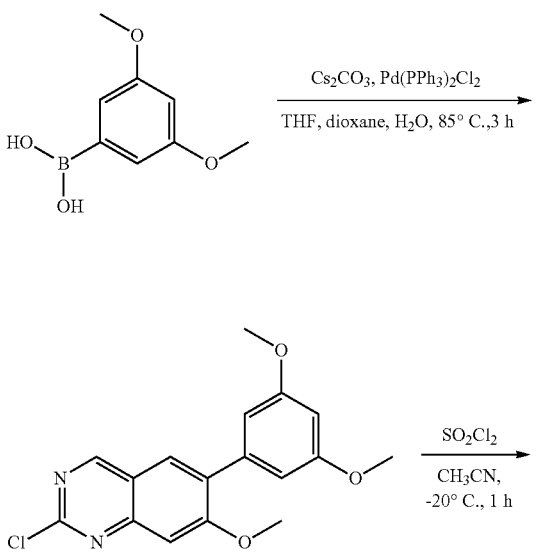

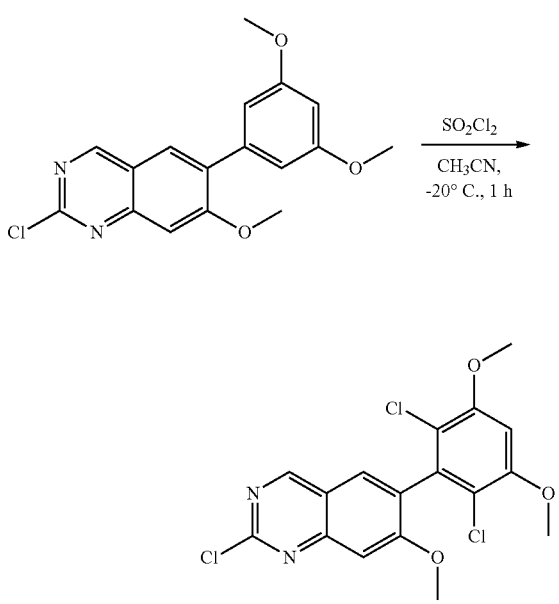

Step 1: Synthesis of (2-amino-4-methoxyphenyl)methanol

To a solution of 2-amino-4-methoxybenzoic acid (15.0 g, 89.8 mmol) in THF (300 mL) was added borohydride in THF (450 mL, 450 mmol) at 0° C., and the reaction mixture was stirred at room temperature overnight. The reaction was quenched with water (150 mL) and extracted with ethyl acetate (500 mL×3). The organic layers were separated, combined, washed with water (200 mL) and brine (200 mL), dried over sodium sulfate, filtered and concentrated to afford the title compound. MS (ES+) $C_8H_{11}NO_2$ requires: 153, found: 154 [M+H]$^+$.

Step 2: Synthesis of 2-amino-4-methoxybenzaldehyde

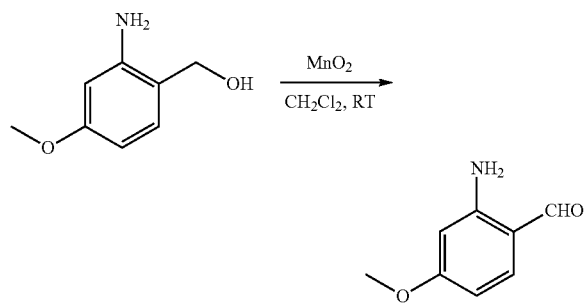

A mixture of (2-amino-4-methoxyphenyl)methanol (20 g, 131.0 mmol) and manganese oxide (68 g, 786.0 mmol) in dichloromethane (300 mL) was stirred at room temperature overnight. The solid was filtered off, and the filtrate was concentrated. The residue was purified by silica gel chromatography (petroleum ether:ethyl acetate=6:1) to give the title compound (7 g, 35%) as a yellow solid. MS (ES+) $C_8H_9NO_2$ requires: 151, found: 152 $[M+H]^+$.

Step 3: Synthesis of 2-amino-5-bromo-4-methoxybenzaldehyde

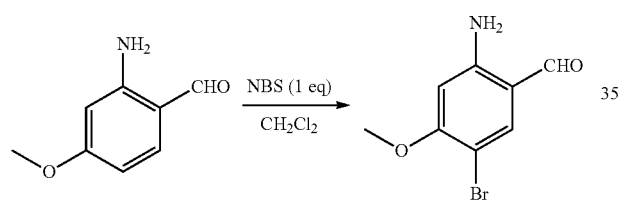

To a stirred solution of 2-amino-4-methoxybenzaldehyde (6 g, 39.7 mmol) in dichloromethane (100 mL) was added N-bromosuccinimide (7 g, 39.7 mmol). The reaction mixture was diluted with dichloromethane and water. The separated organic layer was dried sodium sulfate, filtered and concentrated to give the title compound (5 g, 56%) as a yellow solid. MS (ES+) $C_8H_8BrNO_2$ requires: 229, 231, found: 230, 232 $[M+H]^+$.

Step 4: Synthesis of 6-bromo-7-methoxyquinazolin-2-ol

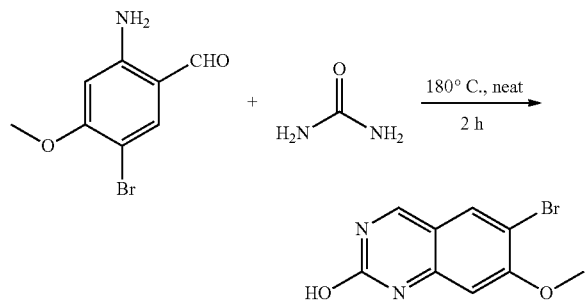

A mixture of 2-amino-5-bromo-4-methoxybenzaldehyde (3 g, 13.1 mmol) and urea (12 g, 196.5 mmol) was stirred at 180° C. for 2 hours. The reaction mixture was cooled to room temperature and washed with water (3×100 mL). The precipitate was collected and dried to give the title compound (3 g, crude) as a yellow solid. MS (ES+) $C_8H_7BrN_2O_2$ requires: 254, 256, found: 255, 257 $[M+H]^+$.

Step 5: Synthesis of 6-bromo-2-chloro-7-methoxyquinazoline

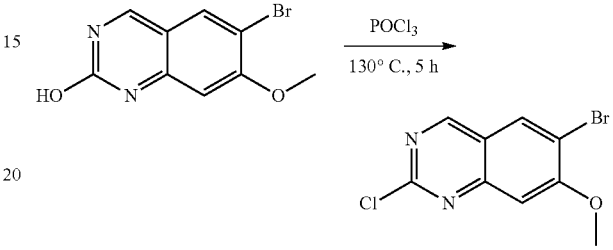

To a solution of 6-bromo-7-methoxyquinazolin-2-ol (3.0 g, 11.8 mmol) in phosphoryl trichloride (30 mL) was refluxed at 130° C. for 5 hours. The reaction was cooled to room temperature, and most of phosphoryl trichloride was evaporated. The residue was dropwise added to ice water (100 mL), and the resulting precipitate was collected via filtration to give the title compound as a yellow solid (2.4 g, 75%). MS (ES+) $C_9H_6BrClN_2O$ requires: 272, 274, found: 273, 275 $[M+H]^+$.

Step 6: Synthesis of 2-chloro-6-(3,5-dimethoxyphenyl)-7-methoxyquinazoline

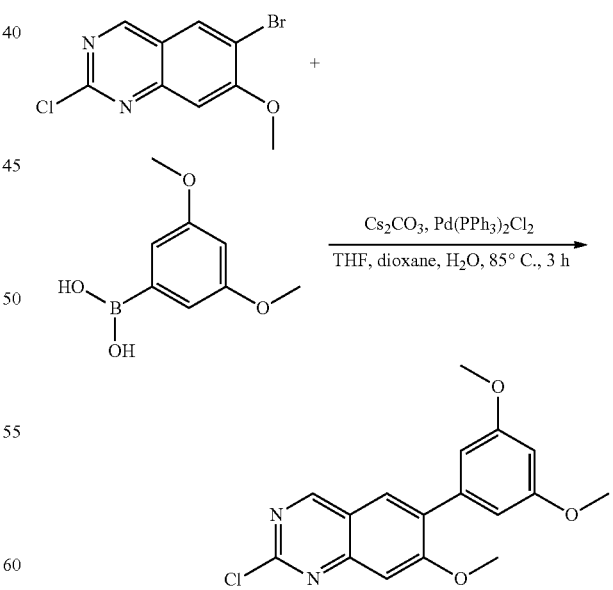

A mixture of 6-bromo-2-chloro-7-methoxyquinazoline (2.4 g, 8.82 mmol), 3,5-dimethoxyphenylboronic acid (1.6 g, 8.82 mmol), cerium carbonate (8.6 g, 26.46 mmol) and $Pd(PPh_3)_2Cl_2$ (1.4 g, 2.1 mmol) in THF (10 mL), dioxane (10 mL) and water (2 mL) was degassed with nitrogen three times and stirred at 85° C. for 3 hours. The mixture was cooled to room temperature and extracted with dichloromethane (3×50 mL). The organic layers were separated, combined, washed with water and brine, dried over sodium sulfate, filtered and concentrated. The residue was purified by silica gel chromatography (petroleum ether: ethyl acetate=1:4) to give the title compound (1.1 g, 38%) as a white solid. MS (ES+) $C_{17}H_{15}ClN_2O_3$ requires: 330, 332, found: 331, 333 [M+H]$^+$.

Step 7: Synthesis of 2-chloro-6-(2,6-dichloro-3,5-dimethoxyphenyl)-7-methoxyquinazoline

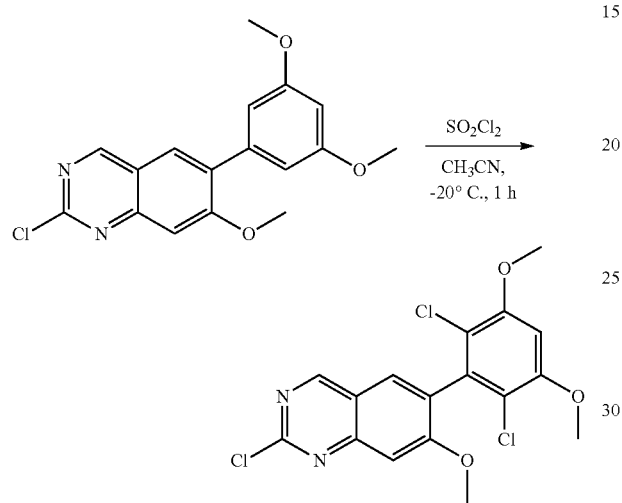

To a solution of 2-chloro-6-(3,5-dimethoxyphenyl)-7-methoxyquinazoline (200 mg, 0.61 mmol) in acetonitrile (5 mL) was added sulfuryl chloride (205 mg, 1.52 mmol), and the mixture was stirred at −20° C. for 1 hour. The reaction was quenched with water (1 mL) and concentrated under reduced pressure. The precipitate was washed by acetonitrile and dried to give the title compound as a white solid (120 mg, 50%). MS (ES+) $C_{17}H_{13}Cl_3N_2O_3$ requires: 398, found: 399, 401 [M+H]$^+$.

NMR and LC-MS data for certain compounds is shown in the table below. The synthetic protocol used to prepare the compounds is also indicated.

| Compound Number | Synthetic Protocol | $^1$H NMR | LC-MS (M + 1) |
|---|---|---|---|
| 1 | 1 | | 358 |
| 2 | 1 | 1H NMR (400 MHz, DMSO-d6) δ 9.19 (s, 1H), 8.47 (d, J = 8.0 Hz, 1H), 8.12 (s, 1H), 8.01 (d, J = 2.2 Hz, 1H), 7.96-7.84 (m, 2H), 7.82 (dd, J = 8.7, 2.1 Hz, 1H), 7.69 (d, J = 8.3 Hz, 1H), 7.62-7.45 (m, 2H), 7.12 (d, J = 8.1 Hz, 1H), 4.45 (s, 1H), 4.34 (s, 1H), 1.97 (dd, J = 17.7, 9.8 Hz, 3H), 1.81-1.62 (m, 3H), 1.56 (s, 1H). | 423 |
| 3 | 2 | 1H NMR (400 MHz, DMSO-d6) δ 9.19 (s, 1H), 8.47 (d, J = 8.0 Hz, 1H), 8.12 (s, 1H), 8.01 (d, J = 2.2 Hz, 1H), 7.96-7.84 (m, 2H), 7.82 (dd, J = 8.7, 2.1 Hz, 1H), 7.69 (d, J = 8.3 Hz, 1H), 7.62-7.45 (m, 2H), 7.12 (d, J = 8.1 Hz, 1H), 4.45 (s, 1H), 4.34 (s, 1H), 1.97 (dd, J = 17.7, 9.8 Hz, 3H), 1.81-1.62 (m, 3H), 1.56 (s, 1H). | 434 |
| 4 | 1 | $^1$H NMR (400 MHz, DMSO-d$_6$) δ 9.11 (s, 1H), 8.41 (d, J = 8.0 Hz, 1H), 7.77 (d, J = 1.9 Hz, 1H), 7.59 (dd, J = 8.6, 2.0 Hz, 1H), 7.49 (d, J = 8.7 Hz, 1H), 7.36 (dd, J = 9.0, 1.8 Hz, 1H), 7.21 (t, J = 9.0 Hz, 1H), 7.09 (d, J = 8.0 Hz, 1H), 4.39 (s, 1H), 4.28 (s, 1H), 3.84 (s, 3H), 1.91 (m, 1H), 1.88 (m, 1H), 1.71 (m, 1H), 1.62 (m, 2H), 1.51 (s, 1H). | 439 |
| 5 | 1 | | 439 |
| 6 | 1 | $^1$H NMR (400 MHz, DMSO-d$_6$) δ 9.11 (s, 1H), 8.41 (d, J = 8.0 Hz, 1H), 7.75 (s, 1H), 7.64-7.43 (m, 2H), 7.26 (t, J = 9.0 Hz, 1H), 7.17 (dd, J = 9.3, 5.0 Hz, 1H), 7.07 (d, J = 8.1 Hz, 1H), 4.39 (m, 1H), 4.28 (m, 1H), 4.11 (q, J = 7.0 Hz, 2H), 4.03 (s, 1H), 1.89 (m, 2H), 1.67 (m, 3H), 1.50 (m, 1H), 1.32 (t, J = 7.0 Hz, 3H). | 453 |
| 7 | 2 | $^1$H NMR (400 MHz, DMSO-d$_6$) δ 9.17 (s, 1H), 8.44 (dd, J = 20.1, 6.1 Hz, 2H), 7.81 (d, J = 2.1 Hz, 1H), 7.78-7.71 (m, 3H), 7.54 (d, J = 8.6 Hz, 1H), 7.40 (d, J = 8.5 Hz, 1H), 7.05 (d, J = 8.1 Hz, 1H), 4.51-4.40 (m, 1H), 4.33 (m, 1H), 2.85 (tq, J = 7.9, 4.1 Hz, 1H), 2.31 (s, 3H), 1.96 (m, 2H), 1.84-1.62 (m, 3H), 1.55 (m, 1H), 0.67 (m, 2H), 0.56 (m, 2H). | 454 |
| 8 | 3 | 1H NMR (400 MHz, DMSO-d6) δ 9.17 (s, 1H), 8.06 (d, J = 8.3 Hz, 1H), 7.86 (d, J = 2.1 Hz, 1H), 7.75 (dd, J = 8.7, 2.1 Hz, 1H), 7.52 (d, J = 8.7 Hz, 1H), 7.15 (d, J = 7.9 Hz, 1H), 6.75 (d, J = 2.8 Hz, 1H), 6.61 (d, J = 2.8 Hz, 1H), 6.21 (dd, J = 17.1, 10.2 Hz, 1H), 6.00 (dd, J = 17.1, 2.2 Hz, 1H), 5.54 (dd, J = 10.2, 2.2 Hz, 1H), 4.78 (p, J = 6.8 Hz, 1H), 4.65 (dt, J = 12.8, 6.1 Hz, 1H), 4.09 (dd, J = 8.6, 6.9 Hz, 1H), 4.04-3.98 (m, 1H), 3.88 (s, 3H), 3.80 (s, 3H), 3.68 (ddd, J = 14.0, 8.8, 5.7 Hz, 2H). | 455 |
| 9 | 2 | $^1$H NMR (400 MHz, DMSO-d$_6$) δ 9.14 (s, 1H), 8.42 (d, J = 4.3 Hz, 1H), 7.83 (d, J = 8.0 Hz, 1H), 7.80 (d, J = 2.1 Hz, 1H), 7.78-7.69 (m, 3H), 7.52 (d, J = 8.6 Hz, 1H), 7.40 (d, J = 8.5 Hz, 1H), 7.00 (d, J = 7.8 Hz, 1H), 6.20 (dd, J = 17.1, 10.1 Hz, 1H), 6.00 (dd, J = 17.1, 2.3 Hz, 1H), 5.52 (dd, J = 10.2, 2.3 Hz, 1H), 4.50-4.43 (m, 1H), 4.38 (q, J = 6.6 Hz, 1H), 2.85 (td, J = 7.3, 3.7 Hz, 1H), 2.31 (s, 3H), 2.06-1.97 (m, 1H), 1.93 (dd, J = 12.4, 6.4 Hz, 1H), 1.76 (d, J = 5.9 Hz, 1H), 1.75-1.55 (m, 3H), 0.73-0.63 (m, 2H), 0.60-0.51 (m, 2H). | 456 |
| 10 | 2 | 1H NMR (400 MHz, DMSO-d6) δ 9.14 (s, 1H), 8.54 (t, J = 5.7 Hz, 1H), 8.42 (d, J = 7.9 Hz, 1H), 8.15 (d, J = 2.2 Hz, 1H), 8.07 (dd, J = 8.8, 2.2 Hz, 1H), 7.75 (s, 1H), 7.51 (d, J = 8.8 Hz, 1H), 7.41-7.30 (m, 2H), 7.02 (d, J = 8.1 Hz, 1H), 4.44- | 458 |

| Compound Number | Synthetic Protocol | ¹H NMR | LC-MS (M + 1) |
|---|---|---|---|
| | | 4.36 (m, 1H), 4.31-4.22 (m, 1H), 4.03 (s, 1H), 3.84 (s, 3H), 1.89 (dq, J = 15.6, 7.7, 6.3 Hz, 2H), 1.77-1.57 (m, 3H), 1.50 (dd, J = 9.4, 5.1 Hz, 1H), 1.20 (d, J = 6.6 Hz, 1H), 1.10 (t, J = 7.2 Hz, 3H). | |
| 11 | 2 | ¹H NMR (400 MHz, DMSO-d6) δ 9.18 (s, 1H), 8.61 (t, J = 5.6 Hz, 1H), 8.46 (d, J = 8.0 Hz, 1H), 7.94 (dd, J = 13.2, 2.1 Hz, 2H), 7.83 (ddd, J = 21.0, 8.5, 2.2 Hz, 2H), 7.68 (d, J = 8.4 Hz, 1H), 7.55 (t, J = 8.3 Hz, 1H), 7.10 (d, J = 8.1 Hz, 1H), 6.76 (d, J = 7.9 Hz, 1H), 4.51-4.39 (m, 1H), 4.33 (s, 1H), 2.95 (s, 2H), 2.05-1.82 (m, 1H), 1.82-1.63 (m, 3H), 1.54 (d, J = 7.9 Hz, 1H), 1.29-1.20 (m, 3H), 0.91-0.77 (m, 1H). | 462 |
| 12 | 2 | ¹H NMR (400 MHz, DMSO-d6) δ 11.93 (s, 1H), 9.19 (s, 1H), 8.92 (s, 1H), 8.48 (d, J = 7.9 Hz, 1H), 7.94 (d, J = 2.1 Hz, 1H), 7.87 (d, J = 2.1 Hz, 1H), 7.81 (td, J = 8.8, 2.1 Hz, 2H), 7.72 (d, J = 8.4 Hz, 1H), 7.56 (d, J = 8.9 Hz, 1H), 7.14 (d, J = 7.9 Hz, 1H), 4.39 (d, J = 46.7 Hz, 2H), 3.72 (s, 3H), 2.03-1.85 (m, 1H), 1.83-1.64 (m, 2H), 1.61-1.50 (m, 1H), 1.41 (ddd, J = 17.0, 11.1, 6.3 Hz, 1H), 0.88-0.78 (m, 1H). | 464 |
| 13 | 2 | ¹H NMR (400 MHz, DMSO-d6) δ 9.18 (s, 1H), 8.53 (d, J = 4.1 Hz, 1H), 8.46 (d, J = 8.0 Hz, 1H), 8.18 (d, J = 2.2 Hz, 1H), 8.10 (dd, J = 8.8, 2.2 Hz, 1H), 7.75 (d, J = 1.5 Hz, 1H), 7.55 (d, J = 8.7 Hz, 1H), 7.42 (t, J = 2.0 Hz, 1H), 7.35 (t, J = 1.8 Hz, 1H), 7.06 (d, J = 8.1 Hz, 1H), 4.49-4.40 (m, 1H), 4.31 (m, 1H), 3.88 (s, 3H), 2.87 (dd, J = 7.4, 3.8 Hz, 1H), 1.93 (m, 2H), 1.81-1.60 (m, 3H), 1.55 (m, 1H), 0.71 (dt, J = 6.8, 3.3 Hz, 2H), 0.59 (p, J = 4.5 Hz, 2H). | 470 |
| 14 | 3 | | 471 |
| 15 | 3 | 1H NMR (400 MHz, DMSO-d6) δ 9.13 (s, 1H), 8.48 (d, J = 8.1 Hz, 1H), 7.87 (d, J = 8.5 Hz, 1H), 7.65 (s, 1H), 7.54-7.44 (m, 2H), 7.00 (s, 1H), 6.28-6.12 (m, 1H), 6.04 (dd, J = 17.1, 2.3 Hz, 1H), 5.56 (dd, J = 10.1, 2.3 Hz, 1H), 4.66-4.51 (m, 1H), 4.51-4.32 (m, 1H), 3.97 (s, 6H), 2.22-1.93 (m, 2H), 1.77-1.47 (m, 2H). | 473 |
| 16 | 2 | 1H NMR (400 MHz, DMSO-d6) δ 9.19 (s, 1H), 8.57 (d, J = 4.3 Hz, 1H), 8.46 (d, J = 8.0 Hz, 1H), 7.93 (dd, J = 8.4, 2.2 Hz, 2H), 7.83 (ddd, J = 20.7, 8.5, 2.2 Hz, 2H), 7.69 (d, J = 8.3 Hz, 1H), 7.55 (d, J = 8.8 Hz, 1H), 7.12 (d, J = 8.1 Hz, 1H), 4.45 (s, 1H), 4.34 (s, 1H), 3.61 (dd, J = 18.4, 11.5 Hz, 1H), 3.15 (dd, J = 7.3, 4.4 Hz, 2H), 2.86 (td, J = 7.3, 3.7 Hz, 2H), 1.95 (d, J = 8.2 Hz, 3H), 1.87-1.61 (m, 3H), 1.56 (s, 1H). | 474 |
| 17 | 2 | ¹H NMR (400 MHz, DMSO-d6) δ 9.18 (s, 1H), 8.57 (d, J = 4.2 Hz, 1H), 7.93 (dd, J = 8.6, 2.2 Hz, 2H), 7.83 (ddd, J = 19.8, 8.6, 2.2 Hz, 2H), 7.69 (d, J = 8.4 Hz, 1H), 7.52 (dd, J = 21.6, 8.4 Hz, 2H), 7.07 (s, 1H), 4.47-4.38 (m, 1H), 4.36-4.20 (m, 1H), 2.86 (td, J = 7.3, 3.7 Hz, 1H), 2.01 (qd, J = 7.5, 2.7 Hz, 3H), 1.88 (dd, J = 12.1, 6.9 Hz, 1H), 1.82-1.50 (m, 3H), 1.25 (q, J = 7.1, 6.6 Hz, 1H), 1.14 (d, J = 13.2 Hz, 1H), 0.88 (t, J = 7.6 Hz, 2H), 0.69 (dt, J = 6.9, 3.3 Hz, 2H), 0.61-0.51 (m, 2H). | 478 |
| 18 | 1 | 1H NMR (400 MHz, DMSO-d6) δ 9.18 (s, 1H), 8.57 (d, J = 4.2 Hz, 1H), 7.93 (dd, J = 8.6, 2.2 Hz, 2H), 7.83 (ddd, J = 19.8, 8.6, 2.2 Hz, 2H), 7.69 (d, J = 8.4 Hz, 1H), 7.52 (dd, J = 21.6, 8.4 Hz, 2H), 7.07 (s, 1H), 4.47-4.38 (m, 1H), 4.36-4.20 (m, 1H), 2.86 (td, J = 7.3, 3.7 Hz, 1H), 2.01 (qd, J = 7.5, 2.7 Hz, 3H), 1.88 (dd, J = 12.1, 6.9 Hz, 1H), 1.82-1.50 (m, 3H), 1.25 (q, J = 7.1, 6.6 Hz, 1H), 1.14 (d, J = 13.2 Hz, 1H), 0.88 (t, J = 7.6 Hz, 2H), 0.69 (dt, J = 6.9, 3.3 Hz, 2H), 0.61-0.51 (m, 2H). | 478 |
| 19 | 2 | 1H NMR (400 MHz, DMSO-d6) δ 11.72 (s, 1H), 9.16 (s, 1H), 8.45 (d, J = 8.1 Hz, 1H), 7.89 (s, 1H), 7.80-7.64 (m, 2H), 7.53 (d, J = 8.6 Hz, 1H), 7.11 (d, J = 8.0 Hz, 1H), 4.43 (s, 1H), 4.32 (s, 1H), 3.71 (s, 3H), 1.94 (s, 2H), 1.71 (d, J = 33.6 Hz, 3H), 1.55 (s, 1H), 1.24 (q, J = 7.0, 6.5 Hz, 2H). | 482 |
| 20 | 3 | 1H NMR (400 MHz, DMSO-d6) δ 9.15 (s, 1H), 8.46 (d, J = 8.0 Hz, 1H), 7.67 (s, 1H), 7.59-7.45 (m, 2H), 7.10 (d, J = 8.0 Hz, 1H), 7.01 (s, 1H), 4.44 (s, 1H), 4.33 (s, 1H), 3.97 (s, 6H), 2.05-1.85 (m,2H), 1.72 (d, J = 30.6 Hz, 3H), 1.55 (s, 1H). | 486 |
| 21 | 3 | 1H NMR (400 MHz, DMSO-d6) δ 9.36 (br s, 1H), 8.65 (br s, 1H), 7.87-7.60 (m, 4H), 7.04 (s, 1H), 6.28 (dd, J = 17.0, 10.2 Hz, 1H), 6.22 (dd, J = 17.0, 2.3 Hz, 1H), 5.70 (dd, J = 10.2, 2.3 Hz, 1H), 4.23 (m, 2H), 3.97 (s, 6H), 2.14 (m, 2H), 2.01 (m, 2H), 1.81-1.65 (m, 2H). | 487 |
| 22 | 3 | 1H NMR (400 MHz, DMSO-d6) δ 9.49 (br s, 1H), 8.95 (br s, 1H), 7.99-7.86 (m, 4H), 7.05 (s, 1H), 6.34 (dd, J = 17.0, 10.2 Hz, 1H), 6.25 (dd, J = 17.0, 2.3 Hz, 1H), 5.76 (dd, J = 10.2, 2.3 Hz, 1H), 4.24 (m, 2H), 3.99 (s, 6H), 2.13 (m, 2H), 2.02 (m, 2H), 1.87-1.74 (m, 2H). | 487 |

| Compound Number | Synthetic Protocol | ¹H NMR | LC-MS (M + 1) |
|---|---|---|---|
| 23 | 3 | ¹H NMR (400 MHz, DMSO-d₆) δ 9.3 (s, 1H), 8.01-7.72 (m, 5H), 7.04 (s, 1H), 6.21 (dd, J = 17.0, 10.2 Hz, 1H), 5.94 (dd, J = 17.0, 2.3 Hz, 1H), 5.50 (dd, J = 10.2, 2.3 Hz, 1H), 4.49 (m, 2H), 3.96 (s, 6H), 2.04 (m, 2H), 1.85 (m, 2H), 1.69-1.61 (m, 2H). | 487 |
| 24 | 3 | 1H NMR (400 MHz, DMSO-d6) δ 9.13 (s, 1H), 7.82 (d, J = 8.1 Hz, 1H), 7.65 (s, 1H), 7.57-7.38 (m, 2H), 7.09-6.92 (m, 2H), 6.21 (dd, J = 17.1, 10.2 Hz, 1H), 6.00 (dd, J = 17.1, 2.2 Hz, 1H), 5.52 (dd, J = 10.2, 2.2 Hz, 1H), 4.41 (d, J = 31.7 Hz, 2H), 3.97 (s, 6H), 2.11-1.88 (m, 1H), 1.84-1.52 (m, 3H), 1.25 (m, J = 10.0 Hz, 1H). | 488 |
| 25 | 3 | | 488 |
| 26 | 3 | 1H NMR (400 MHz, DMSO-d6) δ 9.16 (s, 1H), 8.06 (d, J = 8.2 Hz, 1H), 7.73-7.64 (m, 1H), 7.61-7.46 (m, 2H), 7.18 (d, J = 7.9 Hz, 1H), 7.00 (s, 1H), 6.22 (dd, J = 17.0, 10.2 Hz, 1H), 6.01 (dd, J = 17.0, 2.2 Hz, 1H), 5.54 (dd, J = 10.2, 2.2 Hz, 1H), 4.79-4.75 (m, 1H), 4.69-4.64 (m, 1H), 4.17-4.05 (m, 1H), 4.04-3.99 (m, 1H), 3.96 (s, 6H), 3.75-3.69 (m, 2H). | 489 |
| 27 | 3 | 1H NMR (400 MHz, DMSO-d6) δ 9.16 (s, 1H), 8.07 (d, J = 8.2 Hz, 1H), 7.71-7.65 (m, 1H), 7.59-7.50 (m, 2H), 7.18 (d, J = 7.9 Hz, 1H), 7.00 (s, 1H), 6.22 (dd, J = 17.1, 10.2 Hz, 1H), 6.01 (dd, J = 17.1, 2.2 Hz, 1H), 5.54 (dd, J = 10.2, 2.2 Hz, 1H), 4.79-4.75 (m, 1H), 4.69-4.64 (m, 1H), 4.17-4.05 (m, 1H), 4.04-3.99 (m, 1H), 3.96 (s, 6H), 3.73-3.66 (m, 2H). | 489 |
| 28 | 3 | | 489 |
| 29 | 3 | | 490 |
| 30 | 2 | 1H NMR (400 MHz, DMSO-d6) δ 9.17 (s, 1H), 8.49 (dd, J = 20.3, 6.2 Hz, 2H), 7.90 (d, J = 2.1 Hz, 1H), 7.78 (dd, J = 8.7, 2.2 Hz, 1H), 7.67 (dd, J = 20.4, 8.7 Hz, 2H), 7.54 (d, J = 8.7 Hz, 1H), 7.12 (d, J = 8.0 Hz, 1H), 4.44 (s, 1H), 4.33 (s, 1H), 2.83 (td, J = 7.3, 3.7 Hz, 1H), 2.04-1.88 (m, 2H), 1.84-1.64 (m, 3H), 1.55 (d, J = 7.7 Hz, 1H), 0.70 (td, J = 7.0, 4.7 Hz, 2H), 0.59-0.48 (m, 2H). | 492 |
| 31 | 3 | ¹H NMR (400 MHz, DMSO-d₆) δ 9.16 (s, 1H), 8.51 (d, J = 7.5 Hz, 1H), 7.67 (d, J = 1.9 Hz, 1H), 7.57-7.45 (m, 2H), 7.04 (d, J = 7.6 Hz, 1H), 7.01 (s, 1H), 4.21 (s, 2H), 3.97 (s, 6H), 1.89 (s, 1H), 1.79 (m, 2H), 1.62 (s, 2H), 1.54 (m, 2H), 1.39 (s, 2H). | 499 |
| 32 | 3 | ¹H NMR (400 MHz, DMSO-d₆) δ 9.13 (s, 1H), 7.71 (d, J = 8.5 Hz, 1H), 7.66-7.60 (m, 1H), 7.55-7.42 (m, 2H), 7.05 (d, J = 8.1 Hz, 1H), 6.99 (s, 1H), 6.09 (dd, J = 17.1, 10.1 Hz, 1H), 5.95 (dd, J = 17.0, 2.3 Hz, 1H), 5.44 (dd, J = 10.0, 2.3 Hz, 1H), 4.52 (t, J = 7.2 Hz, 1H), 4.18-4.07 (m, 1H), 3.96 (s, 6H), 2.00 (td, J = 11.8, 4.4 Hz, 1H), 1.89 (dd, J = 12.3, 7.5 Hz, 1H), 1.44 (s, 1H), 1.40-1.32 (m, 1H), 0.48 (m, 1H), 0.45-0.39 (m, 1H). | 499 |
| 33 | 4 | | 501 |
| 34 | 3 | 1H NMR (400 MHz, DMSO-d6) δ 9.22 (br s, 2H), 7.86 (d, J = 8.2 Hz, 1H), 7.74 (m, 1H), 7.59 (m, 2H), 7.02 (s, 1H), 6.34 (dd, J = 17.0, 10.2 Hz, 1H), 6.03 (dd, J = 17.0, 2.3 Hz, 1H), 5.55 (dd, J = 10.2, 2.3 Hz, 1H), 4.31 (m, 2H), 3.97 (s, 6H), 1.76 (m, 4H), 1.61 (m, 2H), 1.42 (m, 2H) | 501 |
| 35 | 3 | 1H NMR (400 MHz, DMSO-d6) δ 9.21 (br s, 2H), 7.84 (d, J = 8.2 Hz, 1H), 7.73 (m, 1H), 7.58 (m, 2H), 7.01 (s, 1H), 6.34 (dd, J = 17.0, 10.2 Hz, 1H), 6.03 (dd, J = 17.0, 2.3 Hz, 1H), 5.55 (dd, J = 10.2, 2.3 Hz, 1H), 4.27 (m, 2H), 3.97 (s, 6H), 1.75 (m, 4H), 1.60 (m, 2H), 1.43 (m, 2H). | 501 |
| 36 | 3 | 1H NMR (400 MHz, DMSO-d6) δ 9.10 (br s, 1H), 8.07 (br s, 1H), 7.64 (br s, 1H), 7.54 (m, 1H), 7.47 (m, 1H), 7.12 (br s, 1H), 7.02 (s, 1H), 6.11 (dd, J = 17.0, 10.0 Hz, 1H), 6.02 (dd, J = 17.0, 2.3 Hz, 1H), 5.48 (dd, J = 10.0, 2.3 Hz, 1H), 3.97 (s, 6H), 3.85 (m, 2H), 2.15 (m, 1H), 1.93 (m, 1H), 1.71 (m, 2H), 1.33 (m, 4H). | 501 |
| 37 | 3 | | 501 |
| 38 | 3 | | 502 |
| 39 | 3 | | 502 |
| 40 | 3 | 1H NMR (500 MHz, DMSO-d6) δ 9.17 (s, 1H), 8.01 (d, J = 7.7 Hz, 1H), 7.68 (d, J = 1.9 Hz, 1H), 7.58-7.45 (m, 2H), 6.99 (d, J = 10.5 Hz, 2H), 6.25 (dd, J = 17.1, 10.2 Hz, 1H), 6.07 (dd, J = 17.0, 2.3 Hz, 1H), 5.55 (dd, J = 10.2, 2.3 Hz, 1H), 4.33 (d, J = 13.4 Hz, 2H), 3.97 (s, 6H), 3.84 (dd, J = 10.8, 5.8 Hz, 2H), 3.65 (dd, J = 11.7, 2.6 Hz, 1H), 3.54 (ddd, J = 11.9, 8.8, 3.2 Hz, 1H), 1.96 (dq, J = 10.9, 7.0, 5.4 Hz, 1H), 1.76-1.62 (m, 1H). | 503 |
| 41 | 3 | 1H NMR (400 MHz, DMSO-d6) δ 9.14 (s, 1H), 8.02 (d, J = 8.1 Hz, 1H), 7.67 (s, 1H), 7.51 (t, J = 11.2 Hz, 2H), 7.14 (d, J = 7.3 Hz, 1H), 7.00 (s, 1H), 6.44 (dd, J = 17.0, 10.2 Hz, 1H), 6.03 (d, J = 17.0 Hz, 1H), 5.56 (d, J = 10.4 Hz, 1H), 4.36 (s, 1H), 3.96 (s, 7H), 3.78 (d, J = 11.7 Hz, 1H), 3.68-3.50 (m, 1H), 1.96 (d, J = 11.9 Hz, 1H), 1.80 (s, 1H), 1.23 (s, 1H), 0.84 (d, J = 9.5 Hz, 1H). | 503 |
| 42 | 4 | | 503 |
| 43 | 3 | 1H NMR (400 MHz, DMSO-d6) δ 9.16 (s, 1H), 8.00 (d, J = 7.6 Hz, 1H), 7.68-7.60 (m, 1H), 7.59-7.39 (m, 2H), 6.97 (d, J = 16.3 Hz, 2H), 6.23 (dd, J = 17.1, 10.1 Hz, 1H), 6.05 (dd, J = 17.1, 2.2 Hz, 1H), 5.54 (dd, J = 10.1, 2.3 Hz, 1H), 4.32 (s, 2H), 3.96 (s, 6H), 3.88-3.80 (m, 2H), 3.64 (d, J = 10.6 Hz, 1H), 3.54 (d, J = 9.1 Hz, 1H), 2.04-1.90 (m, 1H), 1.69 (s, 1H). | 503 |

-continued

| Compound Number | Synthetic Protocol | ¹H NMR | LC-MS (M + 1) |
|---|---|---|---|
| 44 | 3 | | 504 |
| 45 | 3 | 1H NMR (400 MHz, DMSO-d6) δ 9.17 (s, 1H), 7.80 (s, 1H), 7.50 (s, 1H), 7.43 (d, J = 11.4 Hz, 1H), 7.33 (s, 1H), 7.00 (s, 1H), 6.19 (dd, J = 17.0, 10.0 Hz, 1H), 5.98 (d, J = 17.0 Hz, 1H), 5.50 (d, J = 10.2 Hz, 1H), 4.53-4.33 (m, 3H), 3.96 (s, 6H), 2.11-1.89 (m, 2H), 1.81-1.43 (m, 3H). | 505 |
| 46 | 3 | 1H NMR (400 MHz, DMSO-d6) δ 9.22 (s, 1H), 8.05 (d, J = 7.7 Hz, 1H), 7.54 (s, 1H), 7.51-7.40 (m, 1H), 7.01 (s, 1H), 6.22 (dd, J = 17.1, 10.2 Hz, 1H), 6.05-5.97 (m, 1H) 5.58-5.49 (m, 1H), 4.79 (dt, J = 16.9, 9.3 Hz, 1H), 4.72-4.59 (m, 1H), 4.16-4.06 (m, 1H), 4.06-3.99 (m, 1H), 3.96 (s, 6H), 3.70 (ddd, J = 15.5, 8.6, 5.7 Hz, 2H). | 507 |
| 47 | 3 | ¹H NMR (400 MHz, DMSO-d₆) δ 9.16 (s, 1H), 8.28 (s, 1H), 7.67 (d, J = 1.6 Hz, 1H), 7.57-7.45 (m, 2H), 7.00 (m, 2H), 4.21 (s, 1H), 4.16 (s, 1H), 3.97 (s, 6H), 1.91 (s, 3H), 1.77 (m, 2H), 1.67-1.49 (m, 4H), 1.38 (m, 2H). | 513 |
| 48 | 3 | 1H NMR (400 MHz, DMSO-d6) δ 9.12 (s, 1H), 8.48 (s, 1H), 7.22 (s, 1H), 7.00 (s, 1H), 6.96 (s, 1H), 4.46 (s, 1H) 4.30 (s, 1H), 3.97 (s, 6H), 3.86 (s, 4H), 1.97 (s, 2H), 1.75 (s, 5H). | 515 |
| 49 | 5 | | 515 |
| 50 | 3 | ¹H NMR (400 MHz, DMSO-d₆) δ 9.32 (s, 1H), 7.99 (d, J = 7.6 Hz, 1H), 7.51 (t, J = 8.3 Hz, 1H), 7.35 (d, J = 8.8 Hz, 1H), 7.30 (m, 1H), 7.03 (s, 1H), 6.23 (dd, J = 17.1, 10.1 Hz, 1H), 6.05 (dd, J = 17.1, 2.3 Hz, 1H), 5.53 (dd, J = 10.1, 2.3 Hz, 1H), 4.32 (m, 2H), 3.97 (s, 6H), 3.89-3.80 (m, 2H), 3.68-3.60 (m, 1H), 3.59-3.49 (m, 1H), 1.97 (m, 1H), 1.67 (d, J = 13.1 Hz, 1H). | 521 |
| 51 | 3 | ¹H NMR (400 MHz, DMSO-d₆) δ 9.14 (s, 1H), 7.98 (d, J = 7.4 Hz, 1H), 7.80 (d, J = 8.1 Hz, 1H), 7.29 (d, J = 11.3 Hz, 1H), 7.17 (s, 1H), 7.04 (s, 1H), 6.24 (dd, J = 17.1, 10.1 Hz, 1H), 6.10-6.00 (m, 1H), 5.54 (dd, J = 10.1, 2.3 Hz, 1H), 4.32 (m, 2H), 3.97 (s, 6H), 3.84 (m, 2H), 3.63 (d, J = 11.5 Hz, 1H), 3.53 (t, J = 10.1 Hz, 1H), 1.96 (m, 1H), 1.67 (m, 1H). | 521 |
| 52 | 3 | ¹H NMR (400 MHz, DMSO-d₆) δ 9.23 (d, J = 1.6 Hz, 1H), 7.99 (s, 1H), 7.53 (d, J = 1.8 Hz, 1H), 7.45 (dd, J = 11.5, 1.8 Hz, 1H), 7.30 (d, J = 7.7 Hz, 1H), 7.01 (s, 1H), 6.24 (dd, J = 17.0, 10.1 Hz, 1H), 6.05 (dd, J = 17.1, 2.3 Hz, 1H), 5.54 (dd, J = 10.1, 2.3 Hz, 1H), 4.33 (s, 2H), 3.96 (s, 6H), 3.90-3.79 (m, 2H), 3.64 (d, J = 11.6 Hz, 1H), 3.53 (t, J = 10.4 Hz, 1H), 1.97 (m, 1H), 1.68 (s, 1H). | 521 |
| 53 | 3 | ¹H NMR (400 MHz, DMSO-d₆) δ 9.17 (s, 1H), 7.82 (s, 1H), 7.68 (dd, J = 16.3, 1.9 Hz, 1H), 7.41 (d, J = 6.8 Hz, 1H), 7.01 (s, 1H), 6.20 (dd, J = 17.0, 10.2 Hz, 1H), 5.99 (d, J = 16.9 Hz, 1H), 5.51 (d, J = 10.2 Hz, 1H), 4.44 (s, 2H), 3.96 (s, 6H), 2.00 (m, 2H), 1.87-1.46 (m, 4H). | 521 |
| 54 | 3 | ¹H NMR (400 MHz, DMSO-d₆) δ 9.22 (s, 1H), 8.10 (s, 1H), 7.72 (m, 2H), 7.53 (d, J = 7.1 Hz, 1H), 7.01 (s, 1H), 6.24 (dd, J = 17.1, 10.2 Hz, 1H), 6.02 (m, 1H), 5.55 (d, J = 10.1 Hz, 1H), 4.75 (m, 2H), 4.16 (m, 1H), 4.04 (m, 1H), 3.96 (s, 6H), 3.80-3.65 (m, 2H). | 523 |
| 55 | 3 | ¹H NMR (400 MHz, DMSO-d₆) δ 9.16 (s, 1H), 8.05 (d, J = 8.2 Hz, 1H), 7.76 (s, 1H), 7.67 (s, 1H), 7.40 (d, J = 7.7Hz, 1H), 7.02 (s, 1H), 6.21 (dd, J = 17.1, 10.2 Hz, 1H), 6.00 (dd, J = 17.1, 2.2 Hz, 1H), 5.53 (dd, J = 10.2, 2.2 Hz, 1H), 4.71 (m, 2H), 4.09 (m, 1H), 4.05-3.99 (m, 1H), 3.97 (s, 6H), 3.69 (m, 2H). | 523 |
| 56 | 4 | 1H NMR (400 MHz, DMSO-d6) δ 9.17 (s, 1H), 8.17 (dd, J = 14.3, 7.6 Hz, 1H), 7.73-7.67 (m, 1H), 7.61-7.48 (m, 2H), 7.43 (t, J = 6.8 Hz, 1H), 7.00 (d, J = 1.4 Hz, 1H), 6.23 (dtd, J = 18.7, 9.2, 8.5, 1.5 Hz, 1H), 6.04 (dt, J = 17.1, 1.9 Hz, 1H), 5.56 (dt, J = 10.1, 1.9 Hz, 1H), 4.82-4.59 (m, 2H), 3.96 (s, 6H), 3.93-3.77 (m, 1H), 3.72 (m, 1H), 3.59 (m, 1H), 3.55-3.37 (m, 2H), 1.94 (dd, J = 3.6, 1.4 Hz, 3H). | 530 |
| 57 | 4 | 1H NMR (400 MHz, DMSO-d6) δ 9.17 (s, 1H), 8.18 (dd, J = 13.2, 7.5 Hz, 1H), 7.69 (t, J = 1.4 Hz, 1H), 7.59-7.48 (m, 2H), 7.44 (t, J = 7.1 Hz, 1H), 7.00 (s, 1H), 6.23 (ddd, J = 16.7, 10.1, 8.6 Hz, 1H), 6.04 (dd, J = 17.1, 2.2 Hz, 1H) 5.56 (dd, J = 10.1, 2.2 Hz, 1H), 4.83-4.59 (m, 3H), 3.96 (s, 6H), 3.93-3.79 (m, 1H), 3.70 (m, 1H), 3.59 (m, 1H), 3.55-3.46 (m, 1H), 3.45-3.37 (m, 2H), 1.94 (d, J = 3.4 Hz, 3H). | 530 |
| 58 | 4 | | 530 |
| 59 | 3 | 1H NMR (400 MHz, DMSO-d6) δ 9.16 (s, 1H), 7.89 (d, J = 7.4 Hz, 1H), 7.67 (t, J = 1.4 Hz, 1H), 7.49 (s, 2H), 6.99 (s, 1H), 6.90 (s, 1H), 6.15 (dd, J = 17.0, 10.0 Hz, 1H), 6.03 (dd, J = 17.1, 2.4 Hz, 1H), 5.50 (dd, J = 10.0, 2.5 Hz, 1H), 4.34 (s, 2H), 3.80 (m, 2H), 1.87 (t, J = 13.0 Hz, 1H), 1.51 (d, J = 13.0 Hz, 1H), 1.25 (s, 3H), 1.23 (s, 3H). | 531 |
| 60 | 3 | ¹H NMR (400 MHz, DMSO-d₆) δ 9.16 (s, 1H), 7.89 (br s, 1H), 7.67 (s, 1H), 7.48 (s, 2H), 6.99 (s, 1H), 6.91 (s, 1H), 6.15 (dd, J = 17.0, 10.0 Hz, 1H), 6.03 (dd, J = 17.0, 2.5 Hz, 1H), 5.50 (dd, J = 10.0, 2.5 Hz, 1H), 4.34 (s, 2H), 3.96 (s, 6H), 3.78 (d, J = 11.7 Hz, 2H), 1.87 (t, J = 13.0 Hz, 1H), 1.51 (d, J = 13.0 Hz, 1H), 1.25 (s, 3H), 1.23 (s, 3H). | 531 |

-continued

| Compound Number | Synthetic Protocol | ¹H NMR | LC-MS (M + 1) |
|---|---|---|---|
| 61 | 3 | | 531 |
| 62 | | 1H NMR (400 MHz, DMSO-d6) δ 9.17 (s, 1H), 7.80 (s, 1H), 7.50 (s, 1H), 7.43 (d, J = 11.4 Hz, 1H), 7.33 (s, 1H), 7.00 (s, 1H), 6.19 (dd, J = 17.0, 10.0 Hz, 1H), 5.98 (d, J = 17.0 Hz, 1H), 5.50 (d, J = 10.2 Hz, 1H), 4.53-4.33 (m, 3H), 3.96 (s, 6H), 2.11-1.89 (m, 2H), 1.81-1.43 (m, 3H). | 532 |
| 63 | 5 | 1H NMR (300 MHz, DMSO-d6) δ 8.73 (d, J = 13.2 Hz, 1H), 8.05-7.73 (m, 2H), 7.03 (s, 1H), 6.13 (dd, J = 17.0, 10.0 Hz, 1H), 5.99-5.85 (m, 1H), 5.52-5.38 (m, 1H), 4.37 (dd, J = 26.9, 6.6 Hz, 2H), 4.32-4.15 (m, 1H), 3.97 (s, 6H), 1.83 (d, J = 19.8 Hz, 4H), 1.61 (d, J = 27.5 Hz, 2H), 1.22 (t, J = 6.8 Hz, 3H), 0.96-0.77 (m, 1H). | 533 |
| 64 | 5 | | 533 |
| 65 | 3 | 1H NMR (400 MHz, Chloroform-d) δ 9.18 (s, 1H), 7.77 (d, J = 8.6 Hz, 1H), 7.73-7.60 (m, 2H), 7.43 (d, J = 7.5 Hz, 1H), 7.30 (s, 1H), 7.15 (s, 1H), 6.66 (s, 1H), 5.95-5.82 (m, 1H), 5.14-4.95 (m, 1H), 3.99 (s, 7H), 3.42-3.32 (m, OH), 3.24-3.10 (m, 1H), 2.68 (d, J = 13.4 Hz, 1H), 0.93-0.78 (m, 3H). | 533 |
| 66 | 3 | ¹H NMR (400 MHz, DMSO-d6) δ 9.18 (s, 1H), 7.68 (d, J = 1.9 Hz, 1H), 7.58-7.46 (m, 2H), 7.18 (d, J = 7.1 Hz, 1H), 7.01 (s, 1H), 6.95 (d, J = 7.8 Hz, 1H), 6.50 (dd, J = 16.5, 9.9 Hz, 1H), 5.84 (d, J = 16.5 Hz, 1H), 5.51 (d, J = 9.9 Hz, 1H), 4.13 (s, 1H), 3.62 (s, 1H), 3.38 (m, 1H), 1.78 (m, 1H), 1.62 (m, 3H), 1.38 (m, 1H), 1.18 (t, J = 7.1 Hz, 1H), 1.09 (t, J = 7.0 Hz, 1H). | 537 |
| 67 | 3 | ¹H NMR (400 MHz, DMSO-d6) δ 9.22 (s, 1H), 8.00 (d, J = 7.7 Hz, 1H), 7.70 (m, 1H), 7.44-7.29 (m, 1H), 7.01 (s, 1H), 6.24 (dd, J = 17.0, 10.2 Hz, 1H), 6.05 (dd, J = 17.1, 2.2 Hz, 1H), 5.55 (dd, J = 10.2, 2.2 Hz, 1H), 4.35 (m, 2H), 3.96 (s, 6H), 3.85 (m, 2H), 3.67 (m, 1H), 3.54 (m, 1H), 1.98 (m, 1H), 1.68 (m, 1H). | 537 |
| 68 | 5 | 1H NMR (400 MHz, DMSO-d6) δ 8.52 (d, J = 8.1 Hz, 1H), 8.37 (s, 1H), 7.63 (s, 1H), 6.97 (s, 1H), 6.73 (d, J = 8.2 Hz, 1H), 6.51 (s, 1H), 4.27 (m, 1H), 4.15-4.06 (m, 3H), 3.95 (s, 6H), 2.69 (s, 1H), 1.73 (m, 3H), 1.59 (m, 3H), 1.38 (m, 2H), 1.21 (t, J = 7.1 Hz, 3H). | 543 |
| 69 | 4 | ¹H NMR (400 MHz, DMSO-d6) δ 9.17 (d, J = 23.3 Hz, 1H), 8.01 (dd, J = 22.5, 7.8 Hz, 1H), 7.73-7.63 (m, 1H), 7.61-7.44 (m, 2H), 7.16 (dd, J = 19.0, 7.3 Hz, 1H), 7.00 (d, J = 1.7 Hz, 1H), 6.26 (ddd, J = 16.9, 10.1, 6.6 Hz, 1H), 6.12-6.01 (m, 1H), 5.56 (ddd, J = 23.8, 10.1, 2.2 Hz, 1H), 4.26 (m, 2H), 4.16-3.99 (m, 1H), 3.96 (s, 6H), 3.90 (m, 1H), 3.63 (m, 1H), 3.14 (m, 1H), 1.99-1.85 (m, 1H), 1.81 (s, 3H), 1.66 (m, 1H). | 544 |
| 70 | 4 | ¹H NMR (400 MHz, DMSO-d6) δ 9.17 (d, J = 23.3 Hz, 1H), 8.01 (dd, J = 22.4, 7.8 Hz, 1H), 7.74-7.63 (m, 1H), 7.61-7.45 (m, 2H), 7.22-7.10 (m, 1H), 7.00 (d, J = 1.7 Hz, 1H), 6.26 (ddd, J = 17.0, 10.2, 6.7 Hz, 1H), 6.12-6.01 (m, 1H), 5.56 (ddd, J = 23.8, 10.2, 2.2 Hz, 1H), 4.26 (d, J = 46.4 Hz, 2H), 4.16-4.04 (m, 1H), 3.96 (s, 6H), 3.63 (dd, J = 56.7, 14.0 Hz, 1H), 3.14 (s, 1H), 1.85 (d, J = 36.3 Hz, 3H), 1.66 (s, 1H). | 544 |
| 71 | 4 | ¹H NMR (400 MHz, DMSO-d6) δ 9.16 (s, 1H), 7.93 (d, J = 7.0 Hz, 1H), 7.68 (d, J = 2.1 Hz, 1H), 7.61-7.45 (m, 2H), 7.10 (d, J = 7.8 Hz, 1H), 7.00 (s, 1H), 6.39 (dd, J = 17.1, 10.2 Hz, 1H), 6.05 (dd, J = 17.1, 2.2 Hz, 1H), 5.58 (dd, J = 10.1, 2.3 Hz, 1H), 4.33 (m, 3H), 3.96 (s, 6H), 3.83-3.73 (m, 1H), 3.38 (m, 1H), 2.87 (m, 1H), 1.86 (s, 3H), 1.78 (m, 2H). | 544 |
| 72 | 3 | ¹H NMR (400 MHz, DMSO-d6) δ 9.15 (s, 1H), 7.90 (d, J = 8.0 Hz, 1H), 7.66 (br s, 1H), 7.55-7.42 (m, 2H), 7.19-7.11 (m, 1H), 7.00 (m, 2H), 6.70 (s, 1H), 6.17 (dd, J = 17.0, 10.1 Hz, 1H), 6.02 (dd, J = 17.0, 2.3 Hz, 1H), 5.50 (dd, J = 10.1, 2.3 Hz, 1H), 4.47 (m, 1H), 4.00 (m, 1H), 3.96 (s, 6H), 2.49 (m, 1H), 2.13 (s, 1H), 1.81 (m, 2H), 1.65 (m, 2H), 1.51 (m, 1H). | 544 |
| 73 | 6 | 1H NMR (400 MHz, DMSO-d6) δ 9.13 (s, 1H), 7.86 (d, J = 8.3 Hz, 1H), 7.65 (s, 1H), 7.50 (q, J = 9.2 Hz, 1H), 7.00 (d, J = 7.1 Hz, 1H), 6.15 (dd, J = 17.1, 10.1 Hz, 1H), 5.98 (d, J = 15.1 Hz, OH), 5.60-5.47 (m, 1H), 4.52 (s, 1H), 4.40 (s, 1H), 3.97 (d, J = 10.8 Hz, 6H), 3.61 (d, J = 11.6 Hz, 2H), 3.26 (s, 3H), 3.03-2.87 (m, 1H), 2.29 (d, J = 15.3 Hz, 1H), 2.10-1.90 (m, 2H), 1.25-1.08 (m, 1H), 0.88 (dd, J = 41.1, 7.4 Hz, 1H). | 545 |
| 74 | 4 | | 545 |
| 75 | 4 | ¹H NMR (400 MHz, DMSO-d6) δ 9.17 (s, 1H), 8.16 (dd, J = 12.1, 7.6 Hz, 1H), 7.69 (br s, 1H), 7.60-7.47 (m, 2H), 7.44 (d, J = 6.6 Hz, 1H), 7.00 (s, 1H), 6.21 (ddd, J = 16.8, 10.2, 6.5 Hz, 1H), 6.08-6.00 (m, 1H), 5.56 (dt, J = 10.2, 2.1 Hz, 1H), 4.84-4.54 (m, 3H), 4.00 (m, 2H), 3.96 (s, 6H), 3.86-3.71 (m, 2H), 3.52-3.37 (m, 2H). | 546 |

| Compound Number | Synthetic Protocol | ¹H NMR | LC-MS (M + 1) |
|---|---|---|---|
| 76 | 4 | ¹H NMR (400 MHz, DMSO-d₆) δ 9.17 (s, 1H), 8.17 (dd, J = 12.3, 7.7 Hz, 1H), 7.69 (br s, 1H), 7.61-7.47 (m, 2H), 7.45 (d, J = 7.5 Hz, 1H), 7.00 (s, 1H), 6.21 (ddd, J = 16.9, 10.1, 6.6 Hz, 1H), 6.08-5.99 (m, 1H), 5.56 (dt, J = 10.1, 2.1 Hz, 1H), 4.84-4.62 (m, 3H), 4.00 (m, 2H), 3.96 (s, 6H), 3.86-3.62 (m, 2H), 3.52-3.38 (m, 2H). | 546 |
| 77 | 5 | ¹H NMR (400 MHz, DMSO-d₆) δ 8.63 (s, 1H), 7.80 (d, J = 8.5 Hz, 1H), 7.63 (m, 2H), 6.96 (s, 1H), 6.31 (m, 1H), 6.00 (m, 1H), 5.51 (m, 1H), 4.40-4.13 (m, 4H), 3.94 (s, 6H), 1.85-1.49 (m, 6H), 1.40 (s, 2H), 1.19 (t, J = 7.1 Hz, 3H). | 546 |
| 78 | 5 | ¹H NMR (400 MHz, DMSO-d₆) δ 8.72 (s, 1H), 7.95 (d, J = 7.7 Hz, 1H), 7.81 (d, J = 8.3 Hz, 1H), 7.75 (d, J = 8.0 Hz, 1H), 7.02 (s, 1H), 6.42-6.22 (m, 1H), 5.99 (m, 1H), 5.52 (m, 1H), 4.26 (m, 4H), 3.96 (s, 6H), 1.63 (m, 6H), 1.40 (m, 2H), 1.22 (t, J = 7.3 Hz, 3H). | 547 |
| 79 |  | ¹H NMR (400 MHz, DMSO-d₆) δ 9.18 (s, 1H), 8.16 (d, J = 9.2 Hz, 1H), 7.70 (s, 1H), 7.64-7.41 (m, 3H), 7.00 (s, 1H), 6.28 (dd, J = 17.1, 10.2 Hz, 1H), 6.06 (dd, J = 17.1, 2.2 Hz, 1H), 5.60 (dd, J = 10.2, 2.2 Hz, 1H), 4.69 (m, 2H), 3.96 (s, 6H), 3.45 (m, 3H), 3.15 (m, 1H), 2.12 (s, 2H). | 551 |
| 80 | 4 | 1H NMR (400 MHz, DMSO-d6) δ6 9.18 (s, 1H), 8.27-8.14 (m, 1H), 7.69 (dq, J = 2.4, 1.2 Hz, 1H), 7.62-7.48 (m, 2H), 7.44 (dd, J = 10.7, 7.1 Hz, 1H), 7.00 (s, 1H), 6.32-6.18 (m, 1H), 6.05 (dq, J = 17.1, 1.7 Hz, 1H), 5.62-5.52 (m, 1H), 4.73 (m, 2H), 4.16-4.07 (m, 1H), 3.96 (s, 6H), 3.79-3.58 (m, 2H), 3.45 (m, 1H), 1.74 (m, 1H), 0.80-0.66 (m, 4H). | 556 |
| 81 | 6 | 1H NMR (400 MHz, DMSO-d6) δ 9.12 (s, 1H), 7.86 (d, J = 8.0 Hz, 1H), 7.65 (s, 1H), 7.50 (q, J = 8.7 Hz, 2H), 7.17 (d, J = 7.9 Hz, 1H), 6.99 (s, 1H), 6.18 (dd, J = 17.0, 10.1 Hz, 1H), 6.00 (dd, J = 17.0, 2.3 Hz, 1H), 5.51 (dd, J = 10.1, 2.3 Hz, 1H), 4.55 (s, 1H), 4.44 (s, 1H), 3.95 (s, 6H), 3.28-3.14 (m, 3H), 2.99 (s, 2H), 2.84 (s, 2H), 2.18-1.81 (m, 3H), 1.27-1.15 (m, 1H). | 558 |
| 82 | 6 | 1H NMR (400 MHz, DMSO-d6) δ 9.10 (s, 1H), 7.93 (d, J = 8.3 Hz, 1H), 7.64 (d, J = 1.5 Hz, 1H), 7.47 (d, J = 3.1 Hz, 2H), 7.13 (d, J = 8.3 Hz, 1H), 6.99 (s, 1H), 6.08 (dd, J = 17.1, 10.0 Hz, 1H), 5.96 (dd, J = 17.1, 2.4 Hz, 1H), 5.47 (dd, J = 10.0, 2.4 Hz, 1H), 4.65-4.47 (m, 1H), 4.46-4.24 (m, 1H), 3.95 (s, 6H), 3.61 (td, J = 6.6, 3.9 Hz, 1H), 3.04 (s, 3H), 2.86 (s, 3H), 2.23 (s, 2H), 1.82 (ddt, J = 33.1, 14.2, 7.2 Hz, 2H). | 558 |
| 83 | 4 | ¹H NMR (400 MHz, DMSO-d₆) δ 9.18 (s, 1H), 8.15 (d, J = 7.6 Hz, 1H), 7.69 (s, 1H), 7.61-7.47 (m, 2H), 7.31 (d, J = 7.2 Hz, 1H), 7.00 (s, 1H), 6.26 (dd, J = 17.1, 10.2 Hz, 1H), 6.17 (t, J = 5.6 Hz, 1H), 6.05 (dd, J = 17.1, 2.2 Hz, 1H), 5.58 (dd, J = 10.1, 2.2 Hz, 1H), 4.75-4.55 (m, 2H), 3.96 (s, 6H), 3.69 (t, J = 8.6 Hz, 1H), 3.57 (dd, J = 10.8, 6.1 Hz, 1H), 3.41-3.32 (m, 2H), 3.03 (p, J = 6.8 Hz, 2H), 1.00 (t, J = 7.1 Hz, 3H). | 559 |
| 84 | 4 |  | 560 |
| 85 | 4 | ¹H NMR (400 MHz, DMSO-d₆) δ 9.17 (s, 1H), 8.16 (dd, J = 11.6, 7.7 Hz, 1H), 7.69 (br s, 1H), 7.59-7.48 (m, 2H), 7.44 (dd, J = 7.7, 3.1 Hz, 1H), 7.00 (s, 1H), 6.22 (ddd, J = 16.9, 10.2, 6.7 Hz, 1H), 6.04 (dt, J = 17.1, 2.2 Hz, 1H), 5.56 (dt, J = 10.1, 2.5 Hz, 1H), 4.82-4.59 (m, 2H), 4.04-3.98 (m, 2H), 3.96 (s, 6H), 3.87-3.62 (m, 2H), 3.45 (m, 2H), 3.31 (s, 3H). | 560 |
| 86 | 4 | 1H NMR (400 MHz, DMSO-d6) δ 9.17 (s, 1H), 8.16 (dd, J = 11.8, 7.6 Hz, 1H), 7.72-7.66 (m, 2H), 7.61-7.49 (m, 2H), 7.44 (dd, J = 7.5, 3.1 Hz, 1H), 7.00 (s, 1H), 6.22 (ddd, J = 16.9, 10.2, 6.7 Hz, 1H), 6.04 (dt, J = 17.2, 2.2 Hz, 1H), 5.56 (dt, J = 10.2, 2.5 Hz, 1H), 4.81-4.58 (m, 2H), 4.00 (s, 1H), 3.96 (s, 6H), 3.88-3.71 (m, 2H), 3.65 (m, 1H), 3.51-3.41 (m, 2H), 3.30 (s, 3H). | 560 |
| 87 | 3 | ¹H NMR (400 MHz, DMSO-d₆) δ 9.10 (s, 1H), 7.82 (d, J = 8.7 Hz, 1H), 7.64 (d, J = 1.7 Hz, 1H), 7.60-7.43 (m, 2H), 7.18 (d, J = 7.9 Hz, 1H), 6.99 (s, 1H), 6.40 (dd, J = 17.1, 10.2 Hz, 1H), 6.03 (dd, J = 17.1, 2.3 Hz, 1H), 5.58 (dd, J = 10.2, 2.3 Hz, 1H), 4.59 (s, 1H), 4.08 (s, 1H), 3.96 (s, 6H), 3.04 (m, 1H), 2.99 (s, 3H), 2.80 (s, 3H), 1.86-1.62 (m, 5H), 1.51 (m, 1H). | 572 |
| 88 | 4 | ¹H NMR (400 MHz, DMSO-d₆) δ 9.17 (s, 1H), 8.15 (t, J = 8.1 Hz, 1H), 7.72-7.66 (m, 1H), 7.59-7.47 (m, 2H), 7.41 (d, J = 7.4 Hz, 1H), 7.00 (s, 1H), 6.22 (ddd, J = 17.1, 10.1, 4.3 Hz, 1H), 6.04 (dt, J = 17.1, 2.1 Hz, 1H), 5.56 (dt, J = 10.1, 2.8 Hz, 1H), 4.82-4.56 (m, 2H), 3.96 (s, 6H), 3.86 (m, 1H), 3.79-3.65 (m, 1H), 3.56 (m, 1H), 3.45 (m, 2H), 3.10-2.94 (m, 2H), 2.20 (s, 3H), 2.19 (s, 3H) | 573 |

| Compound Number | Synthetic Protocol | $^1$H NMR | LC-MS (M + 1) |
|---|---|---|---|
| 89 | 4 | 1H NMR (400 MHz, DMSO-d6) δ 9.20 (s, 1H), 8.16 (d, J = 7.4 Hz, 1H), 7.70 (d, J = 1.7 Hz, 1H), 7.61-7.49 (m, 2H), 7.39 (d, J = 7.1 Hz, 1H), 7.00 (s, 1H), 6.26 (dd, J = 17.0, 10.2 Hz, 1H), 6.05 (dd, J = 17.1, 2.1 Hz, 1H), 5.59 (dd, J = 10.2, 2.1 Hz, 1H), 4.72 (m, 2H), 3.96 (s, 6H), 3.73 (m, 2H), 3.39 (ddd, J = 21.7, 10.1, 5.6 Hz, 2H), 3.15 (q, J = 7.4 Hz, 2H), 1.23 (t, J = 7.3 Hz, 3H). | 580 |
| 90 | 3 |  | 588 |
| 91 | 4 | $^1$H NMR (400 MHz, DMSO-d$_6$) δ 9.18 (s, 1H), 8.15 (t, J = 7.6 Hz, 1H), 7.69 (br s, 1H), 7.60-7.47 (m, 2H), 7.43 (d, J = 6.6 Hz, 1H), 7.00 (s, 1H), 6.22 (ddd, J = 17.2, 10.2, 7.1 Hz, 1H), 6.05 (ddd, J = 17.1, 3.8, 2.2 Hz, 1H), 5.57 (ddd, J = 10.2, 4.9, 2.2 Hz, 1H), 4.68 (m, 2H), 3.96 (s, 6H), 3.92-3.70 (m, 2H), 3.69-3.51 (m, 2H), 3.45 (m, 3H), 2.67 (m, 3H), 1.71 (m, 4H). | 599 |
| 92 | 3 |  | 602 |

Biochemical Activity Assessment

In order to assess the activity of chemical compounds against the relevant kinase of interest, the Caliper LifeSciences electrophoretic mobility shift technology platform is utilized. Fluorescently labeled substrate peptide is incubated in the presence dosed levels of compounds, a set concentration of kinase and of ATP, so that a reflective proportion of the peptide is phosphorylated. At the end of the reaction, the mix of phosphorylated (product) and non-phosphorylated (substrate) peptides are passed through the microfluidic system of the Caliper LabChip® EZ Reader II, under an applied potential difference. The presence of the phosphate group on the product peptide provides a difference in mass and charge between the product peptide and the substrate peptide, resulting in a separation of the substrate and product pools in the sample. As the pools pass the LEDS within the instrument, these pools are detected and resolved as separate peaks. The ratio between these peaks therefore reflects the activity of the chemical matter at that concentration in that well, under those conditions.

FGFR-4 wild type assay at Km: In each well of a 384-well plate, 0.5 ng/ul of wild type FGFR-4 (Carna Biosciences, Inc.) was incubated in a total of 12.5 ul of buffer (100 mM HEPES pH 7.5, 0.015% Brij 35, 10 mM MgCl$_2$, 1 mM DTT) with 1 uM CSKtide (5-FAM-KKKKEEIYFFFG-NH$_2$) and 400 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper LabChip® EZ Reader II (protocol settings: −1.9 psi, upstream voltage −700, downstream voltage −3000, post sample sip 35 s).

Detection of pMAPK (Thr202/Tyr204) Using Alpha Elisa

MDA-MB453 or DMS 114 cells were plated in 96-well cell culture plates at a density of 1×105 cells or 3×104 cells, respectively. Cells were allowed to attach, and growth media was replaced with serum free media. Compounds were added at the indicated concentrations. Following 1 hr incubation in the presence of compound, cells were collected. For the DMS 114 cells, 100 ng/mL FGF2 was added for 10 min prior to cell collection. Cell lysates were prepared and processed according to manufacturer instruction (AlphaScreen® SureFire™ Phospho-ERK 1/2 Kit (Perkin Elmer).

The table below summarizes biochemical data for Compounds 1-92. In the table below, for FGFR4 and pERK alphaLISA: "A" means that the IC$_{50}$ is less than 10 nM; "B" means the IC$_{50}$ is greater than or equal to 10 and less than 100 nM; "C" means that the IC$_{50}$ is greater than or equal to 100 and less than 1000 nM; "D" means that the IC$_{50}$ is greater than 1000 nM.

| Compound Number | INH-FGFR4 | pERK alphaLISA |
|---|---|---|
| 1 | D |  |
| 2 | B |  |
| 3 | C |  |
| 4 | B |  |
| 5 | B |  |
| 6 | C |  |
| 7 | B |  |
| 8 | B |  |
| 9 | C |  |
| 10 | D |  |
| 11 | B |  |
| 12 | A |  |
| 13 | C |  |
| 15 | C |  |
| 16 | B |  |
| 17 | D |  |
| 18 | D |  |
| 19 | B |  |
| 20 | A |  |
| 21 | D |  |
| 22 | C |  |
| 23 | C |  |
| 24 | B | B |
| 25 | B |  |
| 26 | B | C |
| 27 | A | A |
| 28 | A | B |
| 29 | B | A |
| 30 | B |  |
| 31 | A |  |
| 32 | A | A |
| 33 | B |  |
| 34 | B | B |
| 35 | D |  |
| 36 | D |  |
| 37 | D |  |
| 38 | C |  |
| 39 | D |  |
| 40 | A | A |
| 41 | B | C |
| 42 | B |  |
| 43 | C |  |
| 44 | B | B |
| 45 | B | B |
| 46 | A | A |
| 47 | D |  |
| 48 | A |  |
| 49 | A |  |
| 50 | B |  |
| 51 | A | A |
| 52 | A | A |
| 53 | B |  |
| 54 | A | A |
| 55 | A | A |
| 56 | A | A |
| 57 | C |  |
| 58 | A | B |
| 59 | C |  |

-continued

| Compound Number | INH-FGFR4 | pERK alphaLISA |
|---|---|---|
| 60 | D | |
| 61 | C | |
| 62 | A | B |
| 63 | B | C |
| 64 | A | A |
| 65 | C | |
| 66 | B | |
| 67 | A | |
| 68 | A | |
| 69 | C | |
| 70 | C | |
| 71 | B | |
| 72 | C | |
| 73 | B | |
| 74 | B | C |
| 75 | A | B |
| 76 | A | B |
| 77 | B | B |
| 78 | C | |
| 79 | B | |
| 80 | A | A |
| 81 | B | |
| 82 | D | |
| 83 | A | A |
| 84 | A | B |
| 85 | A | B |
| 86 | A | A |
| 87 | C | |
| 88 | A | B |
| 89 | A | B |
| 90 | B | C |
| 91 | A | B |
| 92 | D | |

Efficacy in an in vivo Model

The effects of Compound 27 on tumor growth inhibition in Hep3B liver cancer cell subcutaneous xenograft model with different dosages were studied.

Female nude mice (Mus Musculus) age 6 to 8 weeks were used. Tumor cell culture and inoculation: Hep3B cells were cultured with EMEM medium (Invitrogen, USA) supplemented with 10% FBS (Gibco, Australia). The cells were harvested in 90% confluence, and the viability was no less than 90%. Mice were implanted subcutaneously (s.c.) with 200 μL of 10×10$^6$ Hep3B cells in 50% Matrigel in the right flank at the beginning of the study.

Animal grouping and dosing schedule: Ten days after cell implantation, when tumors reached an average volume of 284 mm$^3$, 36 mice were selected based on tumor volume and randomly assigned to 5 treatment groups (n=9). The day of randomization was denoted as day 0 and the treatment was started from then on.

Tumor volume and body weight measurements: Tumor size was measured twice per week in two dimensions using a caliper, and the volume was expressed in mm$^3$ using the formula: $V=0.5 \times a \times b^2$ where a and b were the long and short diameters of the tumor, respectively. Body weight was measured at least twice weekly.

Tumor volumes of Hep3B-bearing nude mice: FIG. 1 is a line graph depicting the growth inhibition of Compound 27-treated groups against Hep3B xenograft tumors in nude mice. Statistically significant reduction of tumor volumes was observed in 30 and 100 mg/kg PO BID efficacy groups when compared with vehicle group. Increasing dosage of Compound 27 enhanced the tumor inhibition efficiency. Tumors in the Compound 27-treated (100 mg/kg PO BID) group regressed.

Figure 2:
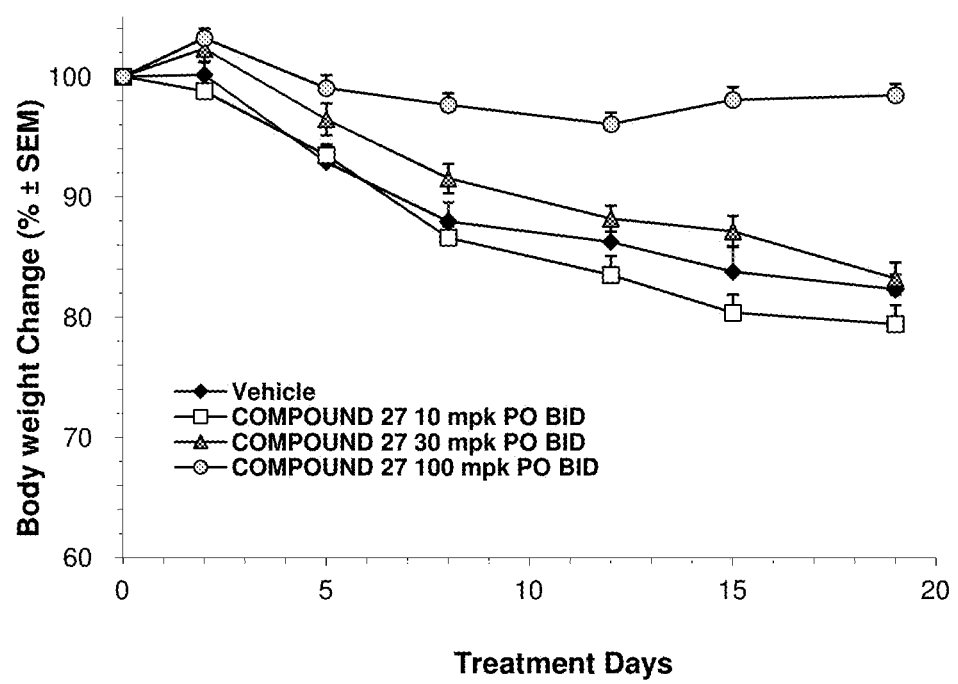
FIG. 2 is a graph depicting the body weight change (%) of Hep3B-bearing nude mice over the course of the study period.

Body weight change (%) of Hep3B-bearing nude mice: FIG. 2 is a line graph depicting the body weight change (%) during the entire study period. All the mice except for the mice in the Compound 27-treated (100 mg/kg PO BID) groups showed significant loss in bodyweight. The body weight of mice in the vehicle group decreased by approximately 15% by Day 10 for the burden of tumor. This result indicated that Compound 27 was well tolerated at the current dosages and dosing schedule in nude mice, and that Compound 27 could alleviate body weight loss by inhibiting tumor growth.

Mice treated with Compound 27 exhibited a significant reduction of tumor volume as compared with the vehicle group during the entire study. Increasing the dosage of Compound 27 from 10 mg/kg to 100 mg/kg enhanced the tumor inhibition efficiency. Tumors of mice in the Compound 27-treated (100 mg/kg PO BID) group regressed and almost disappeared. All mice except for those in the Compound 27-treated (100 mg/kg PO BID) groups lost bodyweight. The bodyweight of the mice in the vehicle group decreased by approximately 15% by Day 10 for the burden of tumor. These results indicated that Compound 27 was well tolerated at the current dosages and at the dosing schedule in nude mice, and that Compound 27 could alleviate body weight loss by inhibiting tumor growth.

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound or pharmaceutically acceptable salt thereof, wherein the compound is:

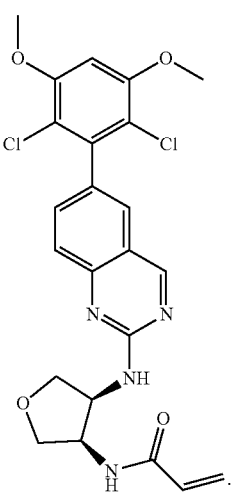 [SMILES: C=CC(=O)N[C@H]1COC[C@H]1Nc1ncc2cc(-c3c(Cl)c(OC)cc(OC)c3Cl)ccc2n1]

2. A pharmaceutical composition comprising the compound of claim 1 or pharmaceutically acceptable salt thereof, and a pharmaceutically acceptable carrier.

3. A compound or pharmaceutically acceptable salt thereof, wherein the compound is:
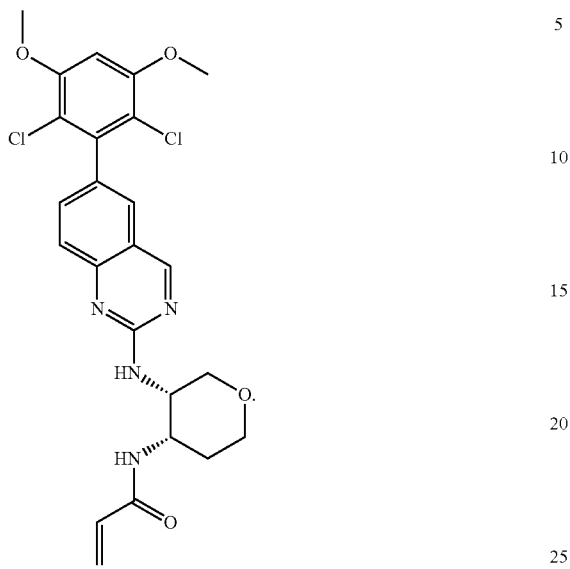
4. A pharmaceutical composition comprising the compound of claim 3 or pharmaceutically acceptable salt thereof, and a pharmaceutically acceptable carrier.
* * * * *